(12) United States Patent
Czech et al.

(10) Patent No.: US 12,372,537 B2
(45) Date of Patent: Jul. 29, 2025

(54) DETERMINATION OF PARKINSON'S DISEASE

(71) Applicants: Hoffmann-La Roche Inc., Little Falls, NJ (US); Roche Diagnostics Operations, Inc., Indianapolis, IN (US); Ventana Medical Systems, Inc., Tucson, AZ (US); Prothena Biosciences Limited, Dublin (IE)

(72) Inventors: Christian Czech, Basel (CH); Sebastian Dziadek, Basel (CH); Lidija Pestic-Dragovich, Tucson, AZ (US); Lei Tang, Tucson, AZ (US); Thomas Kremer, Basel (CH); Wagner Marcelo Zago, Dublin (IE); Tsu-Shuen Tsao, Tucson, AZ (US); Adriana Racolta, Tucson, AZ (US); Marta Canamero, Penzberg (DE); Ronald Torres, Dublin (IE); Mirko Ritter, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 1208 days.

(21) Appl. No.: 17/265,154

(22) PCT Filed: Aug. 8, 2019

(86) PCT No.: PCT/US2019/045793
§ 371 (c)(1),
(2) Date: Feb. 1, 2021

(87) PCT Pub. No.: WO2020/033756
PCT Pub. Date: Feb. 13, 2020

(65) Prior Publication Data
US 2022/0018851 A1    Jan. 20, 2022

Related U.S. Application Data

(60) Provisional application No. 62/716,504, filed on Aug. 9, 2018.

(51) Int. Cl.
*G01N 33/68*    (2006.01)

(52) U.S. Cl.
CPC . *G01N 33/6893* (2013.01); *G01N 2800/2835* (2013.01)

(58) Field of Classification Search
None
See application file for complete search history.

(56) References Cited

U.S. PATENT DOCUMENTS

| | | | |
|---|---|---|---|
| 6,426,195 B1 * | 7/2002 | Zhong | G01N 1/30 435/243 |
| 8,092,801 B2 | 1/2012 | Schenk et al. | |
| 8,609,820 B2 | 12/2013 | Saldanha et al. | |
| 8,790,644 B2 | 7/2014 | Saldanha et al. | |
| 8,940,276 B2 | 1/2015 | Weihofen et al. | |
| 9,580,493 B2 | 2/2017 | Weihofen et al. | |
| 2006/0259986 A1 * | 11/2006 | Chilcote | A61P 43/00 435/7.1 |
| 2015/0140003 A1 | 5/2015 | Kaluza et al. | |

FOREIGN PATENT DOCUMENTS

| | | | | |
|---|---|---|---|---|
| WO | WO-2007130677 A2 * | 11/2007 | | G01N 33/5035 |
| WO | WO 2011/106885 | 9/2011 | | |
| WO | WO-2016166073 A1 * | 10/2016 | | G01N 1/312 |
| WO | WO-2017096113 A1 * | 6/2017 | | A01N 1/0231 |
| WO | WO 2018/002015 | 1/2018 | | |
| WO | WO-2018222665 A1 * | 12/2018 | | A61K 31/575 |

OTHER PUBLICATIONS

Buus et al., High-resolution Mapping of Linear Antibody Epitopes Using Ultrahigh-density Peptide Microarrays, Molecular & Cellular Proteomics, 11(12), (2012), p. 1790-1800 (Year: 2012).*
Barrenschee et al., Distinct pattern of enteric phospho-alpha-synuclein aggregates and gene expression profiles in patients with Parkinson's disease, Acta Neuropathologica Communications, 5(1), (2017), (14 pages) (Year: 2017).*
Lebouvier et al., Pathological Legions in Colonic biopsies during Parkinson's disease, Gut, 57(12), (2008), p. 1741-1743 (Year: 2008).*
Desmet et al., Distinct subcellular localization of the Neuronal Marker HuC/D reveals hypoxia-induced damage in enteric neurons, Neurogastroenterology & Motility, 26(8), (2014), (abstract only) (Year: 2014).*
Abcam, "Anti-PGP9.5 antibody [EPR4118]-Neuronal Marker", ab108986. https://www.abcam.com/en-us/products/primary-antibodies/pgp95-antibody-epr4118-neuronal-marker-ab108986#. Accessed [Sep. 30, 2024] (4 pages) (Year: 2024).*
Smith, C., "FFPE or Frozen? Working with Human Clinical Samples", https://www.biocompare.com/Editorial-Articles/168948-FFPE-or-Frozen-Working-with-Human-Clinical-Samples/. (2014), 2 pages. Accessed [Sep. 30, 2024]. (Year: 2014).*
Lan et al., A Novel, Simple, Reliable, and Sensitive Method for Multiple Immunoenzyme Staining: Use of Microwave Oven Heating to Block Antibody Crossreactivity and Retrieve Antigens, The Journal of Histochemistry and Cytochemistry, 43(1), (1995), p. 97-102 (Year: 1995).*
Howat et al., Antibody validation of immunohistochemistry for biomarker discovery: Recommendations of a consortium of academic and pharmaceutical based histopathology researchers, Methods, 70, (2014), p. 34-38 (Year: 2014).*
Doppler, et al., "Dermal phospho-alpha-synuclein deposits confirm REM sleep behaviour disorder as prodromal Parkinson's disease", ACTA Neuropathologica, 133:535-545 (2017).

(Continued)

*Primary Examiner* — Ellen J Marcsisin
(74) *Attorney, Agent, or Firm* — McDonnell Boehnen Hulbert & Berghoff LLP

(57) ABSTRACT

Methods and compositions for accurate identification of Parkinson's disease are disclosed. More particularly, the disclosure is directed to the determination of Parkinson's disease in ante-mortem tissue samples.

30 Claims, 65 Drawing Sheets

Specification includes a Sequence Listing.

(56) References Cited

OTHER PUBLICATIONS

Beach, et al., "Submandibular Gland Biopsy for the Diagnosis of Parkinson Disease", Journal of Neuropathology and Experimental Neurology, 72:130-136 (2013).
Zhong, et al., "Age-Dependent Alpha-Synclein Accumulation and Phosphorylation in the Enteric Nervous System in a Transgenic Mouse Model of Parkinson's Disease", Neuroscience Bulletin, 33:483-492 (2017).
Bottner, et al., "Expression pattern and localization of alpha-synuclein in the human enteric nervous system", Neurobiology of Disease, 48:474-480 (2012).
Muntane, et al., "Phosphorylation of tau and @a-synuclein in synaptic-enriched fractions of the frontal cortex in Alzheimer's disease, and in Parkinson's disease and related @a-synucleinopathies", Neuroscience, 152:913-923 (2008).
Colom-Cadena et al., "Synaptic phosphorylated a-synuclein in dementia with Lewy bodies" Brain 140(12):3204-14 (Dec. 2017).
Fujiwara et al., "alpha-Synuclein is phosphorylated in synucleinopathy lesions" Nat Cell Biol, 4(2):160-64 (Feb. 2002).
Kramer et al., "Presynaptic alpha-synuclein aggregates, not Lewy bodies, neurodegeneration in dementia with Lewy bodies" J Neurosci, 27(6):1405-1410 (Feb. 2007).
Ikenoue et al., "Cold denaturation of alpha-synuclein amyloid fibrils" Angew Chem Int Ed Engl., 53(30):7799-7804 (Jun. 2014).
Lee et al., "The Search for a Peripheral Biopsy Indicator of alpha-Synuclein Pathology for Parkinson Disease" J Neuropathol Exp Neurol, 76(1):2-15 (Jan. 2017).
Ortuno-Lizaran et al., "Phosphorylated alpha-synuclein in the retina is a biomarker of Parkinson's disease pathology severity" Mov Disord., 33(8):1315-24 (May 2018).
Wilson et al., "The immunolocalization of protein gene product 9.5 using rabbit polyclonal and mouse monoclonal antibodies" Br J Exp Pathol., 69(1):91-104 (Feb. 1988).
International Search Report for International Application No. PCT/US2019/045793; dated Nov. 13, 2019, pp. 1-5.

\* cited by examiner

MJF-R13 (8-8)
0.4 ug/mL

P-syn/81A
2.0 ug/mL

5H5
0.4 ug/mL

2G11
0.4 ug/mL

7E2
0.4 ug/mL

3G2
0.4 ug/mL

11A5
0.4 ug/mL pSyn#64 (WAKO)
1:50,000

No Phosphatase

+Phosphatase

No Phosphatase

+Phosphatase

No Phosphatase

+Phosphatase

No Phosphatase

+Phosphatase

No Phosphatase

+Phosphatase

No Phosphatase

+Phosphatase

No Phosphatase

+Phosphatase

No Protease 1

Protease 1 for 4 min

No Protease 1

Protease 1 for 4 min

No Protease 1

Protease 1 for 4 min

Stained the day slide was cut
Protease 1 for 4 min; OptiView HQ Linker + OptiView Multimer Stained 5 months after slide was cut Protease 1 for 4 min;
OptiView HQ Linker + OptiView Multimer Phosph-S129 alpha-Syn: Black
PGP9.5: Yellow Phosph-S129 alpha-Syn: Black
PGP9.5: Yellow P-Syn/81A, 2 µg/mL, no CC1

P-Syn/81A, 2 µg/mL, CC1 32min

CC1 – 0 min

CC1 – 16 min

CC1 – 64 min

DETERMINATION OF PARKINSON'S DISEASE

RELATED APPLICATION

This application claims the benefit of U.S. Provisional Patent Application Ser. No. 62/716,504, filed Aug. 9, 2018, which is incorporated by reference herein in its entirety.

BACKGROUND

Field

The disclosure is directed to methods and compositions for accurate identification of Parkinson's disease. More particularly, the disclosure is directed to the determination of Parkinson's disease in ante-mortem tissue samples.

Description of Related Art

Parkinson's disease (PD) is currently evaluated by clinical examination of a subject's symptoms and imaging of dopamine transporter function in the brain (DaTscan). Development of therapeutic agents for Parkinson's disease is hampered by a lack of diagnostic tests that accurately identify subjects with PD. The definitive diagnosis of PD is the presence of aggregated alpha-synuclein (aSyn) in neurons combined with loss of dopaminergic neurons in substantia nigra region of the brain, and can only take place post-mortem.

SUMMARY

The inventors have identified a need in the art to definitively and accurately identify Parkinson's Disease in a living subject.

Provided herein are methods for determining whether a subject has Parkinson's Disease (PD), the method comprising: (a) contacting a biological sample comprising at least one nerve feature from the subject with a primary antibody capable of binding phosphorylated alpha-synuclein; (b) detecting whether the primary antibody capable of binding phosphorylated alpha-synuclein localizes within the nerve feature of the biological sample; and (c) determining the subject has PD when the primary antibody capable of binding phosphorylated alpha-synuclein localizes within the nerve feature.

In some of the methods, the sample comprises a tissue sample. In some of the methods, the nerve feature comprises a nerve cell. In some of the methods, the nerve feature comprises a former nerve cell. In some of the methods, the nerve feature is adjacent to a nerve cell.

In some of the methods, the sample is contacted with at least one protease before being contacted with the primary antibody capable of binding phosphorylated alpha-synuclein. In some embodiments, the method further comprises contacting the sample with at least one phosphatase.

In some of the methods, the method further comprises contacting the biological sample from the subject with a primary antibody capable of binding the nerve feature. In some embodiments, the primary antibody capable of binding to the nerve feature is selected from an antibody capable of binding a protein selected from the group consisting of: ubiquitin C-terminal hydrolase L1 (PGP9.5, UCHL1, NDGOA; PARK5; PGP95; SPG79; Uch-L1; HEL-117; PGP 9.5; HEL-S-53), RNA binding fox-1 homolog 3 (RBFOX3, FOX3, NEUN, FOX-3, HRNBP3), microtubule associated protein 2 (MAP2, MAP2A, MAP2B, MAP2C), 160 kDa neurofilament medium (NEFM, NFM, NEF3, NF-M), 200 kDa neurofilament heavy (NEFH, NFH, CMT2CC), synaptophysin (SYP, MRX96, MRXSYP), and discs large MAGUK scaffold protein 4 (DLG4, DLGH4, PSD-95, PSD95, SAP-90, SAP90, SAP90A).

In some of the methods, the detecting comprising histochemical analysis. In some of the methods, the primary antibody capable of binding phosphorylated alpha-synuclein detects alpha-synuclein phosphorylated at residue S129.

In some of the methods, the sample is fixed. In some embodiments, the sample is a formalin fixed, paraffin embedded (FFPE) sample. In some of the methods, the sample is a frozen sample. In some of the methods, the sample comprises a section of the nerve feature. In some of the methods, the sample is selected from the group consisting of skin tissue, colon tissue, and submandibular gland.

In some of the methods, the primary antibody capable of binding phosphorylated alpha-synuclein and the primary antibody capable of binding to the nerve feature are from the same host species, wherein the host species is a mouse or a rabbit.

In some of the methods, step (a) further comprises contacting the sample with a first secondary antibody having a first label conjugated thereto, wherein the first secondary antibody is immunoreactive with the primary antibody capable of binding phosphorylated alpha-synuclein. In some embodiments, the method comprises contacting the sample with a set of reagents reactive with the first label of the first secondary antibody to generate a first detectable signal in proximity to phosphorylated alpha-synuclein in the sample.

In some of the methods, before contacting the sample with the primary antibody capable of binding to the nerve feature, the method comprises denaturing the immunocomplexes in the sample by incubating the sample at 100° C. for at least 15 minutes. In some embodiments, the method further comprises contacting the sample with a second secondary antibody having a second label conjugated thereto, wherein the second secondary antibody is immunoreactive with the primary antibody capable of binding the nerve feature. In some embodiments, the method comprises contacting the sample with a set of reagents reactive with the second label of the second secondary antibody to generate a second detectable signal in proximity to the nerve feature in the sample. In some embodiments, the first detectable signal and the second detectable signal are different. In some embodiments, the first detectable signal is silver stain and the second detectable signal is QM-Dabsyl or Fast-Red.

In some of the methods, the subject is suspected of having PD.

Also provided herein are kits comprising: (a) a primary antibody capable of binding phosphorylated alpha-synuclein; and (b) a primary antibody capable of binding to a nerve feature. In some embodiments, the kit further comprises: (c) a first secondary antibody having a first label conjugated thereto, wherein the first secondary antibody is immunoreactive with the primary antibody capable of binding phosphorylated alpha-synuclein; (d) a set of reagents that generates a first detectable single when reacted with the first label of the first secondary antibody; (e) a second secondary antibody having a second label conjugated thereto, wherein the second secondary antibody is immunoreactive with the primary antibody capable of binding the nerve feature; and (f) a set of reagents that generates a second detectable single when reacted with the second label of the second secondary antibody; wherein the first detectable signal and the second detectable signal are different. In some embodiments, the first detectable signal is silver stain and the second detectable signal is QM-Dabsyl or Fast-Red.

In some of the kits, the primary antibody capable of binding to the nerve feature is selected from an antibody capable of binding a protein selected from the group consisting of: ubiquitin C-terminal hydrolase L1 (PGP9.5, UCHL1, NDGOA; PARK5; PGP95; SPG79; Uch-L1; HEL-117; PGP 9.5; HEL-S-53), RNA binding fox-1 homolog 3 (RBFOX3, FOX3, NEUN, FOX-3, HRNBP3), microtubule associated protein 2 (MAP2, MAP2A, MAP2B, MAP2C), 160 kDa neurofilament medium (NEFM, NFM, NEF3, NF-M), 200 kDa neurofilament heavy (NEFH, NFH, CMT2CC), synaptophysin (SYP, MRX96, MRXSYP), and discs large MAGUK scaffold protein 4 (DLG4, DLGH4, PSD-95, PSD95, SAP-90, SAP90, SAP90A).

Also provided herein are methods for determining whether a subject has Parkinson's Disease (PD), the method comprising: (a) preparing a fixed or frozen section of a biological sample from a subject suspected of having PD; (b) detecting whether phosphorylated alpha-synuclein localizes within a nerve feature in the section; and (c) diagnosing the subject with PD when phosphorylated alpha-synuclein localizes within a nerve feature. In some embodiments, step (c) further comprises: (d) contacting the section with a primary antibody capable of binding phosphorylated alpha-synuclein and a primary antibody capable of binding the nerve feature.

In some of the methods, the primary antibody capable of binding to the nerve feature is selected from an antibody capable of binding a protein selected from the group consisting of: ubiquitin C-terminal hydrolase L1 (PGP9.5, UCHL1, NDGOA; PARK5; PGP95; SPG79; Uch-L1; HEL-117; PGP 9.5; HEL-S-53), RNA binding fox-1 homolog 3 (RBFOX3, FOX3, NEUN, FOX-3, HRNBP3), microtubule associated protein 2 (MAP2, MAP2A, MAP2B, MAP2C), 160 kDa neurofilament medium (NEFM, NFM, NEF3, NF-M), 200 kDa neurofilament heavy (NEFH, NFH, CMT2CC), synaptophysin (SYP, MRX96, MRXSYP), and discs large MAGUK scaffold protein 4 (DLG4, DLGH4, PSD-95, PSD95, SAP-90, SAP90, SAP90A).

In some of the methods, the method further comprises: contacting the section with a first secondary antibody having a first label conjugated thereto, wherein the first secondary antibody is immunoreactive with the primary antibody capable of binding phosphorylated alpha-synuclein, and contacting the section with a second secondary antibody having a second label conjugated thereto, wherein the second secondary antibody is immunoreactive with the primary antibody capable of binding the nerve feature. In some embodiments, the method further comprises: contacting the section with a set of reagents reactive with the first label of the first secondary antibody to generate a first detectable signal in proximity to phosphorylated alpha-synuclein in the sample; and contacting the section with a set of reagents reactive with the second label of the second secondary antibody to generate a second detectable signal in proximity to the nerve feature in the sample. In some embodiments, the method further comprises denaturing immunocomplexes in the sample after contacting the section with the primary antibody capable of binding phosphorylated alpha-synuclein and before contacting the section with the primary antibody capable of binding the nerve feature.

In some of the methods, the section is contacted with at least one protease before being contacted with a primary antibody. In some embodiments, the method further comprises contacting the section with at least one phosphatase.

In some of the methods, the primary antibody capable of binding phosphorylated alpha-synuclein and the primary antibody capable of binding the nerve feature are from the same host species.

In some of the methods, the first detectable signal and the second detectable signal are different. In some embodiments, the first detectable signal is silver stain and the second detectable signal is QM-Dabsyl or Fast-Red.

Also provided herein are methods of diagnosing PD in a subject, said method comprising: (a) obtaining a biological sample comprising at least one nerve feature from a subject suspected of having PD; (b) detecting whether phosphorylated alpha-synuclein localizes with the nerve feature in the sample by contacting the sample with an anti-PGP.5 antibody and determining co-localization between phosphorylated alpha-synuclein and PGP9.5; and (c) diagnosing the subject with PD when it is determined in the affirmative that there is co-localization between phosphorylated alpha-synuclein and PGP9.5 in the nerve feature.

Also provided herein are methods of diagnosing and treating PD in a subject, said method comprising: (a) obtaining a biological sample comprising at least one nerve feature from a subject suspected of having PD; (b) detecting whether phosphorylated alpha-synuclein localizes with the nerve feature in the sample by contacting the sample with an anti-PGP.5 antibody and determining co-localization between phosphorylated alpha-synuclein and PGP9.5; (c) diagnosing the subject with PD when it is determined in the affirmative that there is co-localization between phosphorylated alpha-synuclein and PGP9.5 in the nerve feature; and (d) administering a therapy to treat PD in the subject diagnosed as having PD.

Also provided herein are methods of treating a subject diagnosed with PD, comprising administering to the subject an effective regime of an alpha-synuclein antibody, wherein an antibody capable of binding phosphorylated alpha-synuclein and an antibody capable of binding a nerve feature have been shown to co-localize in a nerve feature in a skin sample from the subject.

Also provided herein are methods of treating a subject determined to have PD, comprising administering to the subject an effective regime of an alpha-synuclein antibody, wherein the subject was determined to have PD by any one of the methods disclosed herein.

In some such methods, the effective regime of an alpha-synuclein antibody comprises an alpha-synuclein antibody selected from the group consisting of: a monoclonal antibody binding within residues 1-20 of alpha-synuclein, 1-10 of alpha synuclein, 4-15 of alpha-synuclein, 91-99 of alpha-synuclein, 117-123 of alpha-synuclein, 118-126 of alpha-synuclein, prasinezumab (PRX002), a humanized antibody having the CDR's of antibody clone 1H7 (ATCC Accession No. PTA-8220), a humanized antibody having the CDR's of antibody clone 9E4 (ATCC Accession No. PTA-8221), the CDR's of antibody clone NI-202.21D11, and the CDR's of antibody clone NI-202.12F4, such as, for example, alpha-synuclein antibodies disclosed in U.S. Pat. Nos. 8,092,801, 8,609,820, 8,790,644, 8,940,276, 9,580,493, which are incorporated by reference herein in their entirety. Some such antibodies comprise a VH CDR1 comprising residues 31-35 of SEQ ID NO:49, a VH CDR2 comprising residues 50-68 of SEQ ID NO:49, a VH CDR3 comprising residues 101-102 of SEQ ID NO:49, a VL CDR1 comprising residues 23-33 of SEQ ID NO:50, a VL CDR2 comprising residues 49-55 of SEQ ID NO:50, and a VL CDR3 comprising residues 88-98 of SEQ ID NO:50. Some such antibodies comprise a VH CDR1 comprising SEQ ID NO:51, a VH CDR2 comprising SEQ ID NO:52, a VH CDR3 comprising SEQ ID NO:53, a VL CDR1 comprising SEQ ID NO:54, a VL CDR2 comprising SEQ ID NO:55 and a VL CDR3 comprising SEQ ID NO:56. Some such antibodies comprise a heavy chain comprising SEQ ID NO:57 and a light chain comprising SEQ ID NO:58.

In some such methods, the antibody is prasinezumab (PRX002). In some such methods, the antibody comprises three light CDRs designated SEQ ID NOs: 18-20 respectively and three heavy chain CDRs designated SEQ ID NOs: 22-24 respectively. In some such methods, the antibody comprises a light chain designated SEQ ID NO:17 and a heavy chain designated SEQ ID NO:21

In some such methods, the antibody is 9E4, as disclosed in U.S. Pat. No. 8,609,820, which is incorporated by reference herein in its entirety. In some such methods, the antibody comprises three light CDRs designated SEQ ID NOs:26-28 respectively and three heavy chain CDRs designated SEQ ID NOs:30-32 respectively. In some such methods, the antibody comprises a light chain designated SEQ ID NO:25 and a heavy chain designated SEQ ID NO:29.

In some such methods, the antibody is NI-202.21D11. In some such methods, the antibody comprises three light CDRs designated SEQ ID NOs:34-36 respectively and three heavy chain CDRs designated SEQ ID NOs: 38-40 respectively. In some such methods, the antibody comprises a light chain variable region designated SEQ ID NO:33 and a heavy chain variable region designated SEQ ID NO:37.

In some such methods, the antibody is NI-202.12F4. In some such methods, the antibody comprises light heavy CDRs designated SEQ ID NOs:42-44 respectively and three heavy chain CDRs designated SEQ ID NOs: 46-48 respectively. In some such methods, the antibody comprises a light chain variable region designated SEQ ID NO:41 and a heavy chain variable region designated SEQ ID NO:45.

Also provided herein are methods for detecting phosphorylated alpha-synuclein, the method comprising: contacting a biological sample with a primary antibody capable of binding phosphorylated alpha-synuclein, and detecting the primary antibody capable of binding phosphorylated alpha-synuclein. In some of the methods, the sample is contacted with at least one protease before being contacted with the primary antibody capable of binding phosphorylated alpha-synuclein. In some methods, the method further comprises contacting the sample with at least one phosphatase. In some methods, the detecting comprising histochemical analysis. In some methods, the primary antibody capable of binding phosphorylated alpha-synuclein detects alpha-synuclein phosphorylated at residue S129. In certain methods, the primary antibody capable of binding phosphorylated alpha-synuclein is the 7E2 antibody clone or the 3G2 antibody clone. In some methods, the sample is fixed. In certain methods, the sample is a formalin fixed, paraffin embedded (FFPE) sample. In some methods, the sample is a frozen sample In some methods, the method further comprises contacting the sample with a first secondary antibody having a first label conjugated thereto, wherein the first secondary antibody is immunoreactive with the primary antibody capable of binding phosphorylated alpha-synuclein. In some methods, the method comprises contacting the sample with a set of reagents reactive with the first label of the first secondary antibody to generate a first detectable signal in proximity to phosphorylated alpha-synuclein in the sample.

DESCRIPTION

Figure 1A:
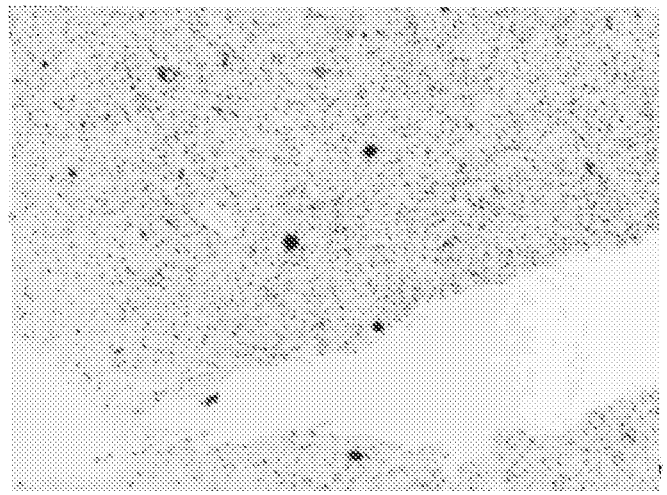
FIG. 1A shows exemplary staining of alpha-synuclein phosphorylated at S129 in brain tissue from a subject with PD using the anti-alpha-synuclein antibody and concentration as indicated (MJF-R13 (8-8) top panel; P-syn/81A middle panel; 5H5 bottom panel).
Figure 1A:
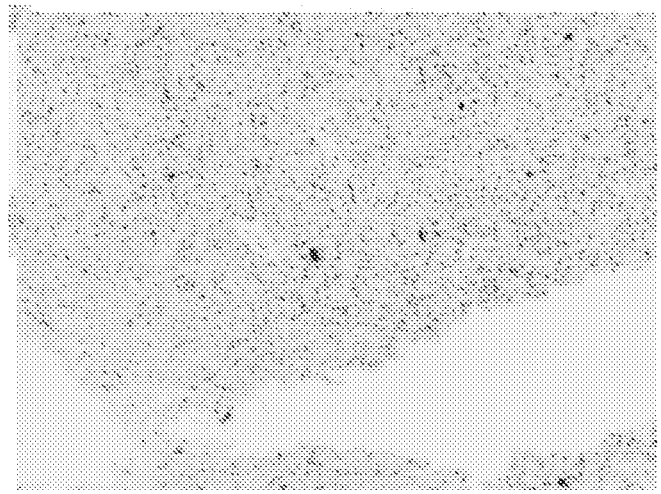
Figure 1A:
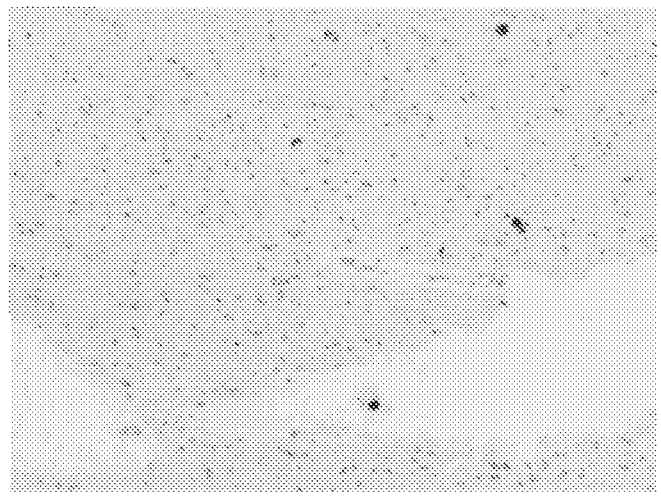

The disclosure involves methods and compositions for accurate and definitive determination of Parkinson's disease (PD) in otherwise undiagnosed subjects with PD, and subjects at risk of or suspected of having Parkinson's Disease. The methods and compositions might also be used to exclude Parkinson's Disease in patients with movement disorders that are sometimes associated with Parkinson's disease-like symptoms, including, but not restricted to, progressive supranuclear palsy, multiple system atrophy, viral parkinsonism, essential tremor, drug- or toxin-induced parkinsonism, post-traumatic parkinsonism, arteriosclerotic parkinsonism, parkinsonism-dementia complex of Guam, cortical basal ganglionic degeneration, or normal pressure hydrocephalus. The disclosed methods include contacting a biological sample comprising at least one nerve feature from the subject with a primary antibody capable of binding phosphorylated alpha-synuclein. By detecting whether the primary antibody capable of binding phosphorylated alpha-synuclein localizes within the nerve feature of the sample, a determination can be made regarding whether a living subject has PD. Subjects may include patients who are pre-symptomatic for PD and those that are in the early stages of disease when accurate diagnosis of PD is currently not routinely possible. In addition, post-mortem analysis can be conducted with biological samples collected after death.

As used herein, the term "biological sample," includes samples which can be tested by the methods and kits of the present disclosure and includes human and animal body, fixed or frozen, tissue specimens, and fixed cell specimens. The term "tissue" refers to a collection of interconnected cells that perform a similar function within an organism. Biological samples can include samples from a healthy or an apparently healthy human subject or from a human subject affected by or suspected of being affected by a condition or disease to be diagnosed or treated, such as Parkinson's Disease. A biological sample can be a sample obtained from any organ or tissue (including a biopsy such as a tumor biopsy). Also, the samples may be from deceased patients, such as a sample taken during an autopsy. Biological samples can also include cytology samples (in some examples, cytology samples can be sourced from tissues, such as tissue sections from skin tissue, colon tissue, submandibular gland tissue, or brain). In other examples, a sample may be a cell, or cell pellet prepared from a biological sample obtained from a subject.

In some examples, biological samples can include normal or cancerous tissue, for example, skin tissue (from for example, the scalp, abdomen or trunk of a subject), colon tissue, submandibular gland tissue, brain tissue, olfactory bulb, lung tissue, ovarian tissue, pancreatic tissue, mesothelial tissue, gastrointestinal tissue, head and neck tissue, breast tissue, liver tissue, kidney tissue, prostate tissue, uterine tissue, cerebrospinal fluid (or cells and/or nerve features isolated from cerebrospinal fluid), bone, lung cells, ovarian cells, pancreatic cells or mesothelial cells, colon cells, head and neck cells, breast cells, liver cells, kidney cells, skin cells, prostate cells, uterine cells, bone cells, brain cells, and lung cells. For example, a sample from skin, the colon, submandibular gland, olfactory bulb, a lung, ovary, liver, or pancreas, or other tumor that contains cellular material, can be obtained by surgical excision of all or part of a tumor, by collecting a fine, needle brain biopsy, a fine needle aspirate from a tumor or a punch biopsy, as well as other methods known in the art.

As used herein, the term "nerve feature" refers to nerve cells and tissue structures known to be innervated. For example, a nerve feature can be part of a nerve cell, a nerve cell, a part of a former nerve cell, a former nerve cell, or both a nerve cell and a former nerve cell, and/or parts thereof. In some of the methods, the nerve feature is adjacent to a nerve cell, for example a former nerve cell adjacent a healthy nerve cell. Other types of nerve features include tissue structures known to be innervated including, but are not limited to: unmyelinated or thinly myelinated intraepidermal nerve fibers that are widely distributed in dermis; adrenergic, noradrenergic, cholinergic sympathetic fibers or vasodilatory peptidergic fibers that innervate autonomic structures including, but not limited to, sweat glands, hair follicles, arrectores pilorum muscle, and blood vessels. In some methods, a nerve feature can comprise components of former nerve cells or nerve cells that are necrotic or apoptotic.

The term "primary antibody", in context of the present disclosure, refers to an antibody binding agent, e.g. a whole antibody molecule, a fragment or a derivative of said molecule (e.g. a conjugate comprising an antibody or a polymerized antibody), that specifically binds to a "target" (for example, phosphorylated alpha-synuclein or a component of a nerve feature), more specifically to a single unit of the target of a sample (e.g. an epitope of the target molecule). In some of the methods disclosed herein, the primary antibody can be an antibody capable of binding phosphorylated alpha-synuclein at residue S129 (pS129 aSyn). In some of the methods disclosed herein, the primary can be an antibody capable of binding a component of a nerve feature. Primary antibodies are more fully described under the heading "Antibodies" in the following disclosure.

In order to detect whether the primary antibody localizes within a nerve feature, the sample is contacted with the antibody and the sample is examined for the presence of the antibody. Determination of the localization of the primary antibody can be accomplished, for example, when the primary antibody is labeled with a detectable label. A detection of the label in the sample corresponds to the localization of the antibody within the nerve feature.

Some of the methods disclosed herein further include contacting the biological sample from the subject with a second primary antibody capable of binding a protein other than phosphorylated alpha-synuclein within the nerve feature. The use of the second primary antibody allows for the determination of the localization of both the first primary antibody and the second primary antibody within the nerve feature. The determination of PD can be accurately and definitively determined upon the detection of the co-localization of both antibodies within the nerve feature.

The second primary antibody may be, for example, selected from an antibody capable of binding a protein that is a component of the nerve feature, and can for example be selected from one of the following: ubiquitin C-terminal hydrolase L1 (PGP9.5, UCHL1, NDGOA; PARK5; PGP95; SPG79; Uch-L1; HEL-117; PGP 9.5; HEL-S-53), RNA binding fox-1 homolog 3 (RBFOX3, FOX3, NEUN, FOX-3, HRNBP3), microtubule associated protein 2 (MAP2, MAP2A, MAP2B, MAP2C), 160 kDa neurofilament medium (NEFM, NFM, NEF3, NF-M), 200 kDa neurofilament heavy (NEFH, NFH, CMT2CC), synaptophysin (SYP, MRX96, MRXSYP), and discs large MAGUK scaffold protein 4 (DLG4, DLGH4, PSD-95, PSD95, SAP-90, SAP90, SAP90A).

In some of the methods disclosed herein, the primary antibody capable of binding phosphorylated alpha-synuclein and the primary antibody capable of binding to the nerve feature are from the same host species, and the host species can be a mouse or a rabbit. In some methods, the primary antibody capable of binding phosphorylated alpha-synuclein and the primary antibody capable of binding to the nerve feature are from different host species, such as mouse or rabbit.

The terms "localization" and "co-localization" refer to the location of a target protein or target proteins within the same nerve feature. In some methods, co-localization of proteins within in a nerve feature is determined when signals independently indicative the proteins are identified in the nerve feature when compared to background for each signal. A signal indicative of a peptide that is outside a nerve feature is not indicative of a protein localized within a nerve feature. As one example, a signal indicative of phosphorylated alpha-synuclein localized in a nerve feature is a signal at one, two, three or four standard deviations higher than a background signal, or at least 1-fold, at least 2 fold, at least 3 fold, at least 4 fold, at least 5 fold, at least 6 fold, at least 7 fold, at least 8 fold, at least 9 fold, or at least 10 fold higher that background signal.

Methods for determining the localization and co-localization of antibodies include, for example, histochemical analysis. As used herein, the terms "immunohistochemistry" or "IHC" refer to method of determining the presence or distribution of an antigen in a fixed or frozen sample by detecting interaction of the antigen with a specific binding agent, such as an antibody, within the sample. Accordingly, the disclosure provides methods for determining whether a subject has Parkinson's Disease (PD) by using a fixed or frozen section of a biological sample from a subject suspected of having PD. Phosphorylated alpha-synuclein localized within a nerve feature in the section may be detected and the subject may be diagnosed with PD when phosphorylated alpha-synuclein localized within a nerve feature. Methods of the disclosure include contacting the section with a first primary antibody capable of binding phosphorylated alpha-synuclein. The method may also include contacting the section with a second primary antibody capable of binding the nerve feature.

Some of the methods disclosed herein may also include an automated histochemical staining platform, such as an automated IHC/ISH slide stainer. Automated IHC/ISH slide stainers typically include at least: reservoirs of the various reagents used in the staining protocols, a reagent dispense unit in fluid communication with the reservoirs for dispensing reagent to onto a slide, a waste removal system for removing used reagents and other waste from the slide, and a control system that coordinates the actions of the reagent dispense unit and waste removal system. In addition to performing staining steps, many automated slide stainers can also perform steps ancillary to staining (or are compatible with separate systems that perform such ancillary steps), including: slide baking (for adhering the sample to the slide), dewaxing (also referred to as deparaffinization), antigen retrieval, counterstaining, dehydration and clearing, and coverslipping. Prichard, *Overview of Automated Immunohistochemistry*, Arch Pathol Lab Med., Vol. 138, pp. 1578-1582 (2014), incorporated herein by reference in its entirety, describes several specific examples of automated IHC/ISH slide stainers and their various features, including the intelliPATH FLX® (Biocare Medical), WAVE® (Celerus Diagnostics), DAKO OMNIS® and DAKO AUTOSTAINER LINK® 48 (Agilent Technologies), BENCHMARK® (Ventana Medical Systems, Inc.), Leica BOND®, and Lab Vision™ Autostainer (Thermo Scientific) automated slide stainers. Additionally, Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901, and 6,943,029, and U.S. Published Patent Application Nos.: 20030211630 and 20040052685, each of which is incorporated herein by reference in its entirety. Commercially-available staining units typically operate on one of the following principles: (1) open individual slide staining, in which slides are positioned horizontally and reagents are dispensed as a puddle on the surface of the slide containing a tissue sample (such as implemented on the DAKO AUTOSTAINER LINK® 48 (Agilent Technologies) and intelliPATH® (Biocare Medical) stainers); (2) liquid overlay technology, in which reagents are either covered with or dispensed through an inert fluid layer deposited over the sample (such as implemented on VENTANA® BenchMark and DISCOVERY® stainers); (3) capillary gap staining, in which the slide surface is placed in proximity to another surface (which may be another slide or a coverplate) to create a narrow gap, through which capillary forces draw up and keep liquid reagents in contact with the samples (such as the staining principles used by DAKO TECHMATE®, Leica BOND®, and DAKO OMNIS® stainers). Some iterations of capillary gap staining do not mix the fluids in the gap (such as on the DAKO TECHMATE® and the Leica BOND®). In variations of capillary gap staining termed dynamic gap staining, capillary forces are used to apply sample to the slide, and then the parallel surfaces are translated relative to one another to agitate the reagents during incubation to effect reagent mixing (such as the staining principles implemented on DAKO OMNIS® slide stainers (Agilent)). In translating gap staining, a translatable head is positioned over the slide. A lower surface of the head is spaced apart from the slide by a first gap sufficiently small to allow a meniscus of liquid to form from liquid on the slide during translation of the slide. A mixing extension having a lateral dimension less than the width of a slide extends from the lower surface of the translatable head to define a second gap smaller than the first gap between the mixing extension and the slide. During translation of the head, the lateral dimension of the mixing extension is sufficient to generate lateral movement in the liquid on the slide in a direction generally extending from the second gap to the first gap. See WO 2011-139978 A1. It has recently been proposed to use inkjet technology to deposit reagents on slides. See WO 2016-170008 A1. This list of staining technologies is not intended to be comprehensive, and any fully or semi-automated system for performing biomarker staining may be incorporated into the histochemical staining platform.

Detection of Antibody Binding

In some of the methods disclosed herein, step (a) further comprises contacting the sample with a first secondary antibody having a first label conjugated thereto, wherein the first secondary antibody is immunoreactive with the primary antibody capable of binding phosphorylated alpha-synuclein. In some of the methods disclosed herein, the methods comprise contacting the sample with a set of reagents reactive with the first label of the first secondary antibody to generate a first detectable signal in proximity to phosphorylated alpha-synuclein in the sample.

In some of the methods disclosed herein, the method further comprises contacting the sample with a second secondary antibody having a second label detectable conjugated thereto, wherein the second secondary antibody is immunoreactive with the primary antibody capable of binding the nerve feature. In some of the methods disclosed herein, the methods comprise contacting the sample with a set of reagents reactive with the second label of the second secondary antibody to generate a second detectable signal in proximity to the nerve feature in the sample. In some of the methods disclosed herein, the first detectable signal and the second detectable signal are different. In certain methods as disclosed herein, the first detectable signal is silver stain and the second detectable signal is QM-Dabsyl or Fast-Red.

The term "secondary antibody," in context of the present disclosure, refers to an antibody binding agent, e.g. a whole antibody molecule, a fragment or a derivative of said molecule (e.g. a conjugate comprising an antibody or a polymerized antibody), that has an antigen binding domain that specifically binds to the primary antibody that is bound to a target antigen. Secondary antibodies can help increase sensitivity and signal amplification due to multiple secondary antibodies binding to a primary antibody. In some embodiments, secondary antibodies can be conjugated to enzymes such as horseradish peroxidase (HRP) or alkaline phosphatase (AP); or fluorescent dyes such as fluorescein isothiocyanate (FITC), rhodamine derivatives, Alexa Fluor dyes; or other molecules to be used in various applications.

In some of the methods disclosed herein, the sample is contacted with at least one protease before being contacted with the primary antibody capable of binding phosphorylated alpha-synuclein. In certain methods as disclosed herein, the methods further comprise contacting the sample with at least one phosphatase. In some of the methods, the sample is contacted with both a protease and a phosphatase. The use of the protease or the protease and the phosphatase may be used according to a method wherein the determination of PD is accomplished with the first primary antibody alone or wherein the determination is accomplished with the use of both the first primary antibody and the second primary antibody. In some of the methods as disclosed herein, the use of the phosphatase enhances detection of phosphorylated alpha-synuclein unique to subjects with Parkinson's disease by removing phosphorylated alpha-synuclein normally seen in subjects without Parkinson's disease. The use of the protease enhances detection of phosphorylated alpha-synuclein by improving accessibility of phosphorylated alpha-synuclein to primary antibody.

In some of the methods disclosed herein, before contacting the sample with the primary antibody capable of binding to the nerve feature, the method comprises denaturing the immunocomplexes in the sample by, for example incubating the sample at 100° C. for at least 15 minutes. In certain methods, denaturing can occur at about 80° C. to at least about 110° C. for about 5 minutes to at least about 60 minutes. For example, denaturing can occur at about 80° C., about 85° C., about 90° C., about 95° C., about 100° C., about 105° C., or about 110° C., for at least about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 25 minutes, about 30 minutes, about 35 minutes, about 40 minutes, about 45 minutes, or about 48 minutes, or about 50 minutes, or about 55 minutes or at least about 60 minutes.

As used herein, the terms "protease" or "peptidase" or "proteinase" refer to an enzyme that performs proteolysis or protein catabolism by hydrolysis of peptide bonds. Proteases can be classified into seven broad groups depending on the catalytic residue. For example, serine proteases (using serine alcohol), cysteine proteases (using a cysteine thiol), threonine proteases (using a threonine secondary alcohol), aspartic proteases (using an aspartate carboxylic acid), glutamic proteases (using a glutamate carboxylic acid), metalloproteases (using a metal, usually zinc), and asparagine peptide lyases (using an asparagine to perform an elimination reaction). Examples of proteases can include, but are not limited to: trypsin, chymotrypsin, enterokinase, endoproteinase GluC, proteinase K, thrombin, Factor Xa, bromelain, alkaline proteases (for example, alkaline VIII protease), papain, collagenase, dispase, pepsin, cathepsin D, and carboxypeptidase A. Examples of commercially available proteases can include, but are not limited to: VENTANA® Protease 1 (P/N 760-2018), VENTANA® Protease 2 (P/N 760-2019), or VENTANA® Protease 3 (P/N 760-2020). Protease incubation times can be determined by a person skilled in the art, but incubation times can range from about 2 minutes or less to at least about 20 minutes, and temperatures can range from about 15° C. or less to at least about 45° C. For example, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, or at least about 20 minutes, at about 15° C., at about 20° C., at about 25° C., at about 30° C., at about 35° C., at about 36° C., at about 37° C., at about 38° C., at about 39° C., or at least about 40° C. In certain examples, the incubation can be for about 4 minutes at about 36° C., or about 4 minutes at 40° C., or about 4 minutes and 30 seconds at 40° C., or about 5 minutes at 40° C., or about 12 minutes at about 36° C.

As used herein, the term "phosphatase" refers to an enzyme that uses water to cleave a phosphoric acid monoester into a phosphate ion and an alcohol (phosphatases remove phosphate groups from molecules). Examples of phosphatases can include, but are not limited to, alkaline phosphatases, acid phosphatases, phosphoprotein phosphatase 1 (PP1), phosphoprotein phosphatase 2A (PP2A), phosphoprotein phosphatase 2B (PP2B), phosphoprotein phosphatase 2C (PP2C), and lambda protein phosphatase. Examples of commercially available phosphatases can include, but are not limited to: bovine alkaline phosphatase from *Pichia pastoris* (Roche P/N 3359123001). Phosphatase incubation times can be determined by a person skilled in the art, but incubation times can range from about 5 minutes to at least about 12 hours, and temperatures can range from about 20° C. to at least about 50° C. For example, about 8 minutes, about 9 minutes, about 10 minutes, about 15 minutes, about 20 minutes, about 25 minutes, about 30 minutes, about 45 minutes, about 60 minutes, about 90 minutes, about 2 hours, about 3 hours, about 4 hours, about 5 hours, about 6 hours, about 7 hours, about 8 hours, about 9 hours, about 10 hours, about 11 hours, or at least about 12 hours, at about 20° C., about 21° C., about 22° C., about 23° C., about 24° C., about 25° C., about 30° C., at about 36° C., at about 37° C., at about 38° C., at about 39° C., or at least about 40° C. In certain examples, the incubation can be for about 2 hours at about 36° C., or about 10 minutes at 37° C., or about 60 minutes at 37° C., or about 45 minutes at 37° C., or about 60 minutes at about 37° C.

In some of the methods disclosed herein, incubation times vary and depend on the temperature of the incubation. Incubation periods for substantially complete antibody binding, color development, and other steps of the method are well known. Many of the steps, e.g. antigen unmasking, antibody binding, and color development, are performed at elevated temperatures of at least about 35° C., preferably from about 400 to about 45° C., or up to 100° C. for a time of about 4 minutes to about 90 minutes. For example, in certain methods, the primary antibodies can be incubated with the samples at 36° C. for 32 minutes or they can be incubated at about 22° C. for 20 minutes. In another example, the protease can be incubated with the samples at 36° C. for 12 minutes or the protease can be incubated with the samples at 36° C. for 4 minutes. In yet another example, antigen unmasking can be performed at least about 100° C. for about 30-90 minutes. However, with the exception of steps dependent on enzyme activity (antigen unmasking and color development), most steps can also be performed at temperatures as low as 4° C., if the incubation period is appropriately increased.

When the antibody staining reagent is specific for an antigen that requires unmasking, the tissue section can be treated with a proteolytic enzyme or protease prior to addition of the primary antibody. The proteolytic enzyme or protease can be added to the evaporation inhibitor liquid covering the tissue section and sinks through the evaporation inhibitor liquid to the tissue section below. Following a sufficient period of incubation for antigen unmasking, for example about 4 to about 30 minutes, the slide can be washed and the evaporation inhibitor liquid can be reapplied.

In some of the methods, prior to antibody application, a sufficient amount of a protease solution to cover the tissue section, conveniently about 100-200 µL, can be applied to paraffin-embedded, formalin-fixed tissue. Treatment with a protease can help expose the antigens to the labeling reagents, allowing for more accurate results. In some of the methods, the incubation period is sufficient to disrupt cross-linking, but not so long that the antigens are destroyed. The period depends on the temperature, enzyme concentration, tissue thickness, tissue type and amount of time in formalin. An appropriate time can be readily determined by one of skill in the art. For example, about 4 minutes at about 36° C., or about 4 minutes at 40° C., or about 4 minutes and 30 seconds at 40° C., or about 5 minutes at 40° C., or about 12 minutes at about 36° C. can be effective. Following incubation, the protease solution can be washed off, and the next reagent in the staining/labeling process is applied. When these ranges are not observed, over and/or under digestion of the tissue by the protease is likely to occur, which can result in destroyed antigens/masked antigens, respectively. Following the incubation, the slide can be rinsed.

Antibodies

As used herein, the term "antibody" refers to a polypeptide ligand comprising at least a light chain or heavy chain immunoglobulin variable region which specifically recognizes and binds an epitope of an antigen. Antibodies include at least a light chain or heavy chain immunoglobulin variable region or immunoglobulin-like molecules (including by way of example and without limitation, IgA, IgD, IgE, IgG and IgM, combinations thereof, and similar molecules produced during an immune response in any vertebrate, for example, in mammals such as humans, goats, rabbits and mice), as well as non-mammalian species, such as shark immunoglobulins. Antibodies include monoclonal antibodies, polyclonal antibodies, or fragments of antibodies as well as others known in the art. In some examples, an antibody is labeled with a detectable label, such as an enzyme or fluorophore. Antibody also includes antibody fragments that specifically bind to a molecule of interest (or a group of highly similar molecules of interest) to the substantial exclusion of binding to other molecules.

The term "antibody" also includes an antigen binding fragment of a naturally occurring or recombinant antibody. Non-limiting examples of binding fragments encompassed within the term antibody include Fab, (Fab')$_2$, Fv, and single-chain Fv (scFv). Fab is the fragment that contains a monovalent antigen-binding fragment of an antibody molecule produced by digestion of whole antibody with the enzyme papain to yield an intact light chain and a portion of one heavy chain or equivalently by genetic engineering. Fab' is the fragment of an antibody molecule obtained by treating whole antibody with pepsin, followed by reduction, to yield an intact light chain and a portion of the heavy chain; two Fab' fragments are obtained per antibody molecule. (Fab')$_2$ is the fragment of the antibody obtained by treating whole antibody with the enzyme pepsin without subsequent reduction or equivalently by genetic engineering. F(Ab')$_2$ is a dimer of two FAb' fragments held together by disulfide bonds. Fv is a genetically engineered fragment containing the variable region of the light chain and the variable region of the heavy chain expressed as two chains. Single chain antibody ("SCA") is a genetically engineered molecule containing the variable region of the light chain, the variable region of the heavy chain, linked by a suitable polypeptide linker as a genetically fused single chain molecule. Methods of making these fragments are routine in the art.

Antibodies and antibody binding fragments that have a binding constant for the molecule of interest (i.e., phosphorylated alpha-synuclein and proteins endogenous in a nerve feature) that is at least $10^3$ M$^{-1}$ greater, at least $10^4$ M$^{-1}$ greater or at least $10^5$ M$^{-1}$ greater than a binding constant for other molecules in a biological sample. In some examples, an antibody has a high binding affinity for phosphorylated alpha-synuclein or PGP9.5 such as a binding affinity of at least about $1\times10^{-8}$ M, at least about $1.5\times10^{-8}$, at least about $2.0\times10^{-8}$, at least about $2.5\times10^{-8}$, at least about $3.0\times10^{-8}$, at least about $3.5\times10^{-8}$, at least about $4.0\times10^{-8}$, at least about $4.5\times10^{-8}$, or at least about $5.0\times10^{-8}$ M. In certain embodiments, an antibody that binds to phosphorylated alpha-synuclein or PGP9.5 has a dissociation constant (Kd) of $\leq10^4$ nM, $\leq10^3$ nM, $\leq100$ nM, $\leq10$ nM, $\leq1$ nM, $\leq0.1$ nM, $\leq0.01$ nM, or $\leq0.001$ nM, or $\leq0.0001$ nM, or $\leq0.00001$ nM (e.g., $10^{-4}$M or to $10^{-6}$M, e.g., from $10^{-7}$M to $10^{-9}$M, e.g., from $10^{-10}$ M to $10^{-12}$ M, or e.g., from $10^{-13}$ M to $10^{-15}$ M). In one embodiment, Kd can be measured by a radiolabeled antigen binding assay (RIA) performed with the Fab version of an antibody of interest and its antigen. In another example, Kd can be measured using a label-free optical scanner for microarray detection based on polarization-modulated oblique-incidence reflectivity difference (OI-RD). In yet another example, Kd can be measured using surface plasmon resonance assays using a BIACORE®-2000 or a BIACORE®-3000 (BIAcore, Inc., Piscataway, N.J.) at 25° C. with immobilized antigen CM5 chips at about 10 response units (RU).

Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., Sequences of Proteins of Immunological Interest, U.S. Department of Health and Human Services, 1991). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds phosphorylated alpha-synuclein will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

Several antibodies to alpha-synuclein (also referred to as, SNCA, PD1; NACP; PARK1; PARK4; aSyn) and phosphorylated alpha-synuclein are known. Alpha-synuclein is a member of the synuclein family, which also includes beta- and gamma-synuclein. Synucleins are expressed in the brain and alpha- and beta-synuclein inhibit phospholipase D2 selectively. Alpha-synuclein may serve to integrate presynaptic signaling and membrane trafficking. Mutations in alpha-synuclein have been implicated in the pathogenesis of Parkinson disease. Alpha-synuclein peptides are a major component of amyloid plaques in the brains of patients with Alzheimers disease. In certain methods, phosphorylated alpha-synuclein can be detected. Alpha-synuclein sequences are publically available, for example from GenBank™ sequence database (e.g., amino acids Accession No. NP_000336.1 encoded by Accession No. NM_000345.3). One of ordinary skill in the art can identify additional alpha-synuclein nucleic acid and protein sequences, including alpha-synuclein variants and isoforms. Antibodies for detecting alpha-synuclein are known in the art, and can include, but are not limited to: rabbit monoclonal antibody clones 7E2, and 3G2 against phospho-S129 alpha-synuclein generated by Roche Diagnostics GmbH CPS R&D Early Development & Reagent Design (DXREAA) with a phospho-peptide corresponding to human alpha-synuclein residues 122-135 as immunogen. Additional monoclonal antibodies against phosphorylated S129 alpha-synuclein (aSyn) can be purchased, for example, from Abcam (clones MJF-R13 (8-8), P/N ab168381 and P-syn/81A, P/N ab184674) or WAKO (clone pSyn #64, P/N 015-25191). Mouse monoclonal antibody clone LB509 against alpha-synuclein regardless of S129 phosphorylation status can be purchased from Abcam (P/N ab27766). Anti-alpha-synuclein mouse monoclonal antibody clone 5C12 (S129 phosphorylation independent; ATCC® No. PTA-9197) and anti-phosphorylated S129-alpha-synuclein mouse monoclonal antibody clone 11A5 (ATCC® No. PTA-8222) from Prothena Corporation may also be used. Also see Table 10 below.

An example of an anti-phosphorylated S129 alpha-synuclein antibody is the rabbit monoclonal antibody clone 7E2, which was generated by Roche Diagnostics GmbH CPS R&D Early Development & Reagent Design (DXREAA) with a phospho-peptide corresponding to human alpha-synuclein residues 122-135 as immunogen. The 7E2 antibody or antigen binding fragment thereof comprises a light chain (LC) variable region comprising the amino acid sequence of SEQ ID NO:01. The 7E2 antibody or antigen binding fragment thereof comprises a heavy chain (HC) variable region comprising the amino acid sequence of SEQ ID NO:05

(7E2 light chain):
SEQ ID NO: 01
AQVLTQTPSPVSAAVGGTVTISCQSSQSVYNNNNLVWYQQKPGQPPKQVI

YKASKVASGVPSRFKGSGSGTQFTLTISDLECDDAATYYCLGGYSGDIYT

FGGGTEVVVKGDPVAPTVLIFPPAADQVATGTVTIVCVANKYFPDVTVTW

EVDGTTQTTGIENSKTPQNSADCTYNLSSTLTLTSTQYNSHKEYTCKVTQ

GTTSVVQSFNRGDC

7E2 LC CDR1:
SEQ ID NO: 02
QSVYNNNN

7E2 LC CDR2:
SEQ ID NO: 03
KASKVAS

7E2 LC CDR3:
SEQ ID NO: 04
LGGYSGDIYT

(7E2 heavy chain):
SEQ ID NO: 05
CQSVEESGGRLVTPGTPLTLTCTASGFTISSYHMSWVRQAPGKGLEWIGY

ISTSGNIYYASWAKGRFTISKTSSTTVDLRMTSLTTEDTATYFCARLGIA

TGYSFWGHGTLVTVSSGQPKAPSVFPLAPCCGDTPSSTVTLGCLVKGYLP

EPVTVTWNSGTLTNGVRTFPSVRQSSGLYSLSSVVSVTSSSQPVTCNVAH

PATNTKVDKTVAPSTCSKPTCPPPELLGGPSVFIFPPKPKDTLMISRTPE

VTCVVVDVSQDDPEVQFTWYINNEQVRTARPPLREQQFNSTIRVVSTLPI

AHQDWLRGKEFKCKVHNKALPAPIEKTISKARGQPLEPKVYTMGPPREEL

SSRSVSLTCMINGFYPSDISVEWEKNGKAEDNYKTTPAVLDSDGSYFLYN

KLSVPTSEWQRGDVFTCSVMHEALHNHYTQKSISRSPGK

7E2 HC CDR1:
SEQ ID NO: 06
GFTISSYHMS

7E2 HC CDR2:
SEQ ID NO: 07
ISTSGNI

7E2 HC CDR3:
SEQ ID NO: 08
ARLGIATGYSF

In some embodiments, there are provided antibodies having a light chain variable region that has an amino acid sequence that shares at least 90% sequence identity with an amino acid sequence represented by SEQ ID NO:01. In a further embodiment, there are provided antibodies having a heavy chain variable region that has an amino acid sequence that shares at least 90% sequence identity with an amino acid sequence represented by SEQ ID NO:05.

Another example of an anti-phosphorylated S129 alpha-synuclein antibody is the rabbit monoclonal antibody clone 3G2, which was generated by Roche Diagnostics GmbH CPS R&D Early Development & Reagent Design (DXREAA) with a phospho-peptide corresponding to human alpha-synuclein residues 122-135 as immunogen. The 3G2 antibody or antigen binding fragment thereof comprises a light chain (LC) variable region comprising the amino acid sequence of SEQ ID NO:09. The 3G2 antibody or antigen binding fragment thereof comprises a heavy chain (HC) variable region comprising the amino acid sequence of SEQ ID NO:13.

(3G2 light chain):
SEQ ID NO: 09
AQVLTQTPSPVSAAVGGTVTISCQSSQSVYNNNNLVWFQKKPGQPPKQLI

YKASKVASGVPSRFKGSGSGTQFTLTISDLECDDAATYYCLGGYSGDIYT

FGGGTEVVVKGDPVAPTVLIFPPAADQVATGTVTIVCVANKYFPDVTVTW

EVDGTTQTTGIENSKTPQNSADCTYNLSSTLTLTSTQYNSHKEYTCKVTQ

GTTSVVQSFNRGDC

3G2 LC CDR1:
SEQ ID NO: 10
QSVYNNNN

3G2 LC CDR2:
SEQ ID NO: 11
KASKVAS

3G2 LC CDR3:
SEQ ID NO: 12
LGGYSGDIYT

(3G2 heavy chain):
SEQ ID NO: 13
QEQLKESGGGLVTPGGTLTLTCTASGFTISSYHMSWVRQAPGKGLEWIGY

ISTSGNIYYATWAKGRFTISKTSSTTVDLRMTSLTTEDTATYFCARLGIA

TGYSFWGHGTLVTVSSGQPKAPSVFPLAPCCGDTPSSTVTLGCLVKGYLP

EPVTVTWNSGTLTNGVRTFPSVRQSSGLYSLSSVVSVTSSSQPVTCNVAH

PATNTKVDKTVAPSTCSKPTCPPPELLGGPSVFIFPPKPKDTLMISRTPE

VTCVVVDVSQDDPEVQFTWYINNEQVRTARPPLREQQFNSTIRVVSTLPI

AHQDWLRGKEFKCKVHNKALPAPIEKTISKARGQPLEPKVYTMGPPREEL

SSRSVSLTCMINGFYPSDISVEWEKNGKAEDNYKTTPAVLDSDGSYFLYN

KLSVPTSEWQRGDVFTCSVMHEALHNHYTQKSISRSPGK

3G2 HC CDR1:
SEQ ID NO: 14
GFTISSYHMS

3G2 HC CDR2:
SEQ ID NO: 15
ISTSGNI

3G2 HC CDR3:
SEQ ID NO: 16
ARLGIATGYSF

In some embodiments, there are provided antibodies having a light chain variable region that has an amino acid sequence that shares at least 90% sequence identity with an amino acid sequence represented by SEQ ID NO:09. In a further embodiment, there are provided antibodies having a heavy chain variable region that has an amino acid sequence that shares at least 90% sequence identity with an amino acid sequence represented by SEQ ID NO:13.

The disclosure also provides methods of detecting one or more proteins that are part of nerve features, as defined herein. Such proteins can be detected by an antibody capable of binding a protein selected from: ubiquitin C-terminal hydrolase L1 (PGP9.5, UCHL1, NDGOA; PARK5; PGP95; SPG79; Uch-L1; HEL-117; PGP 9.5; HEL-S-53; and Accession No's. NM_004181.4→NP_004172.2), RNA binding fox-1 homolog 3 (RBFOX3, FOX3, NEUN, FOX-3, HRNBP3; and Accession No's. NM_001082575.2→NP_001076044.1), microtubule associated protein 2 (MAP2, MAP2A, MAP2B, MAP2C; and Accession No's. NM_001039538.1→NP_001034627.1), 160 kDa neurofilament medium (NEFM, NFM, NEF3, NF-M; and Accession No's. NM_005382.2→NP_005373.2), 200 kDa neurofilament heavy (NEFH, NFH, CMT2CC; and Accession No's. NM_021076.3→NP_066554.2), synaptophysin (SYP, MRX96, MRXSYP; and Accession No's. NM_003179.2→NP_003170.1), or discs large MAGUK scaffold protein 4 (DLG4, DLGH4, PSD-95, PSD95, SAP-90, SAP90, SAP90A; and Accession No's. NM_001365.4→NP_001356.1). One of ordinary skill in the art can identify additional PGP9.5, RBFOX3, MAP2, NEFM, NEFH, SYP, and DLG4 nucleic acid and protein sequences, including variants and isoforms. Antibodies for detecting PGP9.5, RBFOX3, MAP2, NEFM, NEFH, SYP, and DLG4 are known in the art. For example antibodies capable of binding PGP9.5, can include, but are not limited to: anti-human PGP9.5 monoclonal antibodies from rabbit (clone EPR4118, P/N ab108986), or mouse (clone 13C/I3C4, P/N ab8189), can be purchased from Abcam. A rabbit polyclonal antibody with RTD P/N 760-4434 can be obtained from Cell Marque™.

As used herein, the term "contacting" refers to placement that allows association between two or more moieties, particularly direct physical association, for example both in solid form and/or in liquid form (for example, the placement of a biological sample, such as a biological sample affixed to a slide, in contact with an antigen releasing solution).

As used herein, the term "specifically binds" refers to the binding of agent that preferentially binds to a defined target (such as an antibody to a specific antigen or a nucleic acid probe to a specific nucleic acid sequence). A target can be any molecule for which the presence, location and/or concentration is or can be determined. Examples of target molecules include proteins and nucleic acids. Target molecules are typically detected using one or more conjugates of a specific binding molecule and a detectable label. With respect to an antigen, "specifically binds" refers to the preferential association of an antibody or other ligand, in whole or part, with a specific polypeptide. With respect to a nucleic acid sequence, "specifically binds" refers to the preferential association of a nucleic acid probe, in whole or part, with a specific nucleic acid sequence. A specific binding agent binds substantially only to a defined target. It is recognized that a minor degree of non-specific interaction may occur between a molecule, such as a specific binding agent, and a non-target polypeptide or non-target nucleic acid sequence. Although a selectively reactive antibody binds an antigen, it can do so with low affinity. Antibody to antigen specific binding typically results in greater than 2-fold, such as greater than 5-fold, greater than 10-fold, or greater than 100-fold increase in amount of bound antibody or other ligand (per unit time) to a target polypeptide, as compared to a non-target polypeptide. A variety of immunoassay formats are appropriate for selecting antibodies specifically immunoreactive with a particular protein. For example, solid-phase ELISA immunoassays are routinely used to select monoclonal antibodies specifically immunoreactive with a protein.

A sample including an antigen (such as a target antigen) is incubated with an antibody under conditions permitting antibody-antigen binding. Antibody-antigen binding can be detected by means of a detectable label conjugated to the antibody (direct detection) or by means of a detectable label conjugated to a secondary antibody, which is raised against the primary antibody (e.g., indirect detection). Detectable labels can include, but are not limited to, radioactive isotopes, fluorochromes (such as fluorescein, fluorescein isothiocyanate, and rhodamine), and chromogenic molecules.

As used herein, the term "detect" refers to determining if an agent (such as a signal or particular antigen or protein) is present or absent in a sample. In some examples, this can further include quantification. As used herein, the term "detecting" refers to any method of determining if something exists, or does not exist, such as determining if a target molecule is present in a biological sample. For example, detecting can include using a visual or a mechanical device to determine if a sample displays a specific characteristic. In certain examples, detection refers to visually observing a probe bound to a target, or observing that a probe does not bind to a target. For example, light microscopy and other microscopic means are commonly used to detect chromogenic precipitates for methods described here.

Labels

As used herein, "detectable label" refers to a molecule or material that can produce a detectable signal (such as visually, electronically or otherwise) that indicates the presence and/or concentration of a target in a sample. When conjugated to a specific binding molecule, the detectable label can be used to locate and/or quantify the target to which the specific binding molecule is directed. Thereby, the presence and/or concentration of the target in a sample can be detected by detecting the signal produced by the detectable label. A detectable label can be detected directly or indirectly, and several different detectable labels conjugated to different specific-binding molecules can be used in combination to detect one or more targets. Multiple detectable labels that can be separately detected can be conjugated to different specific binding molecules that specifically bind different targets to provide a multiplexed assay that can provide detection of the multiple targets in a sample. A detectable signal can be generated by any known or yet to be discovered mechanism including absorption, emission and/or scattering of a photon (including radio frequency, microwave frequency, infrared frequency, visible frequency and ultra-violet frequency photons).

Detectable labels can include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity). Particular examples of detectable labels include: enzymes, such as horseradish peroxidase, alkaline phosphatase, acid phosphatase, glucose oxidase, β-galactosidase or β-glucuronidase; fluorophores, such as fluoresceins, luminophores, coumarins, BODIPY dyes, resorufins, and rhodamines (many additional examples of fluorescent molecules can be found in The Handbook—A Guide to Fluorescent Probes and Labeling Technologies, Molecular Probes, Eugene, OR); nanoparticles, such as quantum dots; metal chelates, such as DOTA and DPTA chelates of radioactive or paramagnetic metal ions like $Gd^{3+}$; and liposomes, for example, liposomes containing trapped fluorescent molecules. Where the detectable label includes an enzyme, a detectable substrate such as a chromogen, a fluorogenic compound, or a luminogenic compound is used in combination with the enzyme to generate a detectable signal (a wide variety of such compounds are commercially available, for example, from Life Technologies, Carlsbad, Calif.).

As used herein, the term "chromogen" refers to a substance capable of conversion to a colored product, such as a pigment or dye. Certain chromogens are electron donors that, when oxidized, become a colored product. Production of a colored product, or the property of becoming insoluble upon chemical conversion, such as by oxidation, make chromogens useful for IHC. Non-limiting examples of chromogenic compounds, include diaminobenzidine (DAB), 4-Chloro-2-methyl-benzenediazonium (Fast Red), nitro blue tetrazolium (NBT), AP Orange, tetramethylbenzidine (TMB), 2,2'-azino-di-[3-ethylbenzothiazoline sulphonate] (ABTS), New Fuchsin, iodonitrotetrazolium (INT), tetrazolium blue and tetrazolium violet. More chromogens are known to those skilled in the art, for example, 4-nitrophenylphospate (pNPP), bromochloroindolyl phosphate (BCIP), nitro blue tetrazolium (NBT), AP blue, o-dianisidine, 4-chloronaphthol (4-CN), nitrophenyl-.beta.-D-galactopyranoside (ONPG), o-phenylenediamine (OPD), 5-bromo-4-chloro-3-indolyl-.beta.-galactopyranoside (X-Gal), methylumbelliferyl-.beta.-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet. DAB is a chromogen that produces a brown end product that is highly insoluble in alcohol and other organic solvents. Oxidation of DAB causes polymerization, resulting in the ability to react with osmium tetroxide, and thus increasing its staining intensity and electron density.

Alternatively, an enzyme can be used in a metallographic detection scheme. Metallographic detection methods include using an oxido-reductase enzyme (such as horseradish peroxidase) along with a water soluble metal ion (for example, silver or gold), an oxidizing agent and a reducing agent, again to form a detectable precipitate. Under the proper conditions (i.e., the addition of the label enzyme) will reduce soluble metal ions such as silver (+1) or gold (+3) to a silver or gold atom such that it becomes visible to the eye as a specific dot under a brightfield light microscope.

Kits

The disclosure also provides a kit comprising: a primary antibody capable of binding phosphorylated alpha-synuclein; and a primary antibody capable of binding to a nerve feature. In some of the kits disclosed herein, the kits further comprise: (a) a first secondary antibody having a first label conjugated thereto, wherein the first secondary antibody is immunoreactive with the primary antibody capable of binding phosphorylated alpha-synuclein; (b) a set of reagents that generates a first detectable single when reacted with the first label of the first secondary antibody; (c) a second secondary antibody having a second label conjugated thereto, wherein the second secondary antibody is immunoreactive with the primary antibody capable of binding the nerve feature; and (d) a set of reagents that generates a second detectable single when reacted with the second label of the second secondary antibody; wherein the first detectable signal and the second detectable signal are different. In some of the kits, the first detectable signal is silver stain and the second detectable signal is QM-Dabsyl or Fast-Red.

As used herein, the term "kit" refers to a packaged combination of one or more vessels, containers, devices or the like holding the necessary reagents for detecting an analyte of interest. The kit is appended with written or computerized instructions for performing the method. The kit may contain a labeled antibody, nucleic acid, ligand, or the like. The kit for detecting an analyte of interest in a biological sample can comprise one or more containers, each container adapted to hold a specific binding member for the analyte of interest, a redox-inactive reductive species, an enzyme label for rendering said reductive species active, a metal ion, and reagents for metal enhancement. In some embodiments, said specific binding member is immobilized on a solid support.

In some of the methods disclosed herein, the primary antibody capable of binding to alpha-synuclein can be one of the antibodies disclosed in Table 10. For example, antibodies for detecting alpha-synuclein are can include, but are not limited to: rabbit monoclonal antibody clones 7E2, and 3G2 against phosphorylated S129 alpha-synuclein. Additional monoclonal antibodies against phosphorylated S129 alpha-synuclein can include, for example, Abcam clones MJF-R13 (8-8), P/N ab168381 and P-syn/81A, P/N ab184674 or WAKO clone pSyn #64, P/N 015-25191. Mouse monoclonal antibody clone LB509 against alpha-synuclein regardless of S129 phosphorylation status can be used (for example, Abcam (P/N ab27766)). Anti-alpha-synuclein mouse monoclonal antibody clone 5C12 (S129 phosphorylation independent; ATCC® No. PTA-9197) and anti-phosphorylated S129-alpha-synuclein mouse monoclonal antibody clone 11A5 (ATCC® No. PTA-8222) from Prothena Corporation may also be used.

In some of the methods disclosed herein, the primary antibody capable of binding to the nerve feature is selected from an antibody capable of binding a protein selected from the group consisting of: ubiquitin C-terminal hydrolase L1 (PGP9.5, UCHL1, NDGOA; PARK5; PGP95; SPG79; Uch-L1; HEL-117; PGP 9.5; HEL-S-53), RNA binding fox-1 homolog 3 (RBFOX3, FOX3, NEUN, FOX-3, HRNBP3), microtubule associated protein 2 (MAP2, MAP2A, MAP2B, MAP2C), 160 kDa neurofilament medium (NEFM, NFM, NEF3, NF-M), 200 kDa neurofilament heavy (NEFH, NFH, CMT2CC), synaptophysin (SYP, MRX96, MRXSYP), and discs large MAGUK scaffold protein 4 (DLG4, DLGH4, PSD-95, PSD95, SAP-90, SAP90, SAP90A).

In some of the methods disclosed herein, the methods further comprise: contacting the section with a first secondary antibody having a first label conjugated thereto, wherein the first secondary antibody is immunoreactive with the primary antibody capable of binding phosphorylated alpha-synuclein, and contacting the section with a second secondary antibody having a second label conjugated thereto, wherein the second secondary antibody is immunoreactive with the primary antibody capable of binding the nerve feature.

In some of the methods disclosed herein, the methods further comprise: contacting the section with a set of reagents reactive with the first label of the first secondary antibody to generate a first detectable signal in proximity to phosphorylated alpha-synuclein in the sample; and contacting the section with a set of reagents reactive with the second label of the second secondary antibody to generate a second detectable signal in proximity to the nerve feature in the sample.

In some of the methods disclosed herein, the methods further comprise denaturing immunocomplexes in the sample after contacting the section with the primary antibody capable of binding phosphorylated alpha-synuclein and before contacting the section with the primary antibody capable of binding the nerve feature.

In some of the methods disclosed herein, the section is contacted with at least one protease before being contacted with a primary antibody. In certain methods, the method further comprises contacting the section with at least one phosphatase.

In some of the methods disclosed herein, the primary antibody capable of binding phosphorylated alpha-synuclein and the primary antibody capable of binding the nerve feature are from the same host species.

In some of the methods disclosed herein, the first detectable signal and the second detectable signal are different. In some of the methods disclosed herein, the first detectable signal is silver stain and the second detectable signal is QM-Dabsyl or Fast-Red.

Also provided herein are methods for diagnosing PD in a subject, said method comprising: (a) obtaining a biological sample comprising at least one nerve feature from a subject suspected of having PD; (b) detecting whether phosphorylated alpha-synuclein localizes within the nerve feature in the sample by contacting the sample with an anti-PGP.5 antibody and determining co-localization between phosphorylated alpha-synuclein and PGP9.5; and (c) diagnosing the subject with PD when it is determined in the affirmative that there is co-localization between phosphorylated alpha-synuclein and PGP9.5 in the nerve feature. In some instances, the method may be accomplished without the use of the anti-PGP9.5 antibody when nerve features can be identified without the signal associated with the anti-PGP9.5 antibody. For instance, an experienced pathologist may be able to recognize a nerve feature in a tissue sample without such signal. The pathologist can diagnose the subject with PD by presence of the signal associated with the phosphorylated alpha-synuclein localized with the nerve feature.

Some methods can include, for example, scoring phosphorylated alpha-synuclein and nerve features detected in the sample. In some methods, the number of nerve features in an entire slide are counted and expressed as percentage of nerve features containing phosphorylated alpha-synuclein. In certain methods where a nerve feature is identified by the presence of a target nerve feature protein, the presence of phosphorylated alpha-synuclein protein and the target nerve feature protein can include determining an absolute number of nerve features staining with the phosphorylated alpha-synuclein antibody in the sample using a 5×5 ocular grid with an area of 0.25 square millimeter, determining an absolute number of nerve features staining with the target nerve feature antibody in the sample using a 5×5 ocular grid with an area of 0.25 square millimeter, extrapolating the absolute number of cells staining with the phosphorylated alpha-synuclein antibody to a number of nerve features in a 1 square millimeter region, and extrapolating the absolute number of nerve features staining with the target nerve feature antibody to a number of nerve features in a 1 square millimeter region, thereby generating a score of phosphorylated alpha-synuclein protein and the target nerve feature protein. Thus, the method can include counting the number of nerve features staining positive for phosphorylated alpha-synuclein and the number of nerve features staining positive for the target nerve feature protein in the grid (such as phosphorylated alpha-synuclein and/or the target nerve feature positive nerve features). In one specific example, those values are inserted into the following formula: cell count/ (0.0156×# of grids). This formula is dependent on the diameter of the objective which is variable between models even with equal magnification. Other formulas can be used if a different magnification or a different objective is used. In some examples, randomly selected regions of the sample are selected for scoring. Thus, as shown in FIG. 32, each co-localized black and yellow dot in the image represents nerve features staining with phosphorylated alpha-synuclein and the target nerve feature protein.

Provided herein are methods for determining whether a subject has Parkinson's Disease (PD), methods for diagnosing PD in a subject, and methods for diagnosing and treating PD in a subject by, in part, diagnosing a subject with PD when it is determined in the affirmative that there is co-localization between phosphorylated alpha-synuclein and a nerve feature in a biological sample from the subject. For example, if the sample obtained from the subject is analyzed or scored using the methods provided herein as having an increased co-localization of phosphorylated alpha-synuclein with nerve features relative to a normal sample (e.g., non-PD sample of the same tissue type), the subject can be determined to be, or diagnosed, as one having Parkinson's disease. For example, an increase of at least 20%, at least 40%, at least 50%, at least 75%, at least 80%, at least 90%, at least 100%, at least 200% or at least 500% (such as an increase of at least 2-fold, at least 5-fold, or at least 10-fold) in phosphorylated alpha-synuclein within nerve features in the tissue sample as compared to the phosphorylated alpha-synuclein within nerve features in a normal sample (such as a reference value or range of values for such a sample). In contrast, if the biological sample obtained from the subject is analyzed or scored using the methods provided herein as having a similar or decreased phosphorylated alpha-synuclein within nerve features relative to a normal sample (e.g., non-PD sample), the subject can be determined to be, or diagnosed as, one not-likely to have Parkinson's disease. In some examples, the disclosed methods can further include administering one or more therapies or treatments to the subject if the subject is determined to be, or diagnosed, as one having Parkinson's disease.

Also provided herein are methods of treating a subject diagnosed with PD, comprising administering to the subject an effective regime of an alpha-synuclein antibody, wherein an antibody capable of binding phosphorylated alpha-synuclein and an antibody capable of binding a nerve feature have been shown to co-localize in a nerve feature in a skin sample from the subject. In certain methods, a subject determined to have PD, can be treated by administering to the subject an effective regime of an alpha-synuclein antibody, wherein the subject was determined to have PD by any of the methods described herein.

As used herein, the terms "treat", "treatment" and "treating" refer to the amelioration of one or more of the primary or secondary symptoms of Parkinson's disease and related movement disorders. Primary symptoms of Parkinson's disease include, but are not limited to tremor in an extremity while the extremity is at rest, generalized slowness of movement (bradykinesia), increased muscle rigidity or stiffness, gait or balance problems (postural dysfunction). Secondary symptoms of Parkinson's include, but are not limited to, difficulty initiating or resuming movements, loss of fine motor skills, lack of arm swing on the affected side of the body while walking, foot drag on the affected side of the body, decreased facial expression, voice and/or speech changes, cognitive disorders, sleep disorders, gastro-intestinal dysfunction, and feelings of depression or anxiety.

Related movement disorder that may also be treated by the methods of the present disclosure include, but are not limited to, akathisia, akinesia (lack of movement), athetosis (contorted torsion or twisting), ataxia, ballismus (violent involuntary rapid and irregular movements), Cerebral palsy, choreas (e.g. Syndenham's chorea, rheumatic chorea, Huntington's disease), dystonias (e.g. dystonia musularum, belpharospasm, Writer's cramp, spasmodic torticollis), geniospasm (episodic involuntary up and down movements of the chin and lower lip) myoclonus, Restless Legs Syndrome (RLS), spasms, stereotypic movement disorder, stereotypy, Tardive dyskinesia, tic disorders (Tourette's syndrome, postural tremor, kinetic tremor, essential tremor, cerebellar tremor, physiological tremor), and Wilson's disease.

Prior to the initiation of treatment and/or therapy, all subjects should be evaluated and managed by a multidisciplinary team with expertise and experience in neurodegenerative disorders and Parkinson's disease. Subjects with PD typically have a medical professional and multidisciplinary health care team made up of doctors from different specialties including, but not limited to, neurologists, occupational therapists, physical therapists, counselors, social workers, registered dietitians, and speech therapists. After PD is diagnosed in a subject, a medical professional or team of medical professionals will typically recommend one or several treatment options including one or more of prescribed medications (for example, Benztropine mesylate (Cogentin), Entacapone (Comtan), Dopar, Larodopa, Levodopa and carbidopa (Sinemet), Pramipexole (Mirapex), Rasagiline (Azilect), Ropinirole Hcl (Requip), Rotigotine (Neupro), Safinamide (Xadago), Tasmar, or Trihexphenidyl (Artane)), surgery (for example, deep brain stimulation, pallidotomy, thalamotoy, or gamma knife), alternative therapies (Coenzyme Q10, massage, acupuncture, Tai Chi, yoga, Alexander technique, or meditation), and/or healthy eating and exercise. A treatment regimen is determined by a medical professional or team of medical professionals and can be specific to each subject. Those skilled in the art are familiar with various other treatments for PD.

In some such methods, the effective regime of an alpha-synuclein antibody comprises an alpha-synuclein antibody selected from the group consisting of: a monoclonal antibody binding within residues 1-20 of alpha-synuclein, 1-10 of alpha synuclein, 4-15 of alpha-synuclein, 91-99 of alpha-synuclein, 117-123 of alpha-synuclein, 118-126 of alpha-synuclein, prasinezumab (PRX002), a humanized antibody having the CDR's of antibody clone 1H7 (ATCC Accession No. PTA-8220), a humanized antibody having the CDR's of antibody clone 9E4 (ATCC Accession No. PTA-8221), the CDR's of antibody clone NI-202.21D11, and the CDR's of antibody clone NI-202.12F4, such as, for example, alpha-synuclein antibodies disclosed in U.S. Pat. Nos. 8,092,801, 8,609,820, 8,790,644, 8,940,276, 9,580,493, which are incorporated by reference herein in their entirety.

Some such antibodies comprise a VH CDR1 comprising residues 31-35 of SEQ ID NO:49, a VH CDR2 comprising residues 50-68 of SEQ ID NO:49, a VH CDR3 comprising residues 101-102 of SEQ ID NO:49, a VL CDR1 comprising residues 23-33 of SEQ ID NO:50, a VL CDR2 comprising residues 49-55 of SEQ ID NO:50, and a VL CDR3 comprising residues 88-98 of SEQ ID NO:50. Some such antibodies comprise a VH CDR1 comprising SEQ ID NO:51, a VH CDR2 comprising SEQ ID NO:52, a VH CDR3 comprising SEQ ID NO:53, a VL CDR1 comprising SEQ ID NO:54, a VL CDR2 comprising SEQ ID NO:55 and a VL CDR3 comprising SEQ ID NO:56. Some such antibodies comprise a heavy chain comprising SEQ ID NO:57 and a light chain comprising SEQ ID NO:58.

(SEQ ID NO: 9 of U.S. Pat. 8,940,276)
SEQ ID NO: 49
EVQLVQSGGGLVEPGGSLRLSCAVSGFDFEKAWMSWVRQAPGQGLQWVAR

IKSTADGGTTSYAAPVEGRFIISRDDSRNMLYLQMNSLKTEDTAVYYCTS

AHWGQGTLVTVSS (SEQ ID NO: 12 of U.S. Pat. 8,940,276)
SEQ ID NO: 50
QSVLTQPPSVSVSPGQTARITCSGEALPMQFAHWYQQRPGKAPVIVVYKD

SERPSGVPERFSGSSSGTTATLTITGVQAEDEADYYCQSPDSTNTYEVFG

GGTKLTVL (SEQ ID NO: 16 of U.S. Pat. 9,580,493;
NI-202.21D11-VH CDR1)
SEQ ID NO: 51
NYAMH (SEQ ID NO: 17 of U.S. Pat. 9,580,493;
NI-202.21D11-VH CDR2)
SEQ ID NO: 52
WINAGNGERKYSQKFQD (SEQ ID NO: 18 of U.S. Pat. 9,580,493;
NI-202.21D11-VH CDR3)
SEQ ID NO: 53
EEDHAGSGSYLSMDV (SEQ ID NO: 23 of U.S. Pat. 9,580,493;
NI-202.21D11-VK CDR1)
SEQ ID NO: 54
KSSQNVLYSSNNKNYLA (SEQ ID NO: 24 of U.S. Pat. 9,580,493;
NI-202.21D11-VK CDR2)
SEQ ID NO: 55
WASTRES (SEQ ID NO: 25 of U.S. Pat. 9,580,493;
NI-202.21D11-VK CDR3)
SEQ ID NO: 56
QQYYSSPLT (SEQ ID NO: 10 of U.S. Pat. 8,609,820)
SEQ ID NO: 57
EVQLVESGGGLVQPGGSLRLSCAASGFTFSNYGMSWVRQAPGKGLEWVAS

ISSGGGSTYYPDNVKGRFTISRDDAKNSLYLQMNSLRAEDTAVYYCARGG

AGIDYWGQGTLVTSS (SEQ ID NO: 5 of U.S. Pat. 8,609,820)
SEQ ID NO: 58
DIQMTQSPSSLSASVGDRVTITCKSIQTLLYSSNQKNYLAWFQQKPGKAP

KLLIYWASIRKSGVPSRFSGSGSGTDFTLTISSLQPEDLATYYCQQYYSY

PLTFGGGTKLEIK

In some such methods, the antibody is prasinezumab (PRX002). In some such methods, the antibody comprises three light CDRs designated SEQ ID NOs: 18-20 respectively and three heavy chain CDRs designated SEQ ID NOs:

22-24 respectively. In some such methods, the antibody comprises a light chain designated SEQ ID NO:17 and a heavy chain designated SEQ ID NO:21.

SEQ ID NO: 17
>10680L|prasinezumab|Humanized|LC|
DIQMTQSPSSLSASVGDRVTITCKSIQTLLYSSNQKNYLAWFQQKPGKAP

KLLIYWASIRKSGVPSRFSGSGSGTDFTLTISSLQPEDLATYYCQQYYSY

PLTFGGGTKLEIKRTVAAPSVFIFPPSDEQLKSGTASVVCLLNNFYPREA

KVQWKVDNALQSGNSQESVTEQDSKDSTYSLSSTLTLSKADYEKHKVYAC

EVTHQGLSSPVTKSFNRGEC prasinezumab LC CDR1
SEQ ID NO: 18
KSIQTLLYSSNQKNYLA prasinezumab LC CDR2
SEQ ID NO: 19
WASIRKS prasinezumab LC CDR3
SEQ ID NO: 20
QQYYSYPLT

>10680H|prasinezumab|Humanized|HC|
SEQ ID NO: 21
EVQLVESGGGLVQPGSLRLSCAASGFTFSNYGMSWVRQAPGKGLEWVASI

SSGGGSTYYPDNVKGRFTISRDDAKNSLYLQMNSLRAEDTAVYYCARGGA

GIDYWGQGTLVTVSSASTKGPSVFPLAPSSKSTSGGTAALGCLVKDYFPE

PVTVSWNSGALTSGVHTFPAVLQSSGLYSLSSVVTVPSSSLGTQTYICNV

NHKPSNTKVDKRVEPKSCDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEFTISKAKGQPREPQVYTLP

PSREEMTKNQVSLTCLVKGFYPSDIAVEWESNGQPENNYKTTPPVLDSDG

SFFLYSKLTVDKSRWQQGNVFSCSVMHEALHNHYTQKSLSLSPGK prasinezumab HC CDR1
SEQ ID NO: 22
NYGMS prasinezumab HC CDR1
SEQ ID NO: 23
SISSGGGSTYYPDNVKG prasinezumab HC CDR1
SEQ ID NO: 24
GGAGIDY

In some such methods, the antibody is 9E4, as disclosed in U.S. Pat. No. 8,609,820, which is incorporated by reference herein in its entirety. The method provides an antibody comprising a humanized heavy chain comprising the three Kabat CDRs of SEQ ID NO:29 and a humanized light chain comprising the three CDRs of SEQ ID NO:25 provided that position L36 (Kabat numbering) is occupied by F or Y and/or position L83 (Kabat numbering) is occupied by L or F and/or position H73 (Kabat numbering) is occupied by D or N, and/or position H93 (Kabat numbering) is occupied by S or A. In some such antibodies, position L36 (Kabat numbering) is occupied by F and position H73 (Kabat numbering) is occupied by D, and position H93 (Kabat numbering) is occupied by S. In some such antibodies, position L36 is occupied by F. In some such antibodies, position L83 is occupied by L. In some such antibodies position H73 is occupied by D. In some such antibodies, position H93 is occupied by A. In some such antibodies, position L36 is occupied by F and position L83 is occupied by L. In some such antibodies, position L36 is occupied by F and position H73 is occupied by D. In some such antibodies, position L36 is occupied by F and position H93 is occupied by A. In some such antibodies, position L36 is occupied by F, position L83 is occupied by L and position H73 is occupied by D. In some such antibodies, position L36 is occupied by F, position L83 is occupied by L and position H93 is occupied by A. In some such antibodies, position L 36 is occupied by F, position L83 is occupied by L, position I173 is occupied by D and position H93 is occupied by A. In some such antibodies, residues at positions L36, L83, H73 and H93 (Kabat numbering) are occupied by F, and position H73 (Kabat numbering) is occupied by D, and position H93 (Kabat numbering) is occupied by A. In some such antibodies, position L36 (Kabat numbering) is occupied by F and position H93 (Kabat numbering) is occupied by S. In some such antibodies, position H73 (Kabat numbering) is occupied by D and position H93 (Kabat numbering) is occupied by S. In some such antibodies, position 1173 (Kabat numbering) is occupied by D and position 1193 (Kabat numbering) is occupied by A. In some such antibodies, position H93 (Kabat numbering) is occupied by S. In some such antibodies, position 1173 (Kabat numbering) is occupied by N. In some such antibodies, position L36 (Kabat numbering) is occupied by F, position L83 (Kabat numbering) is occupied by L, position H73 (Kabat numbering) is occupied by D, and position H93 (Kabat numbering) is occupied by S. In some such antibodies, position L36 (Kabat numbering) is occupied by F, position L83 (Kabat numbering) is occupied by L and position H93 (Kabat numbering) is occupied by S. In some such methods, the antibody comprises three light CDRs designated SEQ ID NOs:26-28 respectively and three heavy chain CDRs designated SEQ ID NOs:30-32 respectively. In some such methods, the antibody comprises a light chain variable region designated SEQ ID NO:25 and a heavy chain variable region designated SEQ ID NO:29.

9E4 LC Variable Region
SEQ ID NO: 25
DIQMTQSPSSLSASVGDRVTITCKSIQTLLYSSNQKNYLAWYQQKPGKAP

KLLIYWASIRKSGVPSRFSGSGSGTDFTLTISSLQPEDFATYYCQQYYSY

PLTFGGGTKLEIK

9E4 LC CDR1
SEQ ID NO: 26
KSIQTLLYSSNQKNYLA

9E4 LC CDR2
SEQ ID NO: 27
WASIRKS

9E4 LC CDR3
SEQ ID NO: 28
QQYYSYPLT

9E4 HC Variable Region
SEQ ID NO: 29
EVQLVESGGGLVQPGGSLRLSCAASGFTFSNYGMSWVRQAPGKGLEWVAS

ISSGGGSTYYPDNVKGRFTISRDNAKNSLYLQMNSLRAEDTAVYYCARGG

AGIDYWGQGTLVTVSS

9E4 HC CDR1
SEQ ID NO: 30
NYGMS

```
9E4 HC CDR2
                                    SEQ ID NO: 31
SISSGGGSTYYPDNVKG

9E4 HC CDR3
                                    SEQ ID NO: 32
GGAGIDY
```

In some such methods, the antibody is NI-202.21D11. In some such methods, the antibody comprises three light CDRs designated SEQ ID NOs:34-36 respectively and three heavy chain CDRs designated SEQ ID NOs: 38-40 respectively. In some such methods, the antibody comprises a light chain variable region designated SEQ ID NO:33 and a heavy chain variable region designated SEQ ID NO:37.

```
NI-202.21D11 LC variable region
                                    SEQ ID NO: 33
DVVMTQSPDSLAVSLGERATINCKSSQNVLYSSNNKNYLAWYQQKPGHPP

KLLIYWASTRESGVPDRFSGSGSGTDFTLTITSLQTEDVAVYYCQQYYSS

PLTFGGGTKVEIK

NI-202.21D11 LC CDR1
                                    SEQ ID NO: 34
KSSQNVLYSSNNKNYLA

NI-202.21D11 LC CDR2
                                    SEQ ID NO: 35
WASTRES

NI-202.21D11 LC CDR3
                                    SEQ ID NO: 36
QQYYSSPLT

NI-202.21D11 HC variable region
                                    SEQ ID NO: 37
EVQLVESGAEVKKPGASVKVSCKASGYTFTNYAMHWVRQAPGQRLEWMGW

INAGNGKRKYSQKFQDRVTINRDTSASTIYMELSSLGSEDTAVYYCAREE

DHAGSGSYLSMDVWGQGTLVTVSS

NI-202.21D11 HC CDR1
                                    SEQ ID NO: 38
NYAMH

NI-202.21D11 HC CDR2
                                    SEQ ID NO: 39
WINAGNGKRKYSQKFQD

NI-202.21D11 HC CDR3
                                    SEQ ID NO: 40
EEDHAGSGSYLSMDV
```

In some such methods, the antibody is NI-202.12F4. In some such methods, the antibody comprises light heavy CDRs designated SEQ ID NOs:42-44 respectively and three heavy chain CDRs designated SEQ ID NOs: 46-48 respectively. In some such methods, the antibody comprises a light chain variable region designated SEQ ID NO:41 and a heavy chain variable region designated SEQ ID NO:45.

```
NI-202.12F4 LC variable region
                                    SEQ ID NO: 41
QSVLTQPPSVSVSPGQTARITCSGEALPMQFAHWYQQRPGKAPVIVVYKD

SERPSGVPERFSGSSSGTTATLTITGVQAEDEADYYCQSPDSTNTYEVFG

GGTKTLTVL

NI-202.12F4LC CDR1
                                    SEQ ID NO: 42
SGEALPMQFAH

NI-202.12F4LC CDR2
                                    SEQ ID NO: 43
KDSERPS

NI-202.12F4LC CDR3
                                    SEQ ID NO: 44
QSPDSTNTYEV

NI-202.12F4 HC variable region
                                    SEQ ID NO: 45
EVQLVQSGGGLVEPGGSLRLSCAVSGFDFEKAWMSWVRQAPGQGLQWVAR

IKSTADGGTTSYAAPVEGRFIISRDDSRNMLYLQMNSLKTEDTAVYYCTS

AHWGQGTLVTVSS

NI-202.12F4HC CDR1
                                    SEQ ID NO: 46
KAWMS

NI-202.12F4HC CDR2
                                    SEQ ID NO: 47
RIKSTADGGTTSYAAPVEG

NI-202.12F4HC CDR3
                                    SEQ ID NO: 48
TSAH
```

Also provided herein are methods for detecting phosphorylated alpha-synuclein, the method comprising: contacting a biological sample with a primary antibody capable of binding phosphorylated alpha-synuclein, and detecting the primary antibody capable of binding phosphorylated alpha-synuclein. In some of the methods, the sample is contacted with at least one protease before being contacted with the primary antibody capable of binding phosphorylated alpha-synuclein. In some methods, the method further comprises contacting the sample with at least one phosphatase. In some methods, the detecting comprising histochemical analysis. In some methods, the primary antibody capable of binding phosphorylated alpha-synuclein detects alpha-synuclein phosphorylated at residue S129. In certain methods, the primary antibody capable of binding phosphorylated alpha-synuclein is the 7E2 antibody clone or the 3G2 antibody clone. In some methods, the sample is fixed. In certain methods, the sample is a formalin fixed, paraffin embedded (FFPE) sample. In some methods, the sample is a frozen sample In some methods, the method further comprises contacting the sample with a first secondary antibody having a first label conjugated thereto, wherein the first secondary antibody is immunoreactive with the primary antibody capable of binding phosphorylated alpha-synuclein. In some methods, the method comprises contacting the sample with a set of reagents reactive with the first label of the first secondary antibody to generate a first detectable signal in proximity to phosphorylated alpha-synuclein in the sample.

EXAMPLES

Parkinson's disease is a progressive neurodegenerative disease characterized by the presence of Lewy bodies and Lewy neurites in the brain of subjects suffering from the disease. Lewy bodies are highly enriched with the aggregated form of alpha-synuclein (aSyn), a protein with poorly characterized functions. Aggregation of aSyn was also found in peripheral nerves from subject with Parkinson's disease. Aggregated aSyn can be detected using immunohistochemistry (IHC) and can be distinguished from non-aggregated aSyn by virtue of its resistance to protease treatment. However, prolonged protease treatment could degrade tissue morphology in IHC assays, leading to the need for an alternative method to differentiate aggregated aSyn from non-aggregated aSyn. An unusually high proportion of aggregated aSyn is found to be phosphorylated at Ser129 residue (pS129) compared with non-aggregated aSyn. As shown herein, a highly sensitive and specific assay for aggregated aSyn using pS129-aSyn as a surrogate marker for aSyn aggregation was developed.

Materials

Tissue source. Scalp, abdomen area skin, colon, and submandibular gland samples were obtained from Banner Sun Health Research Institute (BSHRI) courtesy of Dr. Thomas G. Beach, director of Brain and Body Donation Program. In addition to standardized clinical assessments diagnosis of Parkinson's disease was confirmed in the tissue donors by the presence of Lewy bodies. Similarly the normal, non-PD control subjects' status was determined by lack of Lewy bodies. The samples (16 males, 8 females; ages 65-95; 15 PD, 9 non-PD) were obtained post-mortem and fixed in formalin. The formalin-fixed paraffin-embedded (FFPE) cortical brain blocks from normal individuals and subjects with PD were obtained from Roche Tissue Diagnostics (RTD) internal tissue bank and Folio Biosciences, respectively. A small cohort of FFPE skin biopsy blocks was obtained from 8 individuals (3 males, 5 females) 1 to 16 years of age through Folio Biosciences to assess the degree of pS129-aSyn staining that does not resemble aggregated aSyn. A much larger cohort of 72 FFPE skin biopsy blocks from 36 subjects were obtained from Dr. Ron Postuma at Montreal General Hospital Department of Neurology. Fifteen of the 36 subjects were diagnosed with PD and five with atypical Parkinsonism based on clinical examination of subjects' presented symptoms. The rest (16 subjects) were control subjects without PD. Two skin punch biopsies were performed on the subjects during clinical visits and FFPE blocks were transferred to Ventana Medical Systems through Prothena. All other tissue specimens were obtained from RTD internal tissue bank. Unless otherwise noted, thickness of all FFPE tissue sections was 4 µm.

Antibodies against alpha-synuclein (aSyn) and PGP9.5. Rabbit monoclonal antibody clones 7E2, and 3G2 against phospho-S129 aSyn were generated by Roche Diagnostics GmbH CPS R&D Early Development & Reagent Design (DXREAA) with a phospho-peptide corresponding to human aSyn residues 122-135 as immunogen. Additional monoclonal antibodies against phospho-S129 aSyn were purchased from Abcam (clones MJF-R13 (8-8), P % N ab168381 and P-syn/81A, P/N ab184674) or WAKO (clone pSyn #64, P/N 015-25191). Mouse monoclonal antibody clone LB509 against aSyn regardless of S129 phosphorylation status was purchased from Abcam (P/N ab27766). Anti-aSyn mouse monoclonal antibody clone 5C12 (S129 phosphorylation independent) and anti-phosphorylated S129 alpha-synuclein mouse monoclonal antibody clone 11A5 were gifts from Prothena Corp. Also see Table 10.

Three anti-human PGP9.5 antibodies were used in the present study. Two monoclonal antibodies, one rabbit (clone EPR4118, P/N ab108986) and the other mouse (clone 13C/13C4, P/N ab8189), were purchased from Abcam. A rabbit polyclonal antibody with RTD P/N 760-4434 was obtained from Cell Marque™.

Enzymes. VENTANA® Protease 1 (P/N 760-2018) was used to remove non-aggregated aSyn in automated protease-resistant alpha-synuclein DAB IHC assay developed by pRED/Prothena. In one specific implementation of automated pS129-aSyn and PGP9.5 silver/yellow dual IHC assay (Bumblebee Assay Protocol 2 described below), recombinant bovine alkaline phosphatase (Roche, at 30 µg/mL in a stabilizing diluent (Roche P/N 06002919001)) and VENTANA® Protease 3 (P/N 760-2020) were used, respectively, to remove pS129-aSyn staining that did not resemble aggregated aSyn and enhance detection of pS129-aSyn.

Commercially available and user-provided reagents for automated phospho-S129-aSyn and PGP9.5 silver/yellow dual IHC assay and protease-resistant alpha-synuclein DAB IHC assay. Table 1 below contains the list of reagents including bulk solutions, enzymes, antibodies, detection kits, and ancillaries used in Bumblebee Assay Protocols 1 and 2 and DAB-based pRED/Prothena Assay Protocol for detection of protease-resistant aSyn (see Methods below).

TABLE 1

List of potential reagents used

| Name | RTD/ Ventana™ Part # | Retire number or overlabel used in protocols |
|---|---|---|
| EZ Prep (10×) | 950-102 | 05279771001 |
| ULTRA LCS | 650-210 | 05424534001 |
| SSC (10×) | 950-110 | 05353947001 |
| Reaction Buffer | 950-300 | 05353955001 |
| ULTRA CC1 | 950-224 | 05424569001 |
| ULTRA CC2 | 950-223 | 05424542001 |
| SilverWash II | 780-003 | 05446724001 |
| Hematoxylin II | 790-2208 | 05277965001 |
| Bluing Reagent | 760-2037 | 05266769001 |
| Protease I | 760-2018 | 05266688001 |
| ISH Protease 3 or Protease 3 | 780-4149/ 760-2020 | 5266718001/ 5266718001 |
| 7E2 Ab 1 µg/mL in DISCOVERY Goat Ig Block | N/A | ANTIBODY 2 |
| 5C12 Ab 1 µg/mL in 95028 DISCOVERY Goat Ig Block | N/A | PREP KIT 9 |
| pH adjust (500 mM Tris pH 10) | 760-6008 | Option 1 |
| 30 µg/mL recombinant bovine AP (Roche)diluted in Roche diluent with P/N 06002919001. | N/A | PRETREATMENT 4 |
| ultraView SISH DNP Detection Kit | N/A | PRETREATMENT 5 |
| OptiView DAB Detection Kit | 760-098 | 5572037001 |
| pH adjust (500 mM Tris pH 10) | 760-700 | 6396500001 |
| QM-Peg8-Dabsyl 480 µM in 25% DMSO/75% QM Buffer (10 mM glycine pH 2/1.05M MgCl₂/0.05% Brij-35) | N/A | ANTIBODY 11 |
| | N/A | ANTIBODY 12 |
| DISCOVERY UltraMap GaR-AP | 760-4314 | ANTIBODY 10 |
| EPR4118 PGP9.5 Ab 0.5 µg/mL in DISCOVERY Goat Ig Block | N/A | ANTIBODY 5 |
| ISH Peroxidase Inhibitor | 780-5061 | 07729014001 |

Equipment. BenchMark ULTRA instruments with the following serial numbers were used: 310520, 310841, 310934, 310940, 311000, 311112, 311276, 311279, and 311311.

Methods

DAB staining of FFPE brain and skin sections from donors with and without Parkinson's disease using antibodies against aSyn or PGP9.5

FFPE brain sections were stained using VENTANA® ultraView Universal DAB Detection Kit or OptiView DAB IHC Detection Kit in an automated VENTANA® BenchMark ULTRA instrument with standard complement of bulk solutions. Following deparaffinization, slides were subjected to one of three antigen retrieval procedures singly or in combination or none at all as indicated. The three antigen retrieval procedures were: 1) VENTANA® Protease 1 (P/N 760-2018) diluted approximately 3.7-fold on slide with Reaction Buffer and incubated for 4 minutes at 36° C., 2) VENTANA® ULTRA CC1 solution (P/N 950-224) for either 32 minutes (for antibodies against alpha-synuclein) or 64 minutes (for antibodies against PGP9.5) at 100° C. unless otherwise noted, and 3) alkaline phosphatase (AP, recombinant from *Pichia pastoris*, highly active EIA grade, Roche) for 2 hours at 36° C. Alkaline phosphatase was cocktailed in a dispenser at 50 µg/mL in a stabilizing solution (Roche P/N 06002919001) and 1 drop was applied to tissue slide immersed in VENTANA® Reaction Buffer following sequential applications of 1 drop of a 1:1 mixture of 0.5M Tris pH 10 and Reaction Buffer and 1 drop of 20 mM MgCl2. Primary antibodies were either hand applied or automatically applied from dispensers at indicated concentrations. Incubations for all primary antibodies were performed at 36° C. for 32 minutes unless otherwise noted. When detection was performed using VENTANA® ultraView Universal DAB Detection Kit (P/N 760-500) or OptiView DAB IHC Detection Kit (P/N 760-700), the ultraView Universal HRP Multimer, the OptiView HQ Universal Linker, and the OptiView HRP Multimer were incubated at 36° C. for 16 minutes unless otherwise noted and DAB stain was deposited using standard conditions in U ultraView DAB or U OptiView DAB IHC procedures. Counterstaining was performed on instrument using VENTANA® Hematoxylin II (P/N 790-2208, 4 minutes at 36° C.) and Bluing Reagent (P/N 760-2037, 4 minutes at 36° C.). Slides were coverslipped in xylene following alcohol dehydration in a Tissue-Tek automated slide stainer & coverslipper (Sakura).

Automated phospho-S129-alpha-synunclein and PGP9.5 silver/yellow dual IHC assay (Bumblebee Assay Protocols). FFPE skin sections were placed in a VENTANA® BenchMark ULTRA instrument with standard complement of bulk solutions including ultraView Silver Wash II (Ventana P/N 780-003). Two protocols (Protocol 1 and Protocol 2) based on the validated U Triplex IHC Silver_QM_DAB procedure were used to stain consecutive skin sections. Following deparaffinization, Bumblebee Assay Protocol 1 (see Table 2 below) had no antigen retrieval steps prior to incubation with 7E2 anti-phosphorylated S129 alpha-synuclein antibody. In contrast, alkaline phosphatase (Roche, diluted to 30 µg/mL in a stabilizing solution (Roche P/N 06002919001)) and VENTANA® Protease 3 (P/N 760-2020) were applied sequentially (with washing in between the treatments) to the slides prior to 7E2 antibody incubation in Bumblebee Assay Protocol 2 (see Table 3 below). Conditions for alkaline phosphatase and protease treatments are 8 minutes at 37° C. and 4 minutes at 36° C., respectively. Both Bumblebee Assay Protocols 1 and 2 had the same antibody incubation and detection steps: 1) incubation with 7E2 antibody for 32 minutes at 36° C., 2) detection of phospho-aSyn with VENTANA® ultraView SISH DNP kit using HRP-conjugated goat anti-rabbit antibody (incubation at 36° C. for 48 minutes) and precipitation of metallic silver, 3) deactivation of primary and secondary antibody complexes with VENTANA® ULTRA CC2 bulk solution (P/N 950-223) at 100° C. for 16 minutes which also serves as antigen retrieval for PGP9.5, 4) incubation with EPR4118 anti-PGP9.5 antibody at 36° C. for 32 minutes, 5) incubation with AP-conjugated goat anti-rabbit antibody (VENTANA® DISCOVERY UltraMap anti-Rb Alk Phos, P/N 760-4314) for 32 minutes at 36C, and 6) detection of PGP9.5 with AP-induced activation of phosphate-protected quinone methide conjugated to 4-(diethylamino)azobenene-4-sulfonamide (DABSYL). Approximate on-slide concentrations of 7E2 and ERP4118 antibodies were, respectively, 0.27 and 0.14 µg/mL after dilution with previously applied 1× Reaction Buffer (Ventana P/N 950-300). Counterstaining was performed on instrument using VENTANA® Hematoxylin II (P/N 790-2208, 8 minutes at 36° C.) and Bluing Reagent (P/N 760-2037, 8 minutes at 36C). Slides were coverslipped in xylene following alcohol dehydration in a Tissue-Tek automated slide stainer & coverslipper (Sakura). See Table 2 for a summary of Protocol 1 and Table 3 for a summary of Protocol 2.

TABLE 2

Summary of Protocol 1

| Step # | Description |
|---|---|
| 1 | Deparaffinization [selected] |
| 2 | Warmup slide to [72° C.] from medium temperatures (deparaffinization) |
| 3 | Pre-primary peroxidase inhibit. [selected] |
| 4 | Inhibitor [selected] |
| 5 | Primary Antibody [selected] |
| 6 | Single reagent application [selected] |
| 7 | Apply one drop of [ANTIBODY 2] (antibody), apply coverslip, and incubate for [32 minutes] |
| 8 | Silver detection [selected] |
| 9 | Detection ultraVIEW SISH [selected] |
| 10 | Apply one drop of SIL, ISH, DNP, HRP, apply coverslip, and incubate for [48 minutes] |
| 11 | Apply one drop of SIL, ISH, DNP, CHRC, and incubate for [12 minutes] |
| 12 | $2^{nd}$ detection [selected] |
| 13 | Antibody denaturation [selected] |
| 14 | Warmup slide to [100° C.] from all temperatures (antibody) |
| 15 | Incubate for [16 minutes] (antibody) |
| 16 | Primary antibody (2) [selected] |
| 17 | Single reagent application (2) [selected] |
| 18 | Apply one drop [ANTIBODY 5] (Antibody 11), apply coverslip, and incubate for [32 minutes] |
| 19 | Secondary Antibody (2) [selected] |
| 20 | Single application (2) [selected] |
| 21 | Blocker (2) [selected] |
| 22 | Apply one drop of [OPTION 1] (Option 2), apply coverslip, and incubate for 4 minutes |
| 23 | Apply one drop of [ANTIBODY 10], (Antibody 12), and incubate for [32 minutes] |
| 24 | Chromogen block (2) [selected] |
| 25 | Apply two drops [ANTIBODY 11] (Antibody 15), apply coverslip, and incubate for 4 minutes |
| 26 | Apply one drop of [ANTIBODY 12] (Antibody 16), and incubate for [32 minutes] |
| 27 | Counterstain [selected] |
| 28 | Apply one drop of [HEMATOXYLIN II] (Counterstain), apply coverslip, and incubate for [8 minutes] |
| 29 | Post counterstain [selected] |
| 30 | Apply one drop of [BLUING REAGENT] (Post-counterstain), apply counterstain, and incubate for [8 minutes] |

TABLE 3

Summary of Protocol 2

| Step # | Description |
|---|---|
| 1 | Deparaffinization [selected] |
| 2 | Warmup slide to [72° C.] from medium temperatures (deparaffinization) |
| 3 | Pretreatment [selected] |
| 4 | Warmup slide to [37° C.] from 37-60° C. temperatures (Pretreatment #1 Temp RB) |
| 5 | Research Fork #36 [selected] |
| 6 | Apply one drop of [PRETREATMENT 4] (Pretreatment #2), apply coverslip, and incubate for 4 minutes |
| 7 | Apply one drop of [PRETREATMENT 5] (Pretreatment #3), and incubate for [8 minutes] |
| 8 | Post cell conditioning enzyme [selected] |
| 9 | Apply one drop of [PROTEASE 3] (Enzyme), apply coverslip, and incubate for [4 minutes] |
| 10 | Pre-primary peroxidase inhibit. [selected] |

TABLE 3-continued

Summary of Protocol 2

| Step # | Description |
|---|---|
| 11 | Inhibitor [selected] |
| 12 | Primary Antibody [selected] |
| 13 | Single reagent application [selected] |
| 14 | Apply one drop of [ANTIBODY 2] (antibody), apply coverslip, and incubate for [32 minutes] |
| 15 | Silver detection [ selected] |
| 16 | Detection ultraVIEW SISH [selected] |
| 17 | Apply one drop of SIL, ISH, DNP, HRP, apply coverslip, and incubate for [48 minutes] |
| 18 | Apply one drop of SIL, ISH, DNP. CHRC, and incubate for [12 minutes] |
| 19 | $2^{nd}$ detection [selected] |
| 20 | Antibody denaturation [selected] |
| 21 | Warmup slide to [100° C.] from all temperatures (antibody) |
| 22 | Incubate for [16 minutes] (antibody) |
| 23 | Primary antibody (2) [selected] |
| 24 | Single reagent application (2) [selected] |
| 25 | Apply one drop [ANTIBODY 5] (Antibody 11), apply coverslip, and incubate for [32 minutes] |
| 26 | Secondary Antibody (2) [selected] |
| 27 | Single application (2) [selected] |
| 28 | Blocker (2) [selected] |
| 29 | Apply one drop of [OPTION 1] (Option 2), apply coverslip, and incubate for 4 minutes |
| 30 | Apply one drop of [ANTIBODY 10], (Antibody 12), and incubate for [32 minutes] |
| 31 | Chromogen block (2) [selected] |
| 32 | Apply two drops [ANTIBODY 11] (Antibody 15), apply coverslip, and incubate for 4 minutes |
| 33 | Apply one drop of [ANTIBODY 12] (Antibody 16), and incubate for [32 minutes] |
| 34 | Counterstain [selected] |
| 35 | Apply one drop of [HEMATOXYLIN II] (Counterstain), apply coverslip, and incubate for [8 minutes] |
| 36 | Post counterstain [selected] |
| 37 | Apply one drop of [BLUING REAGENT] (Post-counterstain), apply counterstain, and incubate for [8minutes] |

Automated protease-resistant alpha-synuclein DAB IHC assay (pRED/Prothena Assay Protocol). As aggregated alpha-synuclein is known to be a poor substrate for proteases, histochemical staining of aggregated aSyn following removal of non-aggregated alpha-synuclein by protease can be employed for detection of Lewy bodies. An assay based on this principle had been developed by Roche pRED in collaboration with Prothena Biosciences to detect aggregated alpha-synuclein in skin biopsy (pRED/Prothena Assay Protocol). This assay relies on the 5C12 antibody whose epitope has been mapped to alpha-synuclein residues 109 to 120, a region outside of the Ser129 phosphorylation site. The pRED/Prothena Protocol is shown in Table 4, and the protocol employed in this study is shown as Table 5. For the pRED/Prothena Assay Protocol, protease treatment was performed for 12 minutes at 36° C. using VENTANA® Protease 1 (P/N 760-2018), and 5C12 antibody was incubated for 20 minutes at ambient temperature (instrument slide heater disabled) with approximate on-slide concentration of 0.27 µg/mL after dilution with previously applied 1×VENTANA® Reaction Buffer (P/N 950-300). As shown in Table 4, dispenser formulation of 5C12 antibody is 1 µg/mL diluted in VENTANA® Antibody Diluent (P/N 251-018, Antibody Diluent without Brij-35, internal P/N 95028). Following incubation with primary antibody, aggregated alpha-synuclein was detected using VENTANA® OptiView DAB IHC Detection Kit (P/N 760-700). Counterstaining was performed on instrument using VENTANA® Hematoxylin II (P/N 790-2208, 8 minutes at 36° C.) and Bluing Reagent (P/N 760-2037, 8 minutes at 36° C.). Slides were coverslipped in xylene following alcohol dehydration in a Tissue-Tek automated slide stainer & coverslipper (Sakura).

TABLE 4

Summary of a protocol for protease-resistant alpha-synuclein

| Step # | Description |
|---|---|
| 1 | Paraffin [selected] |
| 2 | Deparaffinization [selected] |
| 3 | Warmup slide to [75° C.] from medium temperatures (deparaffinization) |
| 4 | Pre cell conditioning enzyme [selected] |
| 5 | Apply one drop of Protease 1 (Catalog No. 760-2018), apply coverslip, and incubate for 12 minutes |
| 6 | Pre-primary peroxidase inhibitor [selected] |
| 7 | Apply coverslip, one drop of Primary Antibody (without heating): alpha-Synuclein 5C12 (1 µg/mL) clone for 20 minutes |
| 8 | Counterstain [selected] |
| 9 | Apply one drop of [HEMATOXYLIN II] (Counterstain), apply coverslip, and incubate for 8 minutes |
| 10 | Post counterstain [selected] |
| 11 | Apply one drop of Bluing Reagent (Post-counterstain), apply counterstain, and incubate for 8 minutes |

TABLE 5

Summary of a protocol for protease-resistant alpha-synuclein

| Step # | Description |
|---|---|
| 1 | Paraffin [selected] |
| 2 | Deparaffinization [selected ] |
| 3 | Warmup slide to [75° C.] from medium temperatures (deparaffinization) |
| 4 | Pre cell conditioning enzyme [selected] |
| 5 | Apply one drop of [PROTEASE 1] (Enzyme), apply coverslip, and incubate for [12 minutes] |
| 6 | Pre-primary peroxidase inhibitor [selected] |
| 7 | Primary Antibody [selected] |
| 8 | Primary Antibody temperature [selected] |
| 9 | Primary Antibody no heat [selected] |
| 10 | Apply coverslip, one drop of [PREP KIT 9] (Antibody), and incubate for [12 minutes] |
| 11 | Counterstain [selected] |
| 12 | Apply one drop of [HEMATOXYLIN II] (Counterstain), apply coverslip, and incubate for [8 minutes] |
| 13 | Post counterstain [selected] |
| 14 | Apply one drop of [BLUING REAGENT] (Post-counterstain), apply counterstain, and incubate for [8 minutes] |

Slide evaluation and scoring of aSyn signals. Slides were scored by a board-certified pathologist or assay development scientists with extensive experience evaluating aSyn staining patterns in skin. For pS129-aSyn and PGP9.5 silver/yellow dual IHC assay, number of total nerve features with yellow PGP9.5 stain was recorded along with number of nerve features exhibiting discrete and/or diffuse granular silver pS129-aSyn stain. In a typical skin section, yellow PGP9.5 stain was observed in nerve bundles and arrector pili muscle and also surrounding eccrine/sebaceous glands and blood vessels. At least 25 nerve features were counted per slide, but often more were counted to ensure assay sensitivity was not adversely affected by low numbers of nerve features evaluated. In slides with limited skin area and total number of nerve features available for evaluation were less than 25, the entire skin area was scanned and total number of nerve features counted. Results were expressed as percentages of nerve features with a particular type of pS129-aSyn stain. Slides stained using protease-resistant aSyn DAB IHC assay were scored similarly except nerve features were recognized by morphology. In cases where tissue morphology was significantly affected by treatment with Protease 1 the numbers of total nerve features were derived from neighboring slides stained using pS129-aSyn and PGP9.5 silver/yellow dual IHC assay.

Statistical Analyses. Association between presence of phosphorylated alpha-synuclein signal and subjects' clinical statuses was evaluated by chi-square test using Minitab 17 statistical software.

Example 1. Characterization of 7E2 Rabbit Monoclonal Antibody Against pS129-aSyn The anti-phosphorylated S129 alpha-synuclein rabbit monoclonal antibody 7E2 was generated by Roche Diagnostics GmbH CPS R&D Early Development & Reagent Design. The immunogen used for the generation of 7E2 is a peptide conjugated to KLH via an N-terminal Cys residue. The sequence of this peptide, NEAYEMPpSEEGYQD (SEQ ID NO:59), corresponds to residue 122-135 of human alpha-synuclein. Surface plasmon resonance (Biacore) experiments showed 7E2 antibody to have high specificity toward the alpha-synuclein (122-135, pS129) immunogen peptide phosphorylated at Ser129 compared with the same peptide not phosphorylated at Ser129. The 7E2 antibody exhibited fast association rate and slow linear dissociation rate toward alpha-synuclein (122-135, pS129) peptide.

Specificity of 7E2 anti-phosphorylated S129 alpha-synuclein antibody in immnohistochemical context was examined using a human tissue microarray containing 30 cores of normal and 29 cores of cancer tissue from various anatomical sites (SuperBioChips Laboratories, Seoul, Korea, P/N BC8). The Tour of Body/Tour of Tumor (ToB/ToT) analysis indicated that the only non-neuronal staining observed with 7E2 antibody was macrophages (expression of alpha-synuclein in macrophages has been reported previously). See Tables 6-9 for summary of ToB/ToT analyses. The ToB/ToT results demonstrate that the protocols are both accurate and specific.

TABLE 6

Summary of Tour of Body analysis for Protocol 1

| No. | Age | Sex | Tissue Type | PGP9.5 Percent Positive Cells | PGP9.5 Average Intensity | aSyn Staining present | Comments |
| --- | --- | --- | --- | --- | --- | --- | --- |
| 1 | 63 | F | Skin | 2 | 2.5 | No | NA |
| 2 | 44 | F | Breast | 1 | 2 | No | Silver dusting around blood vessel |
| 3 | 53 | F | Spleen | 1 | 2.5 | No | NA |
| 4 | 51 | M | Lymph node | 5 | 2.5 | Yes | PGP9.4: blood vessels 2.5+/lymphocytes 1+; Asyn: macrophages |
| 5 | 57 | M | Skeletal muscle | 1 | 2.5 | No | Around blood vessels |
| 6 | 39 | M | Lung | <1 | 2.5 | Yes | PGP9.5: rare stromal cell; A Syn: cytoplasm of macrophages |
| 7 | 69 | M | Salivary gland, sublingual | 10 | 2.5 | No | around glands |
| 8 | 70 | M | Liver | 3 | 2.75 | No | Air under coverslip? |
| 9 | 65 | M | Gallbladder | 2 | 2.75 | No | Silver dusting in nerve and around blood vessel |
| 10 | 73 | F | Pancreas | 10 | 3 | No | PGP9.5 in islet cells; air under coverslip? |
| 11 | 24 | M | Tonsil | 10 | 1 | No | Silver dusting around blood vessels |
| 12 | 69 | M | Esophagus | 10 | 2.75 | No | PGP9.5: around blood vessels |
| 13 | 31 | M | Stomach, antrum | 5 | 2.75 | No | PGP9.5: around blood vessels and in nerve |
| 14 | 59 | M | Stomach, fundus | 5 | 2.75 | No | PGP9.5: around blood vessels and in nerve |
| 15 | 66 | F | Small bowel | 20 | 2.75 | No | PGP9.5: around blood vessels and in nerve and ganglion cells |
| 16 | 73 | M | Colon | 15 | 2.75 | No | PGP9.5: around blood vessels and in nerve and ganglion cells |
| 17 | 67 | M | Rectum | 5 | 2.75 | No | PGP9.5: around blood vessels and in nerve and ganglion cells |
| 18 | 48 | M | Kidney, cortex | 20 | 3 | No | PGP9.5: in tubules |
| 19 | 48 | M | Kidney, medulla | 25 | 3 | No | PGP9.5: in tubules and in nerve |
| 20 | 32 | M | Urinary bladder | 3 | 2.75 | No | NA |
| 21 | 32 | M | Prostate | 2 | 2.5 | No | Around blood vessels |
| 22 | 70 | M | Testis | 20 | 2.75 | No | PGP9.5: stains germ cells |
| 23 | 42 | F | Uterine cervix | 3 | 2.75 | No | NA |
| 24 | 39 | F | Endometrium | 2 | 1.5 | No | Around blood vessels |
| 25 | 42 | F | Myometrium | <1 | 1.5 | No | NA |
| 26 | 34 | F | Placenta | 20 | 2.75 | No | Stains trophoblast cells |
| 27 | 42 | M | Adrenal gland | 15 | 2.75 | No | Around blood vessels |
| 28 | 39 | M | Thyroid | 2 | 2.5 | No | Around blood vessels |
| 29 | 59 | M | Cerebrum | 95 | 2.75 | No | NA |
| 30 | 1 | M | Cerebellum | 95 | 2.75 | No | NA |

TABLE 7

Summary of Tour of Body Analysis for Protocol 2

| No | Age | Sex | Tissue type | PGP9.5 Percent Positive Cells | PGP9.5 Average Intensity | aSyn Staining present | Comments |
|---|---|---|---|---|---|---|---|
| 1 | 63 | F | Skin | 3 | 2.5 | No | stromal cells and nerve staining |
| 2 | 44 | F | Breast | <1 | 2 | No | NA |
| 3 | 53 | F | Spleen | 2 | 2.5 | No | Around blood vessels |
| 4 | 51 | M | Lymph node | 5 | 2 | Yes | PGP9.5: Blood vessels 2+/lymphocytes 1+; Asyn: macrophages |
| 5 | 57 | M | Skeletal muscle | 1 | 2.5 | No | Around blood vessels |
| 6 | 39 | M | Lung | 0 | 0 | Yes | Asyn in macrophages |
| 7 | 69 | M | Salivary gland, sublingual | 10 | 2.5 | No | Around glands, some tissue tearing/folding |
| 8 | 70 | M | Liver | 5 | 2.75 | No | NA |
| 9 | 65 | M | Gallbladder | 3 | 2.75 | No | NA |
| 10 | 73 | F | Pancreas | 10 | 3 | No | Islet cell staining |
| 11 | 24 | M | Tonsil | 10 | 1.5 | No | Germinal center staining |
| 12 | 69 | M | Esophagus | 10 | 2.5 | No | Around blood vessels |
| 13 | 31 | M | Stomach, antrum | 10 | 2.75 | No | Nerve and blood vessels |
| 14 | 59 | M | Stomach, fundus | 15 | 2.75 | No | Nerve and blood vessels |
| 15 | 66 | F | Small bowel | 20 | 2.75 | No | Nerve and blood, vessels |
| 16 | 73 | M | Colon | 15 | 2.75 | No | Nerve and blood vessels |
| 17 | 67 | M | Rectum | 15 | 2.75 | No | Nerve, ganglion cells and blood vessels |
| 18 | 48 | M | Kidney, cortex | 20 | 3 | No | tubules |
| 19 | 48 | M | Kidney, medulla | 25 | 3 | No | tubules |
| 20 | 32 | M | Urinary bladder | 3 | 2.75 | No | Nerve and blood vessels |
| 21 | 32 | M | Prostate | 10 | 2.5 | No | NA |
| 22 | 70 | M | Testis | 20 | 2.75 | No | Germ cells |
| 23 | 42 | F | Uterine cervix | 5 | 2 | No | NA |
| 24 | 39 | F | Endometrium | 0 | 0 | No | NA |
| 25 | 42 | F | Myometrium | 3 | 2 | No | NA |
| 26 | 34 | F | Placenta | 2 | 2.5 | No | trophoblast cells |
| 27 | 42 | M | Adrenal gland | 10 | 2.75 | No | Around blood vessels |
| 28 | 39 | M | Thyroid | 3 | 2.5 | No | NA |
| 29 | 59 | M | Cerebrum | 95 | 2.75 | No | Some staining artifact |
| 30 | 1 | M | Cerebellum | 95 | 2.75 | No | NA |

TABLE 8

Summary of Tour of Tumor analysis for Protocol 1

| No. | Age | Sex | Organ | Diagnosis | PGP9.5 Percent Positive Cells | PGP9.5 Average intensity | aSyn Staining present | Comments |
|---|---|---|---|---|---|---|---|---|
| 31 | 57 | M | Skin | squamous cell carcinoma | 1 | 2 | No | Around blood vessels |
| 32 | 64 | F | Skin | malignant melanoma | NA | NA | NA | Abundant endogenous pigment precludes evaluation |
| 33 | 36 | M | Subcutis | liposarcoma | <1 | 1 | No | Rare lipocyte with staining |
| 34 | 34 | F | Breast | ductal carcinoma in situ | <1 | 2 | No | Around blood, vessels |
| 35 | 35 | F | Breast | infiltrating duct carcinoma | 1 | 1.5 | No | NA |
| 36 | 33 | F | Lymph node | Hodgkin lymphoma | 5 | 2 | No | Scattered non tumor lymphocytes and around blood vessels |
| 37 | 53 | F | Bone | osteosarcoma | <1 | 2 | No | Endogenous pigment present |
| 38 | 60 | M | Lung | adenocarcinoma | 0 | 0 | No | Abundant silver particles |
| 39 | 72 | M | Lung | squamous cell carcinoma | 65 | 2.5 | No | Tumor cell staining; abundant silver particles |
| 40 | 61 | F | Liver | cholangiocarcinoma | 5 | 2 | No | stromal background present |
| 41 | 52 | M | Liver | hepatocellular carcinoma | 0 | 0 | No | Silver particles present |
| 42 | 52 | M | Liver | metastatic adenocarcinoma (from rectum) | 5 | 2.5 | No | TC staining |
| 43 | 56 | M | Esophagus | squamous cell carcinoma | 2 | 2.5 | No | Around blood vessels |
| 44 | 68 | F | Stomach | adenocarcinoma | <1 | 2 | No | Single cell with staining |
| 45 | 52 | M | Stomach | malignant lymphoma, diffuse large B cell | 5 | 2.75 | No | NA |

TABLE 8-continued

Summary of Tour of Tumor analysis for Protocol 1

| No. | Age | Sex | Organ | Diagnosis | PGP9.5 Percent Positive Cells | PGP9.5 Average intensity | aSyn Staining present | Comments |
|---|---|---|---|---|---|---|---|---|
| 46 | 51 | F | Stomach | signet ring cell carcinoma | 10 | 2.75 | No | NA |
| 47 | 61 | M | Duodenum | gastrointestinal stromal tumor, malignant | 80 | 1 | No | TC staining and scattered cells (2%) with 2.5+ staining |
| 48 | uk | M | Descending colon | adenocarcinoma | 0 | 0 | No | Large amount of necrosis, scattered silver particles |
| 49 | 73 | M | Rectum | adenocarcinoma | 5 | 1.5 | No | Scattered silver particles |
| 50 | 56 | M | Kidney | renal cell carcinoma | 1 | 2.5 | No | Around blood vessels and scattered silver particles |
| 51 | 53 | M | Urinary bladder | transitional cell carcinoma | 10 | 2.75 | No | Nerve staining |
| 52 | 70 | M | Prostate | adenocarcinoma | 5 | 2.75 | No | Around blood vessels and nerve |
| 53 | 34 | M | Testis | seminoma | 10 | 1 | No | TC staining |
| 54 | 64 | F | Uterine cervix | squamous cell carcinoma | 5 | 2.75 | No | Nerve staining and around blood vessels |
| 55 | 69 | F | Endometrium | adenocarcinoma | 60 | 3 | No | TC staining |
| 56 | 45 | F | Ovary | metastatic adenocarcinoma (from stomach) | 25 | 1 | No | NA |
| 57 | 15 | F | Ovary | mucinous cystadenocarcinoma | 10 | 1.5 | No | NA |
| 58 | 43 | F | Ovary | serous cystadenoma of low malignant potential | 3 | 1 | No | Around blood vessels |
| 59 | 69 | F | Thyroid | papillary carcinoma | 1 | 1 | No | NA |

TABLE 9

Summary of Tour of Tumor analysis for Protocol 2

| No. | Age | Sex | Organ | diagnosis | PGP9.5 Percent Positive Cells | PGP9.5 Average intensity | aSyn Staining present | Comments |
|---|---|---|---|---|---|---|---|---|
| 31 | 57 | M | Skin | squamous cell carcinoma | 2 | 2.5 | No | Stromal cell staining |
| 32 | 64 | F | Skin | malignant melanoma | NA | NA | NA | Abundant endogenous pigment precludes evaluation |
| 33 | 36 | M | Subcutis | liposarcoma | 0 | 0 | No | Single lipocyte with 1+ membrane staining |
| 34 | 34 | F | Breast | ductal carcinoma in situ | <1 | 2 | No | Around blood vessel |
| 35 | 35 | F | Breast | infiltrating duct carcinoma | 3 | 2 | No | TC staining |
| 36 | 33 | F | Lymph node | Hodgkin lymphoma | 2 | 2.5 | No | NA |
| 37 | 53 | F | Bone | osteosarcoma | <1 | 2 | No | Endogenous pigment present |
| 38 | 60 | M | Lung | adenocarcinoma | 0 | 0 | No | Silver particles present |
| 39 | 72 | M | Lung | squamous cell carcinoma | 60 | 2.5 | No | TC staining |
| 40 | 61 | F | Liver | cholangiocarcinoma | 2 | 2 | No | NA |
| 41 | 52 | M | Liver | hepatocellular carcinoma | 1 | 2.5 | No | NA |
| 42 | 52 | M | Liver | metastatic adenocarcinoma (from rectum) | 10 | 2.5 | No | TC staining |
| 43 | 56 | M | Esophagus | squamous cell carcinoma | 10 | 2.5 | No | stromal background present |
| 44 | 68 | F | Stomach | adenocarcinoma | 0 | 0 | No | NA |
| 45 | 52 | M | Stomach | malignant lymphoma, diffuse large B cell | 3 | 2.5 | No | NA |
| 46 | 51 | F | Stomach | signet ring cell carcinoma | 10 | 2.75 | No | NA |
| 47 | 61 | M | Duodenum | gastrointestinal stromal tumor, malignant | 65 | 1.5 | No | TC staining 1.5+ scattered cells 2.5+ |
| 48 | uk | M | Descending colon | adenocarcinoma | 0 | 0 | No | Large amount of necrosis, silver particles present |

TABLE 9-continued

Summary of Tour of Tumor analysis for Protocol 2

| No. | Age | Sex | Organ | diagnosis | PGP9.5 Percent Positive Cells | PGP9.5 Average intensity | aSyn Staining present | Comments |
|---|---|---|---|---|---|---|---|---|
| 49 | 73 | M | Rectum | adenocarcinoma | 10 | 2.5 | No | NA |
| 50 | 56 | M | Kidney | renal cell carcinoma | 2 | 2.5 | No | NA |
| 51 | 53 | M | Urinary bladder | transitional cell carcinoma | 10 | 2.75 | No | Around blood vessels and nerve |
| 52 | 70 | M | Prostate | adenocarcinoma | 5 | 2.75 | No | Around blood vessels |
| 53 | 34 | M | Testis | seminoma | 10 | 2 | No | TC staining |
| 54 | 64 | F | Uterine cervix | squamous cell carcinoma | 3 | 2.75 | No | Nerve staining; tissue tearing/folding |
| 55 | 69 | F | Endometrium | adenocarcinoma | 60 | 3 | No | TC staining |
| 56 | 45 | F | Ovary | metastatic adenocarcinoma (from stomach) | 3 | 1 | No | NA |
| 57 | 15 | F | Ovary | mucinous cystadenocarcinoma | 20 | 1 | No | NA |
| 58 | 43 | F | Ovary | serous cystadenoma of low malignant potential | 5 | 2 | No | Scattered stromal cells |
| 59 | 69 | F | Thyroid | papillary carcinoma | 1 | 1 | No | NA |

Figure 1B:
FIG. 1B shows exemplary staining in brain tissue from a subject with PD using the anti-phosphorylated S129 alpha-synuclein antibody and concentration as indicated (2G11 top panel; 7E2 middle panel; 3G2 bottom panel).
Figure 1B:
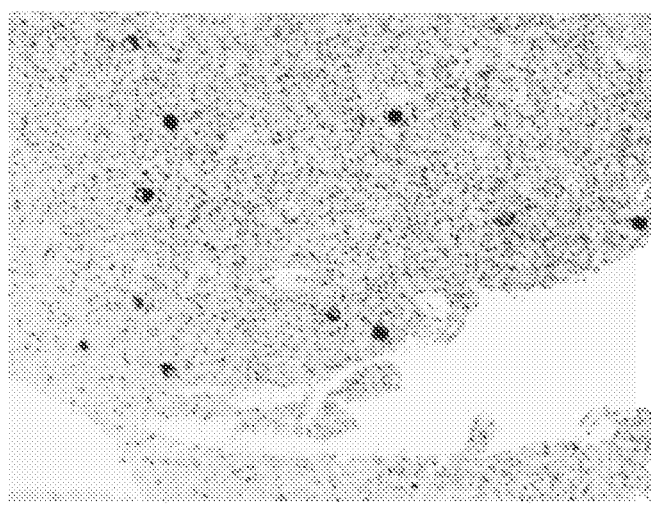
Figure 1B:
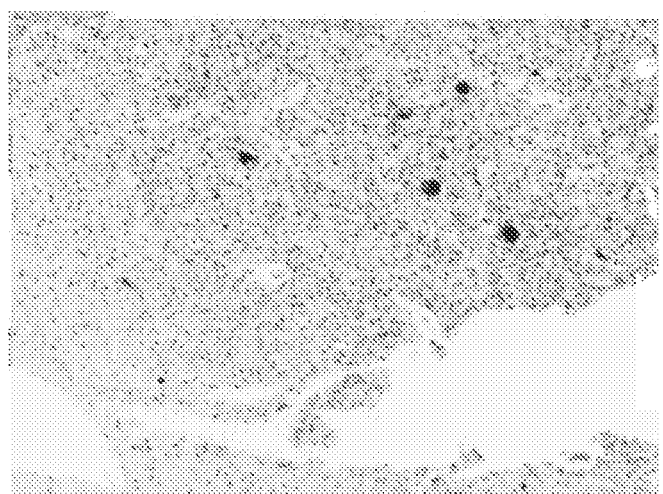
Figure 1C:
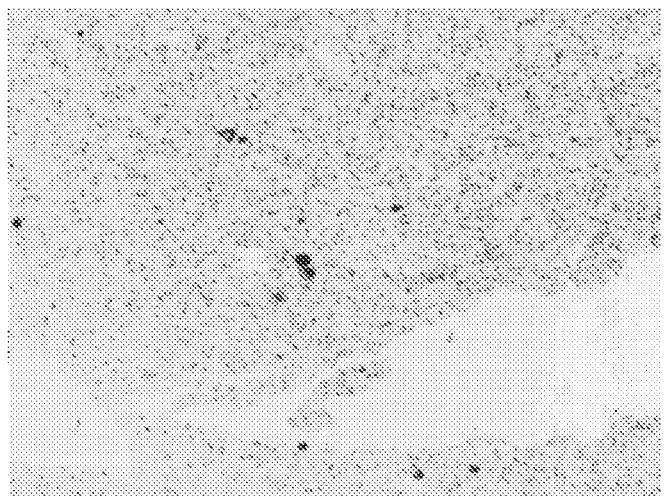
FIG. 1C shows exemplary staining in brain tissue from a subject with PD using the anti-phosphorylated S129 alpha-synuclein antibody and concentration as indicated (11A5 top panel; pSyn #64 (WAKO) bottom panel).
Figure 1C:
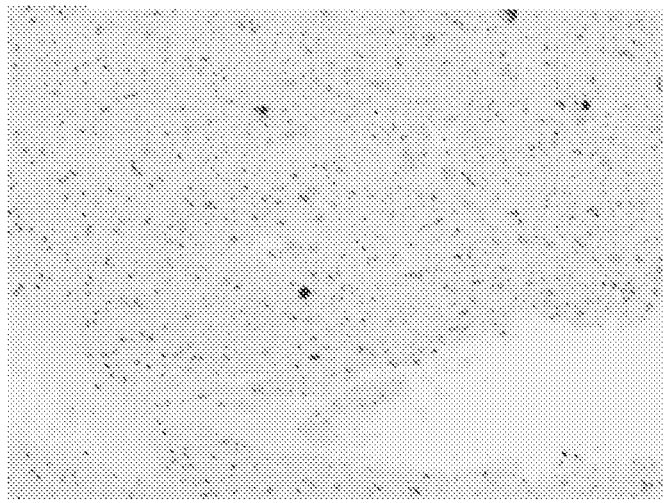

Example 2. Performance of 7E2 Compared with Other pS129-aSyn Antibodies for Immunohistochemical Staining of FFPE Tissue Detection of aggregated alpha-synuclein based on differential sensitivity of aggregated and non-aggregated alpha-synuclein to proteolytic degradation provides the basis for the identification of Lewy bodies in brain and definitive diagnosis of Parkinson's disease. To assess the ability of antibodies against phosphorylated S129 alpha-synuclein including 7E2 to detect Lewy bodies, cortical brain sections from two donors with Parkinson's disease were stained using VENTANA® OptiView DAB IHC Detection Kit. All 8 anti-phosphorylated S129 alpha-synuclein antibodies (81A, #64, MJF-R13(8-8), 5H5, 2G11, 7E2, 3G2, and 11A5) produced DAB stains in PD brain sections that were characteristic of Lewy bodies (see Table 10 for list of non-limiting, exemplary alpha-synuclein antibodies tested). Of the 8 anti-phosphorylated alpha-synuclein antibody clones tested, 7E2, 3G2, 11A5, and MJF-RI3(8-8) exhibited higher sensitivity for pS129-aSyn (see FIG. 1A-1C).

TABLE 10

List of non-limiting, exemplary alpha-synuclein antibodies

| Antibody | Clone | Species | Source | Selected [conc.] for FFPE |
|---|---|---|---|---|
| a-syn | LB 509 | Ms | Abcam | 1.0 µg/mL |
| a-syn | 5C12 | Ms | Prothena | 0.5 µg/mL |
| Phospho a-syn Ab168381 | MJF-R13 (8-8) | Rb | Abcam | 0.4 µg/mL |
| Phospho-a-syn | P-syn/81A | Ms | Abcam/Biolegend/Millipore | 2.0 µg/mL |
| Phospho-a-syn | 5H5 | Rb | Roche Diagnostics GmbH | NA |
| Phospho-a-syn | 2G11 | Rb | Roche Diagnostics GmbH | NA |
| Phospho-a-syn | 7E2 | Rb | Roche Diagnostics GmbH | 0.08 µg/mL |
| Phospho-a-syn | 3G2 | Rb | Roche Diagnostics GmbH | 0.08 µg/mL |
| Phospho-hu-a-syn | 11A5 | Ms | Roche Diagnostics GmbH | 0.4 µg/mL |
| Phospho-a-syn | pSyn#64 | Ms | WAKO | NA |

Figure 2A:
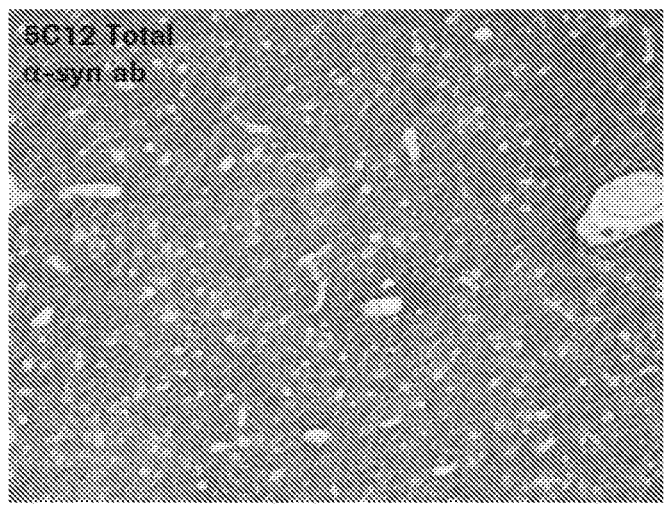
FIG. 2A shows no staining was observed with 3G2 and 7E2 phosphorylated S129 alpha-synuclein antibodies without antigen retrieval in brain tissue from non-PD subjects (7E2 middle panel (0.08 µg/mL); 3G2 bottom panel (0.08 µg/mL)). Staining total alpha-synuclein by antibody 5C12 (0.5 µg/ml) is shown in the top panel. No protease or phosphatase treatment. Images were taken at 10× magnification. Antibodies were diluted in DISCOVERY Goat Ig Block.
Figure 2A:
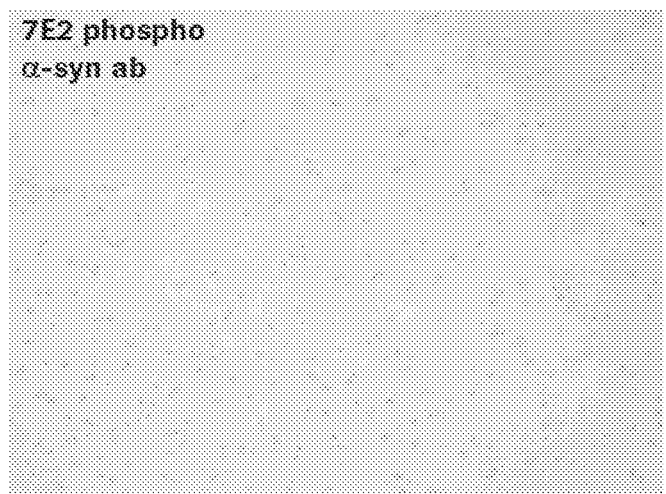
Figure 2A:
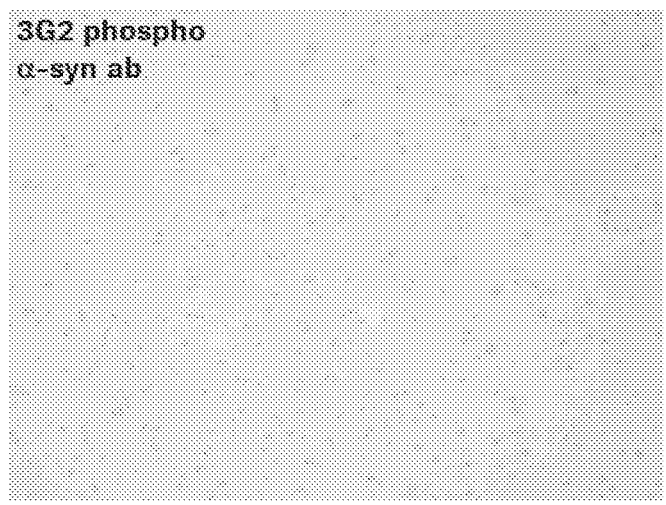
Figure 2B:
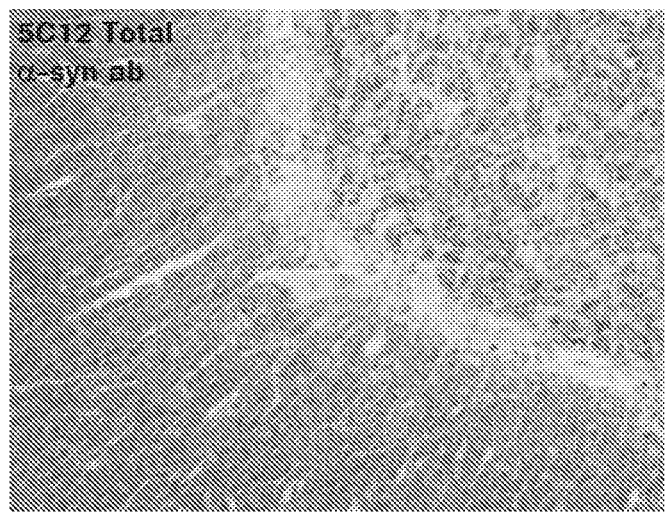
FIG. 2B shows no staining was observed with 3G2 and 7E2 phosphorylated S129 alpha-synuclein antibodies without antigen retrieval in brain tissue from non-PD subjects (7E2 middle panel (0.08 µg/mL); 3G2 bottom panel (0.08 µg/mL)). Staining total alpha-synuclein by antibody 5C12 (0.5 µg/ml) is shown in the top panel. No protease or phosphatase treatment. Images were taken at 10× magnification. Antibodies were diluted in DISCOVERY Goat Ig Block.
Figure 2B:
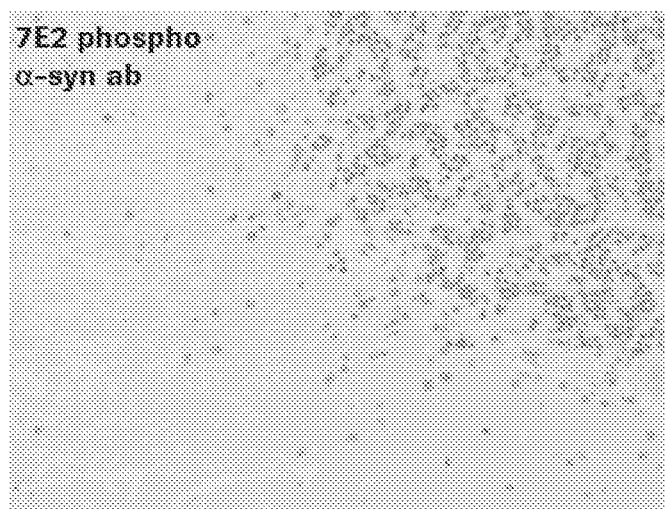
Figure 2B:
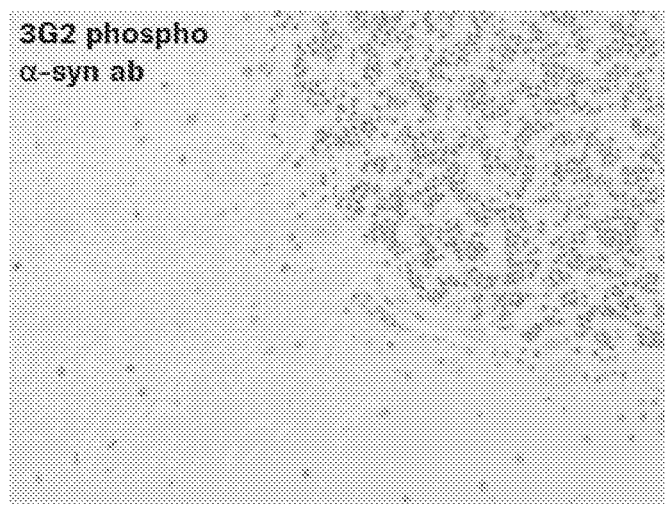
Figure 3A:
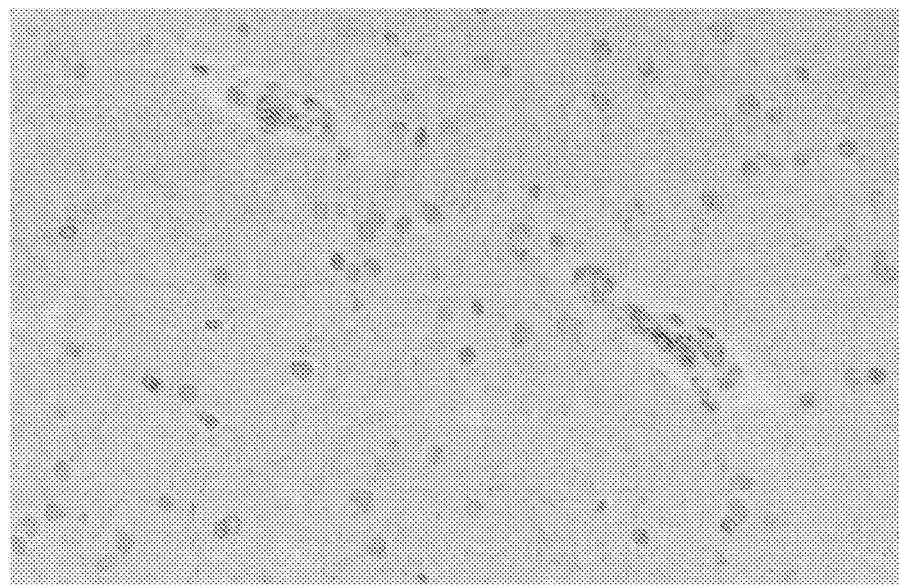
FIG. 3A shows very faint cytoplasmic staining (top panel) in non-PD brain tissue with the anti-phosphorylated S129 alpha-synuclein 7E2 antibody after antigen retrieval (cell conditioning) that is absent after phosphatase treatment (bottom panel). Alkaline phosphatase treatment was 50 µg/mL for 2 hours.
Figure 3A:
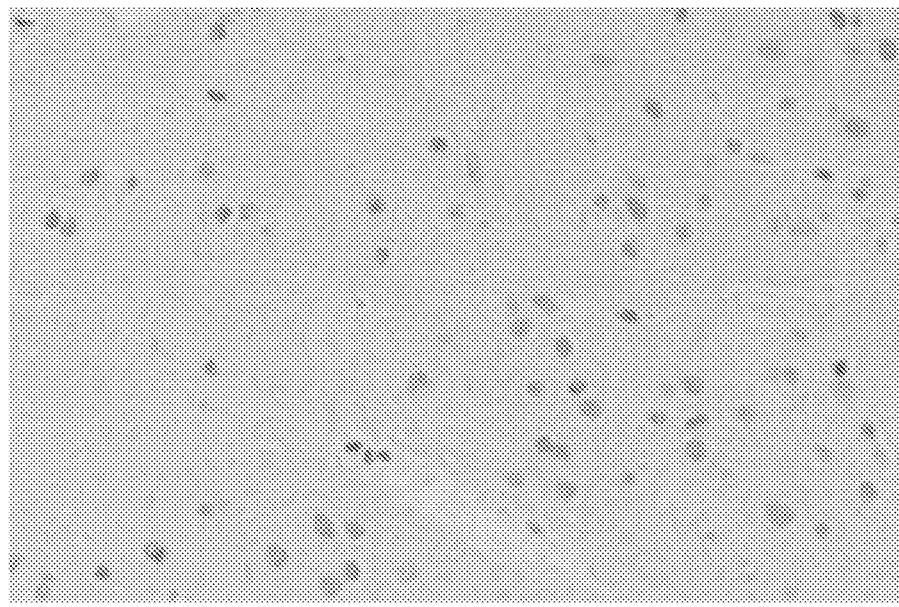
Figure 3B:
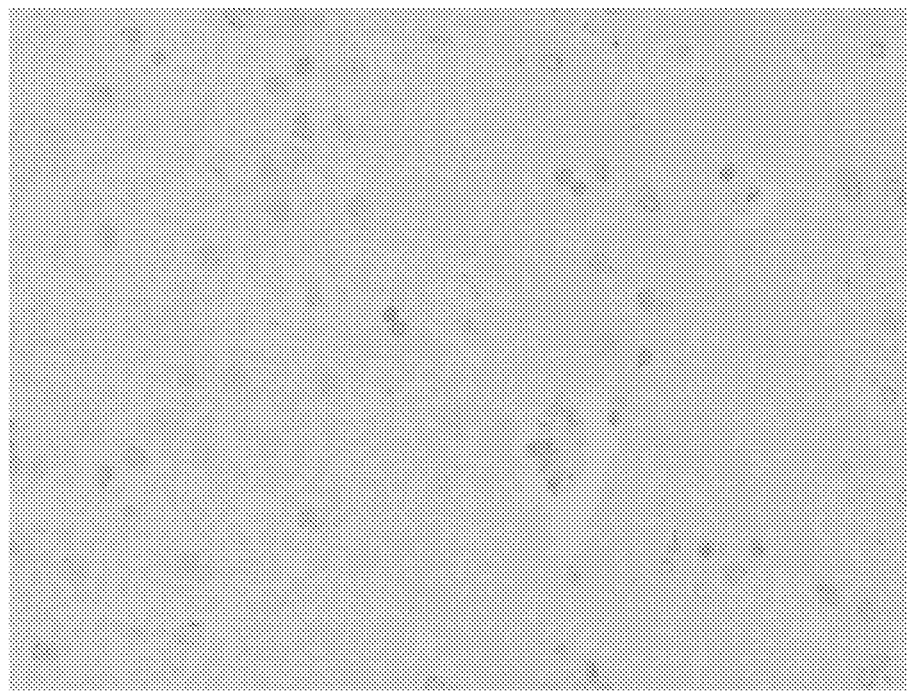
FIG. 3B shows very faint cytoplasmic staining (top panel) in non-PD brain tissue with the anti-phosphorylated S129 alpha-synuclein 3G2 antibody after antigen retrieval (cell conditioning) that is absent after phosphatase treatment (bottom panel). Alkaline phosphatase treatment was 50 µg/mL for 2 hours.
Figure 3B:
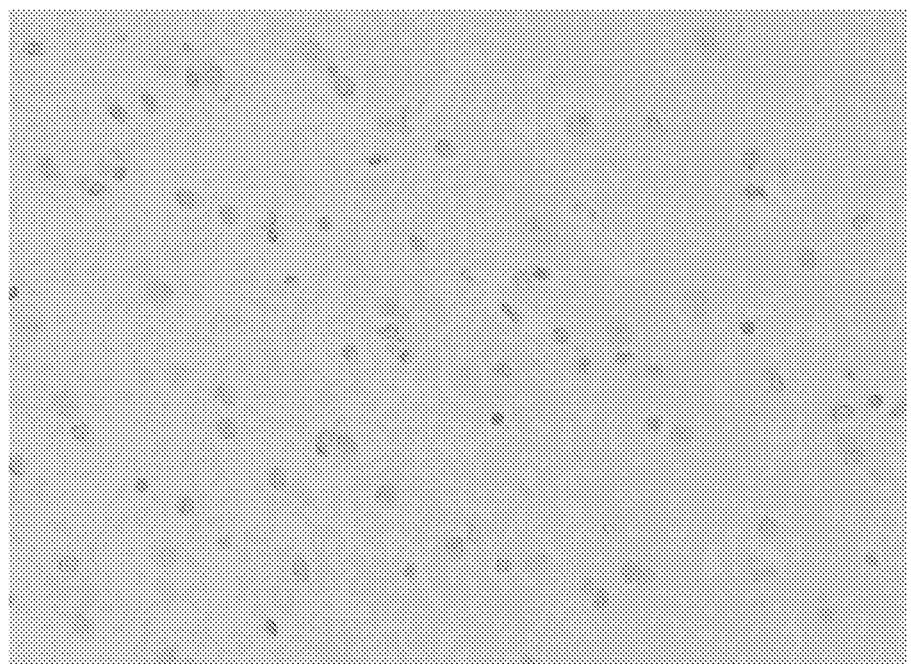
Figure 4A:
FIG. 4A shows that Lewy body staining by the MJF-R13 (8-8) antibody in cortical brain tissue from a subject with PD was severely decreased by alkaline phosphatase treatment (lower panel; 50 µg/mL for 2 hours). Images were taken at 10× magnification. MJF-R13(8-8) antibody (0.4 µg/mL) was diluted in DISCOVERY Goat Ig Block.
Figure 4A:
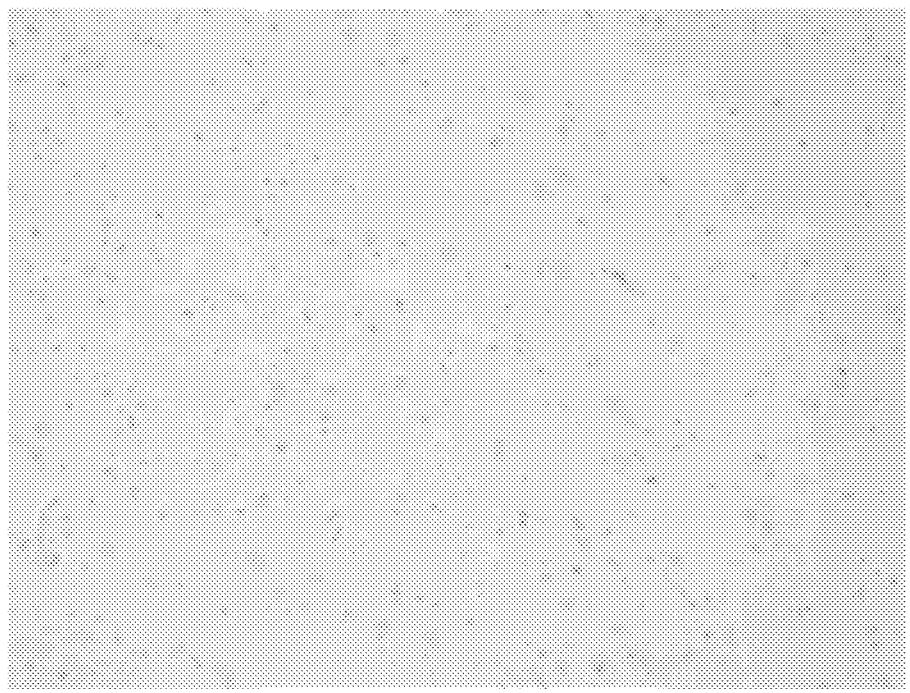
Figure 4B:
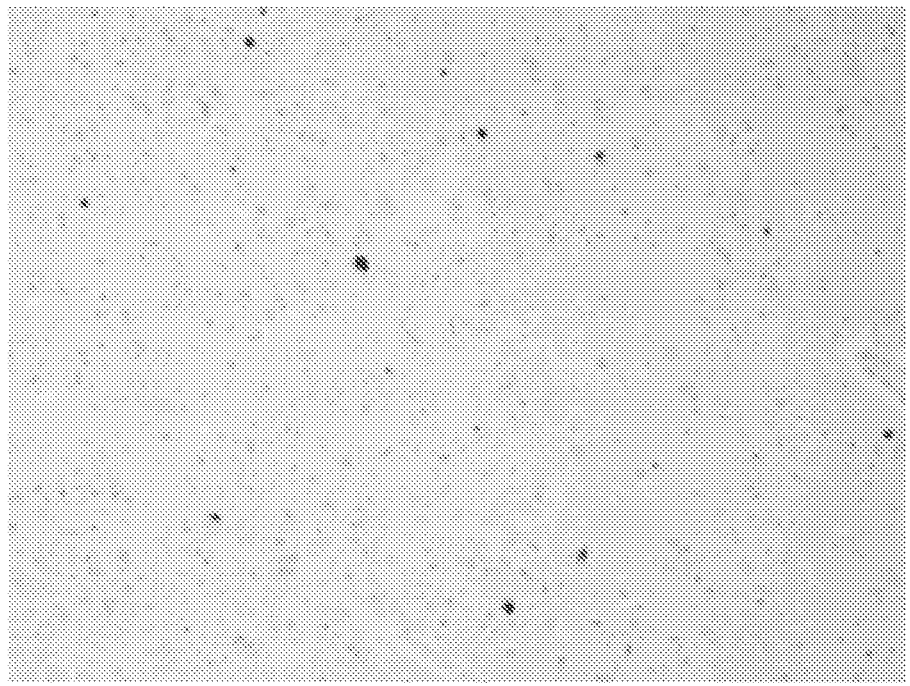
FIG. 4B shows that Lewy body staining by the 81A antibody in cortical brain tissue from a subject with PD was severely decreased by alkaline phosphatase treatment (lower panel; 50 µg/mL for 2 hours). Images were taken at 10× magnification. 81A antibody (2.0 µg/mL) was diluted in DISCOVERY Goat Ig Block.
Figure 4B:
Figure 4C:
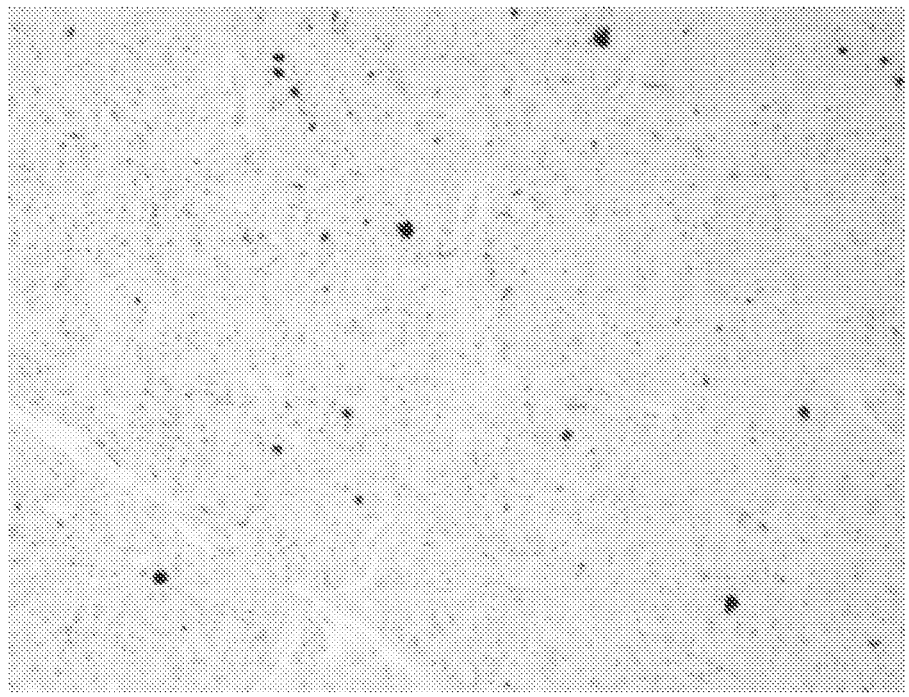
FIG. 4C shows that Lewy body staining by the 11A5 antibody in cortical brain tissue from a subject with PD was moderately decreased by alkaline phosphatase treatment (lower panel; 50 µg/mL for 2 hours). Images were taken at 10× magnification. 11A5 antibody (0.4 µg/mL) was diluted in DISCOVERY Goat Ig Block.
Figure 4C:
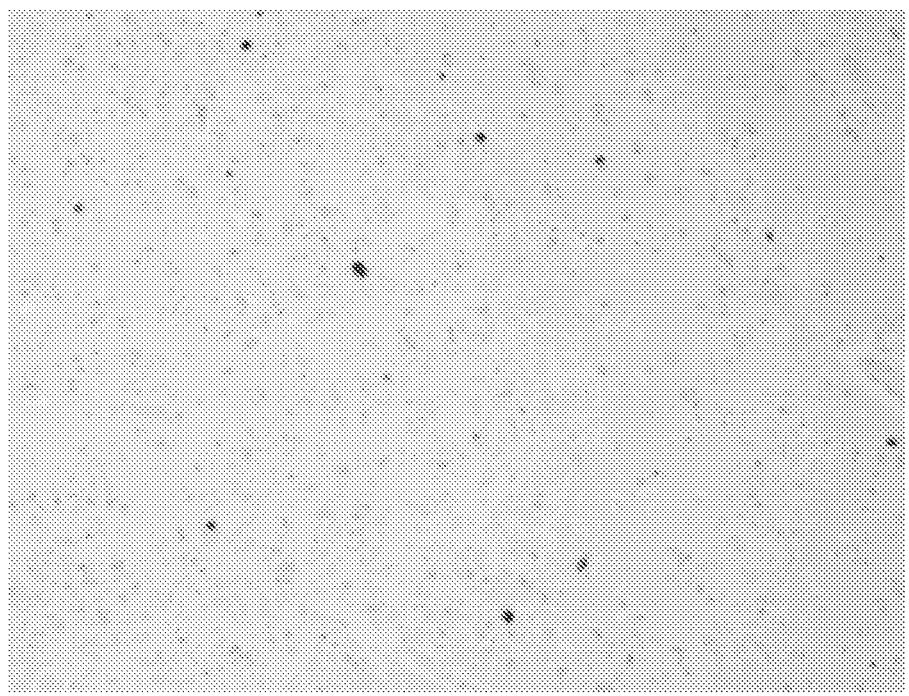
Figure 4D:
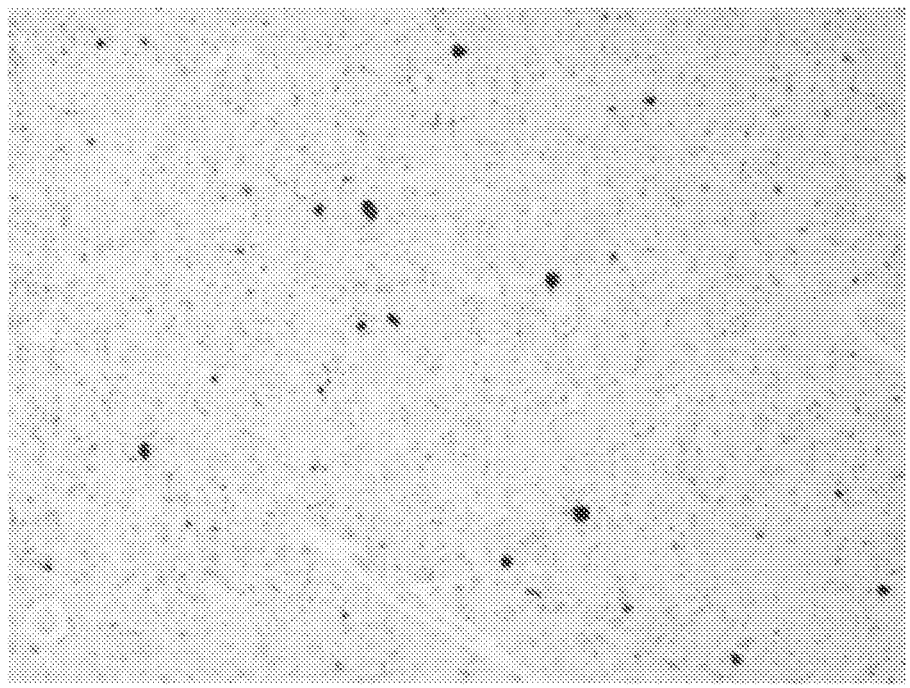
FIG. 4D shows that Lewy body staining by the 7E2 antibody in cortical brain tissue from a subject with PD was moderately decreased by alkaline phosphatase treatment (lower panel; 50 µg/mL for 2 hours). Images were taken at 10× magnification. 7E2 antibody (0.08 µg/mL) was diluted in DISCOVERY Goat Ig Block.
Figure 4D:
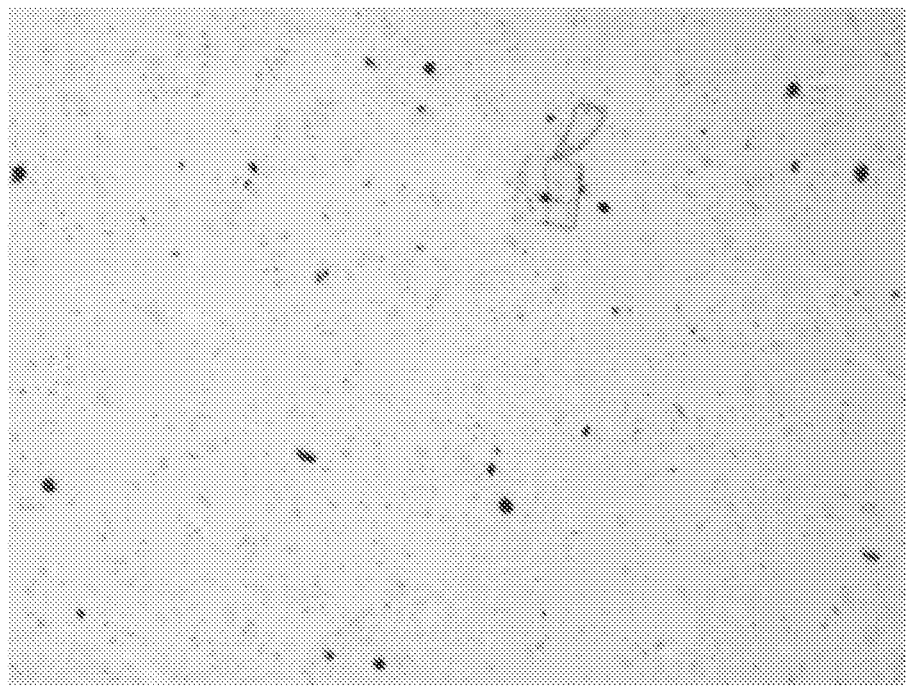
Figure 4E:
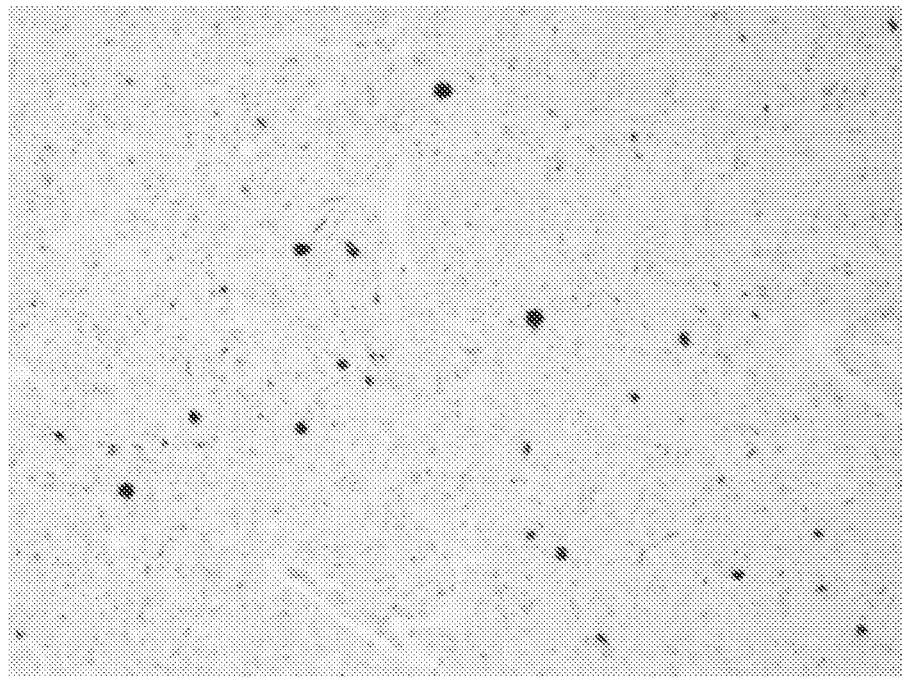
FIG. 4E shows that Lewy body staining by the 3G2 antibody in cortical brain tissue from a subject with PD was moderately decreased by alkaline phosphatase treatment (lower panel; 50 µg/mL for 2 hours). Images were taken at 10× magnification. 3G2 antibody (0.08 µg/mL) was diluted in DISCOVERY Goat Ig Block.
Figure 4E:
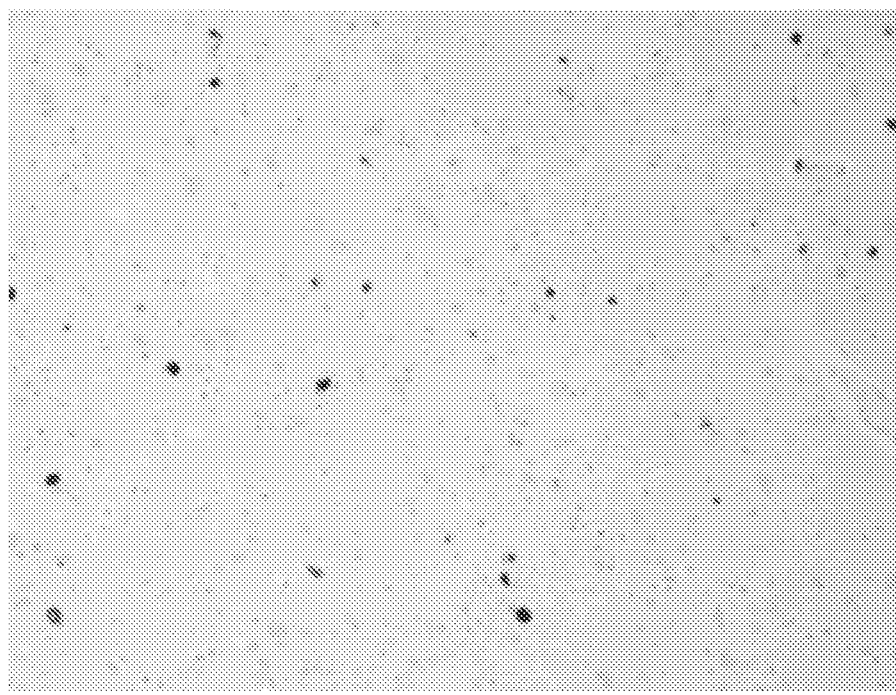
Figure 5A:
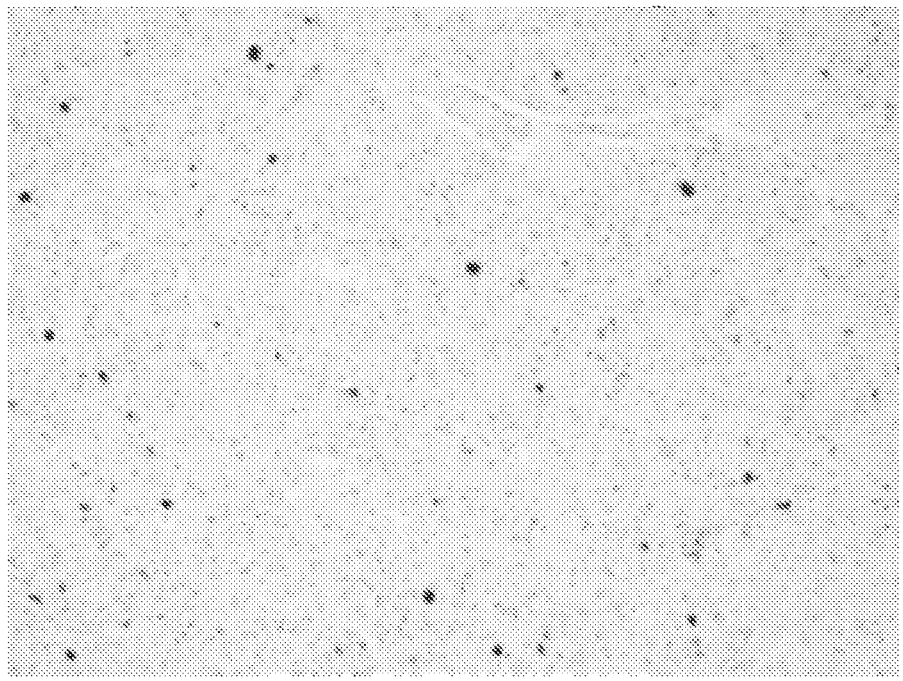
FIG. 5A shows that protease treatment (VENTANA® Protease 1 at 36° C. for 4 minutes) reduced non-Lewy body staining by the 11A5 antibody in cortical brain tissue from a subject with PD without decreasing Lewy body staining. Images were taken at 0x magnification. 11A5 antibody (0.4 µg/mL) was diluted in DISCOVERY Goat Ig Block.
Figure 5A:
Figure 5B:
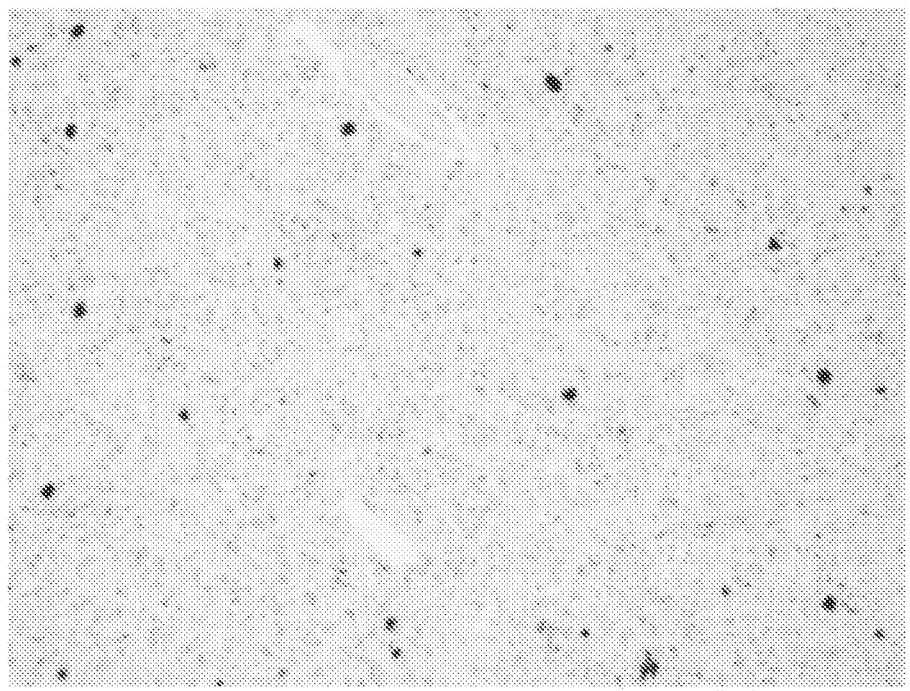
FIG. 5B shows that protease treatment (VENTANA® Protease 1 at 36° C. for 4 minutes) reduced non-Lewy body staining by the 7E2 antibody in cortical brain tissue from a subject with PD without decreasing Lewy body staining. Images were taken at 0x magnification. 7E2 antibody (0.08 µg/mL) was diluted in DISCOVERY Goat Ig Block.
Figure 5B:
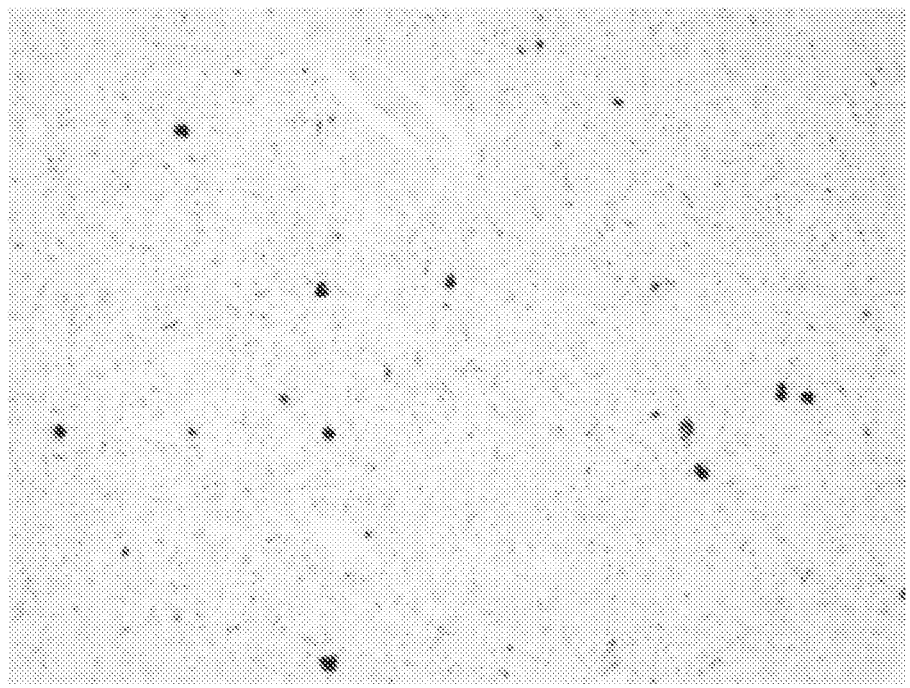
Figure 5C:
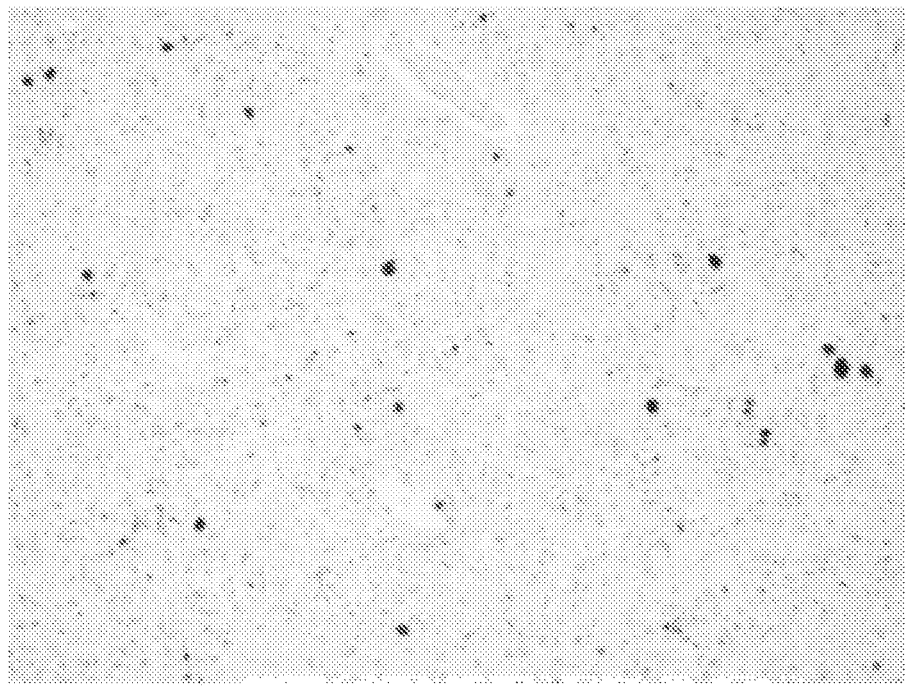
FIG. 5C shows that protease treatment (VENTANA® Protease 1 at 36° C. for 4 minutes) reduced non-Lewy body staining by the 3G2 antibody in cortical brain tissue from a subject with PD without decreasing Lewy body staining. Images were taken at 0x magnification. 3G2 antibody (0.08 µg/mL) was diluted in DISCOVERY Goat Ig Block.
Figure 5C:
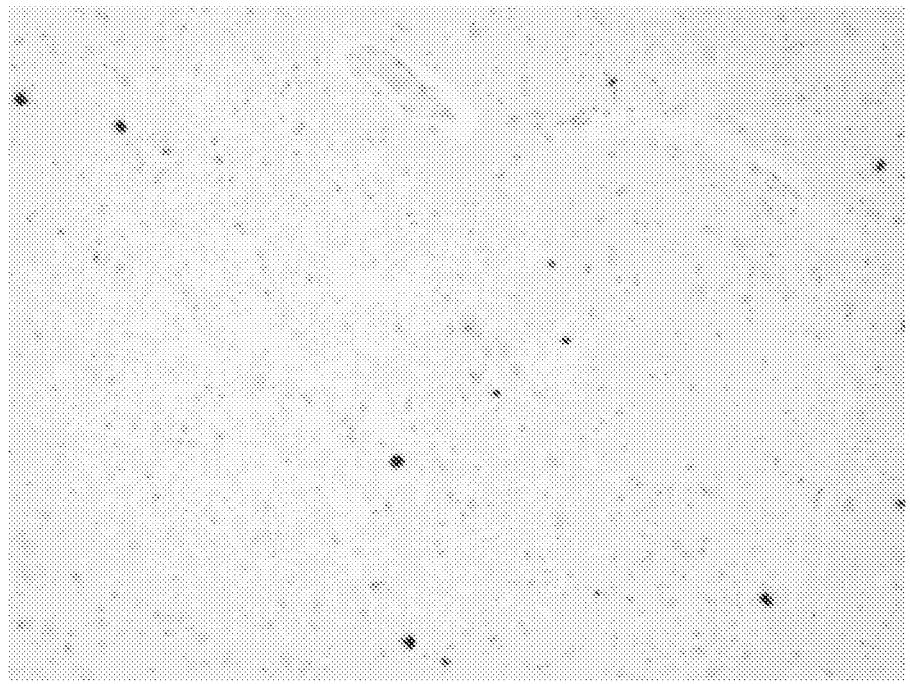

In brain sections from non-PD individuals no staining was observed with 3G2 and 7E2 antibodies without antigen retrieval (see FIGS. 2A and 2B). With ULTRA CC1 antigen retrieval, 3G2 and 7E2 antibodies produced faint cytoplasmic stains that were absent when samples were treated with phosphatase (see FIGS. 3A and 3B). Specificity of 81A, 7E2, 3G2, 11A5, and MJF-R13(8-8) for pS129-aSyn aggregated in Lewy bodies was tested by prolonged phosphatase or moderate protease treatments. Following 2 hours in 8.8 µg/mL highly active recombinant alkaline phosphatase at 36° C., extent of Lewy body staining in cortical brain sections from a PD donor was either severely (with MJF-R13(8-8) and 81A) or moderately (with 11A5, 7E2, and 3G2) decreased (see FIG. 4A-FIG. 4E). Thus phosphatase treatment appears to reduce non-Lewy body staining without significantly affecting Lewy body staining. In contrast, treatment with VENTANA™ Protease 1 at 36° C. for 4 minutes had negligible effect Lewy body staining produced by 11A5, 7E2, or 3G2 antibodies in PD brain sections (see FIG. 5A-FIG. 5C). As control, the same protease treatment removed most alpha-synuclein staining produced by two different antibodies against S129-phosphorylated or non-S129 phosphorylated aSyn (LB509 and 5C12 monoclonal antibodies) in PD brain except for Lewy bodies (data not shown).

Figure 6:
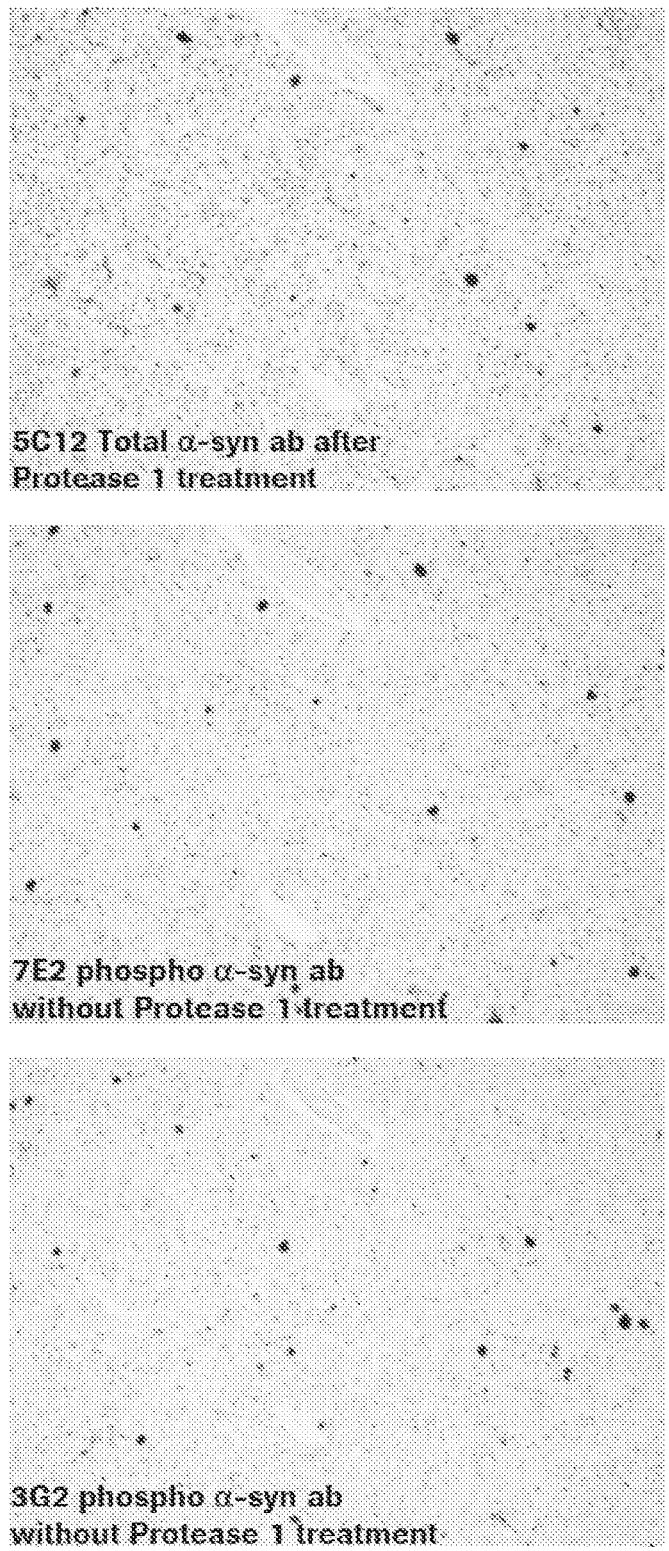
FIG. 6 shows that phosphorylation specific alpha-synuclein antibodies 7E2 (middle panel) and 3G2 (bottom panel), in absence of protease treatment, produced staining patterns in brain tissue from a subject with PD that were identical to total alpha-synuclein antibody 5C12 (top panel) after protease treatment. Images were taken at 10× magnification. All antibodies were diluted in DISCOVERY Goat Ig Block (5C12 antibody at 0.5 µg/mL; 7E2 antibody at 0.08 µg/mL; and 3G2 antibody at 0.08 µg/mL).

Overall, phosphorylation specific alpha-synuclein antibodies 7E2 and 3G2 in absence of protease treatment produced staining patterns in brain sections from a subject with PD that were identical to total alpha-synuclein antibody 5C12 after protease treatment (see FIG. 6). However, 3G2 generally exhibited higher background than 7E2 (data not shown). In addition to poorer staining performance, Abcam's 81A and WAKO's #64 exhibited lower specificity compared with the other anti-phosphorylated S129 alpha-synuclein antibodies. Unlike 3G2 and 7E2, 81A led to neurite staining in brain section from a non-PD individual (data not shown). This may reflect the reported cross-reactivity of 81A for neurofilament light (NFL) phosphorylated at Ser473. At low titer (1:1000), #64 antibody clone from WAKO led to non-specific nuclear staining in brain sections from both PD and non-PD subjects that persisted after phosphatase treatment and was not observed with the other 7 antibody clones (data not shown).

Figure 7A:
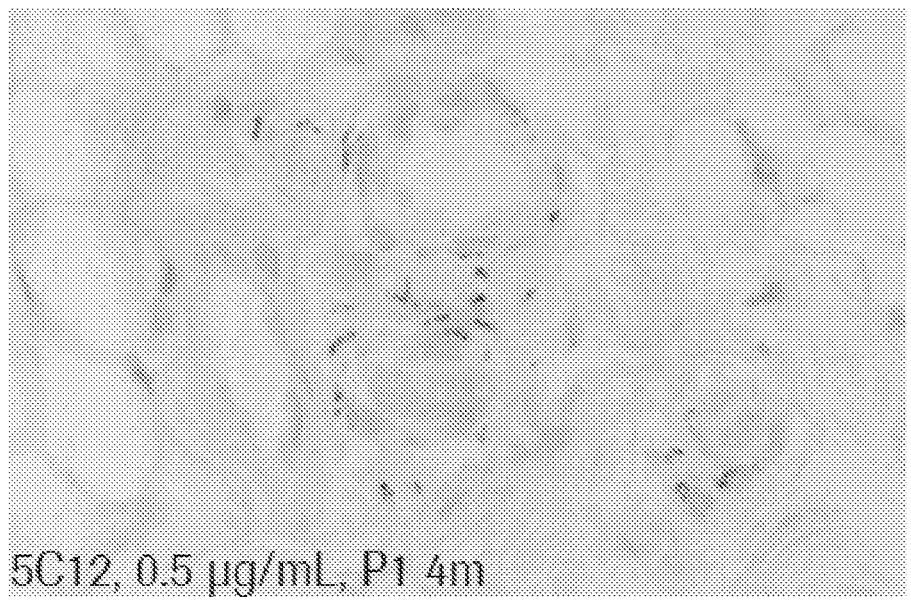
FIG. 7A shows that in absence of protease-based antigen retrieval, the anti-phosphorylated S129 alpha-synuclein 7E2 antibody (bottom panel) detected aggregated alpha-synuclein in skin sections from a subject with PD similar to that detected using the anti-total alpha-synuclein 5C12 antibody (top panel) coupled to VENTANA® Protease 1 treatment (36° C. for 4 minutes).
Figure 7A:
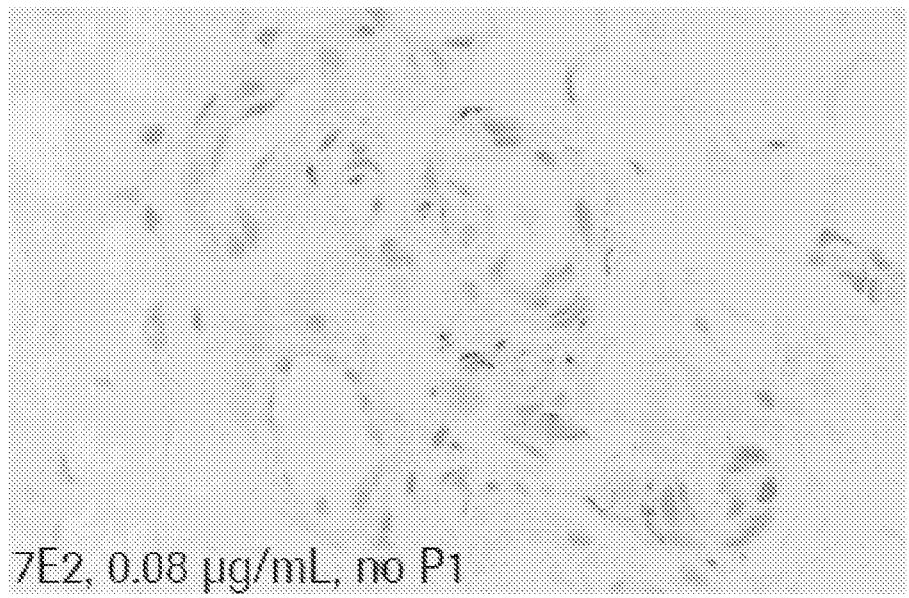
Figure 7B:
FIG. 7B shows that in absence of protease-based antigen retrieval, the anti-phosphorylated 5129 alpha-synuclein 11A5 antibody (top panel) and 3G2 antibody detected aggregated alpha-synuclein in skin sections from a subject with PD similar to that detected using the anti-total alpha-synuclein 5C12 antibody (FIG. 7A top panel) coupled to VENTANA® Protease 1 treatment (36° C. for 4 minutes).
Figure 7B:
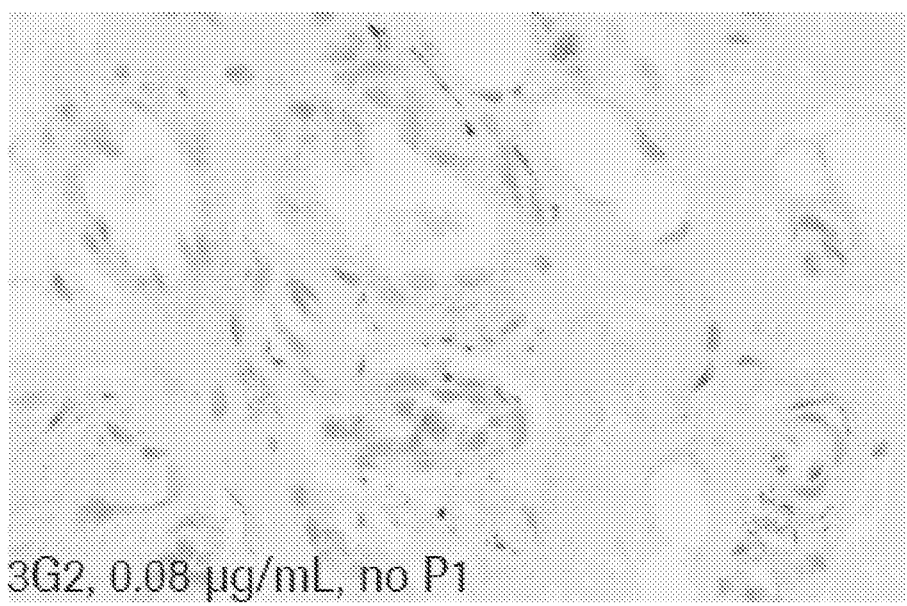
Figure 7C:
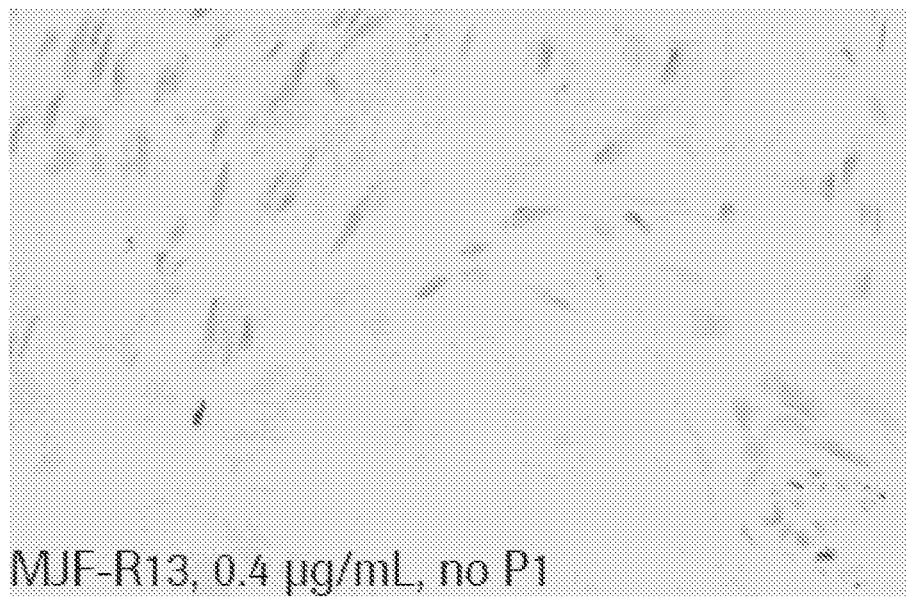
FIG. 7C shows that in absence of protease-based antigen retrieval, the anti-phosphorylated S129 alpha-synuclein MJF-R13 antibody (top panel) and P-Syn/81A antibody detected aggregated alpha-synuclein in skin sections from a subject with PD similar to that detected using the anti-total alpha-synuclein 5C12 antibody (FIG. 7A top panel) coupled to VENTANA® Protease 1 treatment (36° C. for 4 minutes).
Figure 7C:
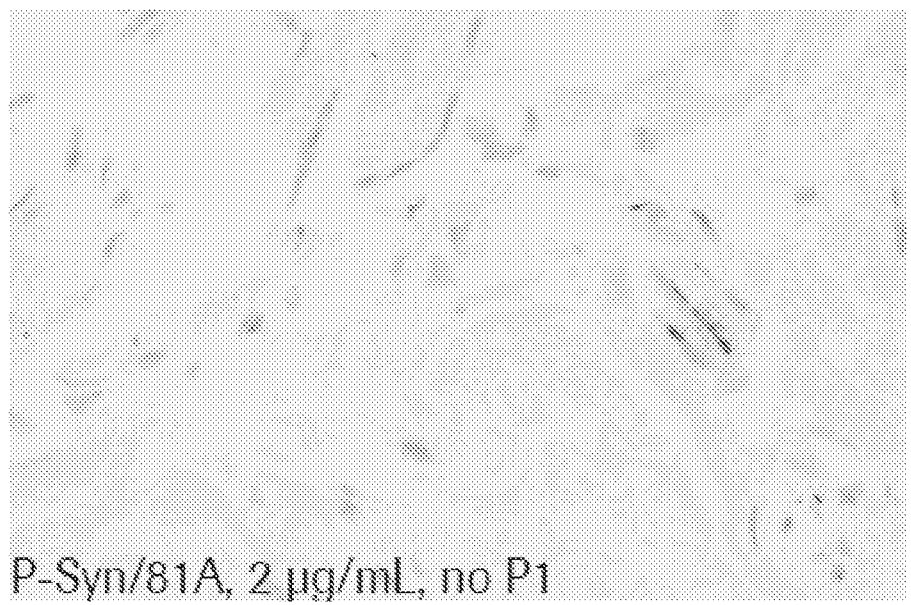

In addition to brain, the ability of anti-pS129-aSyn antibody clones to detect aggregated aSyn in skin samples from subjects with PD was assessed. In absence of protease-based antigen retrieval, all of the anti-pS129-aSyn antibodies were able to detect aggregated aSyn in skin section from a subject with PD similar to that detected using the anti-total aSyn 5C12 antibody coupled to VENTANA™ Protease 1 treatment (see FIG. 7A-FIG. 7C). Antibody clones 81A, 7E2, and MJF-R13(8-8) were further tested on skin sections from subjects with PD and non-PD control subjects. 3G2 was not tested due to its similar staining intensity and pattern and higher background compared with 7E2 antibody on brain samples. Staining with MJF-R13(8-8) was associated with non-specific background in smooth muscle and collagen while 81A led to non-specific nuclear staining (data not shown).

Figure 8A:
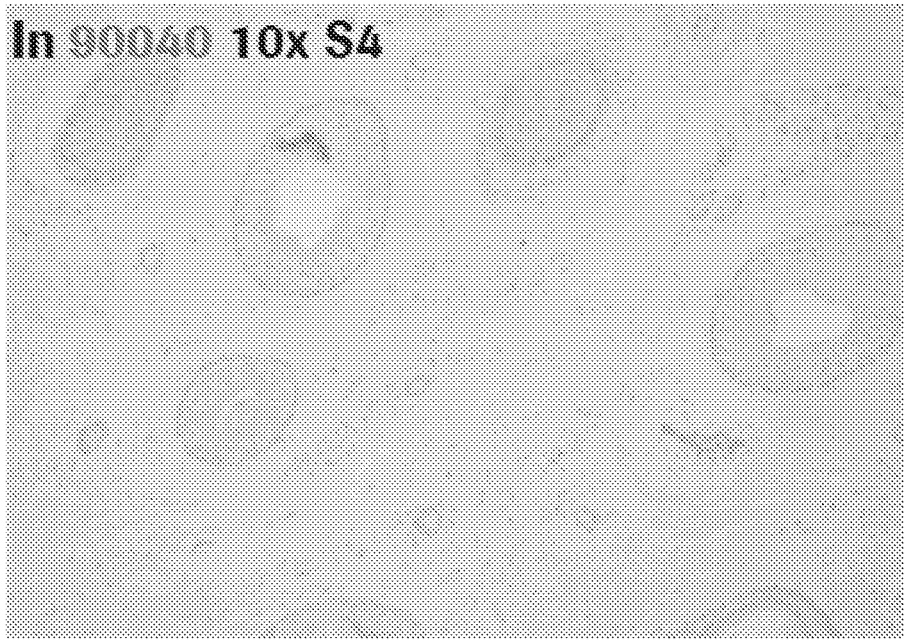
FIG. 8A shows that DISCOVERY Goat Ig Block results in minimal background while preserving staining intensity of the anti-phosphorylated S129 alpha-synuclein 7E2 antibody (1.0 µg/mL) in a PD sample. Images were taken at 10× magnification in top panel and 40× magnification in bottom panel. The images in the top and the bottom panels came from different fields of views of the same tissue section.
Figure 8A:
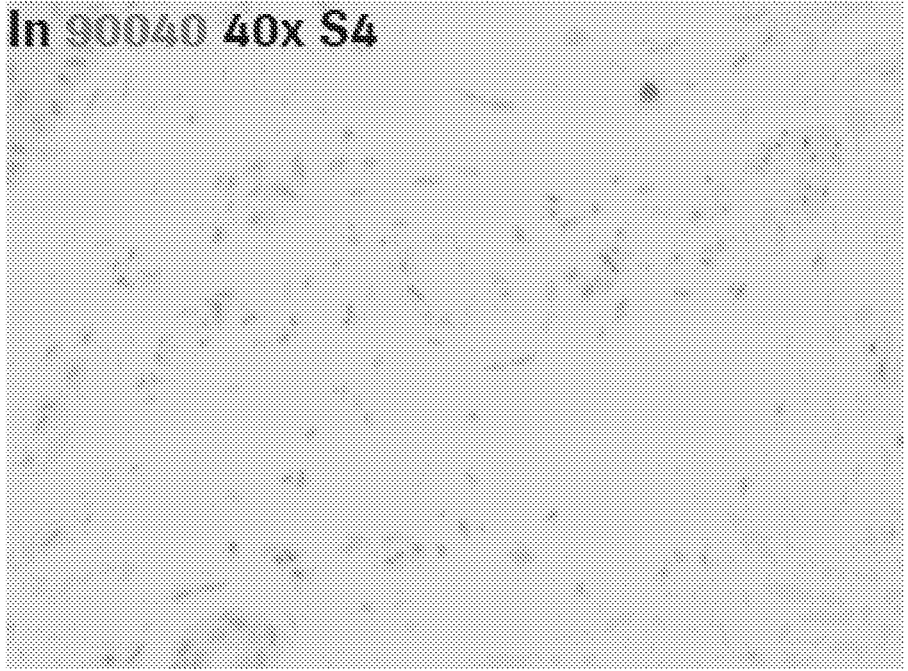
Figure 8B:
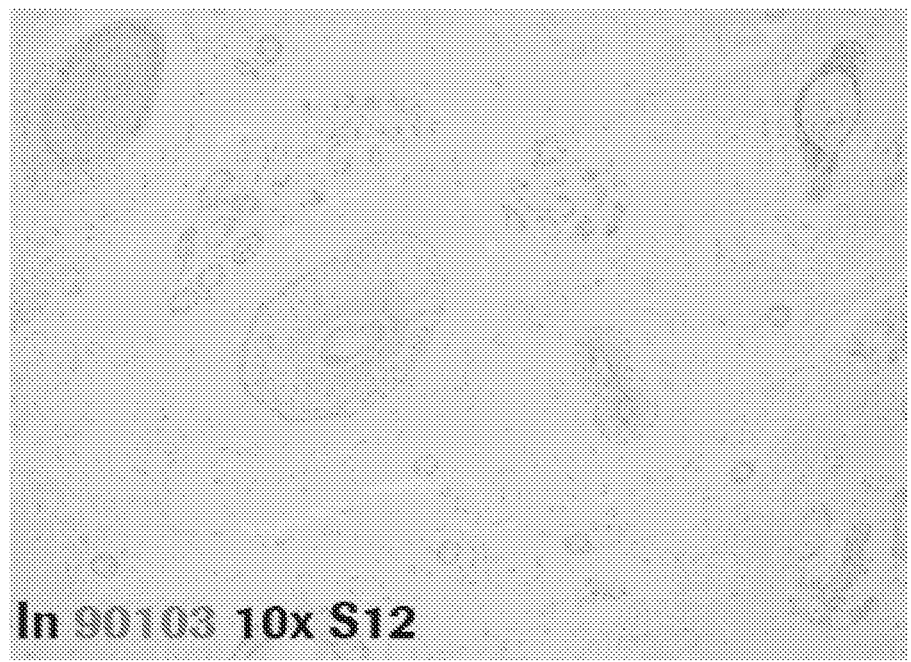
FIG. 8B shows that the 90103 diluent results in minimal background while preserving staining intensity of the anti-phosphorylated S129 alpha-synuclein 7E2 antibody (1.0 µg/mL) in a PD sample. Images were taken at 10× magnification in top panel and 40× magnification in bottom panel. The images in the top and the bottom panels came from different fields of views of the same tissue section.
Figure 8B:
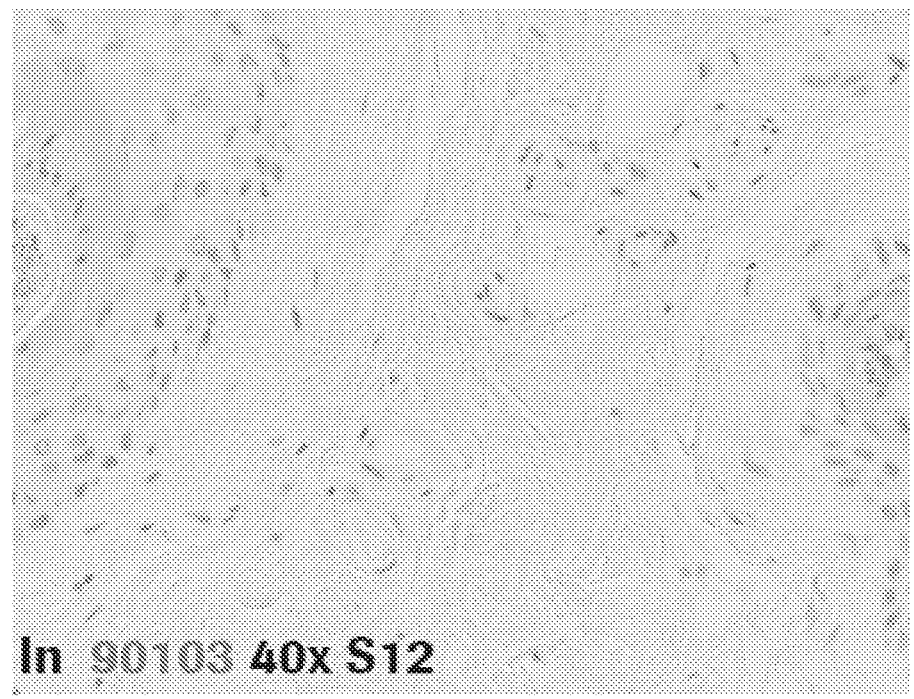
Figure 9:
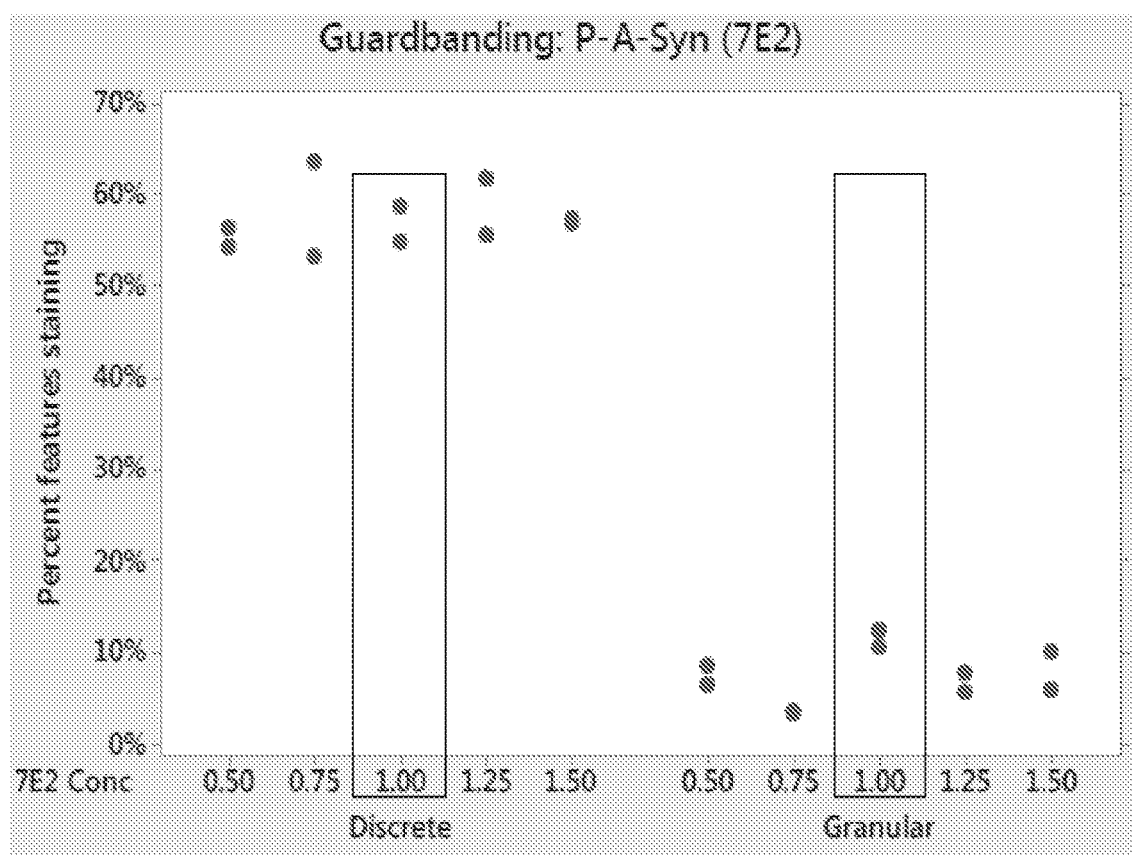
FIG. 9 shows the results of testing the anti-phosphorylated S129 alpha-synuclein 7E2 antibody above and below the nominal concentration of 1.0 µg/mL (guardbanding experiments) in which quantitative measurements in the form of percent neuronal features stained per slide were performed. For this experiment the tissue sections were not treated with protease nor phosphatase prior to antibody application and detection with chromogen. Staining of skin tissue from a subject with PD with the anti-phosphorylated S129 alpha-synuclein 7E2 antibody at 0.5 µg/mL, 0.75 µg/mL, 1.0 µg/mL, 1.25 µg/mL, and 1.5 µg/mL diluted in DISCOVERY Goat Ig Block indicates robust staining with antibody concentrations varying +/−50% around the nominal value of 1.0 µg/mL.

Diluent and titration experiments were performed to optimize phosphorylated S129 alpha-synuclein staining using 7E2 antibody. Results of diluent testing showed diluent 90040 and diluent 90103 to have minimal background while preserving staining intensity (see FIG. 8A and FIG. 8B). Titration experiments showed 7E2 dispenser concentration of 1 µg/mL to have near maximal staining intensity and minimal background (data not shown). The titration experiments results were reinforced by those of guardbanding experiments in which quantitative measurements in the form of percent neuronal features stained per slide were performed (see FIG. 9). Accelerated stability testing performed using both duplex silver/yellow and single-plex DAB detection schemes showed 7E2 to have a predicted shelf-life of 24 months at 4° C. (data not shown).

Example 3. Selection of PGP9.5 Antibody for Immunohistochemical Staining

Figure 10A:
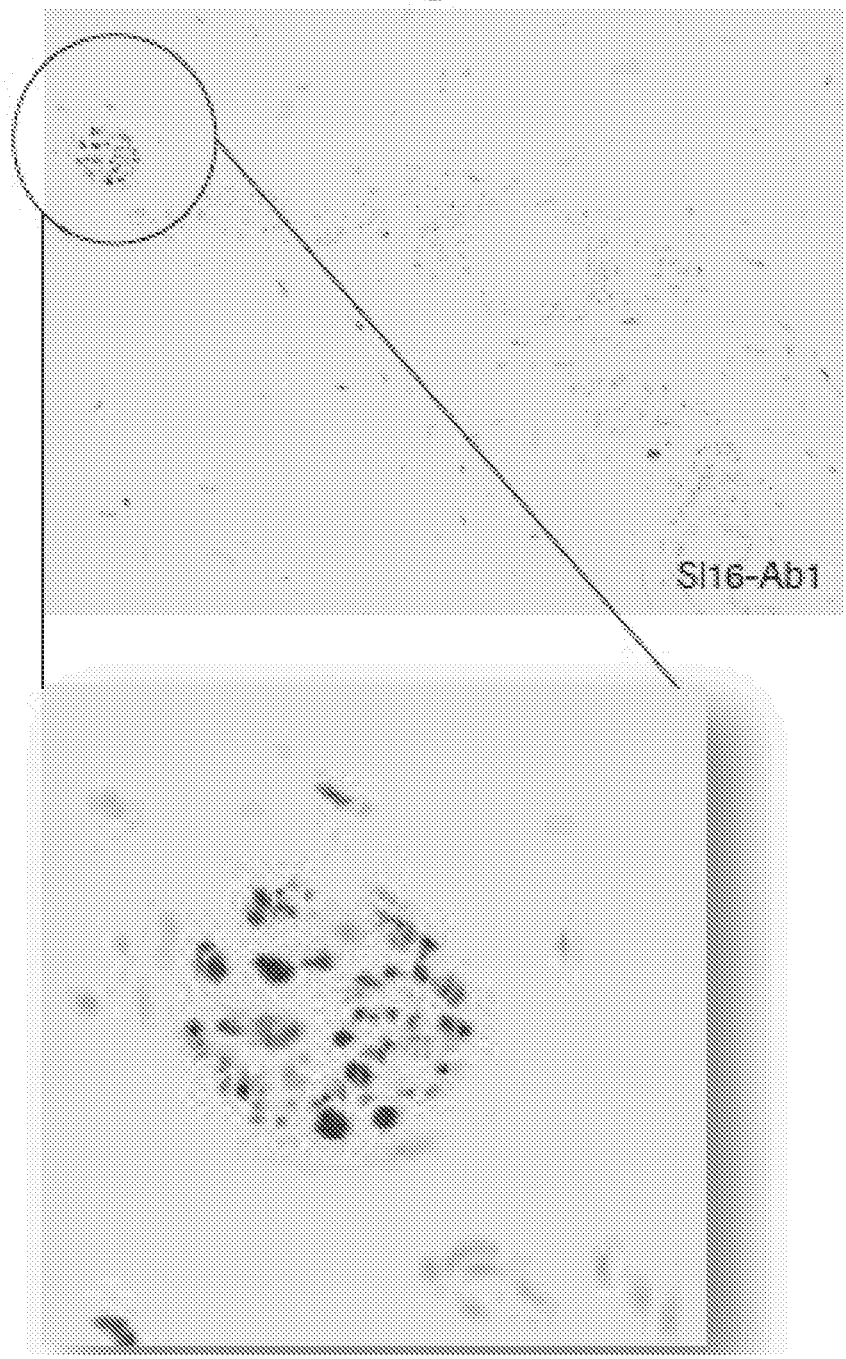
FIG. 10A shows that the anti-PGP9.5 antibody EPR4118 (0.2 µg/mL) stains neuronal features in skin samples from a normal subject (non-PD subject).
Figure 10B:
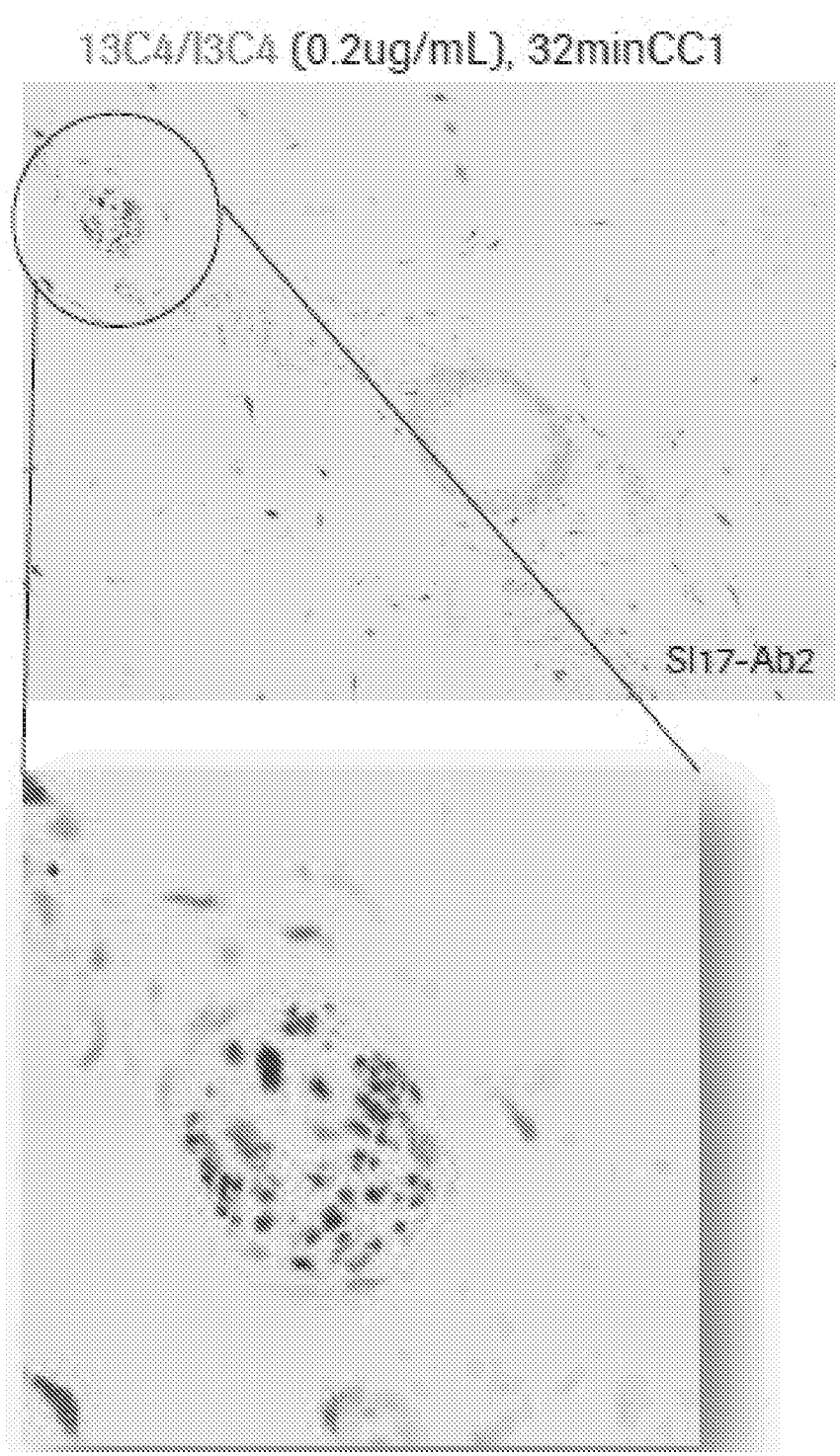
FIG. 10B shows that the anti-PGP9.5 antibody 13C4/I3C4 (0.2 µg/mL) stains neuronal features in skin samples from a normal subject (non-PD subject).
Figure 10C:
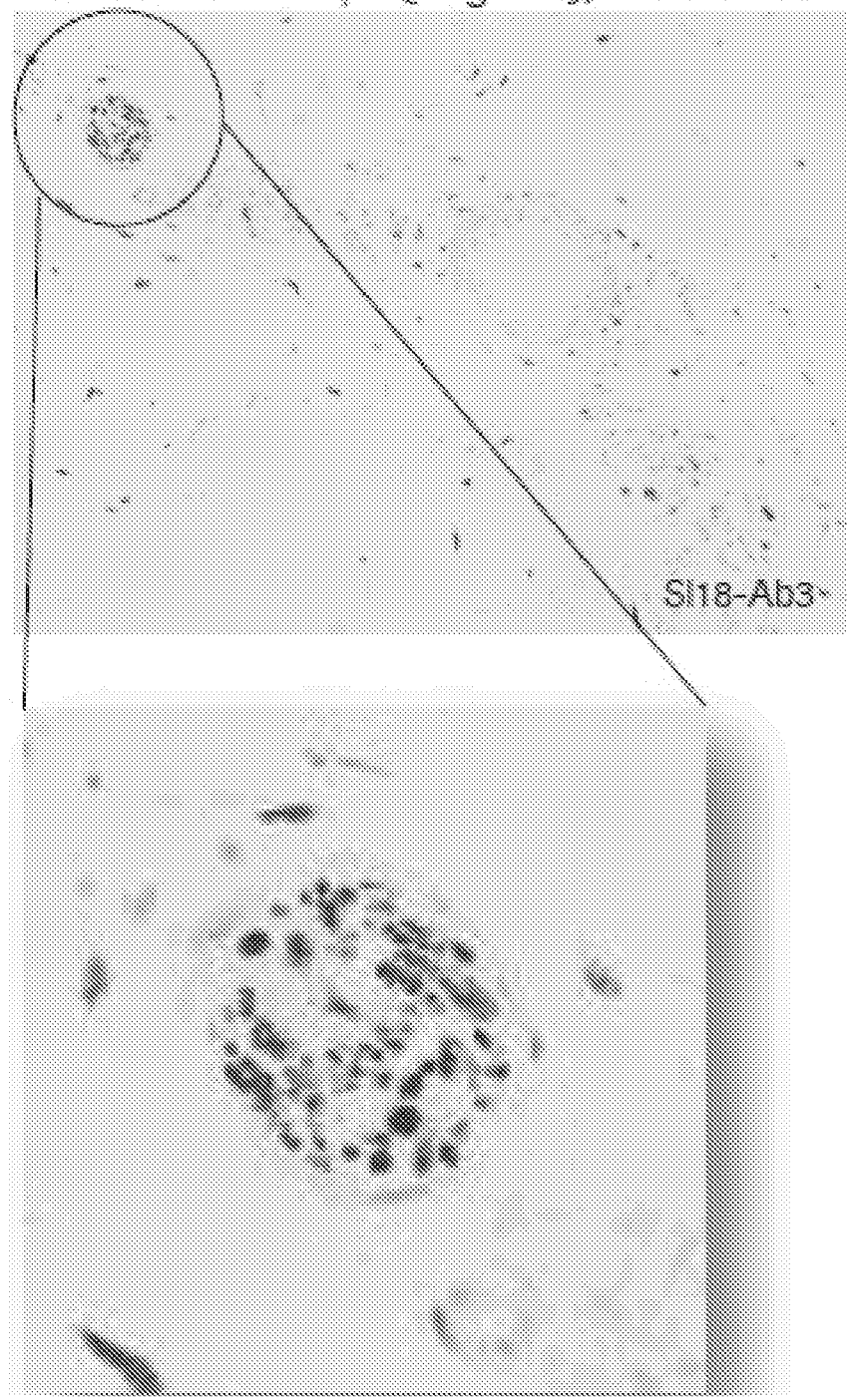
FIG. 10C shows that the polyclonal anti-PGP9.5 antibody by Cell Marque (1.0 µg/mL: VENTANA® catalog number of 760-4434) stains neuronal features in skin samples from a normal subject (non-PD subject).

Protein gene product 9.5 (PGP9.5), more descriptively known as ubiquitin carboxyl-terminal hydrolase L1 (UCHL1), is a thioesterase essential for de-ubiquitination of ubiquitin-conjugated proteins and maintenance of free mono-ubiquitin pool 20-24. It is highly expressed in the brain and has been estimated to comprise 1% to 5% of total neuronal protein. PGP9.5 is commonly used as a marker for neurons and neuroendocrine cells, but the expression of PGP9.5 is not exclusively restricted to those cell types. Three different antibodies against PGP9.5 were evaluated for immunohistochemical detection of nerve features, neurons, or neuroendocrine cells in skin, a polyclonal antibody available in RTD catalog (P/N 760-4434) from Cell Marque™ and two monoclonal antibodies from Abcam, a rabbit (EPR4118) and a mouse (13C/I3C4). All three antibodies were able to specifically stain structures that were recognizably neuronal (see FIG. 10A-FIG. 10C). Following a titration series of three antibody concentrations, EPR4118 and 13C/I3C4 at 0.2 µg/mL were shown to have comparable staining intensity as polyclonal antibody from Cell Marque at dispenser concentration of 1.13 µg/mL (see FIG. 10A-FIG. 10C). However, at these concentrations the 13C/I3C4 antibody exhibited significant amount of non-specific background staining compared with EPR4118 or Cell Marque™ polyclonal antibodies (compare FIG. 10B to FIG. 10A and FIG. 10C).

Specificity of EPR4118 antibody in the immunohistochemical context of phospho-S129-alpha-synuclein and PGP9.5 silver/yellow dual IHC assay was assessed using BC8 human tissue microarray containing 30 normal and 29 cancer tissue cores from various anatomical sites (SuperBioChips Laboratories, Seoul, Korea). The ToB/ToT analysis demonstrates PGP9.5 staining around blood vessels and glands and in nerve and ganglion cells from various tissue sites. Specialized structures with nerve innervation (pancreatic islets) also stained positive for PGP9.5 (see Tables 6-9). PGP9.5 staining was also observed in kidney tubules, rare stromal cells in lung, germ cells in testis, trophoblast cells in placenta, and tumor cells from various types of cancer. These findings are consistent with previously reported expression of PGP9.5 in various types of tumors and non-neuronal cell types.

Results of diluent testing, titrations, guardbanding, and accelerated stability (data not shown) led to the dispenser formulation of EPR4118 at 0.5 µg/mL in DISCOVERY Goat Ig Block (VENTANA P/N 760-6008). In this formulation, EPR4118 is expected to have a shelf-life of 24 months at 4° C. based on accelerated stability testing. Results of the lot-to-lot testing (data not shown) demonstrated the performance of EPR4118 antibody is consistent across four different production lots generated by two different manufacturers (Abcam and Spring).

Example 4. Selection of aSyn and PGP9.5 Assay and Detection Configuration

Figure 11A:
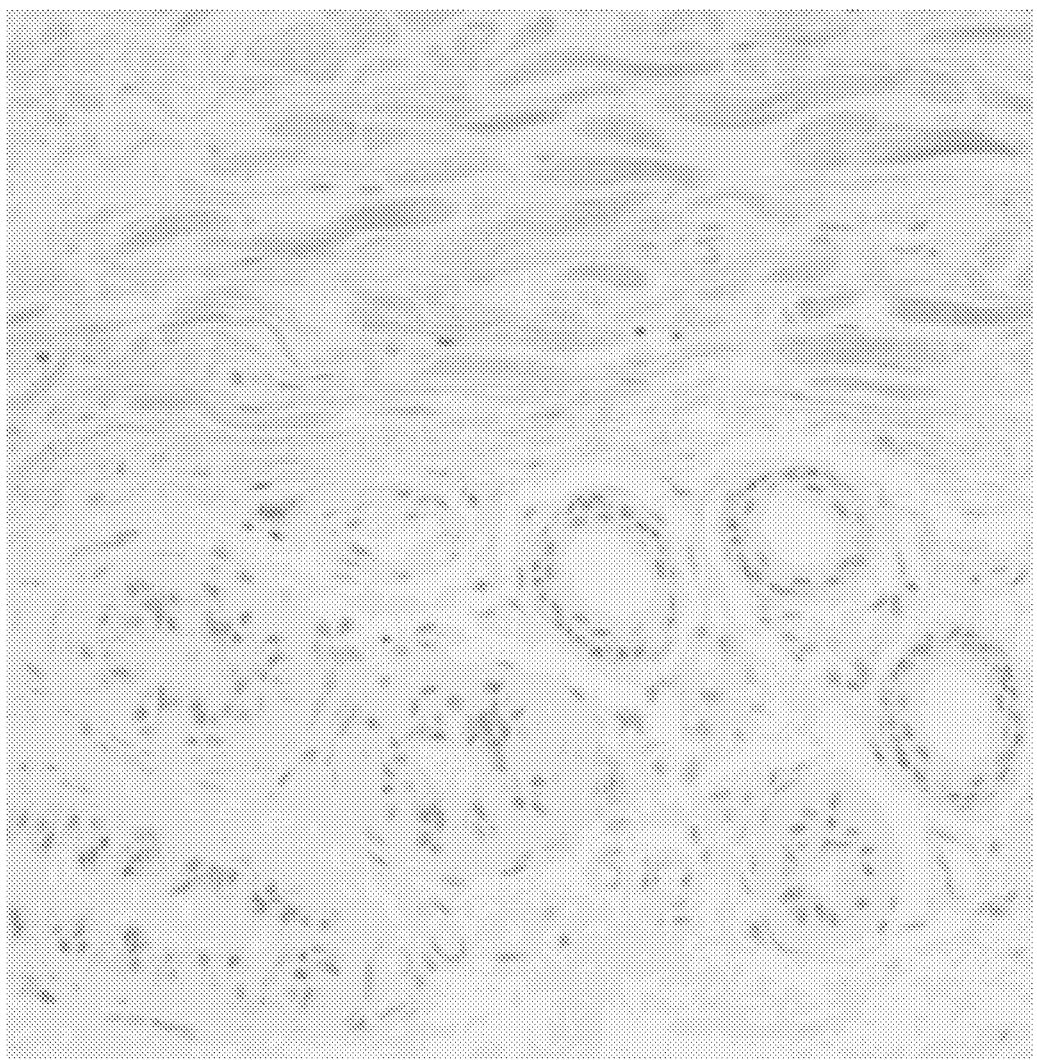
FIG. 11A shows strong background staining of collagen fibers in freshly cut tissue slides (~24-48 hours) from a non-PD subject. Staining was performed using the anti-phosphorylated S129 alpha-synuclein 7E2 antibody at 0.1 µg/mL and VENTANA OptiView DAB IHC Detection Kit. Tissue section did not undergo CC1 antigen retrieval treatment. Similar results were obtained when the anti-phosphorylated S129 alpha-synuclein 7E2 antibody and OptiView HQ Linker were not applied (data not shown), demonstrating the collagen background staining was produced by OptiView Multimer.
Figure 11B:
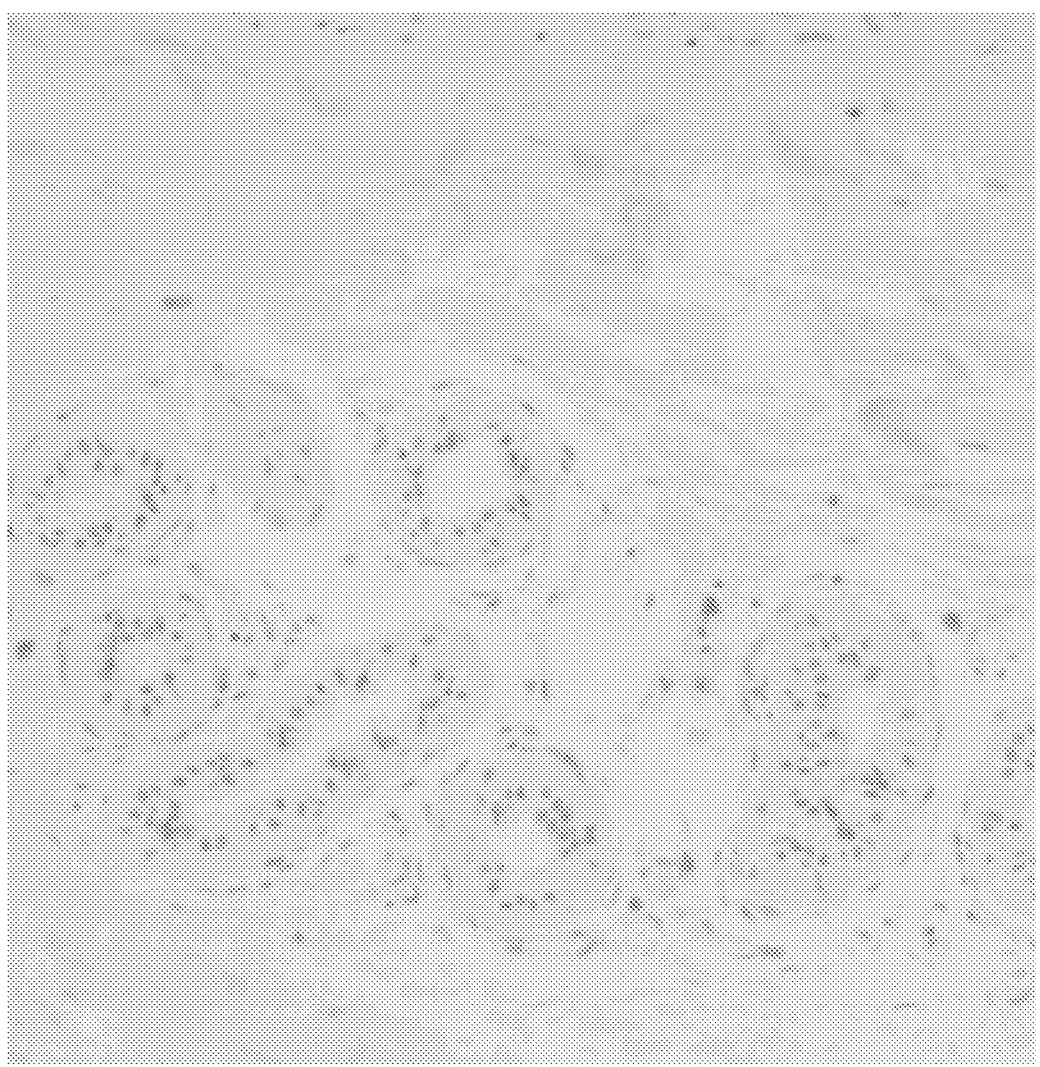
FIG. 11B shows minimal background staining of collagen fibers in tissue slides from a non-PD subject stained approximately 5 months after the slide was cut.
Figure 12A:
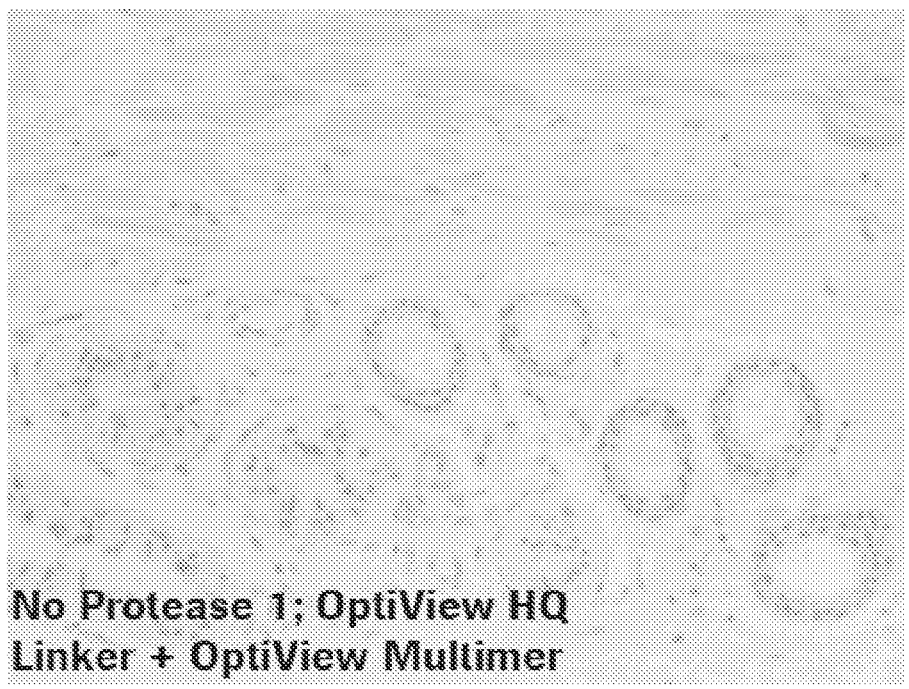
FIG. 12A shows that background staining of collagen fibers in tissue slides can be exacerbated by antigen retrieval with a protease in tissue slides from a non-PD subject. Tissue was tested with the anti-phosphorylated S129 alpha-synuclein 7E2 antibody (0.1 µg/mL) diluted in DISCOVERY Goat Ig Block.
Figure 12A:
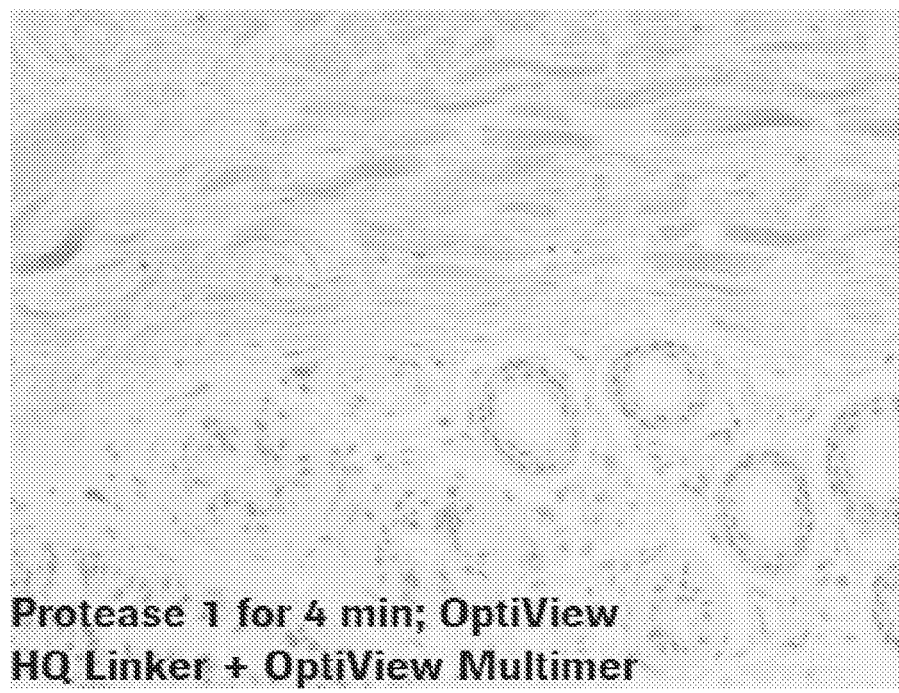
Figure 12B:
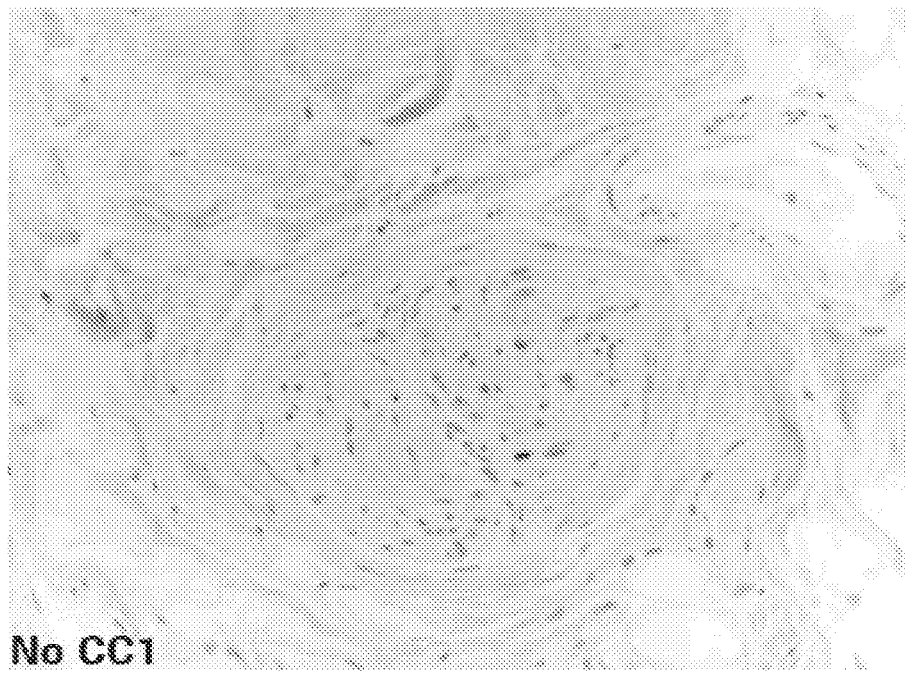
FIG. 12B shows that background staining of collagen fibers in tissue slides can be lessened by CC1 antigen retrieval in tissue slides from a non-PD subject. Tissue was incubated with the anti-phosphorylated S129 alpha-synuclein 7E2 antibody (1.0 µg/mL) diluted in DISCOVERY Goat Ig Block without prior antigen retrieval with CC1 (top panel) or after antigen retrieval using CC1 for 48 minutes at 100° C.; bottom panel) on VENTANA BenchMark ULTRA automated staining instrument.
Figure 12B:
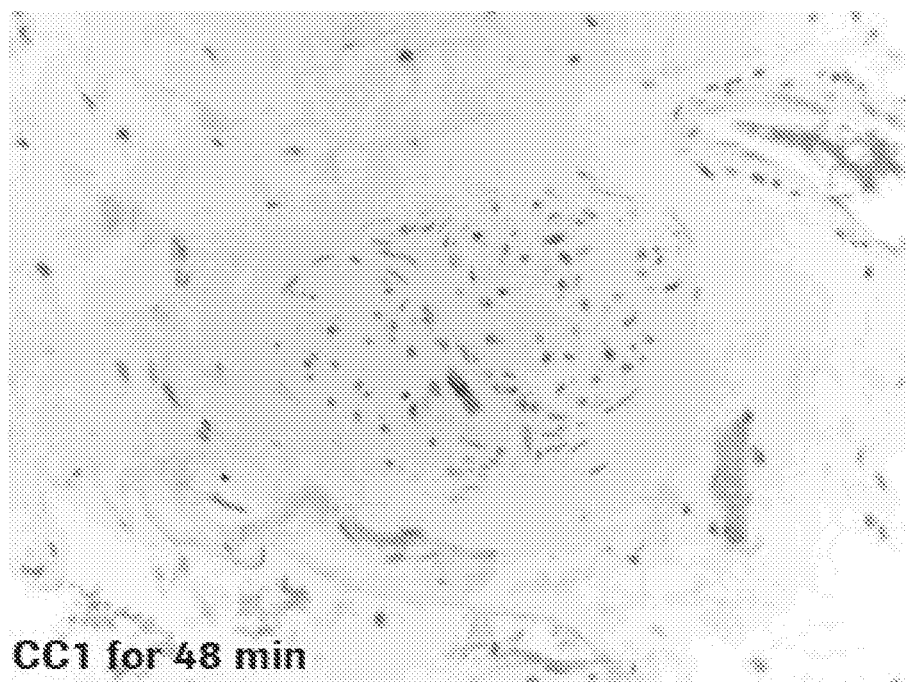

Protease resistance is a hallmark of many aggregated proteins including alpha-synuclein and detection of pathological forms of alpha-synuclein is enhanced with protease treatment. Roche pRED, in collaboration with Prothena, developed an assay (subsequently transferred to Targos) with high specificity toward aggregated alpha-synuclein in a cohort of PD and non-PD samples from BSHRI (see Table 4 and Table 5). The pRED/Prothena aSyn assay is based on the 5C12 antibody that recognizes both phosphorylated and unphosphorylated S129-aSyn, removal of non-aggregated aSyn by VENTANA® Protease 1, and detection using the highly sensitive VENTANA® OptiView DAB IHC Detection kit. However, while minimal background was observed with the pRED/Prothena aSyn assay protocol using skin sections that have been cut for at least several weeks, strong staining of collagen fibers was observed with freshly cut slides (see FIG. 11A and FIG. 11B). The collagen background staining was exacerbated with additional antigen retrieval using Protease 1 (see FIG. 12A) but lessened with Ultra CC1 (see FIG. 12B). The cause of the collagen background staining was not 5C12 antibody as 7E2 antibody gave rise to the same collagen staining using the same detection scheme (data not shown). The background was also not due to non-specific adsorption of DAB by collagen fibers as ultraView DAB IHC Detection kit did not generate any collagen staining (data not shown), but deposition of tyramide-TAMRA (VENTANA Purple kit, DISCOVERY, P/N 760-229) using OptiView HQ Universal Linker and HRP Multimer did (data not shown). Eventually OptiView HRP Multimer was determined to be the cause of collagen fiber staining (data not shown). Physiological cross-linking of collagen fibers leads to formation of many types of adducts. It is possible the anti-HQ IgG cross-reacts with one or more of such adducts. This hypothesis is consistent with lessening of collagen background staining following reversal of collagen cross-linking associated with CC1 treatment.

Figure 13:
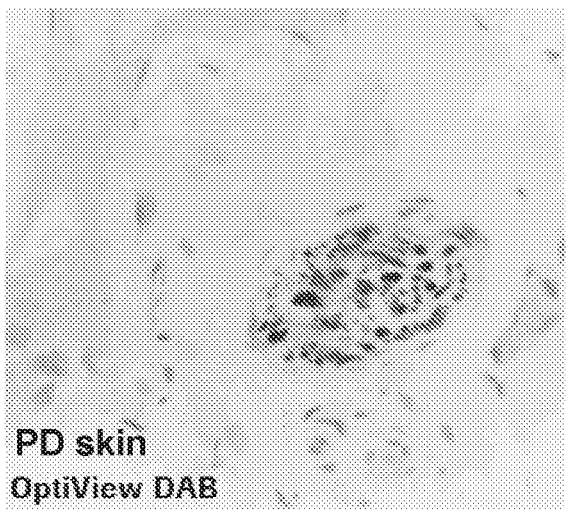
FIG. 13 shows that the ultraView Universal DAB Detection Kit (right panels) results in lower staining intensity for PGP9.5 compared with OptiView DAB IHC Detection Kit (left panels) in both PD skin (top panels) and control skin (bottom panels) samples. OptiView detection: HQ Linker+HRP Multimer. ultraView detection: anti-Rb/Ms HRP Multimer. Tissue samples were pretreated with CC1 at 100° C. for 32 minutes, and the PGP9.5 EPR4118 antibody (0.5 µg/mL) was diluted in DISCOVERY Goat Ig Block. Images were taken at 40× magnification.
Figure 13:
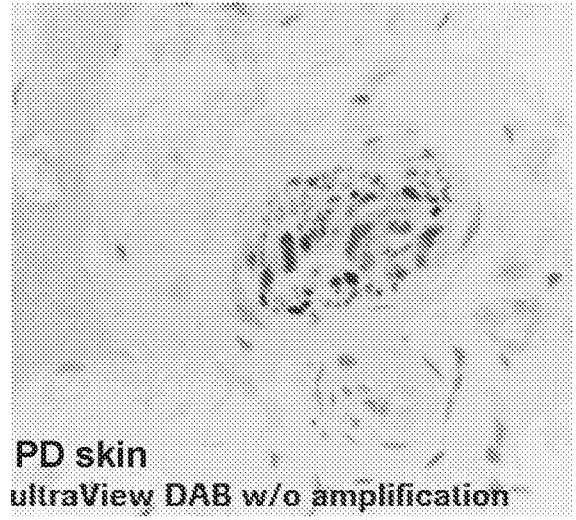
Figure 13:
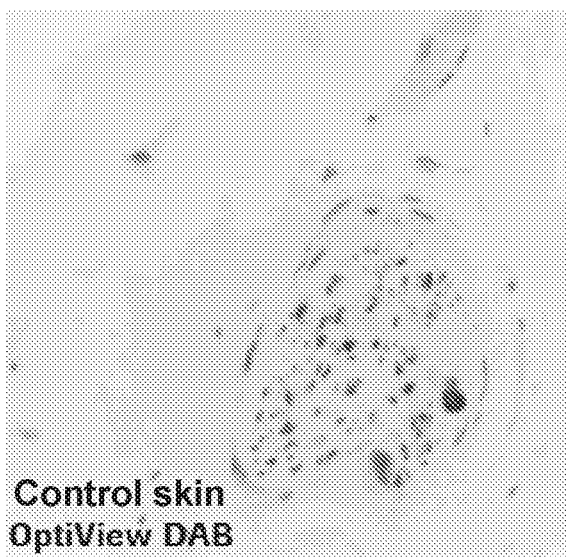
Figure 13:
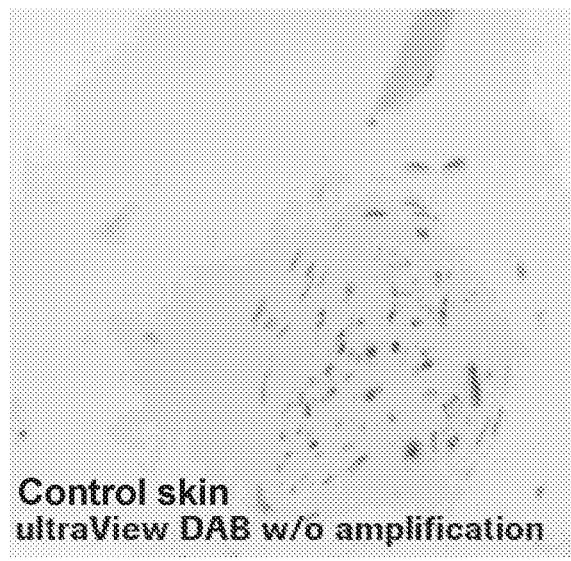
Figure 14:
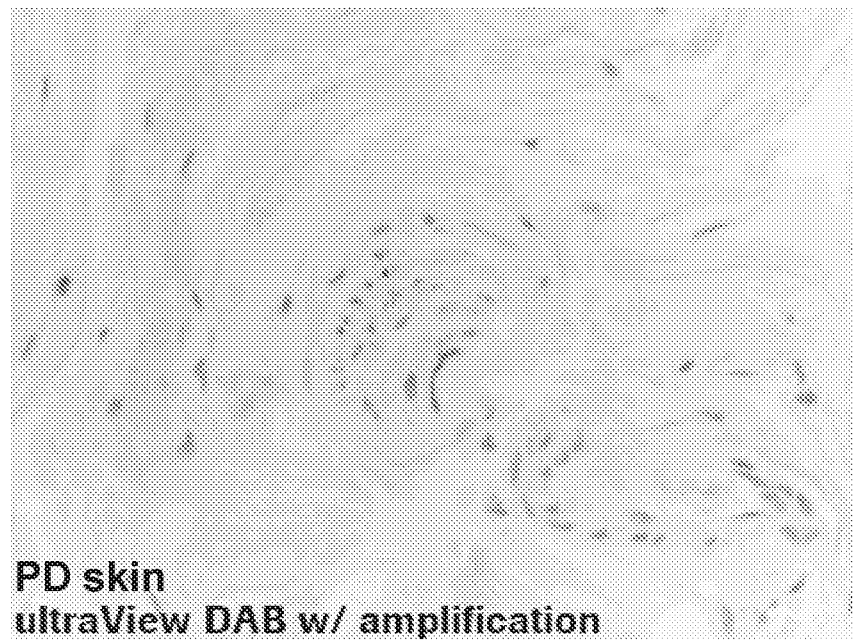
FIG. 14 shows that the amplification process with the ultraView Universal DAB Detection Kit results in a rise in non-specific background staining in both PD skin (top panel) and control skin (bottom panel) samples. Amplification: Ms anti-Rb followed by Rb anti-Ms IgG. ultraView detection: anti-Rb/Ms HRP Multimer. Anti-phosphorylated S129 alpha-synuclein 7E2 antibody (1.0 µg/mL) was diluted in DISCOVERY Goat Ig Block. No pre-treatment with CC1 nor protease. Images were taken at 40× magnification.
Figure 14:
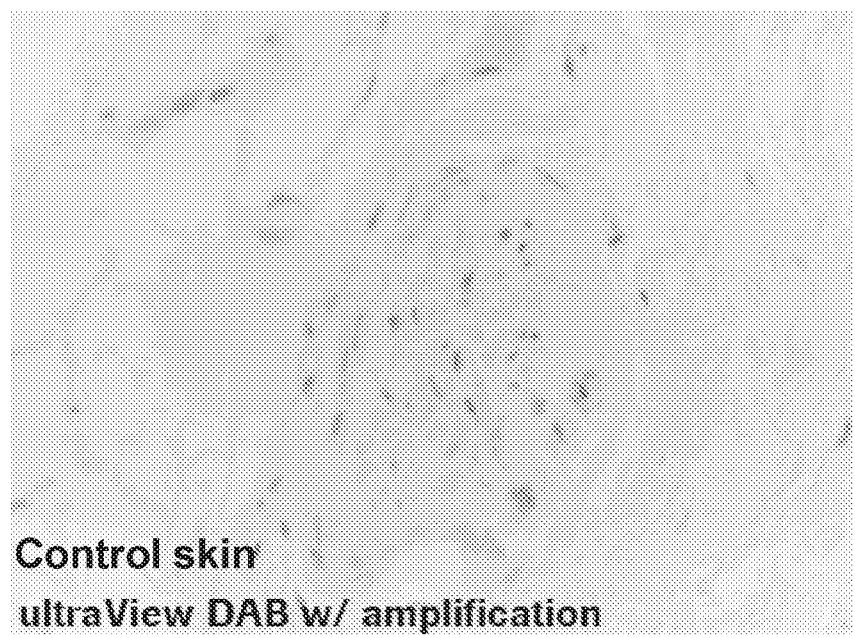

Survey of a collection of scalp samples from the BSHRI cohort showed varying degrees of collagen background DAB staining from light to sufficiently heavy to interfere with interpretation of specific signals from aggregated aSyn (data not shown). This prompted a search for alternative detection methods with comparable sensitivity as OptiView DAB IHC Detection Kit for staining of aggregated aSyn. As shown in FIG. 13, ultraView Universal DAB Detection Kit consistently gave lower staining intensity for PGP9.5 compared with OptiView DAB IHC Detection Kit. As a result, ultraView Universal DAB Detection Kit coupled to amplification using Ms anti-Rb IgG followed by Rb anti-Ms IgG (VENTANA® Amplification Kit, P/N 760-080) was used to stain pS129-aSyn. Even though ultraView Universal DAB Detection Kit with amplification may have similar staining intensity as OptiView DAB IHC Detection Kit, the amplification process gave rise to significant non-specific background (see FIG. 14). High background staining was also observed when the VENTANA iView DAB Detection Kit (P/N 760-091) was used to detect pS129-aSyn or PGP9.5 (data not shown).

Figure 15:
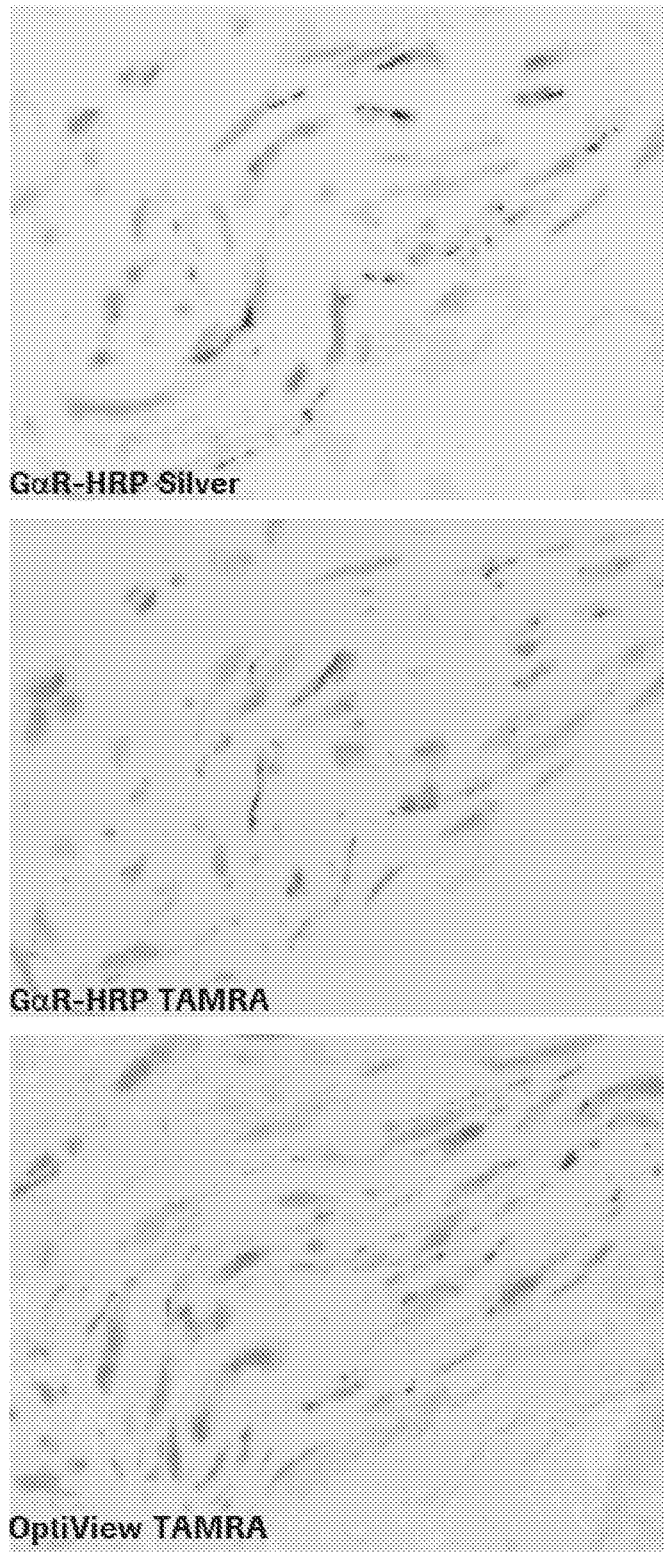
FIG. 15 shows that the ultraView SISH DNP Detection Kit (top panel) and DISCOVERY Purple kit (middle and bottom panels) both detect aggregated anti-phosphorylated S129 alpha-synuclein in skin samples from a subject with PD with little to no background when used with goat anti-rabbit-HRP conjugate stain deposition. Phosphorylated S129 alpha-synuclein stained black (silver stain) or purple (TAMRA). Anti-phosphorylated S129 alpha-synuclein 7E2 antibody at 1.0 µg/mL in DISCOVERY Goat Ig Block. Detection: goat anti-rabbit-HRP with Silver (top panel) or TAMRA (middle panel), or OptiView with TAMRA (HQ-conjugated goat anti-rabbit antibody/anti-HQ-HRP, bottom panel). PGP9.5 antibody EPR4118 at 0.5 µg/mL in DISCOVERY Goat Ig Block is stained yellow. Detection: goat anti-rabbit-AP with Dabsyl (yellow). No pre-treatment with CC1 nor protease.
Figure 16:
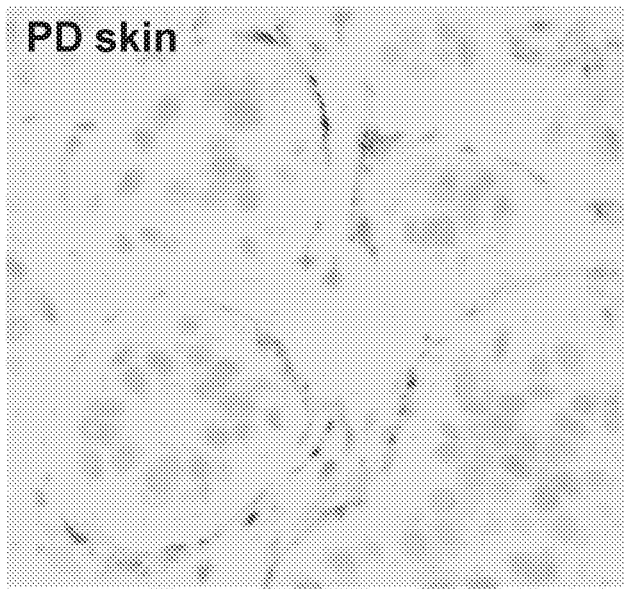
FIG. 16 shows that the black silver stain deposited in skin nerve features by the anti-phosphorylated alpha-synuclein 7E2 antibody and ultraView SISH DNP Detection Kit provided high-contrast visualization of aggregated phosphorylated S129 alpha-synuclein in the background of PGP9.5 stained yellow using EPR4118 antibody and VENTANA® DISCOVERY UltraMap anti-Rb Alkaline Phosphatase and QM-DABSYL. Tissue sample is skin sample from a subject with PD (top panel), and skin sample form a normal subject (non-PD) (bottom panel).
Figure 16:
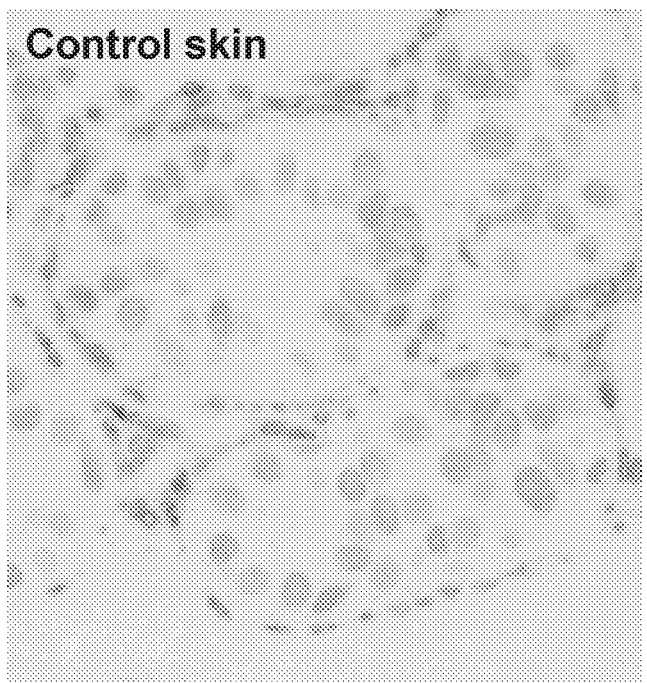
Figure 17A:
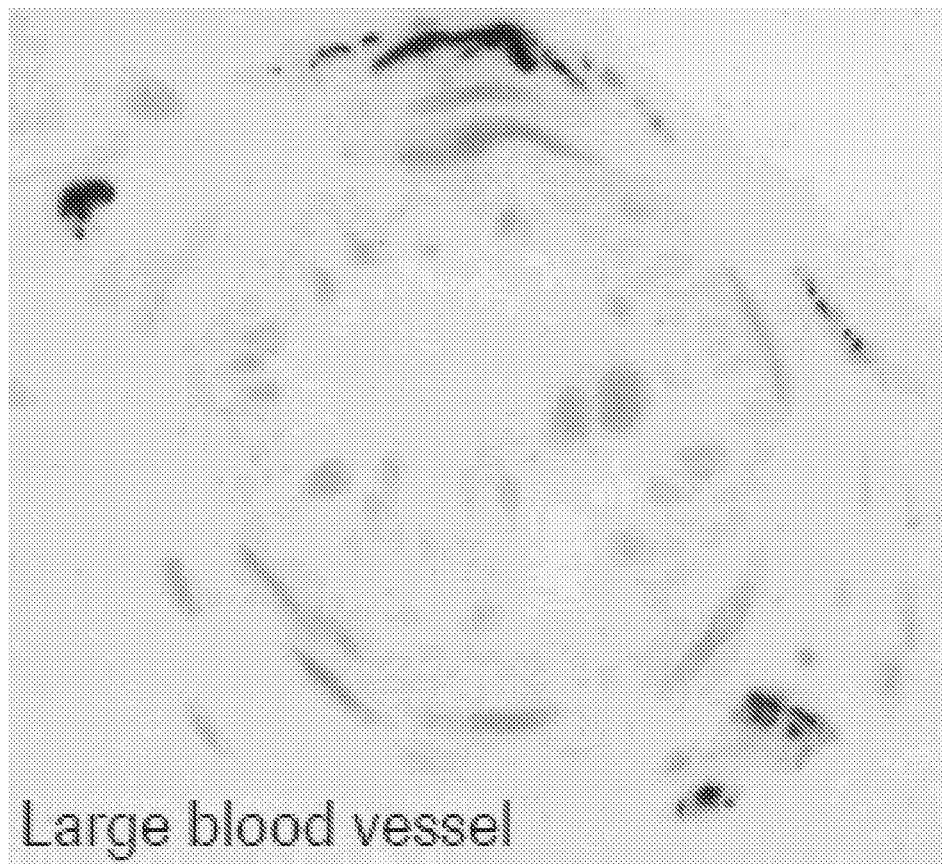
FIG. 17A shows the immunohistochemical detection of phosphorylated S129 alpha-synuclein (black/silver stain) and PGP9.5 (yellow) in nerve features of a large blood vessel in a skin sample from a subject with PD.
Figure 17B:
FIG. 17B shows the immunohistochemical detection of phosphorylated S129 alpha-synuclein (black/silver stain) and PGP9.5 (yellow) in nerve features of a small nerve bundle in a skin sample from a subject with PD.
Figure 17C:
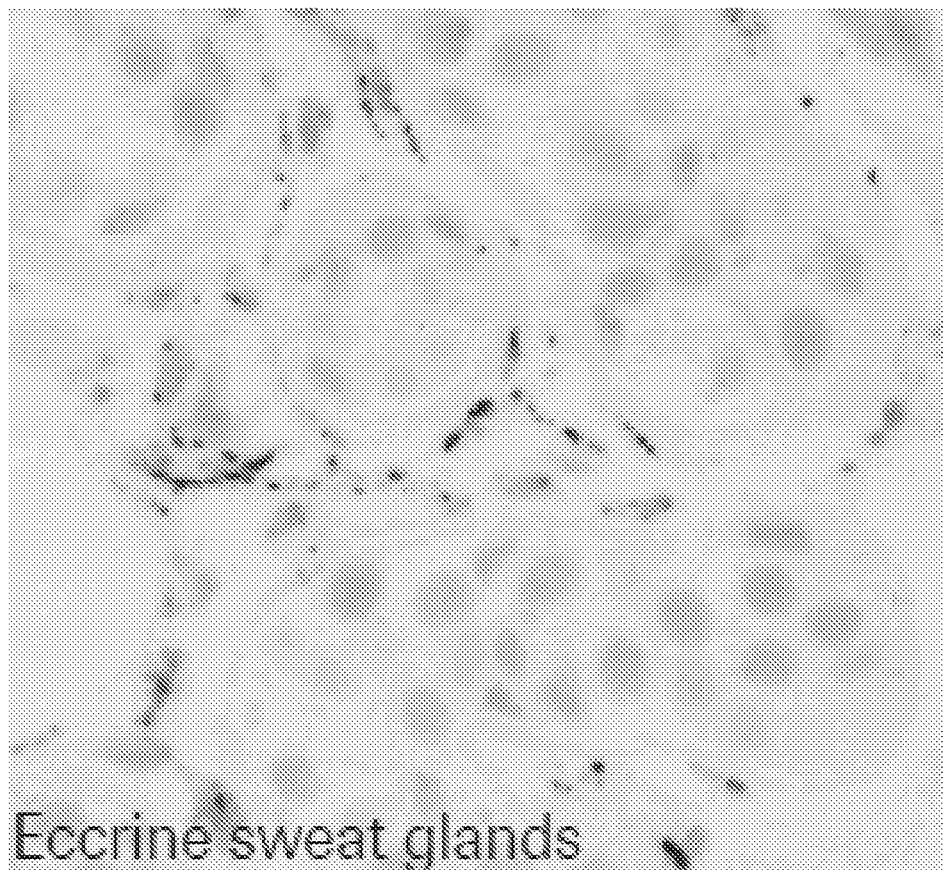
FIG. 17C shows the immunohistochemical detection of phosphorylated S129 alpha-synuclein (black/silver stain) and PGP9.5 (yellow) in nerve features of eccrine sweat glands in a skin sample from a subject with PD.
Figure 17D:
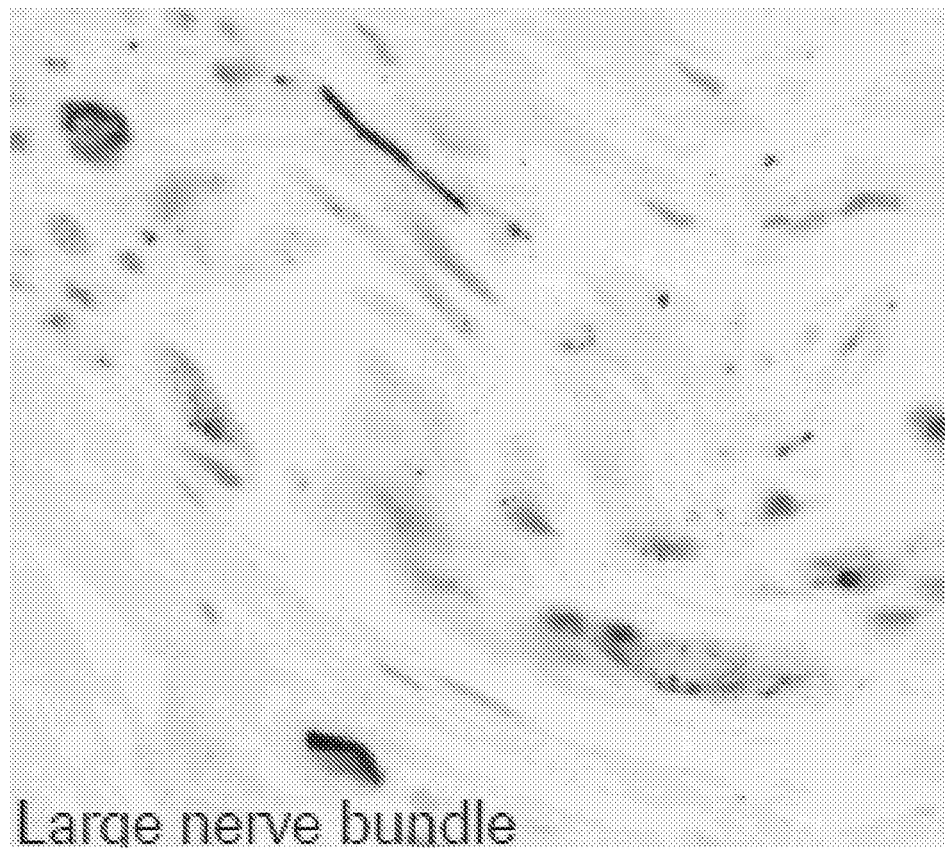
FIG. 17D shows the immunohistochemical detection of phosphorylated S129 alpha-synuclein (black/silver stain) and PGP9.5 (yellow) in nerve features of a large nerve bundle in a skin sample from a subject with PD.
Figure 17E:
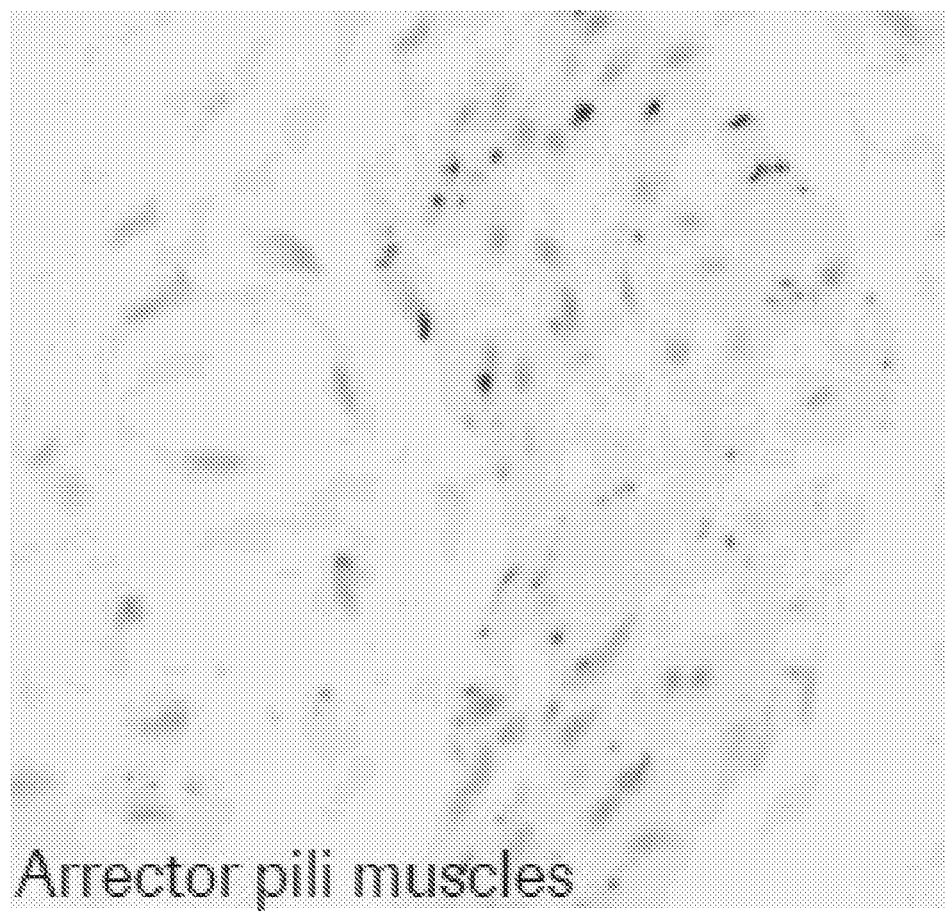
FIG. 17E shows the immunohistochemical detection of phosphorylated S129 alpha-synuclein (black/silver stain) and PGP9.5 (yellow) in nerve features of arrector pili muscles in a skin sample from a subject with PD.
Figure 18:
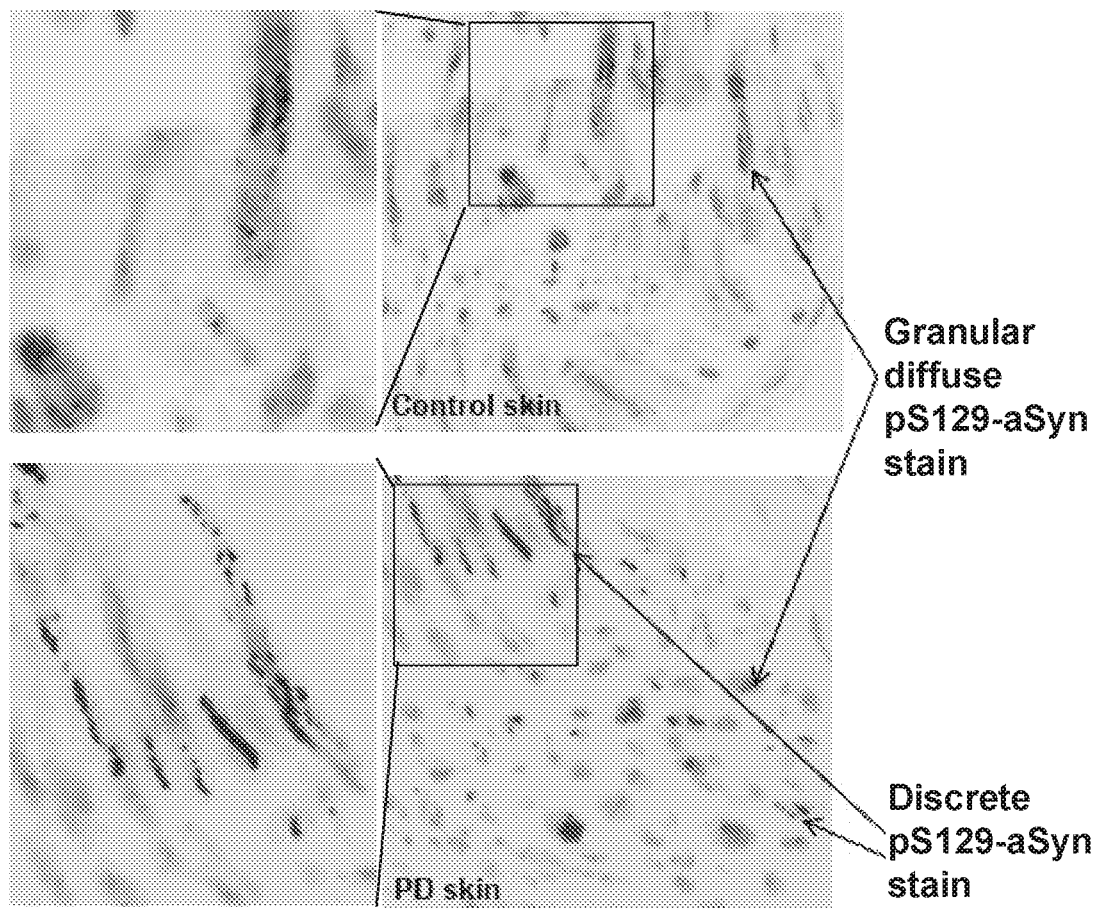
FIG. 18 shows examples of diffuse granular and discrete types of silver phosphorylated S129 alpha-synuclein stain that could be observed in skin nerve bundles from a non-PD control subject (top panels) and PD subject (bottom panels). Sections of scalp biopsies were stained using phosphorylated S129 alpha-synuclein and PGP9.5 silver/yellow dual IHC assay without protease or phosphatase treatments (Protocol 1). Structures stained yellow are nerves expressing PGP9.5.
Figure 19:
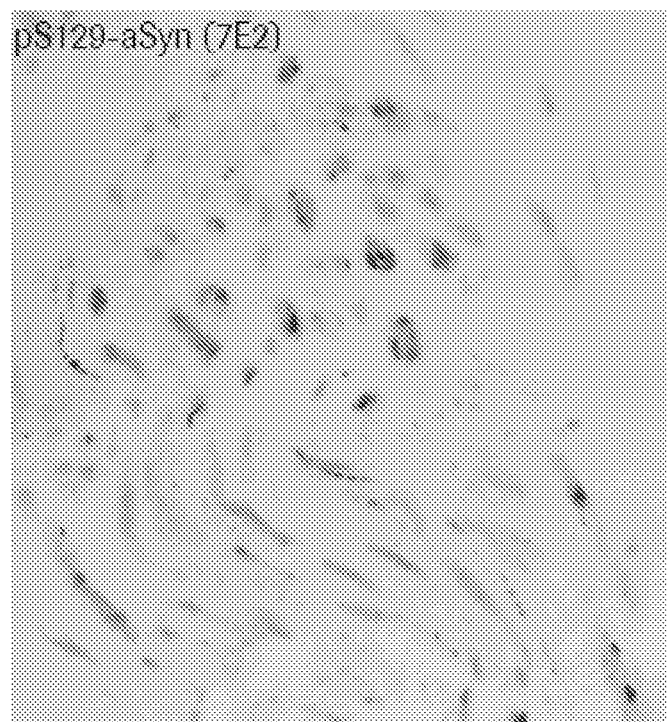
FIG. 19 shows similar circumferential neuronal staining patterns between granular type phosphorylated S129 alpha-synuclein (top panel) and myelin basic protein (bottom panel), which suggests potential localization of diffuse pS129 alpha-synuclein in Schwann cells.
Figure 19:
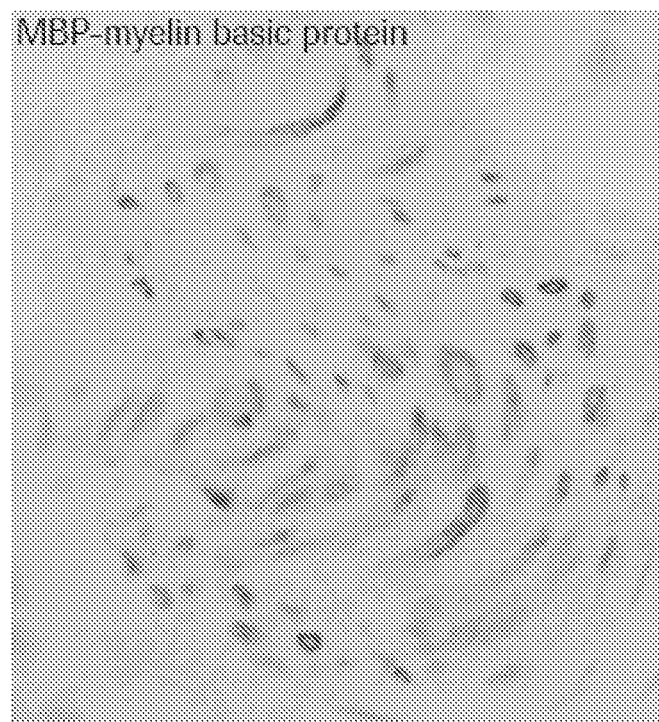
Figure 20A:
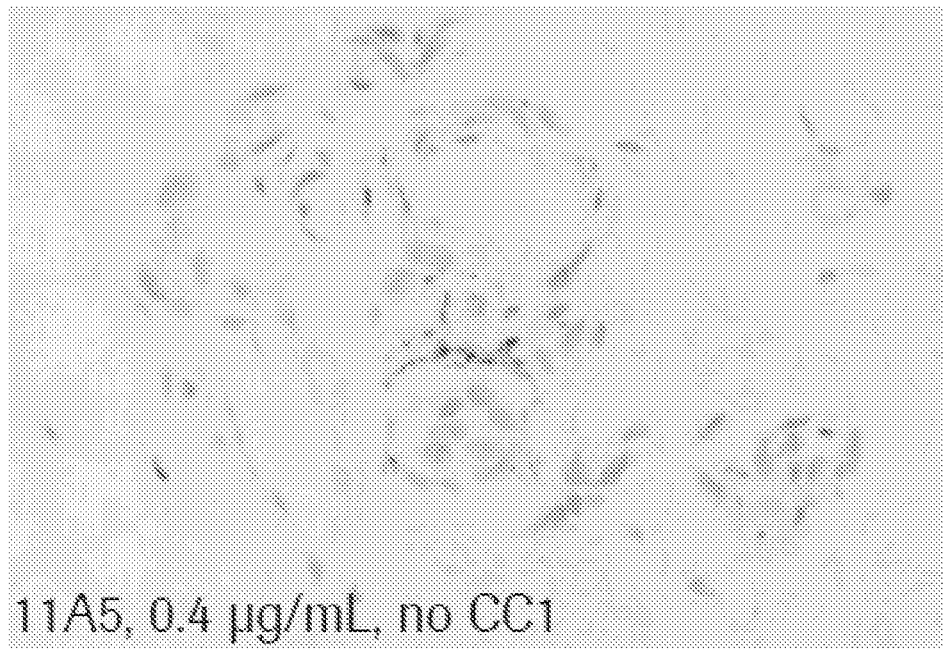
FIG. 20A shows that staining of phosphorylated S129 alpha-synuclein by the 11A5 antibody (0.4 µg/mL) without CC1 treatment (top panel) was decreased after treatment with ULTRA CC1 for 32 minutes at 100° C. (bottom panel).
Figure 20A:
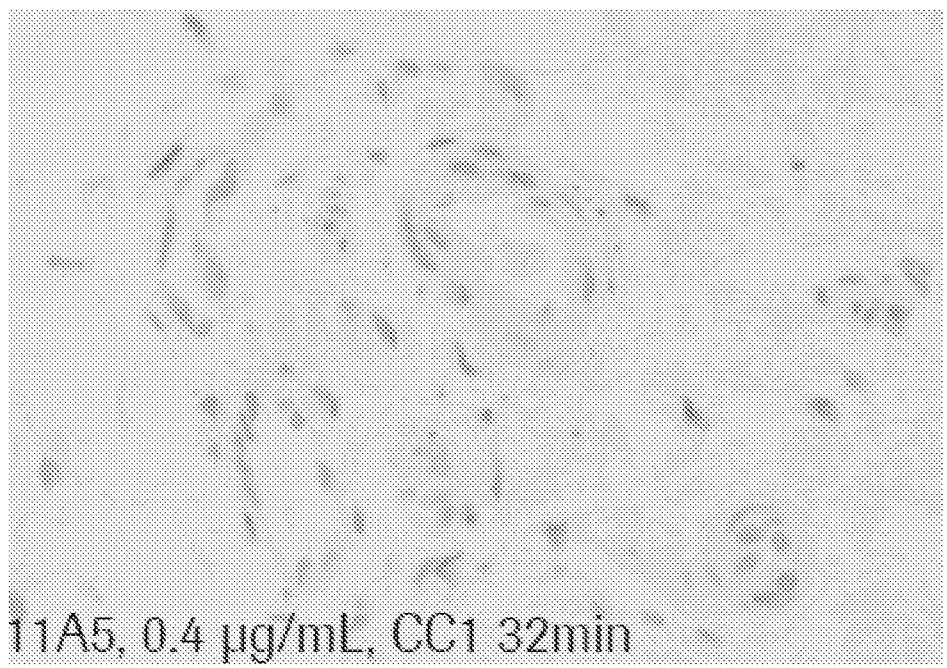
Figure 20B:
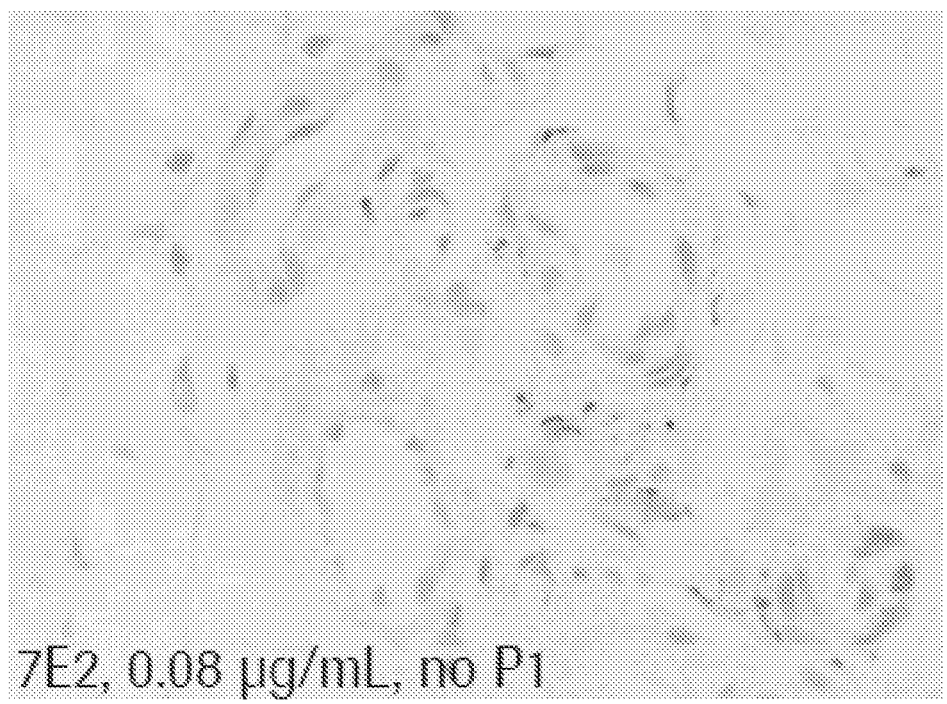
FIG. 20B shows that staining of phosphorylated S129 alpha-synuclein by the 7E2 antibody (0.08 µg/mL) without CC1 treatment (top panel) was decreased after treatment with ULTRA CC1 for 32 minutes at 100° C. (bottom panel).
Figure 20B:
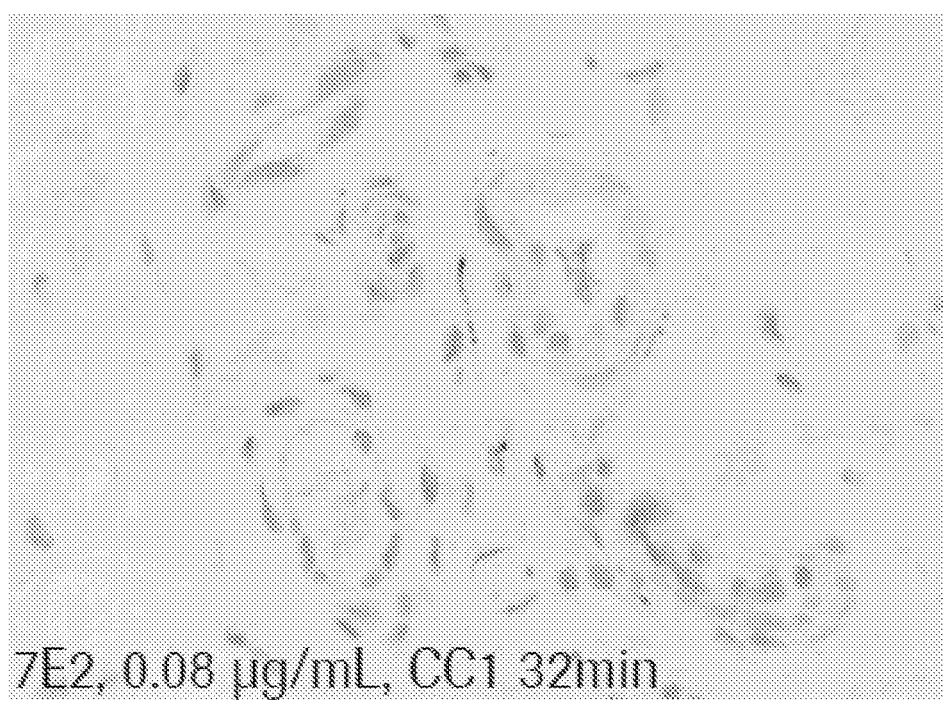
Figure 20C:
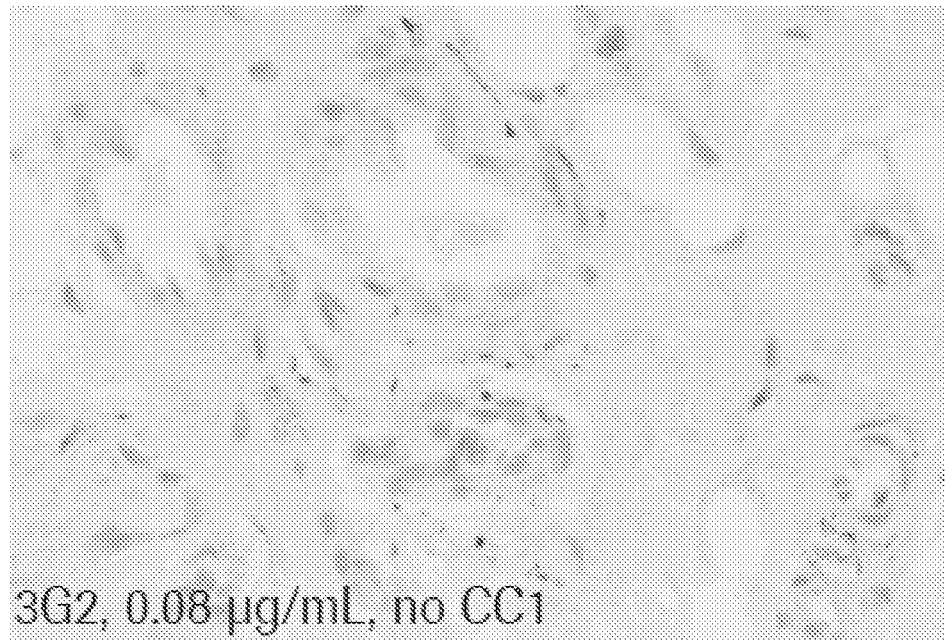
FIG. 20C shows that staining of phosphorylated S129 alpha-synuclein by the 3G2 antibody (0.08 µg/mL) without CC1 treatment (top panel) was decreased after treatment with ULTRA CC1 for 32 minutes at 100° C. (bottom panel).
Figure 20C:
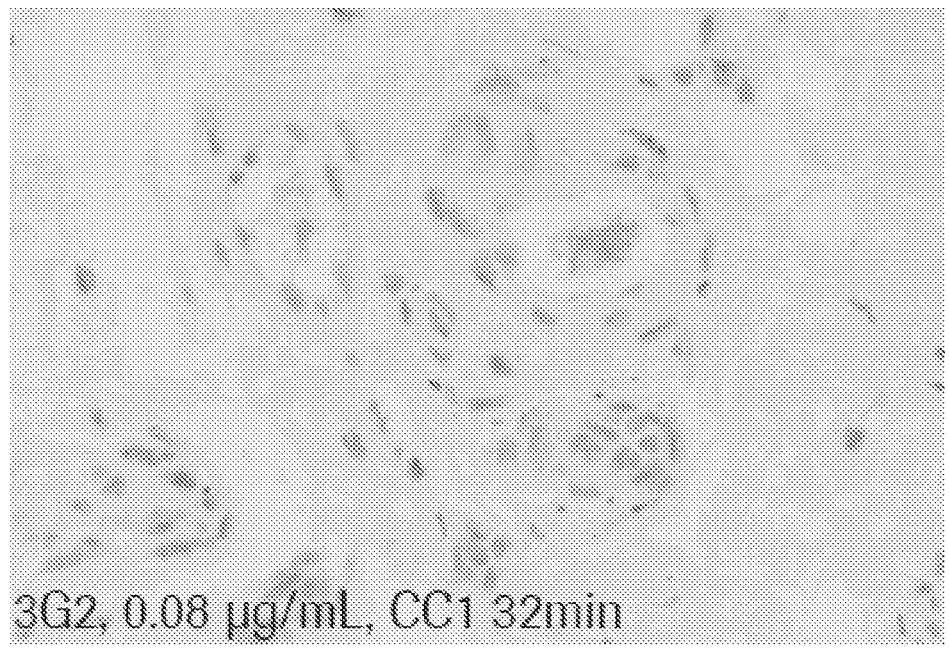
Figure 20D:
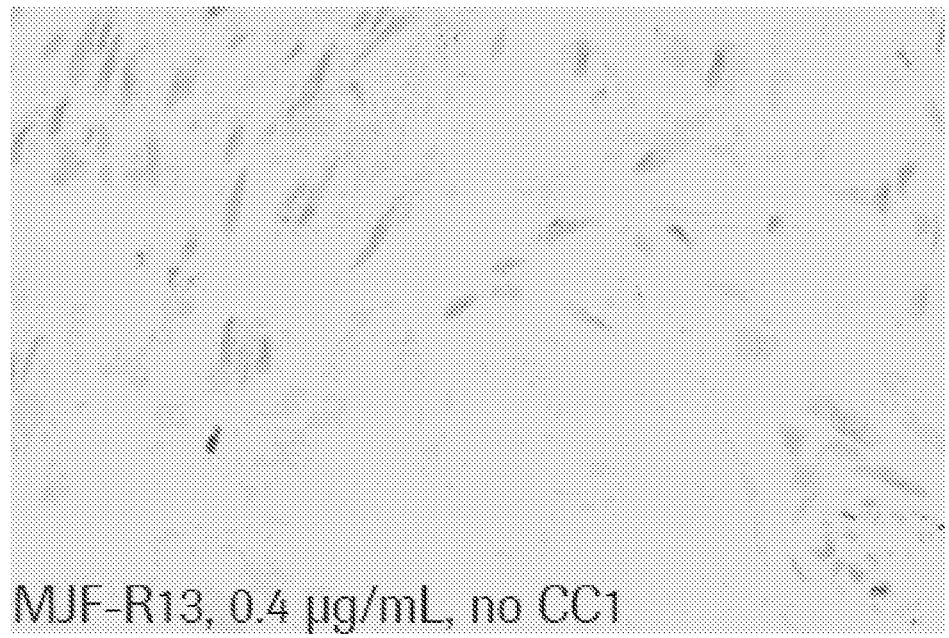
FIG. 20D shows that staining of phosphorylated S129 alpha-synuclein by the MJF-R13 antibody (0.4 µg/mL) without CC1 treatment (top panel) was decreased after treatment with ULTRA CC1 for 32 minutes at 100° C. (bottom panel).
Figure 20D:
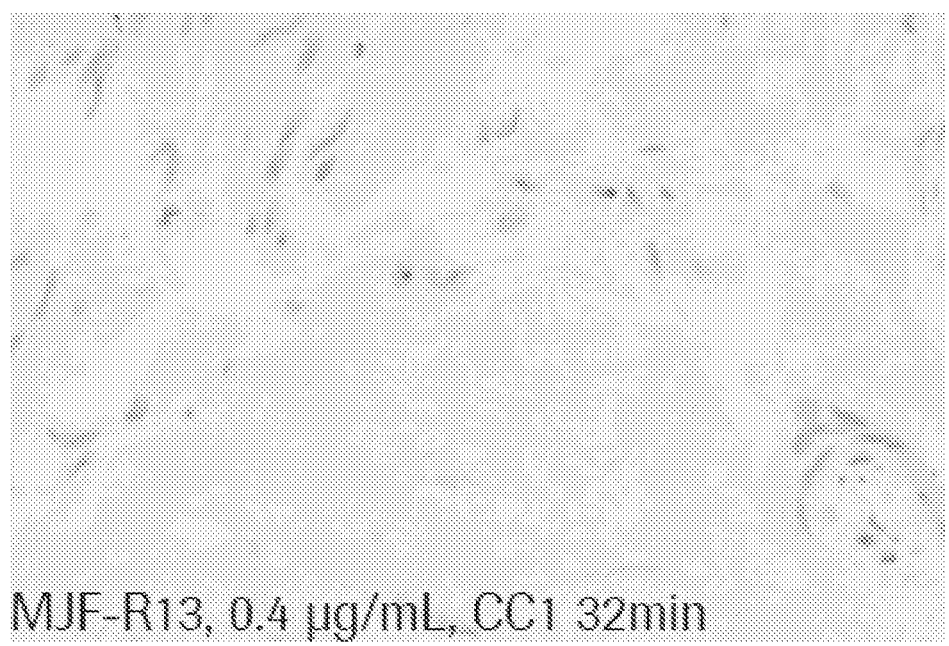
Figure 20E:
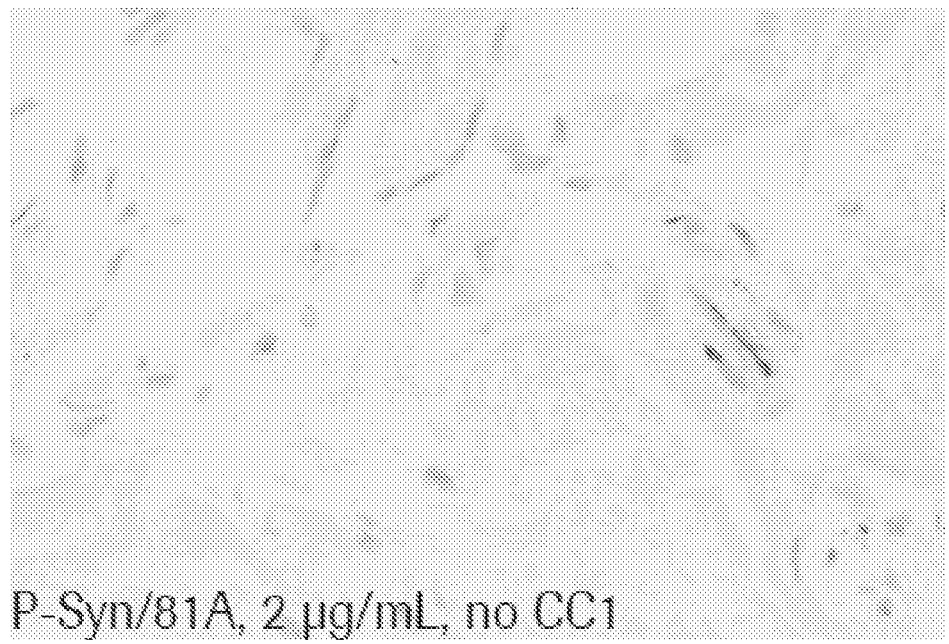
FIG. 20E shows that staining of phosphorylated S129 alpha-synuclein by the P-Syn/81A antibody (2.0 µg/mL) without CC1 treatment (top panel) was decreased after treatment with ULTRA CC1 for 32 minutes at 100° C. (bottom panel).
Figure 20E:
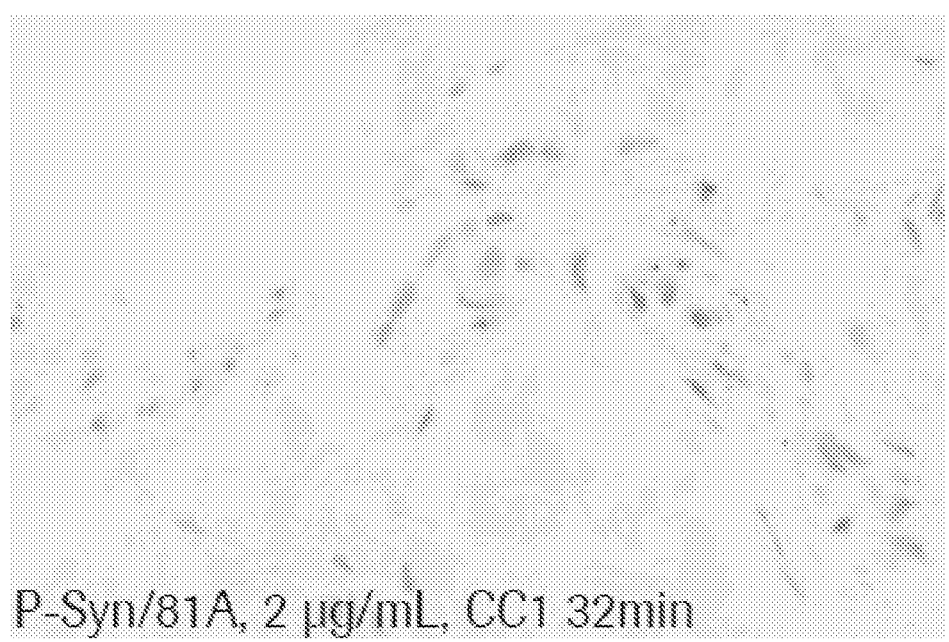

Two additional detection systems were evaluated for staining pS129-aSyn in skin sections using 7E2 antibody, ultraView SISH DNP Detection Kit (P/N 760-098) and DISCOVERY™ Purple kit (P/N 760-229). As shown in FIG. 15, both systems were able to detect aggregated pS129-aSyn with little to no background as long as goat anti-rabbit-HRP conjugate rather than OptiView HQ Universal Linker and HRP Multimer was used for stain deposition. In particular, the black silver stain deposited by the ultraView SISH DNP Detection Kit provided high-contrast visualization of aggregated pS129-aSyn in the background of PGP9.5 stained yellow using VENTANA® DISCOVERY™ UltraMap anti-Rb Alk Phos (P/N 760-4314) and QM-DABSYL as described in Methods section (see FIG. 16). The morphologies of silver/black pS129-aSyn and yellow PGP9.5 stains in different types of nerve features in skin from subjects with PD are shown in FIG. 17A-FIG. 17E. Using Bumblebee detection configuration, two different types of pS129-aSyn stains were observed in large nerve bundles of skin sections from subjects with PD: granular, diffuse-appearing stain and discrete, dense-appearing stain (see FIG. 18). As more fully described in subsequent sections, pS129-aSyn stain of the granular type was observed in FFPE skin sections from both subjects with PD and non-PD subjects in the BSHRI cohort. In contrast, pS129-aSyn stain of the discrete type was almost exclusively restricted to skin from subjects with PD. Subsequent sections also describe the sensitivity of the 7E2 antibody and optimized Bumblebee Assay protocols for aggregated aSyn in comparison with the pRED/Prothena assay based on 5C12 antibody, Protease 1, and OptiView DAB IHC Detection Kit. The granular pS129-aSyn stain often appears as bracketing axons in sagittal nerve sections (see FIG. 18) and as surrounding neurons circumferentially in transverse nerve sections (top panel of FIG. 19). Such staining pattern is similar to that of the Schwann cell marker myelin basic protein (bottom panel of FIG. 19), suggesting the pS129-aSyn protein responsible for the granular stain appearance could be located in Schwann cells. Accumulation of pS129-aSyn within Schwann cells has been previously described in patients with multiple system atrophy.

One assay configuration that was not tested is antigen retrieval with Protease 1 followed by incubation with 5C12 antibody and detection using ultraView SISH DNP Detection Kit. This assay configuration potentially has similar sensitivity for aggregated aSyn as 7E2 antibody detected using ultraView SISH DNP Detection Kit. However, it is not compatible with dual detection incorporating PGP9.5 as neuronal marker because PGP9.5 requires antigen retrieval using Cell Conditioning (CC) 1 or 2 bulk solutions and the combination of Protease 1 with CC1 or CC2 treatments leads to significant loss of tissue morphology (data not shown).

Example 5. Optimization of Antigen Retrieval Conditions for Phospho-aSyn Staining Using 7E2 Antibody Done and PGP9.5 Staining Using EPR4118 Antibody Clone Immunohistochemical detections of many epitopes are enhanced following antigen retrieval procedures. Effects of two different antigen retrieval treatment processes on detection of pS129-aSyn in FFPE skin sections using 7E2 antibody were assessed: VENTANA® ULTRA Cell Conditioning (ULTRA CC1) bulk solution and protease. Effects of treatment with ULTRA CC1 or ULTRA CC2 solutions on PGP9.5 staining using EPR4118 antibody were also evaluated.

In contrast to most targets, staining of pS129-aSyn was paradoxically decreased after treatment with ULTRA CC1 for only 32 minutes at 100° C. (see FIG. 20A-FIG. 20E). The negative effect of ULTRA CC1 on pS129-aSyn staining was observed with five different antibodies against pS129-aSyn: 11A5, 7E2, 3G2, MJF-R13(8-8), and 81A (see FIG. 20A-FIG. 20E), suggesting the phosphorylation of S129 residue itself could have been affected by the treatment.

Figure 21A:
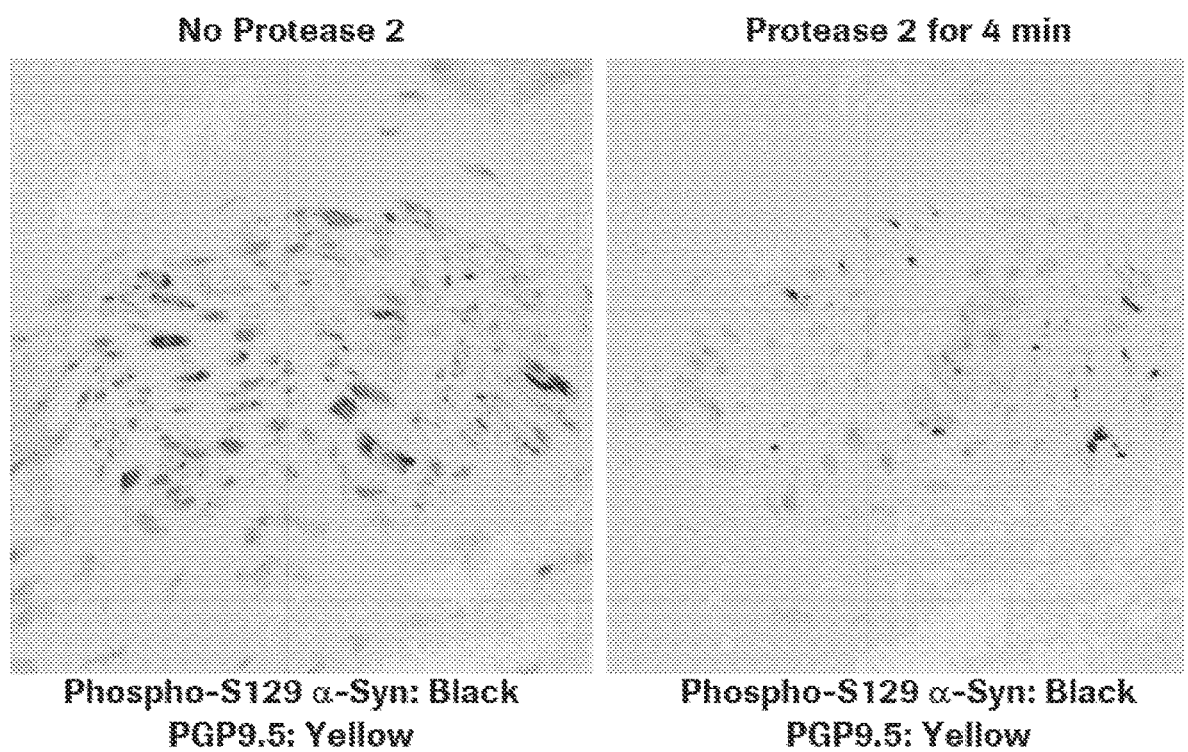
FIG. 21A shows treatment with VENTANA® Protease 2 for 4 minutes (right panel) led to a moderate increase (compared to no treatment; left panel) in the discrete type of phosphorylated S129 alpha-synuclein (detected with 7E2 antibody clone) stain in skin sections from subjects with PD. Treatment with VENTANA® Protease 2 for 4 minutes also dramatically decreased the granular type of phosphorylated S129 alpha-synuclein stain and PGP9.5 stain in skin sections from subjects with PD.
Figure 21B:
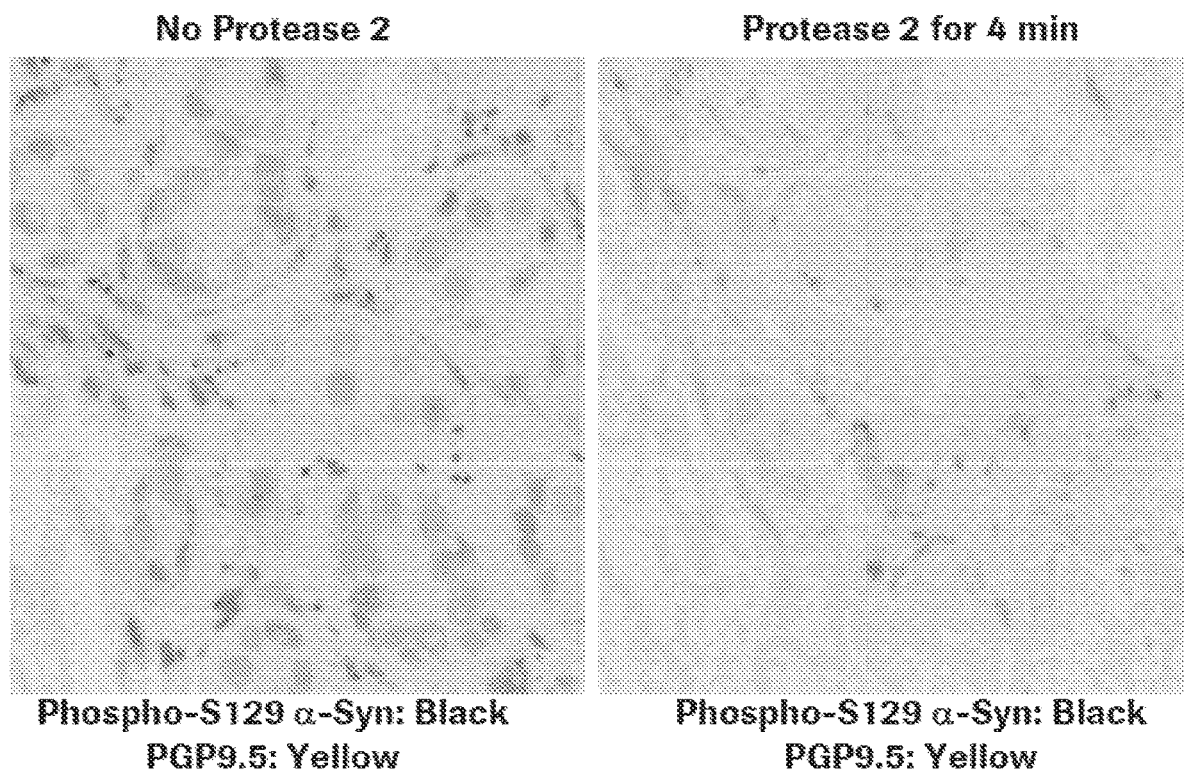
FIG. 21B shows treatment with VENTANA® Protease 2 for 4 minutes (right panel) significantly decreased (compared to no treatment; left panel) the phosphorylated S129 alpha-synuclein (detected with 7E2 antibody clone) stain in skin sections from non-PD subjects that could be mistaken as the discrete type.
Figure 22:
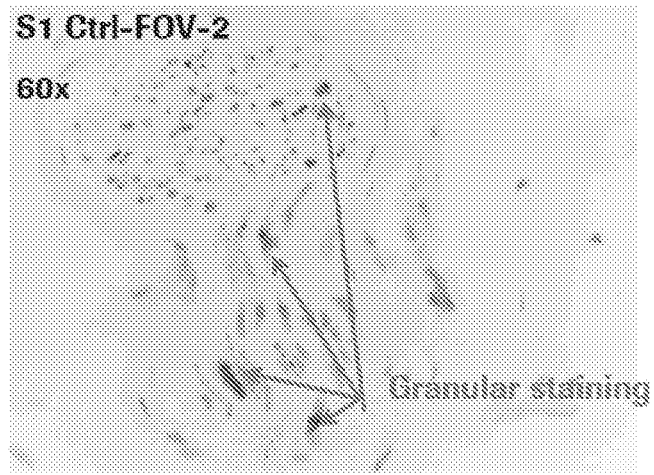
FIG. 22 shows the effect of Protease 3 treatment for 4 minutes (middle panel) or 12 minutes (bottom panel) on staining using phosphorylated S129 alpha-synuclein antibody in skin from a subject with PD compared to no protease treatment (top panel). Phosphorylated S129 alpha-synuclein stained black. 7E2 antibody clone at 1.0 µg/mL in DISCOVERY Goat Ig Block (detection: goat anti-rabbit-HRP with Silver). PGP9.5 antibody EPR4118 at 0.5 µg/mL in DISCOVERY Goat Ig Block stained yellow (detection: goat anti-rabbit-AP with Dabsyl). No pre-treatment with CC1 nor protease.
Figure 22:
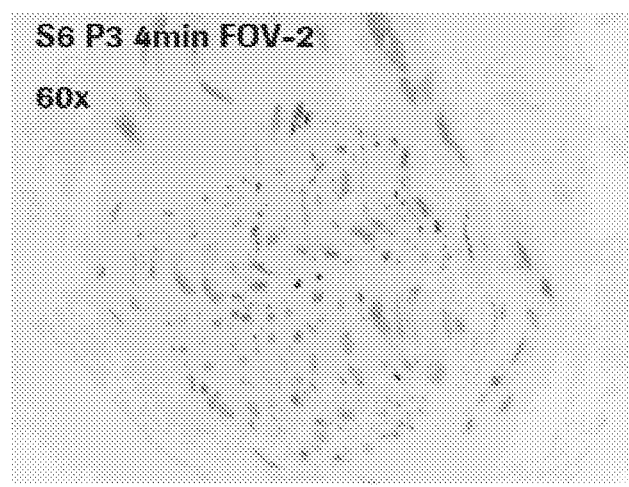
Figure 22:
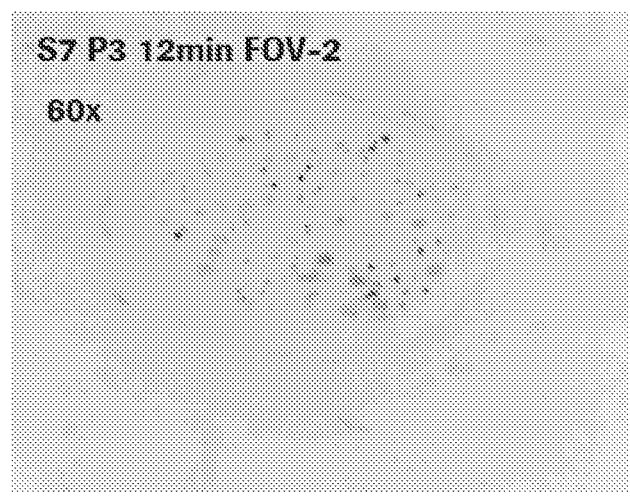

Protease treatment can improve detection of aggregated aSyn, but the underlying cause responsible for this phenomenon is unclear. It could be due to removal of un-aggregated aSyn or improved antibody access to epitopes buried in protein aggregates following protease digestion, or a combination of both. Treatment with VENTANA® Protease 2 for 4 minutes (see FIG. 21A and FIG. 21B) or VENTANA® Protease 3 for 4 minutes or for 12 minutes at 36° C. led to a moderate increase in the discrete type of pS129-aSyn stain in skin sections from subjects with PD (see FIG. 22). A more pronounced effect of protease treatment is the complete (Protease 2 for 4 minutes or Protease 3 for 12 minutes) or partial (Protease 3 for 4 minutes) removal of the granular type of pS129-aSyn stain in skin samples from subjects with PD or non-PD subjects (see FIG. 21 and FIG. 22). This finding presented the opportunity for a pS129-aSyn assay with potentially higher specificity for aggregated aSyn. However, short Protease 3 treatment (4 minutes) did not completely eliminate granular pS129-aSyn stain while Protease 2 or extended Protease 3 treatment (>4 minutes) resulted in poor tissue morphology when tissue was subsequently subjected to CC2 at 100° C. for PGP9.5 detection (data not shown).

Figure 23A:
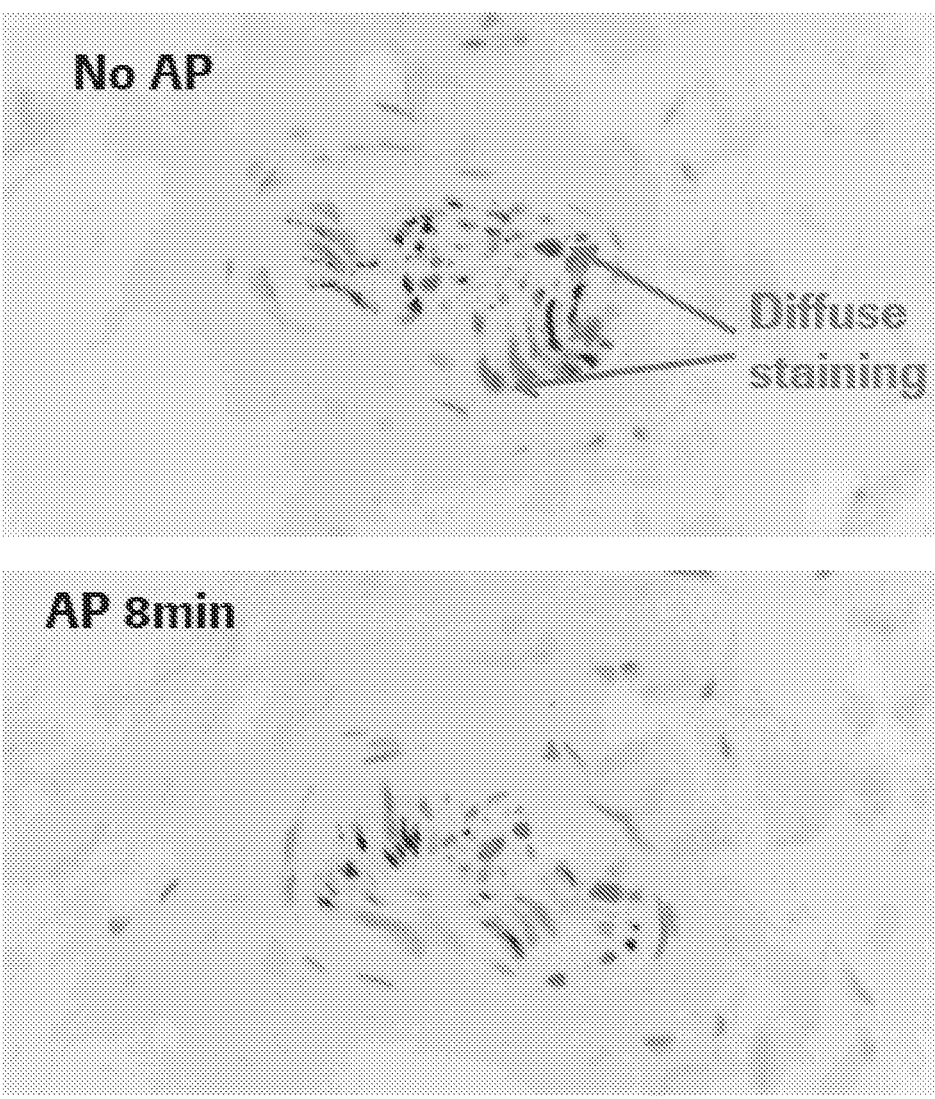
FIG. 23A shows that alkaline phosphatase (purified calf intestinal alkaline phosphatase from NEB) pre-treatment at pH9 for 8 minutes (bottom panel) removes diffuse granular phosphorylated alpha-synuclein staining without affecting staining of the dense discrete type normally observed in tissue that was not treated with alkaline phosphatase (top panel).
Figure 23B:
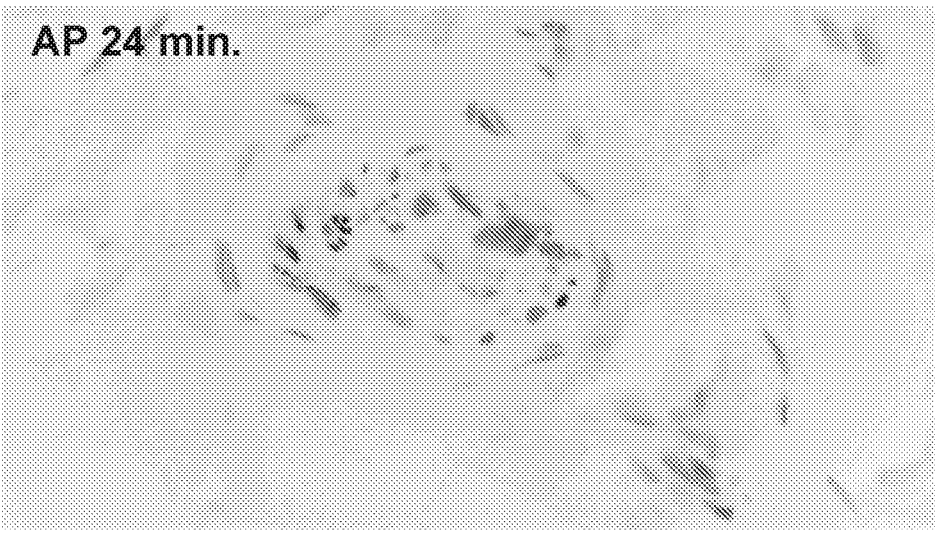
FIG. 23B shows that alkaline phosphatase (purified calf intestinal alkaline phosphatase from NEB) pre-treatment at pH9 for 24 minutes (top panel) or 40 minutes (bottom panel) removes diffuse granular phosphorylated alpha-synuclein staining without affecting staining of the dense discrete type normally observed in tissue that was not treated with alkaline phosphatase.
Figure 23B:
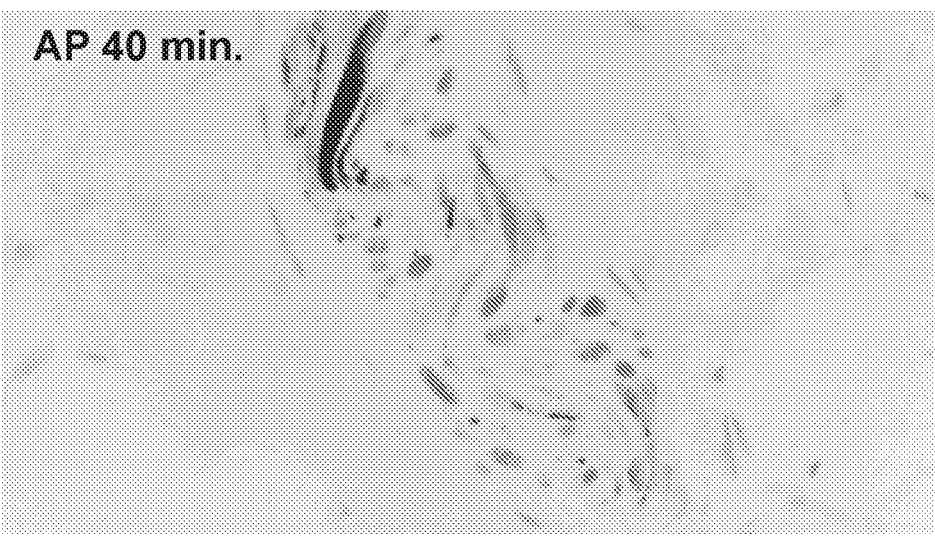
Figure 24:
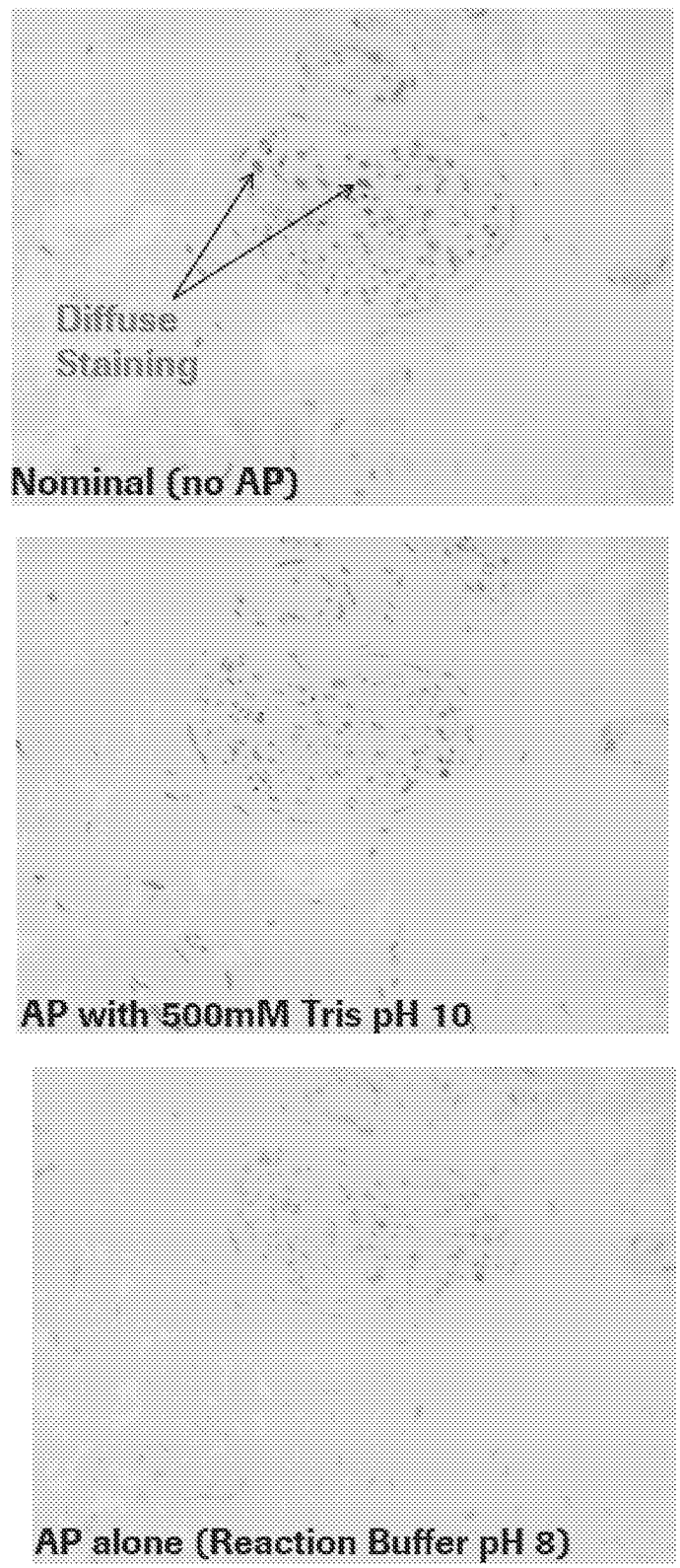
FIG. 24 shows that alkaline phosphatase (recombinant alkaline phosphatase from Roche; 30 µg/mL) treatment at pH8 for 8 minutes resulted in decreased staining of discrete phosphorylated S129 alpha-synuclein (bottom panel) compared to no AP treatment (top panel) or AP treatment at pH10 (middle panel).
Figure 25:
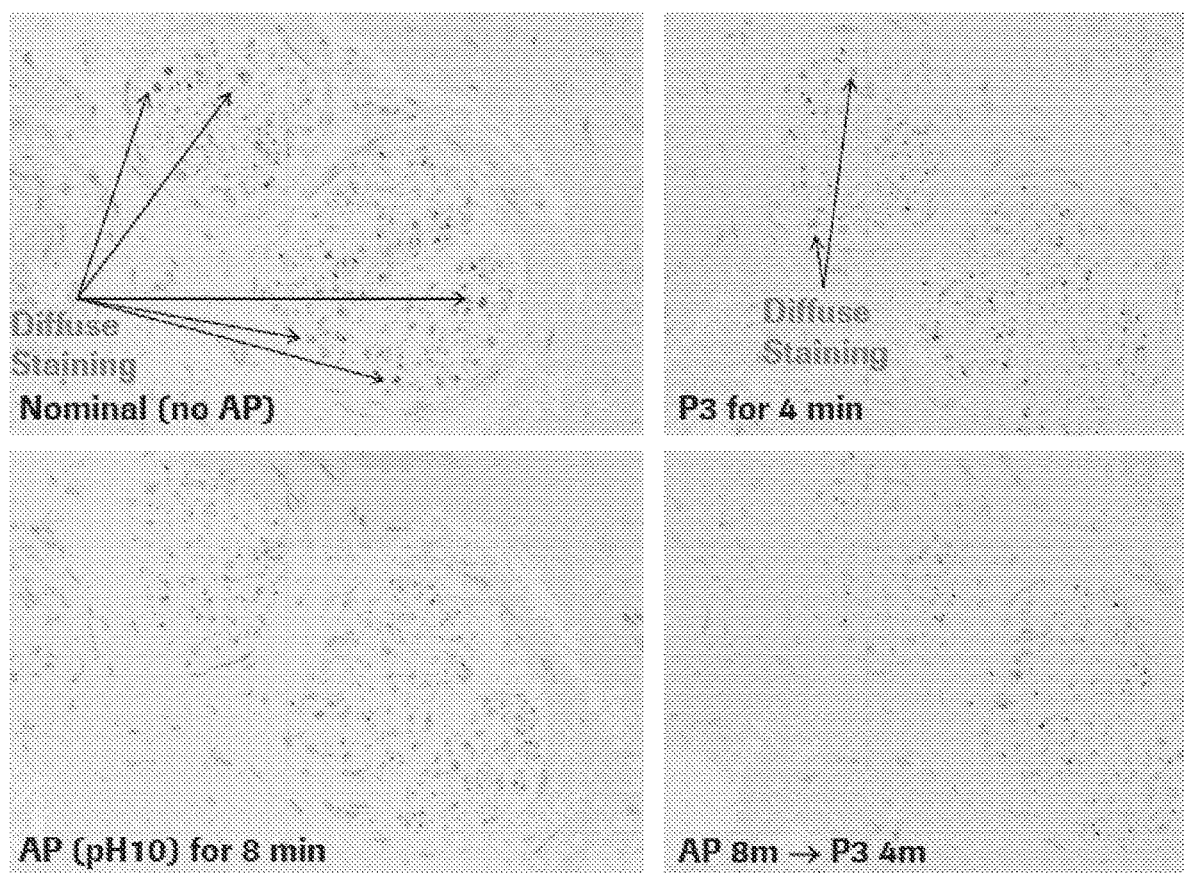
FIG. 25 shows that pretreatment with alkaline phosphatase followed by Protease 3 eliminates diffuse granular phosphorylated alpha-synuclein staining without significant loss of dense discrete staining.

The possibility of a more specific assay protocol that could completely eliminate the granular type of pS129-aSyn stain present in both PD and non-PD samples while preserving the discrete type of pS129-aSyn stain seen only in PD samples led to the search for an alternative method to remove granular pS129-aSyn stain. Once S129 residue becomes phosphorylated in aggregated aSyn, the attached phosphate group is more resistant to removal by protein phosphatases than phospho-S129 in soluble aSyn (Waxman & Giasson, *J Neuropathol Exp Neurol* 67(5):402-416 (May 2008)). The ability of mammalian alkaline phosphatase, a phosphatase with wide substrate specificity and shown to be active toward serine-phosphorylated protein, was tested to selectively remove granular pS129-aSyn stain in FFPE skin sections. Treatment of deparaffinized skin sections with purified endogenous (New England Biolabs, NEB) or recombinant (Roche) calf intestinal alkaline phosphatase at pH 9 or above prior to 7E2 antibody incubation prevented the appearance of granular pS129-aSyn stain without significantly impacting the level of discrete pS129-aSyn stain (see FIG. 23A and FIG. 23B). Interestingly, alkaline phosphatase treatment at pH 8 did result in decreased staining of discrete pS129-aSyn (see FIG. 24). Sequential treatments first with alkaline phosphatase to remove S129 phosphorylation in soluble aSyn followed by protease-mediated enhancement of antigen retrieval formed the basis of an alternative pS129-aSyn and PGP9.5 silver/yellow dual IHC assay protocol (Bumblebee Assay Protocol 2) with potentially higher specificity toward aggregated aSyn (see FIG. 25).

Figure 26:
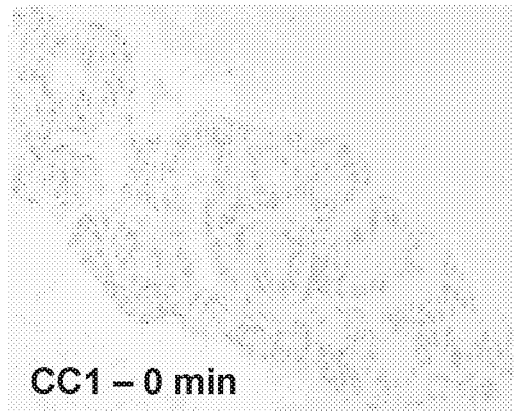
FIG. 26 shows that PGP9.5 detection using EPR4118 antibody (1.0 µg/mL) was enhanced with increasing durations (0 minutes—top panel; 16 minutes—middle panel; or 64 minutes—bottom panel) of antigen retrieval using ULTRA CC1 bulk solution.
Figure 26:
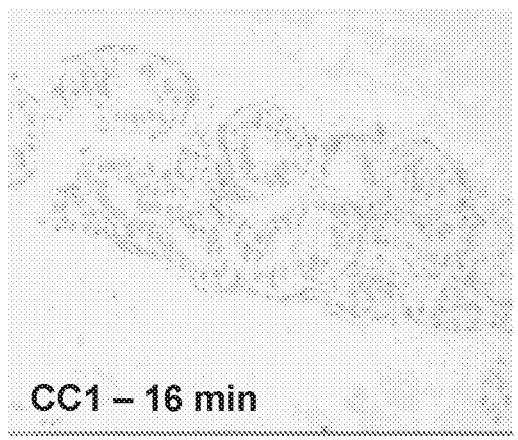
Figure 26:
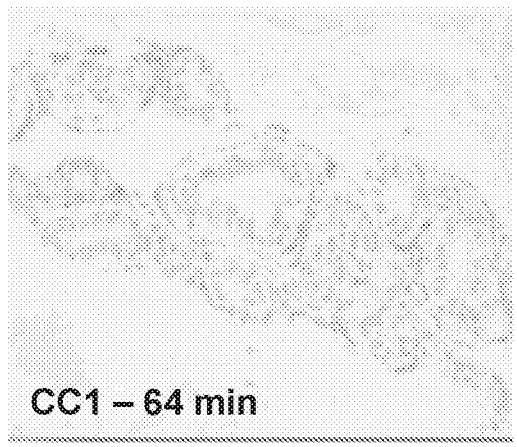
Figure 27:
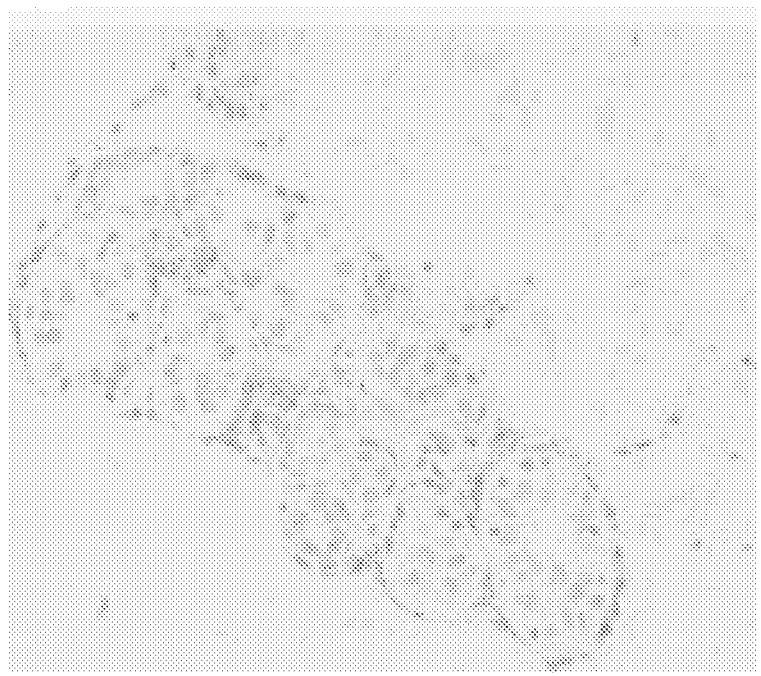
FIG. 27 shows that antigen retrieval with ULTRA CC2 for 16 minutes at 100° C. yielded enhancement in PGP9.5 staining using EPR4118 antibody.
Figure 28:
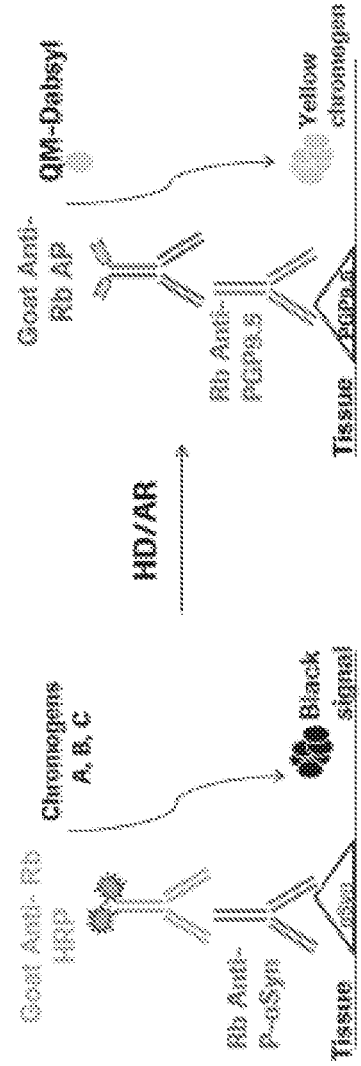
FIG. 28 shows an overview of two protocols for simultaneous detection of alpha-synuclein (aSyn) and PGP9.5 for Parkinson's disease characterization in skin samples.
Figure 28:
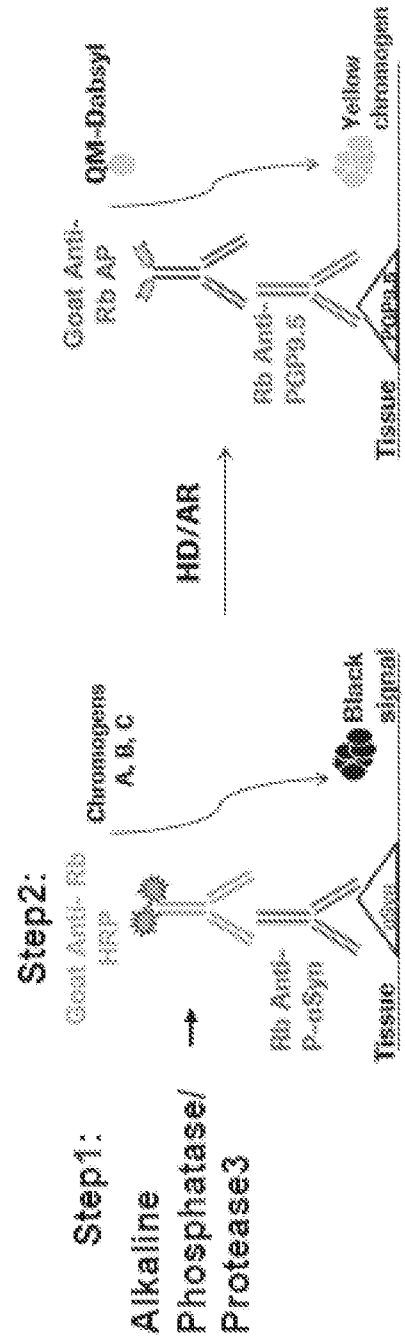

Unlike pS129-aSyn, PGP9.5 detection using EPR4118 antibody was enhanced with increasing durations of antigen retrieval using ULTRA CC1 bulk solution (see FIG. 26). Antigen retrieval with ULTRA CC2 yielded similar enhancement in PGP9.5 staining (see FIG. 27). Automated bright-field duplex IHC assays require sequential antibody incubation and chromogen deposition cycles as shown in FIG. 28. When both primary antibodies of the same species are used in a dual IHC assay protocol, a heat deactivation (HD) step in the form of ULTRA CC2 incubation at 100° C. is needed to remove the primary and secondary antibodies deposited in the first cycle to prevent potential cross-reaction of primary antibody from the first cycle with secondary antibody from the second cycle. Although a heat deactivation step is not necessary when the chromogen deposited in the first cycle is silver/black (yellow stain deposited on top of black stain remains black), treatment with CC2 for 16 minutes at 100° C. serves as antigen retrieval for PGP9.5 staining using EPR4118 antibody.

Example 6. Assay Reproducibility and Precision

The results of the experiments described in preceding sections led to two optimized protocols for the automated phospho-S129-alpha-synunclein and PGP9.5 silver/yellow dual IHC assay (Bumblebee Assay Protocol 1 and Protocol 2). As detailed in the section above, Protocol 1 contains no antigen retrieval steps for pS129-aSyn detection. Protocol 2 is identical to Protocol 1 in every aspect except the samples were treated with alkaline phosphatase followed by protease after deparaffinization and before 7E2 antibody incubation. The intra- and inter-run reproducibility of Bumblebee Assay Protocols 1 and 2 was assessed in scalp samples from three different subjects with PD. For intra-run reproducibility, 5 consecutively sectioned slides from each PD subject were stained using Protocol 1 or 2 as described in Methods and the numbers of nerve features with and without discrete pS129-aSyn were enumerated by a pathologist. The amount of skin nerve features with discrete pS129-aSyn stain as percentage of total nerve features in each PD subject were averaged from the 5 stained sections and shown in Table 11.

TABLE 11

Reproducibility (intra-run) of Protocol 1 and Protocol 2 in Skin Samples

| | Average % of nerve features with discrete p-aSyn staining | Std. Dev. | % CV |
|---|---|---|---|
| Protocol 1 | | | |
| Sample 1 | 91 | 2 | 2 |
| Sample 2 | 87 | 1 | 2 |
| Sample 3 | 87 | 2 | 3 |
| Protocol 2 | | | |
| Sample 1 | 76 | 4 | 5 |
| Sample 2 | 63 | 11 | 17 |
| Sample 3 | 91 | 2 | 3 |

For inter-run reproducibility, triplicate slides from each of three different subjects with PD were stained using Protocol 1 or 2 on three different instruments over non-consecutive days. Within a run, the three slides from each PD subject were consecutively cut sections; however, sections were not continuous between different runs. The average percentages of nerve features with discrete pS129-aSyn stain from each of the three runs are shown in Table 12.

TABLE 12

Reproducibility (inter-run) of Protocol 1 and Protocol 2 in Skin Samples

| | Average % of nerve features with Discrete p-aSyn staining | | | Average | Std. | % |
|---|---|---|---|---|---|---|
| | Run 1 | Run 2 | Run 3 | of 3 runs | Dev. | CV |
| Protocol 1 | | | | | | |
| Sample 1 | 91 | 87 | 89 | 89 | 3 | 3 |
| Sample 2 | 87 | 88 | 82 | 86 | 3 | 4 |
| Sample 3 | 87 | 75 | 69* | 77 | 9 | 12 |
| Protocol 2 | | | | | | |
| Sample 1 | 76 | 77 | 81 | 78 | 2 | 3 |
| Sample 2 | 63 | 61 | 50 | 58 | 7 | 12 |
| Sample 3 | 91 | 87 | 65* | 81 | 14 | 17 |

*slides used in Run 3 were more than 20 cuts away from those in Run 1 and contained half as many features with nerves.

In cases where CV exceeded 15% the most likely source of variation is the difference in numbers of nerve features between consecutively sectioned slides. A study of the continuity of nerve features across consecutively sectioned slides has concluded that a difference of 10% to 20% in number of nerve features could be attributed to slide-to-slide variation in feature distribution over 5 to 10 4-μm sections (see Table 13). The intensity of PGP9.5 stained with yellow DABSYL chromogen was 2.5 across all slides stained for assay reproducibility studies.

TABLE 13

Continuity of nerve features in skin tissue

| | No | Yes | All | % Concordant | % Continuous w/Ref |
|---|---|---|---|---|---|
| Presence/absence concordance of all nerve-containing features in 20 cases | | | | | |
| Row: Ref  No | 23 | 1 | 24 | | |
| Column: Ref + 1  Yes | 4 | 130 | 134 | | 97% |
| All | 27 | 131 | 158 | 97% | |
| Row: Ref  No | 7 | 17 | 24 | | |
| Column: Ref + 5  Yes | 15 | 119 | 134 | | 89% |
| All | 22 | 136 | 158 | 79% | |
| Row: Ref  No | 2 | 22 | 24 | | |
| Column: Ref + 10  Yes | 26 | 108 | 134 | | 81% |
| All | 28 | 130 | 158 | 70% | |
| Presence/absence concordance of transverse nerve bundles in 20 cases | | | | | |
| Row: Ref  No | 9 | 1 | 10 | | |
| Column: Ref + 1  Yes | 3 | 68 | 71 | | 96% |
| All | 12 | 69 | 81 | 95% | |
| Row: Ref  No | 4 | 6 | 10 | | |
| Column : Ref + 5  Yes | 8 | 63 | 71 | | 89% |
| All | 12 | 69 | 81 | 83% | |
| Row: Ref  No | 0 | 10 | 10 | | |
| Column: Ref + 10  Yes | 15 | 56 | 71 | | 79% |
| All | 15 | 66 | 81 | 69% | |
| Presence/absence concordance of sagittal nerve bundles in 20 cases | | | | | |
| Row: Ref  No | 6 | 0 | 6 | | |
| Column: Ref + 1  Yes | 0 | 14 | 14 | | 100% |
| All | 6 | 14 | 20 | 100% | |
| Row: Ref  No | 1 | 5 | 6 | | |
| Column: Ref + 5  Yes | 3 | 11 | 14 | | 79% |
| All | 4 | 16 | 20 | 60% | |
| Row: Ref  No | 2 | 4 | 6 | | |
| Column: Ref + 10  Yes | 4 | 10 | 14 | | 71% |
| All | 6 | 14 | 20 | 60% | |
| Presence/absence concordance of smooth muscle in 20 cases | | | | | |
| Row: Ref  No | 4 | 0 | 4 | | |
| Column: Ref + 1  Yes | 1 | 10 | 11 | | 91% |
| All | 5 | 10 | 15 | 93% | |
| Row: Ref  No | 2 | 2 | 4 | | |
| Column: Ref + 5  Yes | 0 | 11 | 11 | | 100% |
| All | 2 | 13 | 15 | 87% | |
| Row: Ref  No | 0 | 4 | 4 | | |
| Column: Ref + 10  Yes | 1 | 10 | 11 | | 91% |
| All | 1 | 14 | 15 | 87% | |
| Presence/absence concordance of nerves surrounding glands in 20 cases | | | | | |
| Row: Ref  No | 3 | 0 | 3 | | |
| Column: Ref + 1  Yes | 0 | 16 | 16 | | 100% |
| All | 3 | 16 | 19 | 100%% | |
| Row: Ref  No | 0 | 3 | 3 | | |
| Column: Ref + 5  Yes | 3 | 13 | 16 | | 81% |
| All | 3 | 16 | 19 | 68% | |
| Row: Ref  No | 0 | 3 | 3 | | |
| Column: Ref + 10  Yes | 3 | 13 | 16 | | 81% |
| All | 3 | 16 | 19 | 68% | |
| Presence/absence concordance of nerves surrounding vessels in 20 cases | | | | | |
| Row: Ref  No | 1 | 0 | 1 | | |
| Column: Ref + 1  Yes | 0 | 16 | 16 | | 100% |
| All | 1 | 16 | 17 | 100% | |
| Row: Ref  No | 0 | 1 | 1 | | |
| Column: Ref + 5  Yes | 1 | 15 | 16 | | 94% |
| All | 1 | 16 | 17 | 88% | |
| Row: Ref  No | 0 | 1 | 1 | | |
| Column: Ref + 10  Yes | 2 | 14 | 16 | | 88% |
| All | 2 | 15 | 17 | 82% | |

Experiments were performed to analyze the precision of pS129-aSyn and PGP9.5 silver/yellow dual IHC assay, and scored on percent of features staining in each section (~25 features). To analyze inter-run precision, three runs of three slides each on the same instrument were tested at least two days apart (Protocol 1 CV: 2.77% discrete, 5.13% diffuse; Protocol 2 CV: 3.99% discrete, 0.00% diffuse). To analyze inter-instrument precision, two additional runs of three slides each on a new instrument were performed and compared to first run from first instrument (Protocol 1 CV: 3.22% discrete, 11.86% diffuse; Protocol 2 CV: 3.45% discrete, 0.00% diffuse). In summary, the CVs of both inter-run and inter-instrument precision for both Bumblebee Assay Protocol 1 and 2 were below the 15% threshold needed to qualify for transfer.

Example 7. Assay Validation—Scalp Samples

Figure 29:
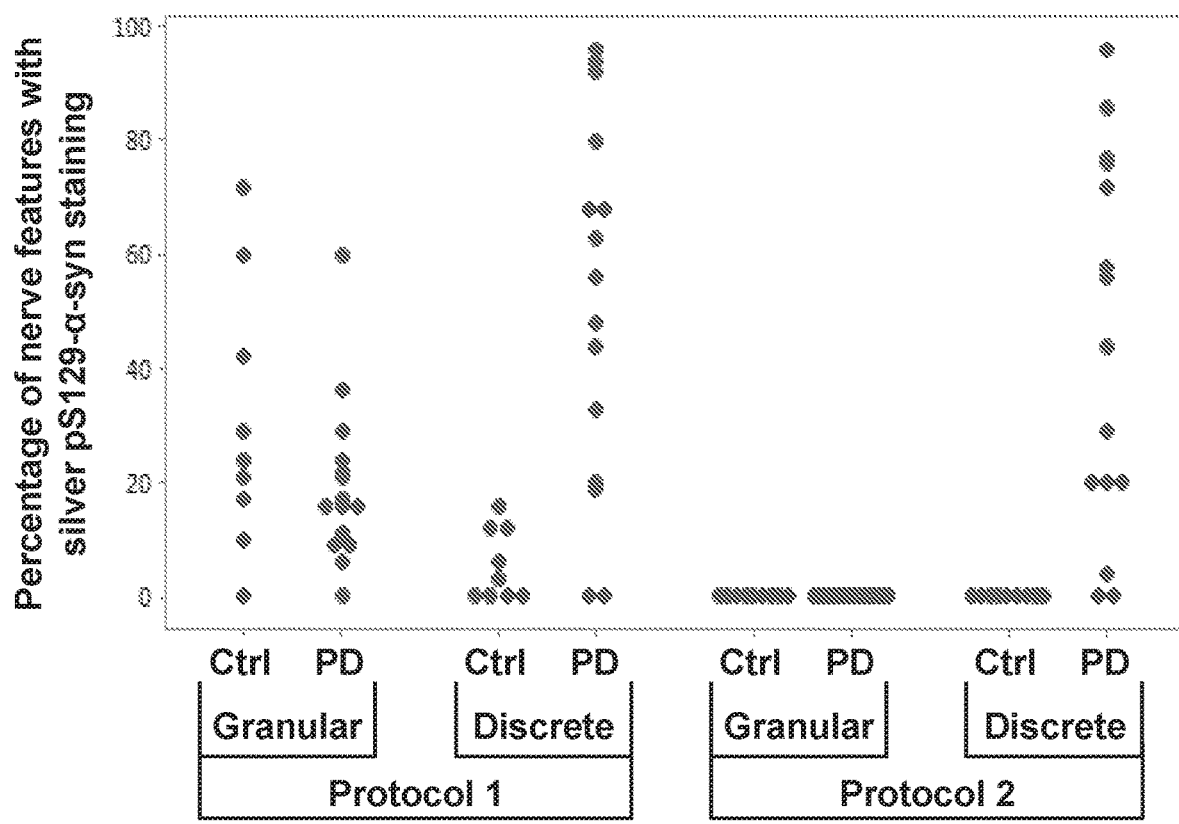
FIG. 29 shows individual value plot showing percentages of nerve features containing phosphorylated S129 alpha-synuclein staining in 4 µm sections of scalp biopsy from subjects with PD and normal, non-PD subjects. A cohort of 15 PD and 9 non-PD control scalp skin samples were stained with two different phosphorylated S129 alpha-synuclein and PGP9.5 silver/yellow dual IHC assay protocols: without Ree (Protocol 1) and with (Protocol 2) protease/phosphatase.

During optimization of phosphorylated-alpha-synuclein and PGP9.5 silver/yellow dual IHC assay (nicknamed Bumblebee Assay) it was observed that smooth discrete phosphorylated-alpha-synuclein staining pattern was exclusively associated with the small cohort of PD scalp samples used for feasibility testing. In order to determine if this trend is extended to a larger cohort of scalp samples from PD and non-PD subjects, scalp sections from 15 PD and 9 non-PD subjects were stained using both Protocol 1 and Protocol 2 of pS129-aSyn and PGP9.5 silver/yellow dual IHC assay (Bumblebee Assay). In addition, sections from a subset of this cohort containing 10 PD and 4 non-PD scalp samples were stained using the automated protease-resistant aSyn DAB IHC assay (pRED/Prothena Assay Protocol). As shown in FIG. 29, 13 of 15 samples (87%) from PD subjects exhibited pS129-aSyn of the discrete type following staining using either Protocol 1 or Protocol 2 of Bumblebee Assay. Of the 9 non-PD scalp samples, 5 (56%) exhibited discrete pS129-aSyn staining using Bumblebee Protocol 1. In contrast, none of the 9 non-PD scalp samples exhibited discrete pS129-aSyn staining using Bumblebee Protocol 2 with mild protease and phosphatase treatments. Diffuse granular type of pS129-aSyn staining was only observed using Protocol 1 but not using Protocol 2.

Figure 30A:
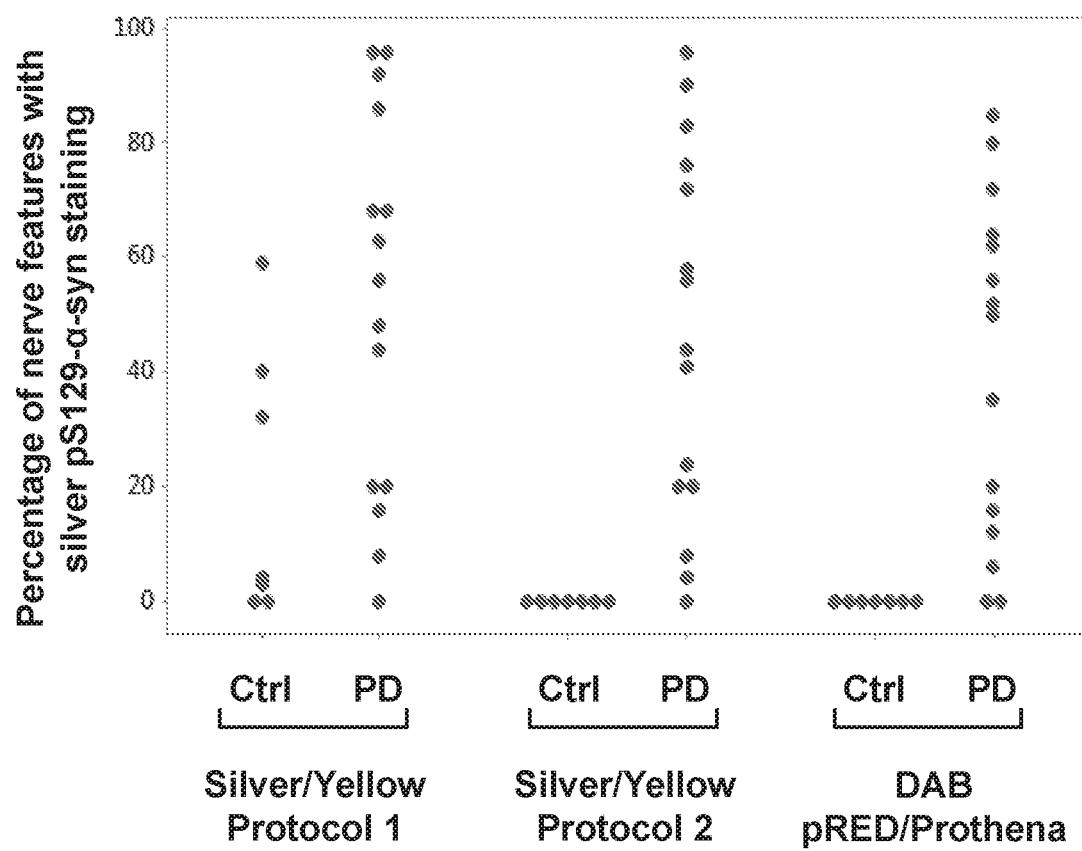
FIG. 30A shows individual value plots showing percentages of nerve features with phosphorylated S129 alpha-synuclein stain of discrete types in 4 µm sections of scalp biopsy from subjects with PD and normal, non-PD subjects. A cohort of 15 PD and 7 non-PD control scalp skin samples were stained with phosphorylated S129 alpha-synuclein and PGP9.5 silver/yellow dual IHC assay protocols without (Protocol 1) and with (Protocol 2) protease/phosphatase and also with protease-resistant alpha-synuclein DAB IHC assay developed by pRED/Prothena.
Figure 30B:
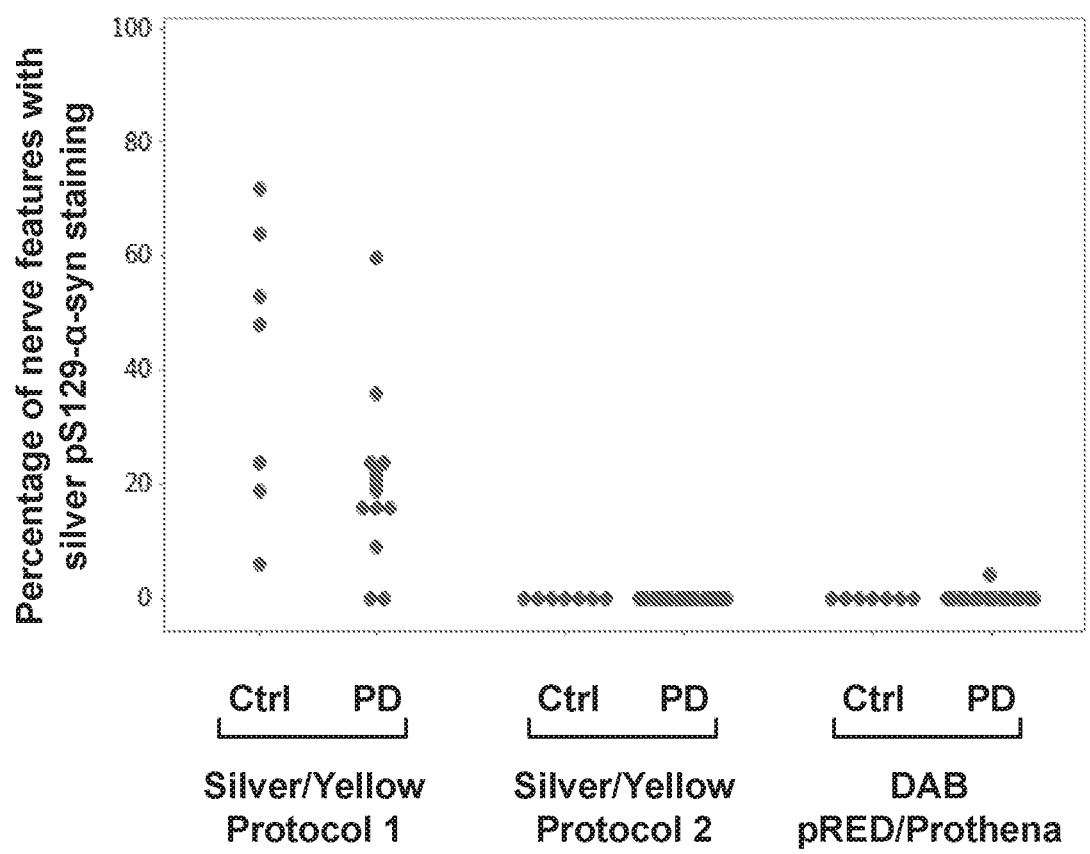
FIG. 30B shows individual value plots showing percentages of nerve features with phosphorylated S129 alpha-synuclein stain of diffuse granular types in 4 µm sections of scalp biopsy from subjects with PD and normal, non-PD subjects. A cohort of 15 PD and 7 non-PD control scalp skin samples were stained with phosphorylated S129 alpha-synuclein and PGP9.5 silver/yellow dual IHC assay protocols without (Protocol 1) and with (Protocol 2) protease/phosphatase and also with protease-resistant alpha-synuclein DAB IHC assay developed by pRED/Prothena.

In the subset of subjects in which results from Bumblebee Assay Protocol 1, Bumblebee Assay Protocol 2, and pRED/Prothena Assay Protocol were available, discrete aSyn signals were observed, respectively, in 14, 14, and 13 PD scalp samples out of 15 stained (see FIG. 30A). Of the 4 non-PD scalp samples stained using all three protocols, discrete aSyn stain was not observed with Bumblebee Protocol 2 or pRED/Prothena Protocol (see FIG. 30A). Diffuse granular aSyn stain was observed in both PD and non-PD scalp samples using Bumblebee Protocol 1 (see FIG. 30B). These results suggest that detection of aggregated aSyn using a combination of highly sensitive detection chemistry (metallic silver precipitation) and antibody against pS129-aSyn is likely to have similar sensitivity as an approach based on antibody against modified or un-modified aSyn combined with protease removal of non-aggregated aSyn.

Example 8. Assay Validation—Abdomen Skin Samples

Figure 31:
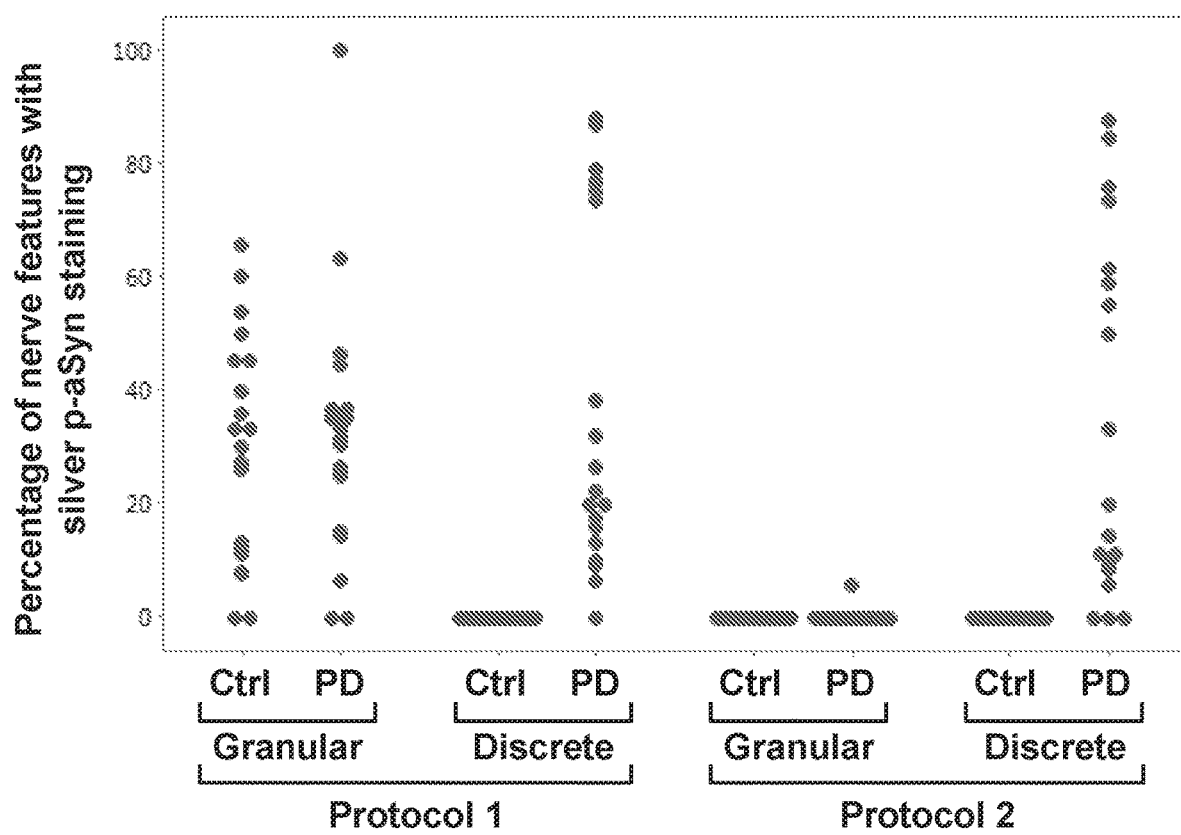
FIG. 31 shows individual value plot showing percentages of nerve features containing phosphorylated S129 alpha-synuclein staining in 4 µm sections of abdomen skin biopsy from subjects with PD and normal, non-PD subjects. A cohort of 20 PD and 20 non-PD control abdomen skin biopsy samples were stained with two different phosphorylated S129 alpha-synuclein and PGP9.5 silver/yellow dual IHC assay protocols: without (Protocol 1) and with (Protocol 2) protease/phosphatase.
Figure 32A:
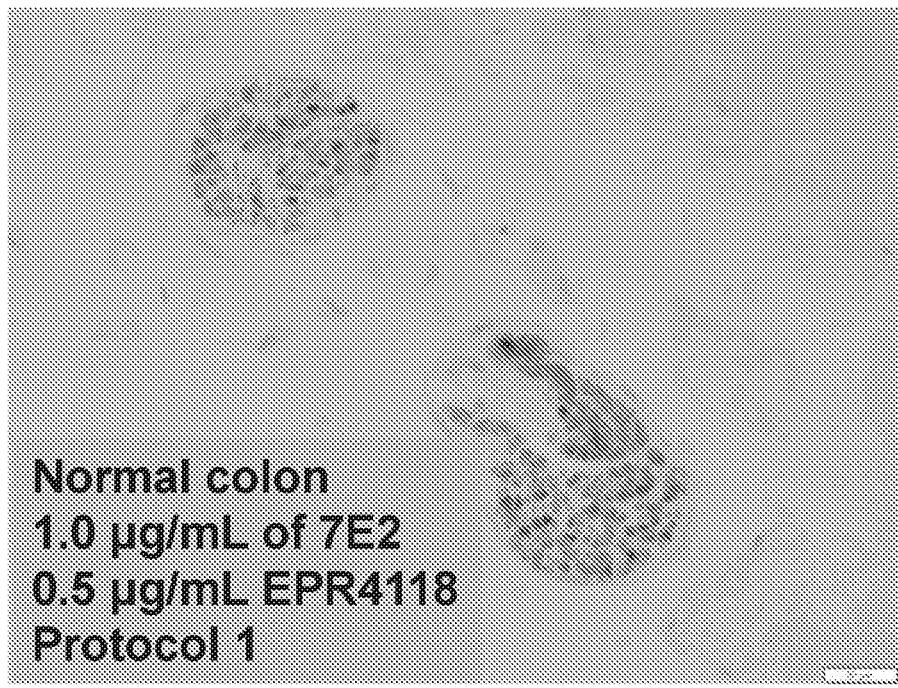
FIG. 32A shows the difference in staining of normal colon tissue by Protocol 1 (top panel) compared to Protocol 2 (bottom panel). Scale bar is 50 µm.
Figure 32A:
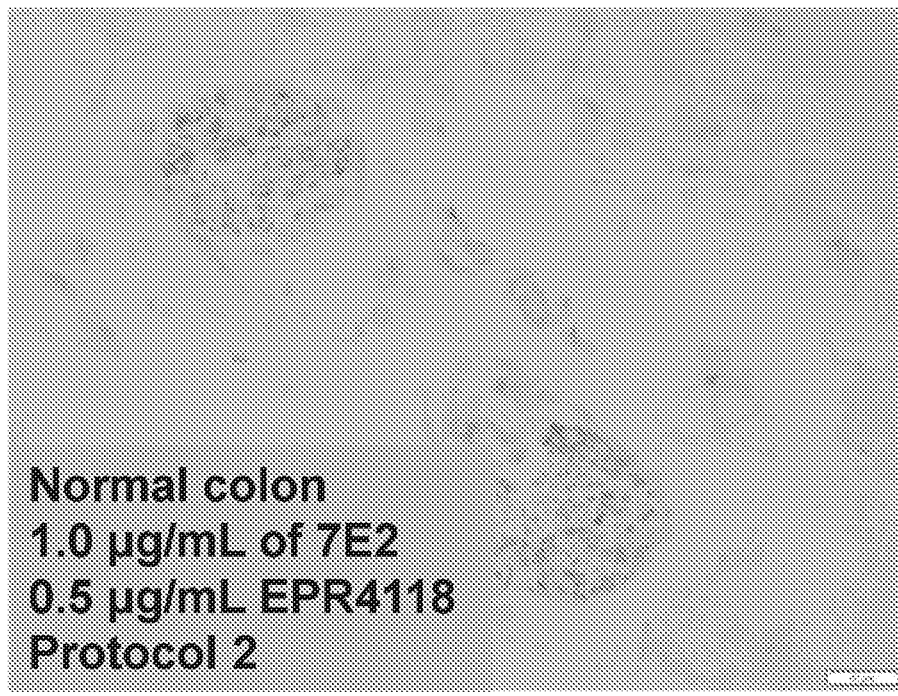
Figure 32B:
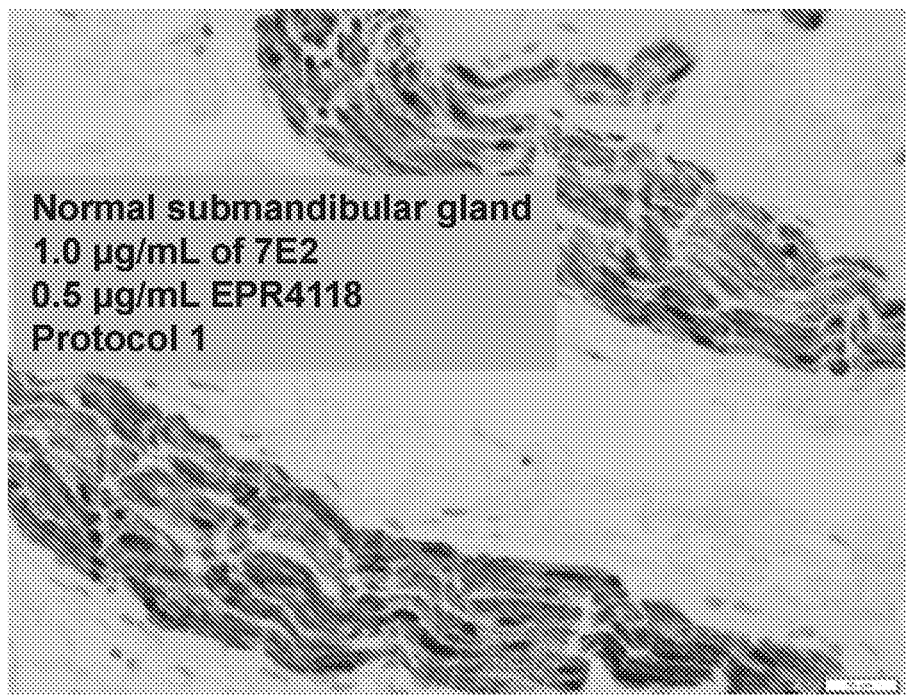
FIG. 32B shows the difference in staining of normal colon tissue by Protocol 1 (top panel) compared to Protocol 2 (bottom panel). Scale bar is 50 µm.
Figure 32B:
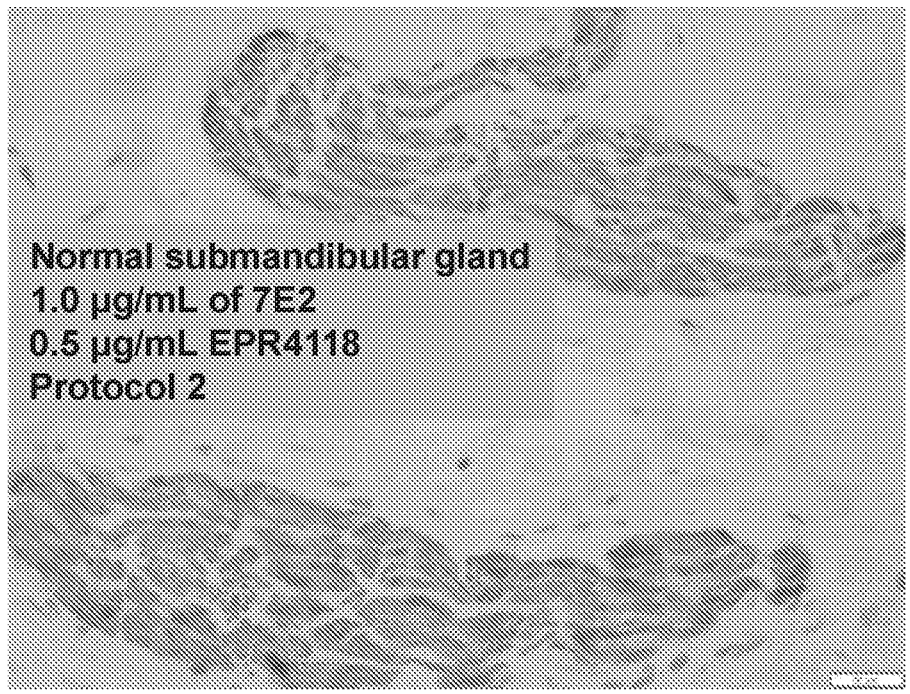

To further assess the sensitivity and specificity of phospho-aSyn and PGP9.5 silver/yellow dual IHC assay, abdomen area skin samples from a cohort of 20 PD and 20 non-PD control subjects were stained using Bumblebee Assay Protocols 1 and 2. The results of the analysis are shown in FIG. 31. Of the 20 PD abdomen skin samples stained using Bumblebee Assay Protocols 1 and 2, discrete pS129-aSyn stain was observed in, respectively, 19 and 17 samples. In contrast, none of the 20 non-PD abdomen skin samples exhibited any discrete pS129-aSyn signal. Also shown in FIG. 31, diffuse granular pS129-aSyn staining was present in most of the PD and non-PD abdomen skin samples stained using Bumblebee Assay Protocol 1 and at a low level in 1 PD sample stained using Bumblebee Assay Protocol 2. These results showed a high degree of association between presence of discrete pS129-aSyn staining and PD clinical status in the expanded cohort of abdomen skin from 20 PD and 20 non-PD subjects (Pearson chi-square=36.2 and 29.6 for Bumblebee Assay Protocols 1 and 2 respectively, P-Values<0.0001 for both protocols).

A cohort of 4 PD and 4 non-PD abdomen skin samples were available in FFPE block format and for testing using both Bumblebee Assay protocols and also the 5C12 antibody- and Protease 1-based pRED/Prothena Assay Protocol. Results of such analysis are shown in the Table 14 below.

TABLE 14

Percentage of nerve features with discrete pS129-aSyn

| Subject # | Subject Status | Bumblebee Assay Protocol 1 | Bumblebee Assay Protocol 2 | pRED/Prothena Protocol |
|---|---|---|---|---|
| 1 | Ctrl | 0% | 0% | 0% |
| 2 | Ctrl | 0% | 0% | 3% |
| 3 | Ctrl | 0% | 0% | 0% |
| 4 | Ctrl | 2% | 0% | 0% |
| 5 | PD | 63% | 52% | 22% |
| 6 | PD | 25% | 22% | 24% |
| 7 | PD | 54% | 58% | 33% |
| 8 | PD | 15% | 23% | 3% |

Three of the four PD abdomen skin samples that were tested using the pRED/Prothena Protocol exhibited decreases in percentage of nerve features with discrete pS129-aSyn compared with those tested using either of the Bumblebee Assay protocols. This was not observed in scalp samples stained using all three protocols (FIG. 30). A likely explanation for the discrepancy is that the tissue morphology of the abdomen skin samples was more prone to degradation by Protease 1 treatment than that of the scalp samples. The cause for the apparent differential sensitivity to Protease 1 treatment is unclear at the present. In addition to anatomical site, the abdomen slides had been cut closer to the time they were stained than the scalp slides. In general, it was observed that slides that have been cut and left at room temperature for long period of time (>30 days) before staining are less susceptible to protease-induced morphology degradation (data not shown).

Figure 33A:
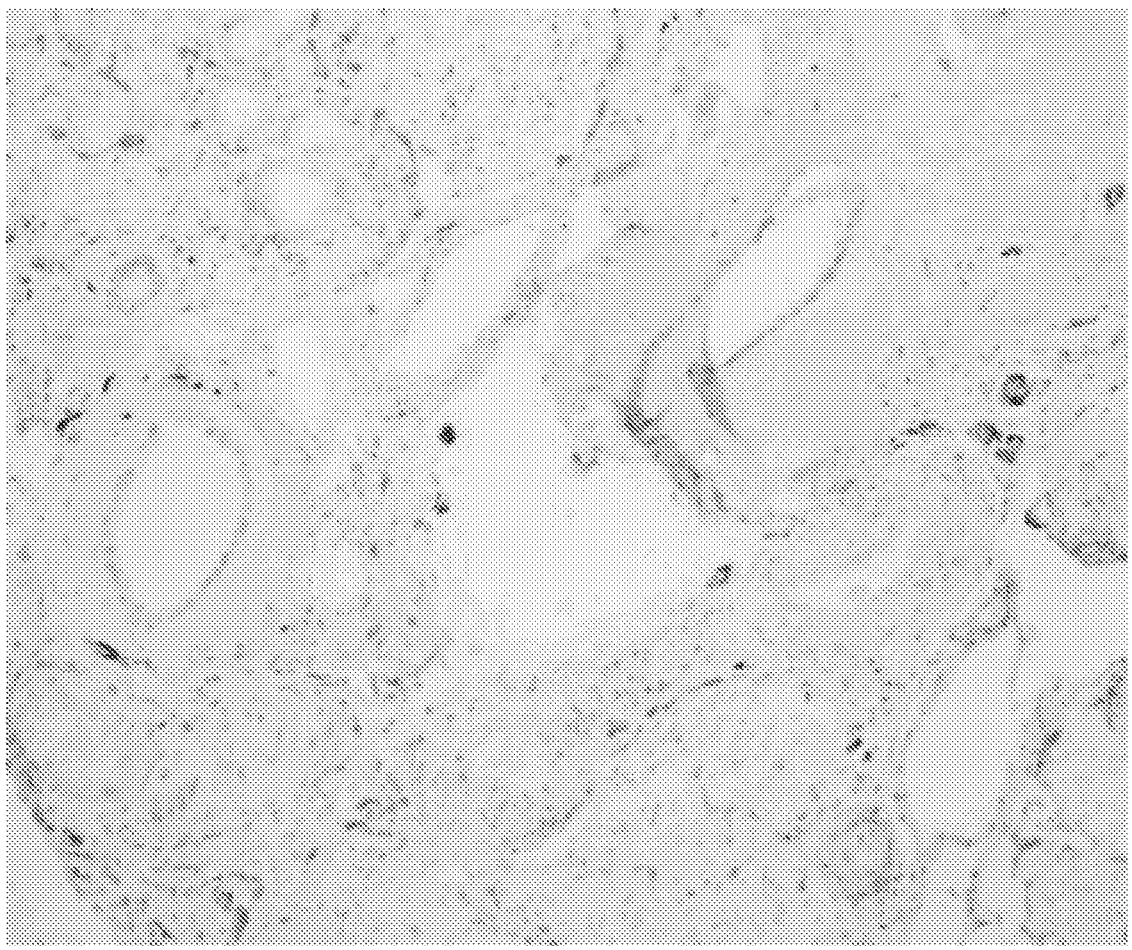
FIG. 33A shows exemplary staining of submandibular gland tissue from a subject with PD using Protocol 2. Images taken at 10× magnification.
Figure 33B:
FIG. 33B shows exemplary staining of sigmoid colon tissue from a subject with PD using Protocol 2. Images taken at 20× magnification.
Figure 33C:
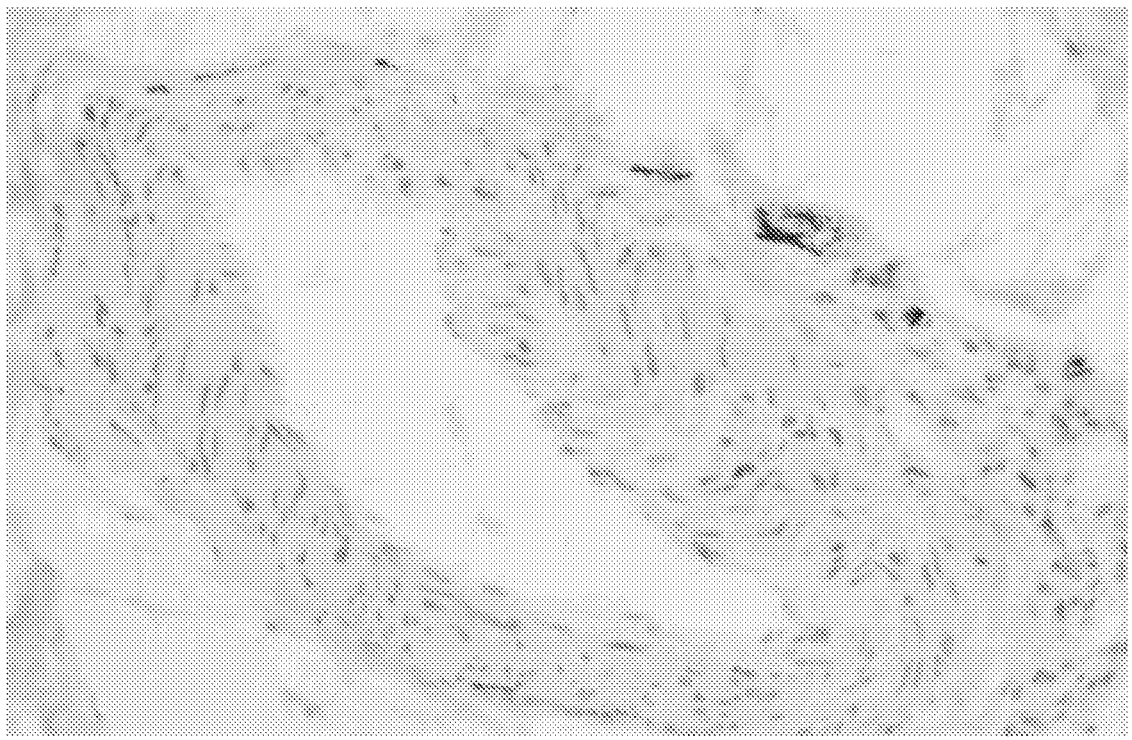
FIG. 33C shows exemplary staining of scalp tissue from a subject with PD using Protocol 2. Images taken at 20× magnification.

Example 9. Assay Validation—Pre-S4 Scalp, Colon, and Submandibular Gland Samples In addition to skin, colon and submandibular gland (SMG) are highly innervated and could be biopsy sites for detection of aggregated alpha-synuclein. Duplicate scalp, colon, and SMG samples from 3 PD and 3 non-PD subjects taken at the time of autopsy were stained using Bumblebee Assay Protocol 2. Protocol 1 was not employed because a previous study of normal colon and SMG samples showed Protocol 1 generated heavy discrete phosphorylated alpha-synuclein stain that could be removed by protease and phosphatase treatment using Protocol 2 (see FIG. 32A and FIG. 32B). Typical images of discrete phosphorylated alpha-synuclein stain in the three different tissue sites are shown in (see FIG. 33A-FIG. 33C). The stained slides were evaluated blindly by three independent readers (data not shown). Even though one of the readers used a different scoring method than the other two, there was total agreement in complete segregation of PD from non-PD samples based on presence of discrete phosphorylated alpha-synuclein stain using Bumblebee Protocol 2. Specificity and sensitivity were both 100%.

Example 10. Assay Validation—Skin Biopsy Samples

Figure 34:
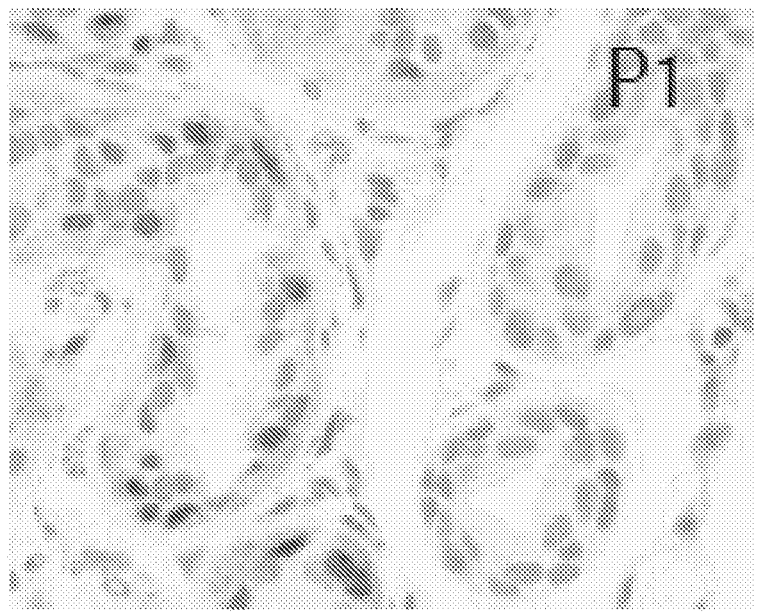
FIG. 34 shows that in pediatric skin tissue Protocol 1 (P1; top panel) generated heavy phosphorylated alpha-synuclein silver stain with discrete morphology that was absent with Protocol 2 (P2; bottom panel).
Figure 34:
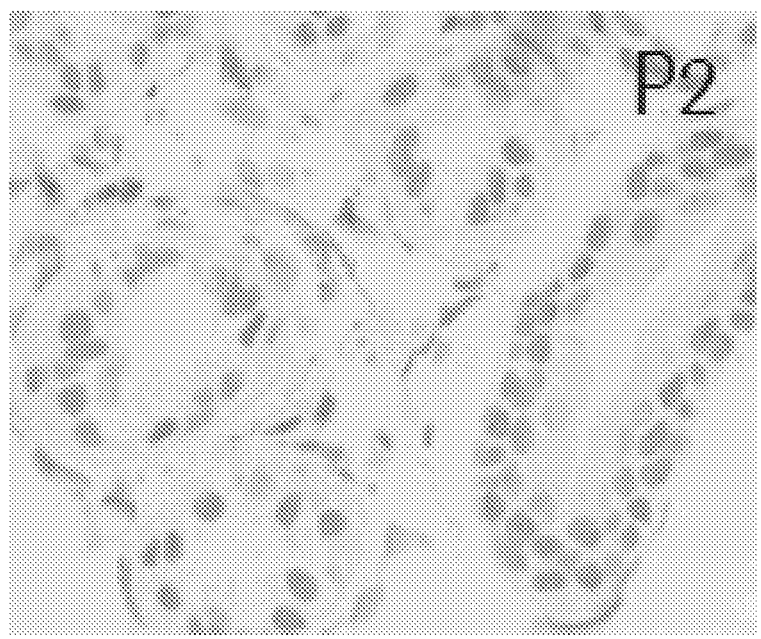

The BSHRI scalp and abdomen skin samples used for assay development and validation were obtained during autopsies. To assess the potential utility of the phosphorylated S129 alpha syncuclein and PGP9.5 silver/yellow dual IHC assay for diagnostic applications, FFPE sections of skin punch biopsies obtained during clinical visits from subjects with and without diagnosed PD symptoms were stained using both Bumblebee Assay Protocols 1 and 2. Tissue sections from a total of 72 FFPE blocks from 36 subjects were stained as duplicate blocks from each subject were available. Stained slides were reviewed by pathologists blinded to the clinical status of the subjects. As the samples were small punch biopsies of the skin, numbers of nerve features available per slide were limited (around 5 to 10). As a result, quantitative measurements in the form of percentage of silver-stained nerve features were not made. A slide was considered positive for phosphorylated-aSyn if there were discrete silver stains that were clearly not granular and of sufficient size to distinguish them from background silver dusting. If sections from one of the duplicate blocks were positive for phosphorylated-aSyn stain, the subject was considered positive overall. As in pediatric skin biopsy samples, Bumblebee Protocol 1 generated heavy phosphorylated-aSyn silver stain with discrete morphology that was absent with Protocol 2 (see FIG. 34). This resulted in 93% of the 15 PD and 50% of the 16 control subjects (69% of all 36 subjects including 5 cases of atypical parkinsonism) with positive discrete phosphorylated-aSyn stain using Protocol 1. With Protocol 2, 60% of the 15 PD and 6% of the 16 control subjects (31% of all 36 subjects) exhibited discrete phosphorylated-aSyn signal (see Tables 15 and 16). The unblinded results of each individual tissue block and corresponding PD status for all 36 subjects are shown in Table 16. Chi-square analysis of the results from all 36 subjects demonstrated a highly significant correlation between presence of discrete phosphorylated-aSyn signal and designation of PD status based on clinical symptoms (Pearson Chi-Square=10.506, DF=1, P-Value=0.001). The association remains significant when the 5 subjects with atypical parkinsonism are excluded from analysis (Pearson Chi-Square=10.236, DF=1, P-Value=0.001).

TABLE 15

Phosphu-Ser129 alpha-synuclein (pS129-aSyn) staining in skin tissue of non-PD subjects using Protocol 1 and Protocol 2

|  | Protocol 1 | Protocol 2 |
|---|---|---|
| # (and %) of subjects with either Block A, or Block B, or both Block A and Block B, showing discrete pS129-aSyn stain | 25 (69%)* | 11 (31%)*+ |
| # (and %) of subjects with either Block A, or Block B, or both Block A and Block B, showing granular pS129-aSyn stain | 36 (100%)** | 2 (6%)++ |

*Presence of discrete pS129-aSyn using Protocol 1 is defined as having significant amount of discrete stain, particularly around glands, rather than any discrete stain. Definition of "significant" is purely subjective as it is based on qualitative impression of the reader. In contrast, presence of discrete pS129-aSyn using Protocol 2 is defined as having any discrete stain that is specific and not background.
**35 of 36 subjects had granular pS129-aSyn stain in both Block A and Block B using Protocol 1.
+Of the 11 subjects with discrete pS129-aSyn stain, 5 had discrete stain in both Block A and Block B.
++No subject had granular pS129-aSyn stain in both Block A and Block B using Protocol 2.

TABLE 16

Unblinded phospho-Ser129 alpha-synuclein (pS129-aSyn) staining in skin tissue of non-PD subjects using Protocol 1 and Protocol 2

|  | Presence of Discrete aSyn Staining Protocol 1 | Presence of Discrete aSyn Staining Protocol 2 |
|---|---|---|
| PD (n = 15) | 14 (93%) | 9 (60%) |
| Control (n = 16) | 8 (50%) | 1 (6%) |

The results demonstrate an automated dual phosphorylated-aSyn and PGP9.5 immunohistochemical assay with high sensitivity and specificity for distinguishing subjects with PD from non-PD control subjects based on presence of the phosphorylated-aSyn stain of the discrete type in skin biopsies. The morphological appearance of discrete phosphorylated-aSyn stain and its resistance to protease and phosphatase treatments are consistent with aggregated aSyn. This assay may have potential value in identifying subjects with PD and/or candidates for therapeutic treatments targeting aggregation of aSyn.

As used herein, the singular forms "a," "an", and "the" include plural referents unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

The foregoing is provided for exemplification purposes only and are not intended to limit the scope of the disclosure described in broad terms above. All references cited in this disclosure are incorporated herein by reference.

Although various specific embodiments of the present disclosure have been described herein, it is to be understood that the disclosure is not limited to those precise embodiments and that various changes or modifications can be affected therein by one skilled in the art without departing from the scope and spirit of the disclosure.

The examples given above are merely illustrative and are not meant to be an exhaustive list of all possible embodiments, applications or modifications of the disclosure. Thus, various modifications and variations of the described methods and systems of the disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure which are obvious to those skilled in molecular biology, immunology, chemistry, biochemistry or in the relevant fields are intended to be within the scope of the appended claims.

It is understood that the disclosure is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the disclosure.

The embodiments of the disclosure and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32, etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Particular methods, devices, and materials are described, although any methods and materials similar or equivalent to those described herein can be used in the practice or testing of the disclosure. The disclosures of all references and publications cited herein are expressly incorporated by reference in their entireties to the same extent as if each were incorporated by reference individually.

What is claimed is:

1. A method for determining whether a subject has Parkinson's Disease (PD), the method comprising:
   (a) contacting a biological sample comprising at least one nerve feature from the subject with a primary antibody capable of binding phosphorylated alpha-synuclein; wherein the primary antibody comprises complementarity determining regions (CDRs) having the following amino acid sequences:

```
   CDR1 VL
                                       (SEQ ID NO: 2)
   QSVYNNNN,

CDR2 VL
                                       (SEQ ID NO: 3)
   KASKVAS,

CDR3 VL
                                       (SEQ ID NO: 4)
   LGGYSGDIYT,

CDR4 VH
                                       (SEQ ID NO: 6)
   GFTISSYHMS,

CDR5 VH
                                       (SEQ ID NO: 7)
   ISTSGNI,
   and CDR6 VH
                                       (SEQ ID NO: 8)
   ARLGIATGYSF;
   ```

(b) detecting whether the primary antibody capable of binding phosphorylated alpha-synuclein localizes within the nerve feature of the biological sample; and
   (c) determining the subject has PD when the primary antibody capable of binding phosphorylated alpha-synuclein localizes within the nerve feature.

2. The method of claim 1, wherein the sample comprises a tissue sample.

3. The method of claim 1, wherein the nerve feature comprises:
   (a) a nerve cell;
   (b) a former nerve cell; or
   (c) is adjacent to a nerve cell.

4. The method of claim 1, wherein the sample is contacted with at least one protease before being contacted with the primary antibody capable of binding phosphorylated alpha-synuclein.

5. The method of claim 4, further comprising contacting the sample with at least one phosphatase.

6. The method of claim 1, further comprising contacting the biological sample from the subject with a primary antibody capable of binding the nerve feature.

7. The method of claim 6, wherein the primary antibody capable of binding to the nerve feature is selected from an antibody capable of binding a protein selected from the group consisting of: ubiquitin C-terminal hydrolase L1, RNA binding fox-1 homolog 3, microtubule associated protein 2, 160 kDa neurofilament medium 200 kDa neurofilament heavy, synaptophysin, and discs large MAGUK scaffold protein 4.

8. The method of claim 1, wherein the detecting comprises histochemical analysis.

9. The method of claim 1, wherein the sample is fixed.

10. The method of claim 9, wherein the sample is a formalin fixed, paraffin embedded (FFPE) sample.

11. The method of claim 1, wherein the sample is a frozen sample.

12. The method of claim 1, wherein the sample comprises a section of the nerve feature.

13. The method of claim 1, wherein the sample is selected from the group consisting of skin tissue, colon tissue, and submandibular gland.

14. The method of claim 6, wherein the primary antibody capable of binding phosphorylated alpha-synuclein and the primary antibody capable of binding to the nerve feature are from the same host species, wherein the host species is a mouse or a rabbit.

15. The method of claim 1, wherein step (a) further comprises contacting the sample with a first secondary antibody having a first label conjugated thereto, wherein the first secondary antibody is immunoreactive with the primary antibody capable of binding phosphorylated alpha-synuclein.

16. The method of claim 15, comprising contacting the sample with a set of reagents reactive with the first label of the first secondary antibody to generate a first detectable signal in proximity to phosphorylated alpha-synuclein in the sample.

17. The method of claim 6, wherein before contacting the sample with the primary antibody capable of binding to the nerve feature, the method comprises denaturing the immunocomplexes in the sample.

18. The method of claim 17, wherein the method further comprises contacting the sample with a second secondary antibody having a second label conjugated thereto, wherein the second secondary antibody is immunoreactive with the primary antibody capable of binding the nerve feature.

19. The method of claim 18, comprising contacting the sample with a set of reagents reactive with the second label of the second secondary antibody to generate a second detectable signal in proximity to the nerve feature in the sample.

20. The method of claim 19, wherein the first detectable signal and the second detectable signal are different.

21. The method of claim 20, wherein the first detectable signal is silver stain.

22. The method of claim 1, wherein the subject is suspected of having PD.

23. The method of claim 1, wherein the antibody capable of binding phosphorylated alpha-synuclein comprises a light chain comprising SEQ ID NO: 01 and the heavy chain comprising SEQ ID NO: 05.

24. The method of claim 7, wherein the primary antibody capable of binding the nerve feature is one of monoclonal antibody clone EPR4118 from Abcam, monoclonal antibody clone 13C/13C4 from Abcam, or polyclonal antibody from Cell Marque™ with RTD PIN 760-4434.

25. The method of claim 24, wherein the primary antibody capable of binding the nerve feature is monoclonal antibody clone EPR4118 from Abcam (PIN ab108986).

26. A kit comprising:
(a) a primary antibody capable of binding phosphorylated alpha-synuclein wherein the primary antibody comprises complementarity determining regions (CDRs) having the following amino acid sequences:

```
CDR1 VL
                             (SEQ ID NO: 2)
QSVYNNNN,

CDR2 VL
                             (SEQ ID NO: 3)
KASKVAS,

CDR3 VL
                             (SEQ ID NO: 4)
LGGYSGDIYT,

CDR4 VH
                             (SEQ ID NO: 6)
GFTISSYHMS,

CDR5 VH
                             (SEQ ID NO: 7)
ISTSGNI,
and

CDR6 VH
                             (SEQ ID NO: 8)
ARLGIATGYSF;
and
```

(b) a primary antibody capable of binding to a nerve feature.

27. The kit of claim 26, further comprising:
(a) a first secondary antibody having a first label conjugated thereto, wherein the first secondary antibody is immunoreactive with the primary antibody capable of binding phosphorylated alpha-synuclein;
(b) a set of reagents that generates a first detectable single when reacted with the first label of the first secondary antibody;
(c) a second secondary antibody having a second label conjugated thereto, wherein the second secondary antibody is immunoreactive with the primary antibody capable of binding the nerve feature;
(d) a set of reagents that generates a second detectable single when reacted with the second label of the second secondary antibody;
wherein the first detectable signal and the second detectable signal are different.

28. The kit of claim 27, wherein the first detectable signal is silver stain.

29. The kit of claim 26, wherein the primary antibody capable of binding to the nerve feature is selected from an antibody capable of binding a protein selected from the group consisting of: ubiquitin C-terminal hydrolase L1, RNA binding fox-1 homolog 3, microtubule associated protein 2, 160 kDa neurofilament medium, 200 kDa neurofilament heavy, and discs large MAGUK scaffold protein 4.

30. The kit of claim 26, wherein the antibody capable of binding phosphorylated alpha-synuclein comprises a light chain comprising SEQ ID NO: 01 and the heavy chain comprising SEQ ID NO: 05.

* * * * *

SEQUENCE LISTING

<160> NUMBER OF SEQ ID NOS: 59

<210> SEQ ID NO 1
<211> LENGTH: 214
<212> TYPE: PRT
<213> ORGANISM: Artificial Sequence
<220> FEATURE:
<223> OTHER INFORMATION: Synthetic peptide

<400> SEQUENCE: 1

```
Ala Gln Val Leu Thr Gln Thr Pro Ser Pro Val Ser Ala Ala Val Gly
1               5                   10                  15

Gly Thr Val Thr Ile Ser Cys Gln Ser Ser Gln Ser Val Tyr Asn Asn
            20                  25                  30

Asn Asn Leu Val Trp Tyr Gln Gln Lys Pro Gly Gln Pro Pro Lys Gln
        35                  40                  45

Val Ile Tyr Lys Ala Ser Lys Val Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Leu Gly Gly Tyr Ser Gly
                85                  90                  95

Asp Ile Tyr Thr Phe Gly Gly Gly Thr Glu Val Val Val Lys Gly Asp
            100                 105                 110

Pro Val Ala Pro Thr Val Leu Ile Phe Pro Pro Ala Ala Asp Gln Val
        115                 120                 125

Ala Thr Gly Thr Val Thr Ile Val Cys Val Ala Asn Lys Tyr Phe Pro
    130                 135                 140

Asp Val Thr Val Thr Trp Glu Val Asp Gly Thr Thr Gln Thr Thr Gly
145                 150                 155                 160

Ile Glu Asn Ser Lys Thr Pro Gln Asn Ser Ala Asp Cys Thr Tyr Asn
                165                 170                 175

Leu Ser Ser Thr Leu Thr Leu Thr Ser Thr Gln Tyr Asn Ser His Lys
            180                 185                 190

Glu Tyr Thr Cys Lys Val Thr Gln Gly Thr Thr Ser Val Val Gln Ser
        195                 200                 205

Phe Asn Arg Gly Asp Cys
    210
```

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

```
Gln Ser Val Tyr Asn Asn Asn Asn
1               5
```

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

```
Lys Ala Ser Lys Val Ala Ser
1               5
```

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide

<400> SEQUENCE: 4

Leu Gly Gly Tyr Ser Gly Asp Ile Tyr Thr
1               5                   10

<210> SEQ ID NO 5
<211> LENGTH: 439
<212> TYPE: PRT
<213> ORGANISM: Artificial Sequence
<220> FEATURE:
<223> OTHER INFORMATION: Synthetic peptide

<400> SEQUENCE: 5

Cys Gln Ser Val Glu Glu Ser Gly Gly Arg Leu Val Thr Pro Gly Thr
1               5                   10                  15

Pro Leu Thr Leu Thr Cys Thr Ala Ser Gly Phe Thr Ile Ser Ser Tyr
            20                  25                  30

His Met Ser Trp Val Arg Gln Ala Pro Gly Lys Gly Leu Glu Trp Ile
        35                  40                  45

Gly Tyr Ile Ser Thr Ser Gly Asn Ile Tyr Tyr Ala Ser Trp Ala Lys
    50                  55                  60

Gly Arg Phe Thr Ile Ser Lys Thr Ser Ser Thr Val Asp Leu Arg
65                  70                  75                  80

Met Thr Ser Leu Thr Thr Glu Asp Thr Ala Thr Tyr Phe Cys Ala Arg
                85                  90                  95

Leu Gly Ile Ala Thr Gly Tyr Ser Phe Trp Gly His Gly Thr Leu Val
            100                 105                 110

Thr Val Ser Ser Gly Gln Pro Lys Ala Pro Ser Val Phe Pro Leu Ala
        115                 120                 125

Pro Cys Cys Gly Asp Thr Pro Ser Ser Thr Val Thr Leu Gly Cys Leu
    130                 135                 140

Val Lys Gly Tyr Leu Pro Glu Pro Val Thr Val Thr Trp Asn Ser Gly
145                 150                 155                 160

Thr Leu Thr Asn Gly Val Arg Thr Phe Pro Ser Val Arg Gln Ser Ser
                165                 170                 175

Gly Leu Tyr Ser Leu Ser Ser Val Val Ser Val Thr Ser Ser Ser Gln
            180                 185                 190

Pro Val Thr Cys Asn Val Ala His Pro Ala Thr Asn Thr Lys Val Asp
        195                 200                 205

Lys Thr Val Ala Pro Ser Thr Cys Ser Lys Pro Thr Cys Pro Pro Pro
    210                 215                 220

Glu Leu Leu Gly Gly Pro Ser Val Phe Ile Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Asp Asp Pro Glu Val Gln Phe Thr Trp Tyr Ile Asn
            260                 265                 270

Asn Glu Gln Val Arg Thr Ala Arg Pro Pro Leu Arg Glu Gln Gln Phe
        275                 280                 285

Asn Ser Thr Ile Arg Val Val Ser Thr Leu Pro Ile Ala His Gln Asp

```
                290                 295                 300
Trp Leu Arg Gly Lys Glu Phe Lys Cys Lys Val His Asn Lys Ala Leu
305                 310                 315                 320

Pro Ala Pro Ile Glu Lys Thr Ile Ser Lys Ala Arg Gly Gln Pro Leu
                325                 330                 335

Glu Pro Lys Val Tyr Thr Met Gly Pro Pro Arg Glu Glu Leu Ser Ser
            340                 345                 350

Arg Ser Val Ser Leu Thr Cys Met Ile Asn Gly Phe Tyr Pro Ser Asp
        355                 360                 365

Ile Ser Val Glu Trp Glu Lys Asn Gly Lys Ala Glu Asp Asn Tyr Lys
    370                 375                 380

Thr Thr Pro Ala Val Leu Asp Ser Asp Gly Ser Tyr Phe Leu Tyr Asn
385                 390                 395                 400

Lys Leu Ser Val Pro Thr Ser Glu Trp Gln Arg Gly Asp Val Phe Thr
                405                 410                 415

Cys Ser Val Met His Glu Ala Leu His Asn His Tyr Thr Gln Lys Ser
            420                 425                 430

Ile Ser Arg Ser Pro Gly Lys
        435

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Gly Phe Thr Ile Ser Ser Tyr His Met Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Ile Ser Thr Ser Gly Asn Ile
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide

<400> SEQUENCE: 8

Ala Arg Leu Gly Ile Ala Thr Gly Tyr Ser Phe
1               5                   10

<210> SEQ ID NO 9
<211> LENGTH: 214
<212> TYPE: PRT
<213> ORGANISM: Artificial Sequence
<220> FEATURE:
<223> OTHER INFORMATION: Synthetic peptide

<400> SEQUENCE: 9

Ala Gln Val Leu Thr Gln Thr Pro Ser Pro Val Ser Ala Ala Val Gly
```

```
                1               5                  10                 15
        Gly Thr Val Thr Ile Ser Cys Gln Ser Ser Gln Ser Val Tyr Asn Asn
                        20                  25                  30

Asn Asn Leu Val Trp Phe Gln Lys Lys Pro Gly Gln Pro Pro Lys Gln
                        35                  40                  45

Leu Ile Tyr Lys Ala Ser Lys Val Ala Ser Gly Val Pro Ser Arg Phe
                        50                  55                  60

Lys Gly Ser Gly Ser Gly Thr Gln Phe Thr Leu Thr Ile Ser Asp Leu
         65                  70                  75                  80

Glu Cys Asp Asp Ala Ala Thr Tyr Tyr Cys Leu Gly Gly Tyr Ser Gly
                        85                  90                  95

Asp Ile Tyr Thr Phe Gly Gly Gly Thr Glu Val Val Lys Gly Asp
                        100                 105                 110

Pro Val Ala Pro Thr Val Leu Ile Phe Pro Pro Ala Ala Asp Gln Val
                        115                 120                 125

Ala Thr Gly Thr Val Thr Ile Val Cys Val Ala Asn Lys Tyr Phe Pro
                        130                 135                 140

Asp Val Thr Val Thr Trp Glu Val Asp Gly Thr Thr Gln Thr Thr Gly
        145                 150                 155                 160

Ile Glu Asn Ser Lys Thr Pro Gln Asn Ser Ala Asp Cys Thr Tyr Asn
                        165                 170                 175

Leu Ser Ser Thr Leu Thr Leu Thr Ser Thr Gln Tyr Asn Ser His Lys
                        180                 185                 190

Glu Tyr Thr Cys Lys Val Thr Gln Gly Thr Thr Ser Val Val Gln Ser
                        195                 200                 205

Phe Asn Arg Gly Asp Cys
        210

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Gln Ser Val Tyr Asn Asn Asn Asn
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Lys Ala Ser Lys Val Ala Ser
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide

<400> SEQUENCE: 12

Leu Gly Gly Tyr Ser Gly Asp Ile Tyr Thr
1               5                  10
```

<210> SEQ ID NO 13
<211> LENGTH: 439
<212> TYPE: PRT
<213> ORGANISM: Artificial Sequence
<220> FEATURE:
<223> OTHER INFORMATION: Synthetic peptide

<400> SEQUENCE: 13

```
Gln Glu Gln Leu Lys Glu Ser Gly Gly Gly Leu Val Thr Pro Gly Gly
1               5                   10                  15

Thr Leu Thr Leu Thr Cys Thr Ala Ser Gly Phe Thr Ile Ser Ser Tyr
            20                  25                  30

His Met Ser Trp Val Arg Gln Ala Pro Gly Lys Gly Leu Glu Trp Ile
        35                  40                  45

Gly Tyr Ile Ser Thr Ser Gly Asn Ile Tyr Tyr Ala Thr Trp Ala Lys
    50                  55                  60

Gly Arg Phe Thr Ile Ser Lys Thr Ser Thr Thr Val Asp Leu Arg
65                  70                  75                  80

Met Thr Ser Leu Thr Thr Glu Asp Thr Ala Thr Tyr Phe Cys Ala Arg
                85                  90                  95

Leu Gly Ile Ala Thr Gly Tyr Ser Phe Trp Gly His Gly Thr Leu Val
            100                 105                 110

Thr Val Ser Ser Gly Gln Pro Lys Ala Pro Ser Val Phe Pro Leu Ala
        115                 120                 125

Pro Cys Cys Gly Asp Thr Pro Ser Ser Thr Val Thr Leu Gly Cys Leu
    130                 135                 140

Val Lys Gly Tyr Leu Pro Glu Pro Val Thr Val Thr Trp Asn Ser Gly
145                 150                 155                 160

Thr Leu Thr Asn Gly Val Arg Thr Phe Pro Ser Val Arg Gln Ser Ser
                165                 170                 175

Gly Leu Tyr Ser Leu Ser Ser Val Val Ser Val Thr Ser Ser Ser Gln
            180                 185                 190

Pro Val Thr Cys Asn Val Ala His Pro Ala Thr Asn Thr Lys Val Asp
        195                 200                 205

Lys Thr Val Ala Pro Ser Thr Cys Ser Lys Pro Thr Cys Pro Pro Pro
    210                 215                 220

Glu Leu Leu Gly Gly Pro Ser Val Phe Ile Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Asp Asp Pro Glu Val Gln Phe Thr Trp Tyr Ile Asn
            260                 265                 270

Asn Glu Gln Val Arg Thr Ala Arg Pro Pro Leu Arg Glu Gln Gln Phe
        275                 280                 285

Asn Ser Thr Ile Arg Val Val Ser Thr Leu Pro Ile Ala His Gln Asp
    290                 295                 300

Trp Leu Arg Gly Lys Glu Phe Lys Cys Lys Val His Asn Lys Ala Leu
305                 310                 315                 320

Pro Ala Pro Ile Glu Lys Thr Ile Ser Lys Ala Arg Gly Gln Pro Leu
                325                 330                 335

Glu Pro Lys Val Tyr Thr Met Gly Pro Pro Arg Glu Glu Leu Ser Ser
            340                 345                 350

Arg Ser Val Ser Leu Thr Cys Met Ile Asn Gly Phe Tyr Pro Ser Asp
        355                 360                 365
```

```
Ile Ser Val Glu Trp Glu Lys Asn Gly Lys Ala Glu Asp Asn Tyr Lys
    370                 375                 380

Thr Thr Pro Ala Val Leu Asp Ser Asp Gly Ser Tyr Phe Leu Tyr Asn
385                 390                 395                 400

Lys Leu Ser Val Pro Thr Ser Glu Trp Gln Arg Gly Asp Val Phe Thr
                405                 410                 415

Cys Ser Val Met His Glu Ala Leu His Asn His Tyr Thr Gln Lys Ser
            420                 425                 430

Ile Ser Arg Ser Pro Gly Lys
        435

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Gly Phe Thr Ile Ser Ser Tyr His Met Ser
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Ile Ser Thr Ser Gly Asn Ile
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic peptide

<400> SEQUENCE: 16

Ala Arg Leu Gly Ile Ala Thr Gly Tyr Ser Phe
1               5                   10

<210> SEQ ID NO 17
<211> LENGTH: 220
<212> TYPE: PRT
<213> ORGANISM: Artificial Sequence
<220> FEATURE:
<223> OTHER INFORMATION: Synthetic peptide

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80
```

```
Ile Ser Ser Leu Gln Pro Glu Asp Leu Ala Thr Tyr Tyr Cys Gln Gln
                85                  90                  95

Tyr Tyr Ser Tyr Pro Leu Thr Phe Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 18
<211> LENGTH: 17
<212> TYPE: PRT
<213> ORGANISM: Artificial Sequence
<220> FEATURE:
<223> OTHER INFORMATION: Synthetic peptide

<400> SEQUENCE: 18

Lys Ser Ile Gln Thr Leu Leu Tyr Ser Ser Asn Gln Lys Asn Tyr Leu
1               5                   10                  15

Ala

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Trp Ala Ser Ile Arg Lys Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide

<400> SEQUENCE: 20

Gln Gln Tyr Tyr Ser Tyr Pro Leu Thr
1               5

<210> SEQ ID NO 21
<211> LENGTH: 446
<212> TYPE: PRT
<213> ORGANISM: Artificial Sequence
<220> FEATURE:
<223> OTHER INFORMATION: Synthetic peptide

<400> SEQUENCE: 21
```

-continued

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Asn Tyr
            20                  25                  30
Gly Met Ser Trp Val Arg Gln Ala Pro Gly Lys Gly Leu Glu Trp Val
        35                  40                  45
Ala Ser Ile Ser Ser Gly Gly Ser Thr Tyr Tyr Pro Asp Asn Val
50                      55                  60
Lys Gly Arg Phe Thr Ile Ser Arg Asp Asp Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly Gly Ala Gly Ile Asp Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
```

420                 425                 430
Asn His Tyr Thr Gln Lys Ser Leu Ser Leu Ser Pro Gly Lys
        435                 440                 445

<210> SEQ ID NO 22
<211> LENGTH: 5
<212> TYPE: PRT
<213> ORGANISM: Artificial Sequence
<220> FEATURE:
<223> OTHER INFORMATION: Synthetic peptide

<400> SEQUENCE: 22

Asn Tyr Gly Met Ser
1               5

<210> SEQ ID NO 23
<211> LENGTH: 17
<212> TYPE: PRT
<213> ORGANISM: Artificial Sequence
<220> FEATURE:
<223> OTHER INFORMATION: Synthetic peptide

<400> SEQUENCE: 23

Ser Ile Ser Ser Gly Gly Gly Ser Thr Tyr Tyr Pro Asp Asn Val Lys
1               5                   10                  15

Gly

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

Gly Gly Ala Gly Ile Asp Tyr
1               5

<210> SEQ ID NO 25
<211> LENGTH: 113
<212> TYPE: PRT
<213> ORGANISM: Artificial Sequence
<220> FEATURE:
<223> OTHER INFORMATION: Synthetic peptide

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys

```
<210> SEQ ID NO 26
<211> LENGTH: 17
<212> TYPE: PRT
<213> ORGANISM: Artificial Sequence
<220> FEATURE:
<223> OTHER INFORMATION: Synthetic peptide

<400> SEQUENCE: 26

Lys Ser Ile Gln Thr Leu Leu Tyr Ser Ser Asn Gln Lys Asn Tyr Leu
1               5                   10                  15

Ala

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide

<400> SEQUENCE: 27

Trp Ala Ser Ile Arg Lys Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide

<400> SEQUENCE: 28

Gln Gln Tyr Tyr Ser Tyr Pro Leu Thr
1               5

<210> SEQ ID NO 29
<211> LENGTH: 116
<212> TYPE: PRT
<213> ORGANISM: Artificial Sequence
<220> FEATURE:
<223> OTHER INFORMATION: Synthetic peptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser
        115

<210> SEQ ID NO 30
<211> LENGTH: 5
<212> TYPE: PRT
```

```
<213> ORGANISM: Artificial Sequence
<220> FEATURE:
<223> OTHER INFORMATION: Synthetic peptide

<400> SEQUENCE: 30

Asn Tyr Gly Met Ser
1               5

<210> SEQ ID NO 31
<211> LENGTH: 17
<212> TYPE: PRT
<213> ORGANISM: Artificial Sequence
<220> FEATURE:
<223> OTHER INFORMATION: Synthetic peptide

<400> SEQUENCE: 31

Ser Ile Ser Ser Gly Gly Gly Ser Thr Tyr Tyr Pro Asp Asn Val Lys
1               5                   10                  15

Gly

<210> SEQ ID NO 32
<211> LENGTH: 7
<212> TYPE: PRT
<213> ORGANISM: Artificial Sequence
<220> FEATURE:
<223> OTHER INFORMATION: Synthetic peptide

<400> SEQUENCE: 32

Gly Gly Ala Gly Ile Asp Tyr
1               5

<210> SEQ ID NO 33
<211> LENGTH: 113
<212> TYPE: PRT
<213> ORGANISM: Artificial Sequence
<220> FEATURE:
<223> OTHER INFORMATION: Synthetic peptide

<400> SEQUENCE: 33

Asp Val Val Met Thr Gln Ser Pro Asp Ser Leu Ala Val Ser Leu Gly
1               5                   10                  15

Glu Arg Ala Thr Ile Asn Cys Lys Ser Ser Gln Asn Val Leu Tyr Ser
                20                  25                  30

Ser Asn Asn Lys Asn Tyr Leu Ala Trp Tyr Gln Gln Lys Pro Gly His
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Thr Ser Leu Gln Thr Glu Asp Val Ala Val Tyr Tyr Cys Gln Gln
                85                  90                  95

Tyr Tyr Ser Ser Pro Leu Thr Phe Gly Gly Gly Thr Lys Val Glu Ile
            100                 105                 110

Lys

<210> SEQ ID NO 34
<211> LENGTH: 17
<212> TYPE: PRT
<213> ORGANISM: Artificial Sequence
<220> FEATURE:
<223> OTHER INFORMATION: Synthetic peptide

<400> SEQUENCE: 34
```

Lys Ser Ser Gln Asn Val Leu Tyr Ser Asn Asn Lys Asn Tyr Leu
1               5                   10                  15

Ala

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide

<400> SEQUENCE: 35

Trp Ala Ser Thr Arg Glu Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic peptide

<400> SEQUENCE: 36

Gln Gln Tyr Tyr Ser Ser Pro Leu Thr
1               5

<210> SEQ ID NO 37
<211> LENGTH: 124
<212> TYPE: PRT
<213> ORGANISM: Artificial Sequence
<220> FEATURE:
<223> OTHER INFORMATION: Synthetic peptide

<400> SEQUENCE: 37

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Lys Arg Lys Tyr Ser Gln Lys Phe
    50                  55                  60

Gln Asp Arg Val Thr Ile Asn Arg Asp Thr Ser Ala Ser Thr Ile Tyr
65                  70                  75                  80

Met Glu Leu Ser Ser Leu Gly Ser Glu Asp Thr Ala Val Tyr Tyr Cys
                85                  90                  95

Ala Arg Glu Glu Asp His Ala Gly Ser Gly Ser Tyr Leu Ser Met Asp
            100                 105                 110

Val Trp Gly Gln Gly Thr Leu Val Thr Val Ser Ser
        115                 120

<210> SEQ ID NO 38
<211> LENGTH: 5
<212> TYPE: PRT
<213> ORGANISM: Artificial Sequence
<220> FEATURE:
<223> OTHER INFORMATION: Synthetic peptide

<400> SEQUENCE: 38

Asn Tyr Ala Met His
1               5

```
<210> SEQ ID NO 39
<211> LENGTH: 17
<212> TYPE: PRT
<213> ORGANISM: Artificial Sequence
<220> FEATURE:
<223> OTHER INFORMATION: Synthetic peptide

<400> SEQUENCE: 39

Trp Ile Asn Ala Gly Asn Gly Lys Arg Lys Tyr Ser Gln Lys Phe Gln
1               5                   10                  15

Asp

<210> SEQ ID NO 40
<211> LENGTH: 15
<212> TYPE: PRT
<213> ORGANISM: Artificial Sequence
<220> FEATURE:
<223> OTHER INFORMATION: Synthetic peptide

<400> SEQUENCE: 40

Glu Glu Asp His Ala Gly Ser Gly Ser Tyr Leu Ser Met Asp Val
1               5                   10                  15

<210> SEQ ID NO 41
<211> LENGTH: 108
<212> TYPE: PRT
<213> ORGANISM: Artificial Sequence
<220> FEATURE:
<223> OTHER INFORMATION: Synthetic peptide

<400> SEQUENCE: 41

Gln Ser Val Leu Thr Gln Pro Pro Ser Val Ser Val Ser Pro Gly Gln
1               5                   10                  15

Thr Ala Arg Ile Thr Cys Ser Gly Glu Ala Leu Pro Met Gln Phe Ala
            20                  25                  30

His Trp Tyr Gln Gln Arg Pro Gly Lys Ala Pro Val Ile Val Val Tyr
        35                  40                  45

Lys Asp Ser Glu Arg Pro Ser Gly Val Pro Glu Arg Phe Ser Gly Ser
    50                  55                  60

Ser Ser Gly Thr Thr Ala Thr Leu Thr Ile Thr Gly Val Gln Ala Glu
65                  70                  75                  80

Asp Glu Ala Asp Tyr Tyr Cys Gln Ser Pro Asp Ser Thr Asn Thr Tyr
                85                  90                  95

Glu Val Phe Gly Gly Gly Thr Lys Leu Thr Val Leu
            100                 105

<210> SEQ ID NO 42
<211> LENGTH: 11
<212> TYPE: PRT
<213> ORGANISM: Artificial Sequence
<220> FEATURE:
<223> OTHER INFORMATION: Synthetic peptide

<400> SEQUENCE: 42

Ser Gly Glu Ala Leu Pro Met Gln Phe Ala His
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide
```

<400> SEQUENCE: 43

Lys Asp Ser Glu Arg Pro Ser
1               5

<210> SEQ ID NO 44
<211> LENGTH: 11
<212> TYPE: PRT
<213> ORGANISM: Artificial Sequence
<220> FEATURE:
<223> OTHER INFORMATION: Synthetic peptide

<400> SEQUENCE: 44

Gln Ser Pro Asp Ser Thr Asn Thr Tyr Glu Val
1               5                   10

<210> SEQ ID NO 45
<211> LENGTH: 113
<212> TYPE: PRT
<213> ORGANISM: Artificial Sequence
<220> FEATURE:
<223> OTHER INFORMATION: Synthetic peptide

<400> SEQUENCE: 45

Glu Val Gln Leu Val Gln Ser Gly Gly Gly Leu Val Glu Pro Gly Gly
1               5                   10                  15

Ser Leu Arg Leu Ser Cys Ala Val Ser Gly Phe Asp Phe Glu Lys Ala
            20                  25                  30

Trp Met Ser Trp Val Arg Gln Ala Pro Gly Gln Gly Leu Gln Trp Val
        35                  40                  45

Ala Arg Ile Lys Ser Thr Ala Asp Gly Gly Thr Thr Ser Tyr Ala Ala
    50                  55                  60

Pro Val Glu Gly Arg Phe Ile Ile Ser Arg Asp Asp Ser Arg Asn Met
65                  70                  75                  80

Leu Tyr Leu Gln Met Asn Ser Leu Lys Thr Glu Asp Thr Ala Val Tyr
                85                  90                  95

Tyr Cys Thr Ser Ala His Trp Gly Gln Gly Thr Leu Val Thr Val Ser
            100                 105                 110

Ser

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide

<400> SEQUENCE: 46

Lys Ala Trp Met Ser
1               5

<210> SEQ ID NO 47
<211> LENGTH: 19
<212> TYPE: PRT
<213> ORGANISM: Artificial Sequence
<220> FEATURE:
<223> OTHER INFORMATION: Synthetic peptide

<400> SEQUENCE: 47

Arg Ile Lys Ser Thr Ala Asp Gly Gly Thr Thr Ser Tyr Ala Ala Pro
1               5                   10                  15

Val Glu Gly

<210> SEQ ID NO 48
<211> LENGTH: 4
<212> TYPE: PRT
<213> ORGANISM: Artificial Sequence
<220> FEATURE:
<223> OTHER INFORMATION: Synthetic peptide

<400> SEQUENCE: 48

Thr Ser Ala His
1

<210> SEQ ID NO 49
<211> LENGTH: 113
<212> TYPE: PRT
<213> ORGANISM: Artificial Sequence
<220> FEATURE:
<223> OTHER INFORMATION: Synthetic peptide

<400> SEQUENCE: 49

Glu Val Gln Leu Val Gln Ser Gly Gly Gly Leu Val Glu Pro Gly Gly
1               5                   10                  15

Ser Leu Arg Leu Ser Cys Ala Val Ser Gly Phe Asp Phe Glu Lys Ala
            20                  25                  30

Trp Met Ser Trp Val Arg Gln Ala Pro Gly Gln Gly Leu Gln Trp Val
        35                  40                  45

Ala Arg Ile Lys Ser Thr Ala Asp Gly Gly Thr Thr Ser Tyr Ala Ala
    50                  55                  60

Pro Val Glu Gly Arg Phe Ile Ile Ser Arg Asp Asp Ser Arg Asn Met
65                  70                  75                  80

Leu Tyr Leu Gln Met Asn Ser Leu Lys Thr Glu Asp Thr Ala Val Tyr
                85                  90                  95

Tyr Cys Thr Ser Ala His Trp Gly Gln Gly Thr Leu Val Thr Val Ser
            100                 105                 110

Ser

<210> SEQ ID NO 50
<211> LENGTH: 108
<212> TYPE: PRT
<213> ORGANISM: Artificial Sequence
<220> FEATURE:
<223> OTHER INFORMATION: Synthetic peptide

<400> SEQUENCE: 50

Gln Ser Val Leu Thr Gln Pro Pro Ser Val Ser Val Ser Pro Gly Gln
1               5                   10                  15

Thr Ala Arg Ile Thr Cys Ser Gly Glu Ala Leu Pro Met Gln Phe Ala
            20                  25                  30

His Trp Tyr Gln Gln Arg Pro Gly Lys Ala Pro Val Ile Val Val Tyr
        35                  40                  45

Lys Asp Ser Glu Arg Pro Ser Gly Val Pro Glu Arg Phe Ser Gly Ser
    50                  55                  60

Ser Ser Gly Thr Thr Ala Thr Leu Thr Ile Thr Gly Val Gln Ala Glu
65                  70                  75                  80

Asp Glu Ala Asp Tyr Tyr Cys Gln Ser Pro Asp Ser Thr Asn Thr Tyr
                85                  90                  95

Glu Val Phe Gly Gly Gly Thr Lys Leu Thr Val Leu
            100                 105

```
<210> SEQ ID NO 51
<211> LENGTH: 5
<212> TYPE: PRT
<213> ORGANISM: Artificial Sequence
<220> FEATURE:
<223> OTHER INFORMATION: Synthetic peptide

<400> SEQUENCE: 51

Asn Tyr Ala Met His
1               5

<210> SEQ ID NO 52
<211> LENGTH: 17
<212> TYPE: PRT
<213> ORGANISM: Artificial Sequence
<220> FEATURE:
<223> OTHER INFORMATION: Synthetic peptide

<400> SEQUENCE: 52

Trp Ile Asn Ala Gly Asn Gly Lys Arg Lys Tyr Ser Gln Lys Phe Gln
1               5                   10                  15

Asp

<210> SEQ ID NO 53
<211> LENGTH: 15
<212> TYPE: PRT
<213> ORGANISM: Artificial Sequence
<220> FEATURE:
<223> OTHER INFORMATION: Synthetic peptide

<400> SEQUENCE: 53

Glu Glu Asp His Ala Gly Ser Gly Ser Tyr Leu Ser Met Asp Val
1               5                   10                  15

<210> SEQ ID NO 54
<211> LENGTH: 17
<212> TYPE: PRT
<213> ORGANISM: Artificial Sequence
<220> FEATURE:
<223> OTHER INFORMATION: Synthetic peptide

<400> SEQUENCE: 54

Lys Ser Ser Gln Asn Val Leu Tyr Ser Ser Asn Asn Lys Asn Tyr Leu
1               5                   10                  15

Ala

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide

<400> SEQUENCE: 55

Trp Ala Ser Thr Arg Glu Ser
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide

<400> SEQUENCE: 56

Gln Gln Tyr Tyr Ser Ser Pro Leu Thr
```

<210> SEQ ID NO 57
<211> LENGTH: 116
<212> TYPE: PRT
<213> ORGANISM: Artificial Sequence
<220> FEATURE:
<223> OTHER INFORMATION: Synthetic peptide

<400> SEQUENCE: 57

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser
        115

<210> SEQ ID NO 58
<211> LENGTH: 113
<212> TYPE: PRT
<213> ORGANISM: Artificial Sequence
<220> FEATURE:
<223> OTHER INFORMATION: Synthetic peptide

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys

<210> SEQ ID NO 59
<211> LENGTH: 14
<212> TYPE: PRT
<213> ORGANISM: Artificial Sequence
<220> FEATURE:
<223> OTHER INFORMATION: corresponds to residues 122-135 of human alpha-
      synuclein
<220> FEATURE:
<221> NAME/KEY: MISC_FEATURE

```
<222> LOCATION: (8)..(8)
<223> OTHER INFORMATION: serine residue is phosphorylated

<400> SEQUENCE: 59

Asn Glu Ala Tyr Glu Met Pro Ser Glu Glu Gly Tyr Gln Asp
1               5                   10
```